US007560118B2

(12) United States Patent
Whitehead et al.

(10) Patent No.: US 7,560,118 B2
(45) Date of Patent: Jul. 14, 2009

(54) ATTENUATED DENGUE VIRUS COMPRISING MUTATIONS IN THE NS3 GENE

(75) Inventors: Stephen S. Whitehead, Montgomery Village, MD (US); Brian R. Murphy, Bethesda, MD (US); Kathryn A. Hanley, Bethesda, MD (US); Joseph E. Blaney, Frederick, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 163 days.

(21) Appl. No.: 11/446,050

(22) Filed: Jun. 2, 2006

(65) Prior Publication Data

US 2007/0092534 A1 Apr. 26, 2007

Related U.S. Application Data

(60) Division of application No. 10/719,547, filed on Nov. 21, 2003, now Pat. No. 7,226,602, which is a continuation of application No. PCT/US02/16308, filed on May 22, 2002.

(60) Provisional application No. 60/293,049, filed on May 22, 2001.

(51) Int. Cl.
A61K 39/12 (2006.01)
C12N 7/04 (2006.01)
(52) U.S. Cl. .................................. 424/218.1; 435/236
(58) Field of Classification Search ....................... None
See application file for complete search history.

(56) References Cited

U.S. PATENT DOCUMENTS

| 5,494,671 A | 2/1996 | Lai et al. |
| 6,074,865 A | 6/2000 | Kelly et al. |
| 6,455,509 B1 | 9/2002 | Kochel et al. |

FOREIGN PATENT DOCUMENTS

WO WO 00/57907 A1 10/2000

OTHER PUBLICATIONS

Angsubhakorn, S. et al. 1994 "Dengue-3 (16562) PGMK 33 vaccine: neurovirulence, viremia and immune responses in *Macaca fascicularis*," *Southeast Asian J. Trop. Med. Public Health* 25:554-559.
Bancroft W.H. et al. 1981 "Dengue-2 vaccine: virological, immunological; and clinical responses of six yellow fever-immune recipients," *Infect. Immun.* 31:698-703.
Bancroft, W.H. et al. 1984 "Dengue virus type 2 vaccine: reactogenicity and immunogenicity in soldiers." *J. Infect. Dis.* 149:1005-1010.

Bhamarapravati, N. et al. 1997 Live attenuated tetravalent dengue vaccine, p. 367-377. In D. J. Gubler, and G. Kuno (ed.), *Dengue and Dengue Hemorrhagic Fever*. CAB International, New York, N.Y.
Bhamarapravati, N. et al. 2000 "Live attenuated tetravalent dengue vaccine." *Vaccine* 18(Suppl. 2):44-47.
Bhamarpravati N. et al. 1987 "Immunization with a live attenuated dengue-2-virus candidate vaccine (16681-PDK 53): clinical, immunological and biological responses in adult volunteers," *Bull World Health Organ.* 65:189-195.
Blaney J.E. Jr., et al. 2001 "Chemical mutagenesis of dengue virus type 4 yields mutant viruses which are temperature sensitive in vero cells or human liver cells and attenuated in mice." *J. Virol.* 75:9731-9740.
Blaney, Jr. J.E. et al. (2002) "Genetic basis of attenuation of dengue virus type 4 small plaque mutants with restricted replication in suckling mice and an SCID mice transplanted with human liver cells" *Virology* 300:125-139.
Blaney, Jr. J.E. et al. (2003) "Mutations which enhance the replication of dengue virus type 4 and an antigenic chimeric Dengue virus type 2/4 vaccine candidate in Vero cells" *Vaccine* 21:4317-4327.
Blaney, Jr. J.E. et al. (2003) "Temperature sensitive mutations in the genes encoding the ns1, ns2a, and ns5 nonstructural proteins of dengue virus type 4 restrict replication in the brains of mice" *Arch. Virol.* 148:999-1006.
Blaney, Jr. J.E. et al. (2004) "Genetically modified, live attenuated dengue virus type 3 vaccine candidates" *Am. J. Trop. Med. Hyg.* 71:811-821.
Blaney, Jr. J.E. et al. (2005) "Recombinant, live-attenuated tetravalent dengue virus vaccine formulations induce a balanced, broad, and protective neutralizing antibody response against each of the four serotypes in Rhesus monkeys" *J. Virol.* 79:5516-5528
Blaney, Jr., J.E. et al. (2001) "Chemical mutagenesis of dengue virus type 4 yields mutant viruses which are temperature sensitive in vero cells or human liver cells and attenuated in mice" *J. Virol.* 75:9731-9740.
Blok, J. et al. 1992 "Comparison of a dengue-2- virus and its candidate vaccine derivative: sequence relationships with the flaviviruses and other viruses." *Virology* 187:573-590.
Bray, M. et al. 1991 "Construction of intertypic chimeric dengue viruses by substitution of structural protein genes," *PNAS USA* 88:10342-10346.
Bray, M. et al. 1996 "Monkeys immunized with intertypic chimeric dengue viruses are protected against wild-type virus challenge," *J. Virol.* 70:4162-4166.
Burke, D.S. et al. 1988 "A prospective study of dengue infections in Bangkok." *Am. J. Trop. Med. Hyg.* 38:172-180.
Butrapet, S. et al. 2000 "Attenuation markers of a candidate dengue type 2 vaccine virus, strain 16681 (PDK-53), are defined by mutations in the 5' noncoding region and nonstructural proteins 1 and 3." *J. Virol.* 74:3011-3019.
CDC, 2000 "Public Health Dispatch: Outbreak of poliomyelitis—Dominican Republic and Haiti, 2000" *MMWR Morb. Mortal Wkly. Rep.* 49:1094-1104.
Chambers, T.J. et al. 1999 "Yellow fever/Japanese encephalitis chimeric viruses: construction and biological properties," *J. Virol.* 73:3095-3101.

(Continued)

*Primary Examiner*—Jeffrey S. Parkin
(74) *Attorney, Agent, or Firm*—Knobbe Martens Olson & Bear LLP

(57) ABSTRACT

A menu of mutations was developed that is useful in fine-tuning the attenuation and growth characteristics of dengue virus vaccines.

16 Claims, 12 Drawing Sheets

OTHER PUBLICATIONS

Chang, G.-J. 1997 Molecular biology of dengue viruses, p. 175-198. In D. J. Gubler, and G. Kuno (ed.), *Dengue and Dengue Hemorrhagic Fever*. CAB International, New York, N.Y.

Chen, W. et al. 1995 "Construction of intertypic chimeric dengue viruses exhibiting type 3 antigenicity and neurovirulence for mice," *J. Virol.* 69:5186-5190.

Cole, G.A. et al. 1969 "Pathogenesis of type 1 dengue virus infection in suckling, weanling and adult mic. 1. The relation of virus replication to interferon and antibody formation." *Am. J. Epidemiol.* 89:669-680.

Cole, G.A. et al. 1973 "Pathogenesis of type 1 dengue virus infection in suckling, weaning and adult mice. II. Immunofluorescent and histological studies." *J. Comp. Pathol.* 83:243-252.

Couvelard, A. et al. 1999 "Report of a fatal case of dengue infection with hepatitis: demonstration of dengue antigens in hepatocytes and liver apoptosis." *Hum. Pathol.* 30:1106-1110.

Database NCBI Jan. 3, 2001, XP0021317338 retrieved from NCBI accession No. GI:12018173; Dateabase accession No. AF 326827.

Database NCBI Jan. 3, 2001, XP002317339 retrieved from NCBI accession No. GI:2018169; Database accession No. AF326825.

Dunster, L.M. et al. 1999 "Molecular and biological changes associated with HeLa cell attenuation of wild-type yellow fever virus." *Virology* 261:309-318.

Durbin A.P. et al. 2001 "Attenuation and immunogenicity in humans of a live dengue virus type-4 vaccine candidate with a 30 nucleotide deletion in its 3'-untranslated region." *Am. J. Trop. Med. Hyg.* 65:405-13.

Durbin, A.P. et al. (2000) "A recombinant live attenuated dengue virus type 4 vaccine candidate is highly attenuated and immunogenic in humans," *Clin. Infect. Dis.* 31:223.

Eckels, K.H. et al. 1980 "Dengue-2 vaccine: preparation from a small-plaque virus clone." *Infect. Immun.* 27:175-180.

Eckels, K.H. et al. 1984 "Selection of attenuated dengue 4 viruses by serial passage in primary kidney cells. V. Human response to immunization with a candidate vaccine prepared in fetal rhesus lung cells." *Am. J. Trop. Med Hyg.* 33:684-689.

Edelman, R. et al. 1994 "A live attenuated dengue-1 vaccine candidate (45AZ5) passaged in primary dog kidney cell culture is attenuated and immunogenic for humans." *J. Infect. Dis.* 170:1448-1455.

Gubler, D. J. 1999 "Impact of dengue/dengue hemorrhagic fever on the developing world." *Adv. Virus Res.* 53:35-70.

Gubler, D.J. et al. 1998 "Dengue and dengue hemorrhagic fever," *Clin. Microbiol. Rev.* 11:480-496.

Guirakhoo, F. et al. 2000 "Recombinant chimeric yellow fever-dengue type 2 virus is immunogenic and protective in nonhuman primates." *J. Virol.* 74:5477-5485.

Halstead, S.B. et al. 1969 "Dengue and chikungunya virus infection in man in Thailand, 1962-1964. IV. Epidemiologic studies in the Bangkok metropolitan area." *Am. J. Trop. Med. Hyg.* 18:997-1021.

Halstead, S.B. et al. 1977 "Dengue viruses and mononuclear phagocytes. II. Identity of blood and tissue leukocytes supporting in vitro infection." *J. Exp. Med.* 146:218-229.

Hanley, K.A. et al. (2002) "Paired charge-to-alanine mutagenesis of dengue virus type 4 ns5 generates mutants with temperature-sensitive, host range, and mouse attenuation phenotypes" *J. Virol.* 76:525-531.

Hanley, K.A. et al. (2002) "Paired charge-to-alanine mutagenesis of dengue virus type 4 NS5 generates mutants with temperature-sensitive, host range, and mouse attenuation phenotypes," *J. Virol.* 76:525-531.

Hanley, K.A. et al. (2003) "A trade-off in replication in mosquito versus mammalian systems conferred by a point mutation in the ns4b protein of dengue virus type 4" *Virology* 312:222-232.

Hanley, K.A. et al. (2004) "Introduction of mutations into the nonstructural genes or 3' untranslated region of an attenuated dengue virus type 4 vaccine candidate further decreases replication in rhesus monkeys while retaining protective immunity" *Vaccine* 22:3440-3448.

Hoke, C.H. Jr. et al. 1990. "Preparation of an attenuated dengue 4 (341750 Carib) virus vaccine. II. Safety and immunogenicity in humans," *Am J. Trop. Med. Hyg.* 43:219-226.

Holbrook, M.R. et al. 2000 "The French neurotropic vaccine strain of yellow fever virus accumulates mutations slowly during passage in cell culture." *Virus Res.* 69:31-39.

Huang, C.Y. et al. 2000 "Chimeric dengue type 2 (vaccine strain PDK-53)/dengue type 1 virus as a potential candidate dengue type 1 virus vaccine." *J. Virol.* 74:3020-3028.

Huerre, M.R. et al. 2001 "Liver histopathology and biological correlates in five cases of fatal dengue fever in Vietnamese children." *Virchows Arch.* 438:107-115.

Igarashi, A. 1997 "Impact of dengue virus infection and its control," *FEMS Immunol. Med. Microbiol.* 18:291-300.

Innis, B L. et al. 1988 "Virulence of a live dengue virus vaccine candidate: a possible new marker of dengue virus attenuation." *J. Infect. Dis.* 158:876-880.

Innis, B.L. 1995 Dengue and dengue hemorrhagic fever, p. 103-146. In J. S. Porterfield (ed.), *Exotic Viral Infections*. Chapman and Hall, London, United Kingdom.

Jennings, A.D. et al. 1994 "Analysis of a yellow fever virus isolated from a fatal case of vaccine-associated human encephalitis." *J. Infect. Dis.* 169:512-518.

Kalayanarooj, S. et al. 1997 "Early clinical and laboratory indicators of acute dengue illness." *J. Infect. Dis.* 176:313-321.

Kanesa-Thasan, N. et al. 2001 "Safety and immunogenicity of attenuated dengue virus vaccines (Aventis Pasteur) in human volunteers." *Vaccine* 19:3179-3188.

Kraiselburd E. et al. 1985 "Quantity of dengue virus required to infect rhesus monkeys," *Trans. R. Soc. Trop. Med. Hyg.* 79:248-251.

Kuo, C.H. et al. 1992 "Liver biochemical tests and dengue fever." *Am. J. Trop. Med. Hyg.* 47:265-270.

Kurane, I. et al. 1990 "Dengue-2 virus infection of human mononuclear cell lines and establishment of persistent infections." *Arc. Virol.* 110:91-101.

Lai, C. J. et al. (1998) "Evaluation of molecular strategies to develop a live dengue vaccine," *Clin. Diagnostic Virol.* 10:173-179.

Lai, C.J. et al. 1991 "Infectious RNA transcribed from stably cloned full-length cDNA of dengue type 4 virus," *Proc Natl Acad Sci USA* 88:5139-5143.

Lee, E. et al. 1997 "Changes in the dengue virus major envelope protein on passaging and their localization on the three-dimensional structure of the protein." *Virology* 232:281-290.

Libraty, D.H. et al. 2001 "Human dendritic cells are activated by dengue virus infection: enhancement by gamma interferon and implications for disease pathogenesis." *J. Virol.* 75:3501-3508.

Lin, Y.L. et al. 1998 "Study of dengue virus infection in SCID mice engrafted with human K562 cells." *J. Virol.* 72:9729-9737.

Lin, Y.L. et al. 2000 "Infection of five human liver cell lines by dengue-2 virus." *J. Med. Virol.* 60:425-431.

Marchette, N. J. et al. (1990) "Preparation of an attenuated dengue 4 (341750 carib) virus vaccine. I. pre-clinical studies," *Amer. J. Tropical Med. Hygiene* 43:212-218.

Marianneau, P. et al. 1996 "Dengue 1 virus binding to human hepatoma HepG2 and simian Vero cell surfaces differs." *J. Gen. Virol.* 77:2547-2554.

Martin, J. et al. 2000 "The vaccine origin of the 1968 epidemic of type 3 poliomyelitis in Poland," *Virology* 278:42-49.

McKee, K.T., Jr. et al. 1087 "Lack of attenuation of a candidate dengue 1 vaccine (45AZ5) in human volunteers." *Am. J. Trop. Med. Hyg.* 36:435-442.

Men, R. et al. 1996 "Dengue type 4 virus mutants containing deletions in the 3' noncoding region of the RNA genome: analysis of growth restriction in cell culture and altered viremia pattern and immunogenicity in rhesus monkeys." *J. Virol.* 70:3930-3937.

Mohan, B. et al. 2000 "Hepatic dysfunction in childhood dengue infection." *J. Trop. Pediatr.* 46:40-43.

Monath, T.P. et al. 1999 "Recombinant, chimaeric live, attenuated vaccine (ChimeriVax™) incorporating the envelope genes of Japanese encephalitis (SA14-14-2) virus and the capsid and nonstructural genes of yellow fever (17D) virus is safe, immunogenic and protective in non-human primates," *Vaccine* 17:1869-1882.

Murgue, B. et al. 2000 "Prospective study of the duration and magnitude of viraemia in children hospitalized during the 1996-1997 dengue-2 outbreak in French Polynesia," *J. Med. Virol.* 60:432-438.

Nakabayashi, H. et al. 1982 "Growth of human hepatoma cell lines with differentiated functions in chemically defined medium." *Cancer Res.* 42:3858-3863.

Ni, H. et al. 1995 "Molecular basis of attenuation of neurovirulence of wild-type Japanese encephalitis virus strain SA14." *J. Gen. Virol.* 76:409-413.

Pletnev, A.G. et al. 1998 "Attenuation of the Langat tick-borne flavivirus by chimerization with mosquito-borne flavivirus dengue type 4," *PNAS USA* 95:1746-1751.

Puri, B. et al. 1997 "Molecular analysis of dengue virus attenuation after serial passage in primary dog kidney cells." *J. Gen. Virol.* 78:2287-2291.

Rosen, L. et al. 1999 "Detection of dengue virus RNA by reverse transcription-polymerase chain reaction in the liver and lymphoid organs but not in the brain in fatal human infection." *Am. J. Trop. Med. Hyg.* 61:720-724.

Sabin, A. 1955 "Recent advances in our knowledge of dengue and sandfly fever," *Am. J. Trop. Med. Hyg.* 4:198-207.

Sabin, A.B. 1952 "Research on dengue during World War II," *Am. J. Trop. Med. Hyg.* 1:30-50.

Sabin, A.B. et al. 1945 "Production of immunity to dengue with virus modified by propagation in mice," *Science* 101:640-642.

Scott, R.M. et al. 1980 "Isolation of dengue viruses from peripheral blood leukocytes of patients with hemorrhagic fever." *J. Infect. Dis.* 141:1-6.

Thein, S. et al. 1997 "Risk factors in dengue shock syndrome." *Am. J. Trop. Med. Hyg.* 56:566-572.

Theofilopoulos, A.N. et al. 1976 "Replication of dengue-2 virus in cultured human lymphoblastoid cells and subpopulations of human peripheral leukocytes." *J. Immunol.* 117:953-961.

Troyer, J.M. et al. 2001 "A live attenuated recombinant dengue-4 virus vaccine candidate with restricted capacity for dissemination in mosquitoes and lack of transmission from vaccinees to mosquitoes," *Am. J. Trop. Med. Hyg.* 65:414-419.

Valle, R.P et al. 1998 "Mutagenesis of the NS3 protease of dengue virus type 2." *J. Virol.* 72:624-632.

Vaughn D.W., et al. 2000 "Dengue viremia titer, antibody response pattern, and virus serotype correlate with disease severity," *J. Infect. Dis.* 181:2-9.

Vaughn, D.W. et al. 1996 "Testing of a dengue 2 live-attenuated vaccine (strain 16681 PDK 53) in ten American volunteers." *Vaccine* 14:329-336.

Wahid, S.F. et al. 2000 "A comparison of the pattern of liver involvement in dengue hemorrhagic fever with classic dengue fever." *Southeast Asian J. Trop. Med. Public Health* 31:259-263.

Wang, E. et al. 1995 "Comparison of the genomes of the wild-type French viscerotropic strain of yellow fever virus with its vaccine derivative French neurotropic vaccine." *J. Gen. Virol.* 76:2749-2755.

Watts, D.M. et al. 1982 "Evaluation of *Toxorhynchites splendens* (Diptera:Culicidae) as a bioassay host for dengue viruses," *J. Med. Entomol.* 19:54-59.

Whitehead, S.S. et al. (2003) "A live attenuated dengue virus type 1 vaccine candidate with a 30-nucleotide deletion in the 3' untranslated region is highly attenuated and immunogenic in monkeys" *J. Virol.* 77:1653-1657.

Whitehead, S.S. et al. (2003) "Substitution of the structural genes of dengue virus type 4 with those of type 2 results in chimeric vaccine candidates which are attenuated for mosquitoes, mice, and rhesus monkeys" *Vaccine* 21:4307-4316.

Wisseman C.L. Jr., et al. 1963 "Attenuated living type 1 dengue vaccines," *Am J. Trop. Med. Hyg.* 12:620-623.

Wu, S.J. et al. 2000 "Human skin Langerhans cells are targets of dengue virus infection." *Nat. Med.* 6:816-820.

European Patent Office Communication dated Sep. 11, 2006 pursuant to European Application 02739358.6.

India Patent Office Communication dated Jan. 4, 2007 pursuant to India Patent Application No. 204/delnp/2005.

|     |            |            |            |            |            |     |
|-----|------------|------------|------------|------------|------------|-----|
| 1   | GTGTTGETLG | EKWKRQLNSL | DRKEFEEYKR | SGILEVDRTE | AKSALKDGSK | SAM |
| 51  | IKHAVSRGSS | KIRWIVERGM | VKPKGKVVDL | GCGRGGWSYY | MATLKNVTEV |     |
| 101 | KGYTKGGPGH | EEPIPMATYG | WNLVKLHSGV | DVFYKPTEQV | DTLLCDIGES |     |
| 151 | SSNPTIEEGR | TLRVLKMVEP | WLSSKPEFCI | KVLNPYMPTV | IEELEKLQRK |     |
| 201 | HGGNLVRCPL | SRNSTHEMYW | VSGASGNIVS | SVNTTSKMLL | NRFTTRHRKP |     |
| 251 | TYEKDVDLGA | GTRSVSTETE | KPDMTIIGRR | LQRLQEEHKE | TWHYDQENPY |     |
| 301 | RTWAYHGSYE | APSTGSASSM | VNGVVKLLTK | PWDVIPMVTQ | LAMTDTTPFG | Importin – binding + NLS |
| 351 | QQRVFKEKVD | TRTPQPKPGT | RMVMTTTANW | LWALLGKKKN | PRLCTREEFI |     |
| 401 | SKVRSNAAIG | AVFQEEQGWT | SASEAVNDSR | FWELVDKERA | LHQEGKCESC |     |
| 451 | VYNMMGKREK | KLGEFGRAKG | SRAIWYMWLG | ARFLEFEALG | FLNEDHWFGR |     |
| 501 | ENSWSGVEGE | GLHRLGYILE | EIDKKDGDLM | YADDTAGWDT | RITEDDLQNE |     |
| 551 | ELITEQMAPH | HKILAKAIFK | LTYQNKVVKV | LRPTPRGAVM | DIISRKDQRG |     |
| 601 | SGQVGTYGLN | TFTNMEVQLI | RQMEAEGVIT | QDDMQNPKGL | KERVEKWLKE |     |
| 651 | CGVDRLKRMA | ISGDDCVVKP | LDERFGTSLL | FLNDMGKVRK | DIPQWEPSKG | Polymerase |
| 701 | WKNWQEVPFC | SHHFHKIFMK | DGRSLVVPCR | NQDELIGRAR | ISQGAGWSLR |     |
| 751 | ETACLGKAYA | QMWSLMYFHR | RDLRLASMAI | CSAVPTEWFP | TSRTTWSIHA |     |
| 801 | HHQWMTTEDM | LKVWNRVWIE | DNPNMTDKTP | VHSWEDIPYL | GKREDLWCGS |     |
| 851 | LIGLSSRATW | AKNIHTAITQ | VRNLIGKEEY | VDYMPVMKRY | SAPSESEGVL |     |

ATTENUATED DENGUE VIRUS COMPRISING MUTATIONS IN THE NS3 GENE

RELATED APPLICATIONS

This application is a divisional of U.S. application Ser. No. 10/719,547, filed Nov. 21, 2003, now U.S. Pat. No. 7,226,602, which is a continuation and claims the benefit of priority of International Application No. PCT/US02/16308 filed May 22, 2002, designating the United States of America and published in English as WO 02/095075 on Nov. 28, 2002, which claims the benefit of priority of U.S. Provisional Application No. 60/293,049 filed May 22, 2001, all of which are hereby expressly incorporated by reference in their entireties.

FIELD OF THE INVENTION

A menu of mutations was developed that is useful in fine-tuning the attenuation and growth characteristics of dengue virus vaccines.

BACKGROUND OF THE INVENTION

Dengue virus is a positive-sense RNA virus belonging to the *Flavivirus* genus of the family Flaviviridae. Dengue virus is widely distributed throughout the tropical and semitropical regions of the world and is transmitted to humans by mosquito vectors. Dengue virus is a leading cause of hospitalization and death in children in at least eight tropical Asian countries (WHO, 1997. *Dengue haemorrhagic fever: diagnosis, treatment prevention and control*—2nd ed. Geneva: WHO). There are four serotypes of dengue virus (DEN-1, DEN-2, DEN-3, and DEN-4) which annually cause an estimated 50-100 million cases of dengue fever and 500,000 cases of the more severe form of dengue virus infection, dengue hemorrhagic fever/dengue shock syndrome (DHF/DSS) (Gubler, D. J. & Meltzer, M. 1999 *Adv Virus Res* 53:35-70). DHF/DSS is seen predominately in children and adults experiencing a second dengue virus infection with a serotype different than that of their first dengue virus infection and in primary infection of infants who still have circulating dengue-specific maternal antibody (Burke, D. S. et al. 1988 *Am J Trop Med Hyg* 38:172-80; Halstead, S. B. et al. 1969 *Am J Trop Med Hyg* 18:997-1021; Thein, S. et al. 1997 *Am J Trop Med Hyg* 56:566-72). A vaccine is needed to lessen the disease burden caused by dengue virus, but none is licensed. Because of the association of more severe disease with secondary dengue virus infection, a successful vaccine must induce immunity to all four serotypes. Immunity is primarily mediated by neutralizing antibody directed against the envelope E glycoprotein, a virion structural protein. Infection with one serotype induces long-lived homotypic immunity and a short-lived heterotypic immunity (Sabin, A. 1955 *Amer J Trop Med Hyg* 4:198-207). Therefore, the goal of immunization is to induce a long-lived neutralizing antibody response against DEN-1, DEN-2, DEN-3, and DEN-4, which can best be achieved economically using live attenuated virus vaccines. This is a reasonable goal since a live attenuated vaccine has already been developed for the related yellow fever virus, another mosquito-borne flavivirus present in tropical and semitropical regions of the world (Monath, T. P. & Heinz, F. X. 1996 in: Fields B. N. et al. eds. *Fields Virology* Philadelphia: Lippincott-Ravan Publishers, 961-1034).

Several live attenuated dengue vaccine candidates have been developed and evaluated in humans or non-human primates. The first live attenuated dengue vaccine candidates were host range mutants developed by serial passage of wild type dengue viruses in the brains of mice and selection of mutants attenuated for humans (Kimura, R. & Hotta, S. 1944 *Japanese J Bacteriology* 1:96-99; Sabin, A. B. & Schlesinger, R. W. 1945 *Science* 101:640; Wisseman, C. L. Jr. et al. 1963 *Am J Trop Med* 12:620-623). Although these candidate vaccine viruses were immunogenic in humans, their poor growth in cell culture discouraged further development. Additional live attenuated DEN-1, DEN-2, DEN-3, and DEN-4 vaccine candidates have been developed by serial passage in tissue culture (Angsubhakorn, S. et al. 1994 *Southeast Asian J Trop Med Public Health* 25:554-9; Bancroft, W. H. et al. 1981 *Infect Immun* 31:698-703; Bhamarapravati, N. et al. 1987 *Bull World Health Organ* 65:189-95; Eckels, K. H. et al. 1984 *Am J Trop Med Hyg* 33:684-9; Hoke, C. H. Jr. et al. 1990 *Am J Trop Med Hyg* 43:219-26; Kanesa-thasan, N. et al. 2001 *Vaccine* 19:3179-88) or by chemical mutagenesis (McKee, K. T. Jr. et al. 1987 *Am J Trop Med Hyg* 36:435-42). It has proven very difficult to achieve a satisfactory balance between attenuation and immunogenicity for each of the four serotypes of dengue virus using these approaches and to formulate a tetravalent vaccine that is safe and satisfactorily immunogenic against each of the four dengue viruses (Kanesa-thasan, N. et al. 2001 *Vaccine* 19:3179-88; Bhamarapravati, N. & Sutee, Y. 2000 *Vaccine* 18 Suppl 2: 44-7).

Two major advances utilizing recombinant DNA technology have recently made it possible to develop additional promising live attenuated dengue virus vaccine candidates. First, methods have been developed to recover infectious dengue virus from cells transfected with RNA transcripts derived from a full-length cDNA clone of the dengue virus genome, thus making it possible to derive infectious viruses bearing attenuating mutations which have been introduced into the cDNA clone by site-directed mutagenesis (Lai, C. J. et al. 1991 *PNAS USA* 88:5139-43). Second, it is possible to produce antigenic chimeric viruses in which the structural protein coding region of the full-length cDNA clone of dengue virus is replaced by that of a different dengue virus serotype or from a more divergent flavivirus (Bray, M. & Lai, C. J. 1991 *PNAS USA* 88: 10342-6; Chen, W. et al. 1995 *J Virol* 69:5186-90; Huang, C. Y. et al. 2000 *J Virol* 74:3020-8; Pletnev, A. G. & Men, R. 1998 *PNAS USA* 95:1746-51). These techniques have been used to construct intertypic chimeric dengue viruses which have been shown to be effective in protecting monkeys against homologous dengue virus challenge (Bray, M. et al. 1996 *J Virol* 70:4162-6). Despite these advances, there is a need to develop attenuated antigenic dengue virus vaccines that specify a satisfactory balance between attenuation and immunogenicity for humans.

SUMMARY OF THE INVENTION

The invention provides mutations that confer temperature sensitivity in Vero cells or human liver cells, host-cell restriction in mosquito or human liver cells, host-cell adaptation for improved replication in Vero cells, or attenuation in mice, which mutations are useful in fine tuning the attenuation and growth characteristics of dengue virus vaccines.

BRIEF DESCRIPTION OF THE DRAWINGS

FIG. 5 shows amino acid sequence of the rDEN4 NS5 gene (SEQ ID NO: 1). Eighty underlined amino acid pairs were mutagenized to alanine pairs; 32 pairs in boldface represent mutant viruses that could be recovered in either Vero or C6/36 cells; pairs in normal type represent mutant viruses that could not be recovered in either Vero or C6/36 cells. Boxed regions indicate putative functional domains, including an S-adenosylmethionine utilizing methyltransferase domain (SAM), an importin-β binding domain adjacent to a nuclear localization sequence (importin-β−binding+NLS) and an RNA-dependent RNA polymerase domain (Polymerase).

Figure 9:
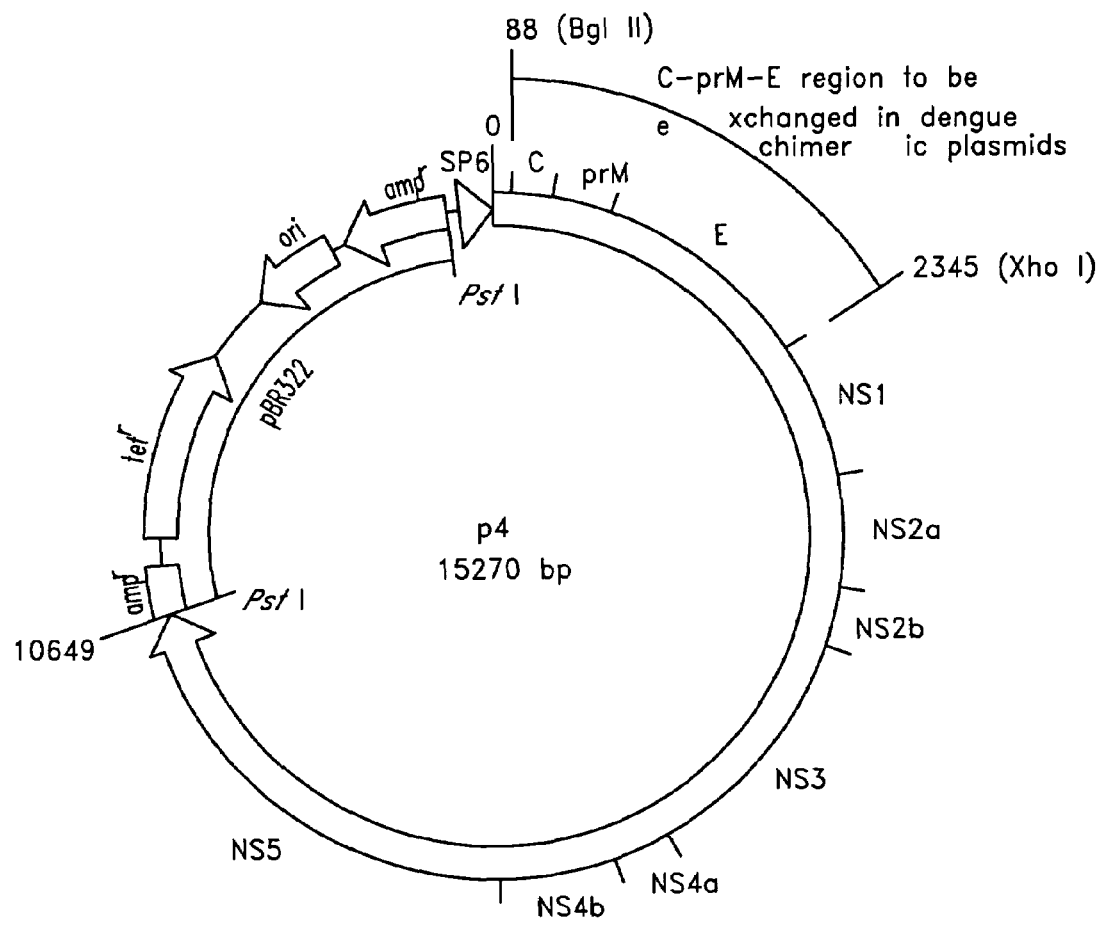

FIG. 9 shows genetic map of plasmid p4. Dengue cDNA is shown as bold line, with the C-prM-E region exchanged during construction of chimeric dengue virus cDNAs indicated.

BRIEF DESCRIPTION OF THE TABLES

Figure 1:
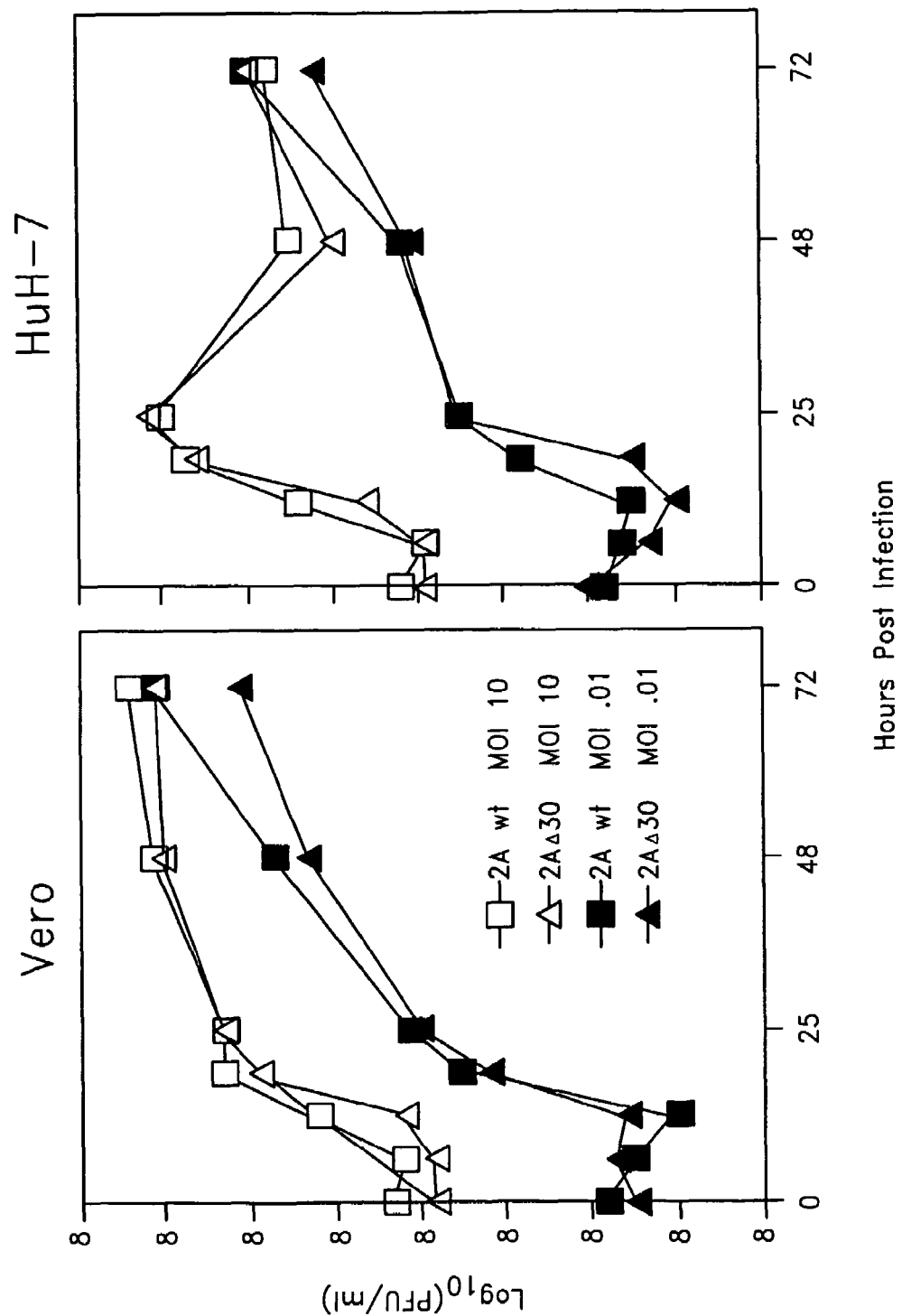
FIG. 1 shows growth of wt DEN4 2A and vaccine candidate, 2AΔ30, in Vero and HuH-7 cells. Vero (A) or HuH-7 (B) cells were infected with DEN4 2A or 2AΔ30 at a multiplicity of infection (MOI) of 10 or 0.01. Confluent cell monolayers in 25-mm tissue culture flasks were washed and overlaid with a 1.5 ml inoculum containing the indicated virus. After a two hour incubation at 37° C., cells were washed three times in PBS and 7 ml of culture media supplemented with 2% FBS was added. A 1 ml aliquot of tissue culture medium was removed, replaced with fresh medium, and designated the 0 hour time-point. At the indicated time points post-infection, samples of tissue culture media were removed and frozen at −70° C. The level of viral replication was assayed by plaque titration in Vero cells. Briefly, serial ten-fold dilutions of cell culture media samples were inoculated onto confluent Vero cell monolayers in 24-well plates in duplicate and overlaid with Opti-MEM containing 0.8% methylcellulose. After five days, plaques were visualized by immunoperoxidase staining as described in Example 1.

Table 1. Susceptibility of mice to intracerebral DEN4 infection is age-dependent.

Table 2. Temperature-sensitive (ts) and mouse brain attenuation (att) phenotypes of 5-FU mutant DEN4 viruses.

Table 3. Nucleotide and amino acid differences of the 5-FU mutant viruses which are ts in both Vero and HuH-7 cells.

Table 4. Nucleotide and amino acid differences of the 5-FU mutant viruses which are ts in only HuH-7 cells.

Table 5. Mutations which are represented in multiple 5-FU mutant DEN4 viruses.

Table 6. Addition of ts mutation 4995 to rDEN4Δ30 confers a ts phenotype and further attenuates its replication in suckling mouse brain.

Table 7. Temperature-sensitive (ts) and mouse brain attenuation (att) phenotypes of 5-FU DEN4 mutant viruses which exhibit a small plaque (sp) phenotype.

Table 8. Viruses with both ts and sp phenotypes are more restricted in replication in mouse brain than those with only a ts phenotype.

Table 9. Nucleotide and amino acid differences of the 5-FU mutant DEN4 viruses which produce small plaques in both Vero and HuH-7 cells.

Table 10. Nucleotide and amino acid differences of the 5-FU mutant DEN4 viruses which produce small plaques in only HuH-7 cells.

Table 11. Putative Vero cell adaptation mutations derived from the full set of 5-FU mutant viruses.

Table 12. Mutagenic oligonucleotides used to generate recombinant DEN4 viruses containing single 5-FU mutations.

Table 13. sp, ts and mouse attenuation phenotypes of rDEN4 mutant viruses encoding single mutations identified in six sp 5-FU mutant viruses.

Table 14. Phenotypes of rDEN4 mutant viruses encoding single mutations identified in 10 5-FU mutant viruses that are ts in both Vero and HuH-7 cells.

Table 15. sp, ts and mouse attenuation phenotypes of rDEN4 mutant viruses encoding single mutations identified in 3 HuH-7 cell-specific ts 5-FU mutant viruses.

Table 16. Temperature-sensitive (ts) and mouse brain attenuation (att) phenotypes of additional rDEN4 viruses encoding single 5-FU mutations.

Table 17. Growth of wt DEN-4 2A-13 in SCID mice transplanted with HuH-7 cells.

Table 18. Combination of ts mutations, NS3 4995 and NS5 7849, in rDEN4 results in an additive ts phenotype.

Table 19. The 5-FU mutations are compatible with the Δ30 mutation for replication in the brain of suckling mice.

Table 20. Temperature-sensitive and mouse brain attenuation phenotypes of viruses bearing charge-cluster-to-alanine mutations in the NS5 gene of DEN4.

Table 21. SCID-HuH-7 attenuation phenotypes of viruses bearing charge-cluster-to-alanine mutations in the NS5 gene of DEN4.

Table 22. Combination of paired charge-cluster-to-alanine mutations into double-pair mutant viruses.

Table 23. Temperature-sensitive and mouse brain attenuation phenotypes of double charge-cluster-to-alanine mutants of the NS5 gene of rDEN4.

Table 24. SCID-HuH-7 attenuation phenotypes of double charge-cluster-to-alanine mutants of the NS5 gene of rDEN4.

Table 25. Phenotypes (temperature sensitivity, plaque size and replication in mouse brain and SCID-HuH-7 mice) of wt DEN4 and viruses containing the Δ30 and 7129 mutations.

Table 26. The 5-fluorouracil 5-1A1 small plaque mutant demonstrates a restriction of midgut infection following oral infection of *Aedes aegypti* mosquitoes.

Table 27. The 5-fluorouracil 5-1A1 small plaque mutant demonstrates a restriction of infection following intrathoracic inoculation of *Toxorhynchites splendens* mosquitoes.

Table 28. Mutagenesis primers for the deletion or swap of sequences in DEN4 showing conserved differences from tick-borne flaviviruses.

Table 29. Virus titer and plaque size of 3' UTR mutant viruses in Vero and C6/36 cells.

Table 30. Infectivity of wt DEN4 and 3' UTR mutants for *Toxorhynchites splendens* via intrathoracic inoculation.

Table 31. Infectivity of 3' UTR swap mutant viruses for *Aedes aegypti* fed on an infectious bloodmeal.

Table 32. Putative Vero cell adaptation mutations derived from the set of 5-FU mutant viruses and other DEN4 viruses passaged in Vero cells.

Table 33. Sequence analysis of rDEN2/4Δ30 clone 27(p4)-2-2A2.

Table 34. Sequence analysis of rDEN2/4Δ30 clone 27(p3)-2-1A1.

Table 35. Recombinant virus rDEN2/4Δ30 bearing Vero adaptation mutations can be recovery and titered on Vero cells.

Table 36. Putative Vero cell adaptation mutations of dengue type 4 virus and the corresponding wildtype amino acid residue in other dengue viruses.

Table 37. Mutations known to attenuate dengue type 4 virus and the corresponding wildtype amino acid residue in other dengue virus.

BRIEF DESCRIPTION OF THE APPENDICES

Appendix 1. Sequence of recombinant dengue type 4 virus strain 2A (amino acid sequence SEQ ID NO: 13 and nucleotide sequence SEQ ID NO: 14).

Appendix 2. Sequence of recombinant dengue type 4 virus strain rDEN4 (amino acid sequence SEQ ID NO: 15 and nucleotide sequence SEQ ID NO: 16).

Appendix 3. Sequence of recombinant dengue type 2 chimeric virus strain rDEN2/4Δ30 (amino acid sequence SEQ ID NO: 17 and nucleotide sequence SEQ ID NO: 18).

Appendix 4. Alignment of dengue virus polyproteins. DEN4 (SEQ ID NO: 19); DEN1-WP (SEQ ID NO: 20); DEN2-NGC (SEQ ID NO: 21); DEN3-H87 (SEQ ID NO: 22).

DETAILED DESCRIPTION OF THE PREFERRED EMBODIMENT

To assemble a collection of useful mutations for incorporation in recombinant live dengue virus vaccines, site-directed and random mutagenesis techniques were used to introduce mutations into the dengue virus genome. The resulting mutant viruses were screened for several valuable phenotypes, including temperature sensitivity in Vero cells or human liver cells, host cell restriction in mosquito cells or human liver cells, host-cell adaptation for improved replication in Vero cells, and attenuation in mice. The genetic basis for each observed phenotype was determined by direct sequence analysis of the virus genome. Mutations identified through these sequencing efforts have been further evaluated by their re-introduction, singly, or in combination, into recombinant dengue virus and characterization of the resulting phenotypes. In this manner, a menu of mutations was developed that is useful in fine-tuning the attenuation and growth characteristics of dengue virus vaccines.

EXAMPLE 1

Chemical Mutagenesis of Dengue Virus Type 4 Yields Temperature-Sensitive and Attenuated Mutant Viruses A recombinant live attenuated dengue virus type 4 (DEN4) vaccine candidate, 2AΔ30, was found previously to be generally well-tolerated in humans, but a rash and an elevation of liver enzymes in the serum occurred in some vaccinees. 2AΔ30, a non-temperature-sensitive (ts) virus, contains a 30 nucleotide deletion in the 3' untranslated region (UTR) of the viral genome. In the present study, chemical mutagenesis of DEN4 has been utilized to generate attenuating mutations which may be useful to further attenuate the incompletely attenuated 2AΔ30 candidate vaccine. Wild-type DEN4 2A virus was grown in Vero cells in the presence of 5-fluorouracil, and, from a panel of 1,248 clones that were isolated in Vero cells, twenty ts mutant viruses were identified which were ts in both Vero and HuH-7 cells (n=13) or in HuH-7 cells only (n=7). Each of the twenty ts mutations possessed an attenuation (att) phenotype as indicated by restricted replication in the brains of seven day old mice. The complete nucleotide sequence of the 20 ts mutant viruses identified nucleotide substitutions in structural and non-structural genes as well as in the 5' and 3' UTR with more than one change occurring, in general, per mutant virus. A ts mutation in the NS3 protein (nucleotide position 4,995) was introduced into a recombinant DEN4 virus possessing the Δ30 deletion creating the rDEN4Δ30-4995 recombinant virus which was found to be ts and to be more attenuated than rDEN4Δ30 in the brains of mice. A menu of attenuating mutations is being assembled that should be useful in generating satisfactorily attenuated recombinant dengue vaccine viruses and in increasing our understanding of the pathogenesis of dengue virus.

The mosquito-borne dengue (DEN) viruses (serotypes 1 to 4) are members of the *Flavivirus* genus and contain a single-stranded positive-sense RNA genome of approximately 10,600 nucleotides (nt) (Monath, T. P. & Heinz, F. X. 1996 in: *Fields Virology* B. N. Fields, et al. Eds. pp. 961-1034 Lippincott-Ravan Publishers, Philadelphia). The genome organization of DEN viruses is 5'-UTR-C-prM-E-NS1-NS2A-NS2B-NS3-NS4A-NS4B-NS5-UTR-3' (UTR—untranslated region, C—capsid, PrM—pre-membrane, E—envelope, NS—non-structural) (Chang, G.-J. 1997 in: *Dengue and dengue hemorrhagic fever* D. J. Gubler & G. Kuno, eds. pp. 175-198 CAB International, New York; Rice, C. M. 1996 in: *Fields Virology* B. N. Fields et al. Eds. pp. 931-959 Lippincott-Ravan Publishers, Philadelphia). A single viral polypeptide is co-translationally processed by viral and cellular proteases generating three structural proteins (C, M, and E) and seven NS proteins. The disease burden associated with DEN virus infection has increased over the past several decades in tropical and semitropical countries. Annually, there are an estimated 50-100 million cases of dengue fever (DF) and 500,000 cases of the more severe and potentially lethal dengue hemorrhagic fever/dengue shock syndrome (DHF/DSS) (Gubler, D. J. & Meltzer, M. 1999 *Adv Virus Res* 53:35-70).

The site of viral replication in DEN virus-infected humans and the pathogenesis of DF and DHF/DSS are still incompletely understood (Innis, B. L. 1995 in: *Exotic viral infections* J. S. Porterfield, ed. pp. 103-146 Chapman and Hall, London). In humans, DEN virus infects lymphocytes (Kurane, I. et al. 1990 *Arch Virol* 110:91-101; Theofilopoulos, A. N. et al. 1976 *J Immunol* 117:953-61), macrophages (Halstead, S. B. et al. 1977 *J Exp Med* 146:218-29; Scott, R. M. et al. 1980 *J Infect Dis* 141:1-6), dendritic cells (Libraty, D. H. et al. 2001 *J Virol* 75:3501-8; Wu, S. J. et al. 2000 *Nat Med* 6:816-20), and hepatocytes (Lin, Y. L. et al. 2000 *J Med Virol* 60:425-31; Marianneau, P. et al. 1996 *J Gen Virol* 77:2547-54). The liver is clearly involved in DEN virus infection of humans, as indicated by the occurrence of transient elevations in serum alanine aminotransferase (ALT) and aspartate aminotransferase (AST) levels in the majority of dengue virus-infected patients and by the presence of hepatomegaly in some patients (Kalayanarooj, S. et al. 1997 *J Infect Dis* 176: 313-21; Kuo, C. H. et al. 1992 *Am J Trop Med Hyg* 47:265-70; Mohan, B. et al. 2000 *J Trop Pediatr* 46:40-3; Wahid, S. F. et al. 2000 *Southeast Asian J Trop Med Public Health* 31:259-63). DEN virus antigen-positive hepatocytes are seen surrounding areas of necrosis in the liver of fatal cases (Couvelard, A. et al. 1999 *Hum Pathol* 30:1106-10; Huerre, M. R. et al. 2001 *Virchows Arch* 438:107-15), and dengue virus sequences were identified in such cases using RT-PCR (Rosen, L. et al. 1999 *Am J Trop Med Hyg* 61:720-4). Of potential importance to the etiology of severe dengue virus infection, three studies have demonstrated that the mean levels of serum ALT/AST were significantly increased in patients with DHF/DSS versus those with DF (Kalayanarooj, S. et al. 1997 *J Infect Dis* 176:313-21; Mohan, B. et al. 2000 *J Trop Pediatr* 46:40-3; Wahid, S. F. et al. 2000 *Southeast Asian J Trop Med Public Health* 31:259-63).

A vaccine for DEN viruses is not presently licensed. Since previous infection with one dengue virus serotype can increase the risk for DHF/DSS following infection with a different serotype (Burke, D. S. et al. 1988 *Am J Trop Med Hyg* 38:172-80; Halstead, S. B. et al. 1969 *Am J Trop Med Hyg* 18:997-1021; Thein, S. et al. 1997 *Am J Trop Med Hyg* 56:566-72), it is clear that a dengue virus vaccine will need to protect against each of the four dengue virus serotypes, namely DEN1, DEN2, DEN3, and DEN4. Several strategies are currently being actively pursued in the development of a live attenuated tetravalent DEN virus vaccine (Bancroft, W. H. et al. 1984 *J Infect Dis* 149:1005-10; Bhamarapravati, N. & Sutee, Y. 2000 *Vaccine* 18:44-7; Guirakhoo, F. et al. 2000 *J Virol* 74:5477-85; Huang, C. Y. et al. 2000 *J Virol* 74:3020-8). Recently, we demonstrated that a live attenuated DEN4 vaccine candidate, 2AΔ30, was attenuated and immunogenic in a group of 20 human volunteers (see Example 8). This recombinant DEN4 virus contains a 30 nt deletion in the 3' UTR which removes nucleotides 10,478-10,507 and was restricted in replication in rhesus monkeys. Levels of viremia in humans were low or undetectable, and virus recovered from the vaccinees retained the Δ30 mutation. An asymptomatic rash was reported in 50% of patients. The only laboratory abnormality observed was an asymptomatic, transient rise in the serum ALT level in 5 of 20 vaccinees. All vaccinees developed serum-neutralizing antibody against DEN4 virus (mean titer:

1:580). Importantly, 2AΔ30 was not transmitted to mosquitoes fed on vaccinees and has restricted growth properties in mosquitoes (Troyer, J. M. et al. 2001 *Am J Trop Med Hyg* 65:414-9). The presence of a rash and of the elevated ALT levels suggests that the 2AΔ30 vaccine candidate is slightly under-attenuated in humans. Because of the overall set of desirable properties conferred by the Δ30 mutation, chimeric vaccine candidates are being constructed which contain the structural genes of dengue virus type 1, 2, and 3 and the DEN4 attenuated backbone bearing the genetically stable Δ30 mutation.

Although the initial findings indicate the utility of the 2AΔ30 vaccine candidate, many previous attempts to develop live attenuated dengue virus vaccines have yielded vaccine candidates that were either over- or under-attenuated in humans (Eckels, K. H. et al. 1984 *Am J Trop Med Hyg* 33:684-9; Bhamarapravati, N. & Yoksan, S. 1997 in: *Dengue and dengue hemorrhagic fever* D. J. Gubler & G. Kuno eds. pp. 367-377 CAB International, New York; Innis, B. L. et al. 1988 *J Infect Dis* 158:876-80; McKee, K. T., Jr. et al. 1987 *Am J Trop Med Hyg* 36:435-42). Therefore, we developed a menu of point mutations which confer temperature-sensitive (ts) and attenuation (att) phenotypes upon DEN4. These mutations are envisioned as being useful to attenuate DEN4 viruses to different degrees and therefore as having purpose in fine-tuning the level of attenuation of vaccine candidates such as 2AΔ30. Addition of such mutations to 2AΔ30 or to other dengue virus vaccine candidates is envisioned as resulting in the generation of a vaccine candidate that exhibits a satisfactory balance between attenuation and immunogenicity for humans.

In the present example, chemical mutagenesis of DEN4 has been utilized to identify point mutations which confer the ts phenotype, since such viruses often are attenuated in humans. Additionally, because of the reported involvement of the liver in natural dengue infection and the elevated ALT levels in a subset of 2AΔ30 vaccinees, mutagenized DEN4 viruses were also evaluated for ts phenotype in HuH-7 liver cells derived from a human hepatoma. Here, we describe the identification of 20 DEN4 ts mutant viruses each of which replicates efficiently in Vero cells, the proposed substrate for vaccine manufacture, and each of which is attenuated in mice. Finally, the feasibility of modifying the attenuation phenotype of the 2AΔ30 vaccine candidate by introduction of a point mutation in NS3 is demonstrated.

Cells and viruses. WHO Vero cells (African green monkey kidney cells) were maintained in MEM (Life Technologies, Grand Island, N.Y.) supplemented with 10% fetal bovine serum (FBS) (Summit Biotechnologies, Fort Collins, Colo.), 2 mM L-glutamine (Life Technologies), and 0.05 mg/ml gentamicin (Life Technologies). HuH-7 cells (human hepatoma cells) (Nakabayashi, H. et al. 1982 *Cancer Res* 42:3858-63) were maintained in D-MEM/F-12 (Life Technologies) supplemented with 10% FBS, 1 mM L-glutamine and 0.05 mg/ml gentamicin. C6/36 cells (*Aedes albopictus* mosquito cells) were maintained in complete MEM as described above supplemented with 2 mM non-essential amino acids (Life Technologies).

The wild type (wt) DEN4 2A virus was derived from a cDNA clone of DEN4 strain 814669 (Dominica, 1981) (Men, R. et al. 1996 *J Virol* 70:3930-7). Sequence of the cDNA of DEN 4 2A virus is presented in Appendix 1. The full-length 2A cDNA clone has undergone several subsequent modifications to improve its ability to be genetically manipulated. As previously described, a translationally-silent XhoI restriction enzyme site was engineered near the end of the E region at nucleotide 2348 to create clone 2A-XhoI (Bray, M. & Lai, C. J. 1991 *PNAS USA* 88:10342-6). The viral coding sequence of the 2A-XhoI cDNA clone was further modified using site-directed mutagenesis to create clone p4: a unique BbvCI restriction site was introduced near the C-prM junction (nucleotides 447-452); an extra XbaI restriction site was ablated by mutation of nucleotide 7730; and a unique SacII restriction site was created in the NS5 region (nucleotides 9318-9320). Each of these engineered mutations is translationally silent and does not change the amino acid sequence of the viral polypeptide. Also, several mutations were made in the vector region of clone p4 to introduce or ablate additional restriction sites. The cDNA clone p4Δ30 was generated by introducing the Δ30 mutation into clone p4. This was accomplished by replacing the MluI-KpnI fragment of p4 (nucleotides 10403-10654) with that derived from plasmid 2AΔ30 containing the 30 nucleotide deletion. The cDNA clones p4 and p4Δ30 were subsequently used to generate recombinant viruses rDEN4 (Appendix 2) and rDEN4Δ30, respectively. (The GenBank accession number for rDEN4 is AF326825 and the accession for rDEN4Δ30 is AF326827).

Chemical mutagenesis of DEN4. Confluent monolayers of Vero cells were infected with wt DEN4 2A at an multiplicity of infection (MOI) of 0.01 and incubated for 2 hours at 32° C. Infected cells were then overlaid with MEM supplemented with 2% FBS and 5-fluorouracil (5-FU) (Sigma, St. Louis, Mo.) at concentrations ranging from 10 mM to 10 nM. After incubation at 32° C. for five days, cell culture medium was harvested, clarified by centrifugation, and frozen at −70° C. Clarified supernatants were then assayed for virus titer by plaque titration in Vero cells. Serial ten-fold dilutions of the clarified supernatant were prepared in Opti-MEM I (Life Technologies) and inoculated onto confluent Vero cell monolayers in 24-well plates. After incubation at 35° C. for two hours, monolayers were overlaid with 0.8% methylcellulose (EM Science, Gibbstown, N.J.) in Opti-MEM I supplemented with 2% FBS, gentamicin, and L-glutamine. Following incubation at 35° C. for five days, plaques were visualized by immunoperoxidase staining. Vero cell monolayers were fixed in 80% methanol for 30 minutes and washed for 10 minutes with antibody buffer which consists of 3.5% (w/v) nonfat dry milk (Nestle, Solon, Ohio) in phosphate buffered saline (PBS). Cells were then incubated for one hour at 37° C. with an anti-DEN4 rabbit polyclonal antibody preparation ($PRNT_{50}$ of >1:2000) diluted 1:1,000 in antibody buffer. After one wash with antibody buffer, cells were incubated for one hour with peroxidase-labeled goat-anti-rabbit IgG (KPL, Gaithersburg, Md.) diluted 1:500 in antibody buffer. Monolayers were washed with PBS, allowed to dry briefly, overlaid with peroxidase substrate (KPL), and plaques were counted.

Virus yields in cultures treated with 1 mM 5-FU were reduced 100-fold compared to untreated cultures, and the virus present in the supernatant from the 1 mM 5-FU-treated culture was terminally diluted to derive clones for phenotypic characterization. Briefly, 96 well plates of Vero cells were inoculated with the 5-FU-treated virus at an MOI that yielded 10 or fewer virus-positive wells per plate. After a five-day incubation at 35° C., cell culture media from the 96 well plates were temporarily transferred to 96 well plates lacking cells, and the positive cultures were identified by immunoperoxidase staining of the infected-cell monolayers. Virus from each positive well was transferred to confluent Vero cell monolayers in 12 well plates for amplification. Cell culture medium was harvested from individual wells five or six days later, clarified by centrifugation, aliquoted to 96 deep-well polypropylene plates (Beckman, Fullerton, Calif.) and frozen at −70° C. A total of 1,248 virus clones were prepared from the 1 mM 5-FU-treated cultures. Two wt virus clones, 2A-1 and 2A-13, were generated in the same manner from the 5-FU untreated control cultures.

Screening of clones for ts and att phenotypes. The 1,248 virus clones were screened for ts phenotype by assessing virus replication at 35° C. and 39° C. in Vero and HuH-7 cells. Cell monolayers in 96 well plates were inoculated with serial ten-fold dilutions of virus in L-15 media (Quality Biologicals, Gaithersburg, Md.) supplemented with 2% FBS, L-glutamine and gentamicin. Cells were incubated at the indicated temperatures for five days in temperature-controlled water baths, and presence of virus was determined by immunoperoxidase staining as described above. Virus clones which demonstrated a 100-fold or greater reduction in titer at 39° C. were terminally diluted an additional two times and amplified in Vero cells. The efficiency of plaque formation (EOP) at permissive and restrictive temperatures of each triply biologically cloned virus suspension was determined as follows. Plaque titration in Vero and HuH-7 cells was performed as described above except virus-infected monolayers were overlaid with 0.8% methylcellulose in L-15 medium supplemented with 5% FBS, gentamicin, and L-glutamine. After incubation of replicate plates for five days at 35, 37, 38, or 39° C. in temperature-controlled water baths, plaques were visualized by immunoperoxidase staining and counted.

The replication of DEN4 5-FU ts mutant viruses was evaluated in Swiss Webster suckling mice (Taconic Farms, Germantown, N.Y.). Groups of six one-week-old mice were inoculated intracranially with $10^4$ PFU of virus diluted in 30 µl Opti-MEM I. Five days later, mice were sacrificed and brains were removed and individually homogenized in a 10% suspension of phosphate-buffered Hank's balanced salt solution containing 7.5% sucrose, 5 mM sodium glutamate, 0.05 mg/ml ciprofloxacin, 0.06 mg/ml clindamycin, and 0.0025 mg/ml amphotericin B. Clarified supernatants were frozen at −70° C. and subsequently virus titer was determined by titration in Vero cells, and plaques were stained by the immunoperoxidase method described above.

Sequence analysis of viral genomes. The nucleotide sequence of the 5-FU-mutagenized DEN4 viruses was determined. Briefly, genomic viral RNA was isolated from virus clones with the QIAamp viral RNA mini kit (Qiagen, Valencia, Calif.) and reverse transcription was performed using the SuperScript First Strand Synthesis System for RT-PCR (Life Technologies) and random hexamer primers. Advantage cDNA polymerase (Clontech, Palo Alto, Calif.) was used to generate overlapping PCR fragments of approximately 2,000 nt which were purified by HighPure PCR Product Purification System (Roche Diagnostics, Indianapolis, Ind.). DEN-specific primers were used in BigDye terminator cycle sequencing reactions (Applied Biosystems, Foster City, Calif.) and reactions were analyzed on a 3100 genetic analyzer (Applied Biosystems). Primers were designed to sequence both strands of the PCR product from which consensus sequences were assembled.

The nucleotide sequence of the 5' and 3' regions of the viral genome were determined as above after circularization of the RNA genome. The 5' cap nucleoside of the viral RNA was excised using tobacco acid pyrophosphatase (Epicentre Technologies, Madison, Wis.) and the genome was circularized by RNA ligase (Epicentre Technologies). A RT-PCR fragment was generated which overlapped the ligation junction (5' and 3' ends) and was sequenced as described above.

Generation of recombinant DEN4 viruses. The mutation at nt position 4,995 in NS3 was introduced into the p4 cDNA construct by site-directed mutagenesis (Kunkel, T. A. 1985 *PNAS USA* 82:488-92). The StuI-BstBI (nt 3,619-5,072) fragment of p4 was sub-cloned into a modified pUC119 vector. The U>C mutation at nt position 4,995 was engineered by site-directed mutagenesis into the p4 fragment, cloned back into the p4 cDNA construct, and the presence of the mutation was confirmed by sequence analysis. The Δ30 mutation was introduced into the 3' UTR of the p4-4995 cDNA clone by replacing the MluI-KpnI fragment with that derived from the p4Δ30 cDNA clone, and the presence of the deletion was confirmed by sequence analysis. Full length RNA transcripts were prepared from the above cDNA clones by in vitro transcription. Briefly, transcription consisted of a 50 μl reaction mixture containing 1 μg linearized plasmid, 60 U SP6 polymerase (New England Biolabs (NEB), Beverly, Mass.), 1X RNA polymerase buffer (40 mM Tris-HCl, pH 7.9, 6 mM $MgCl_2$, 2 mM spermidine, 10 mM dithiothreitol), 0.5 mM m7G(5')ppp(5')G cap analog (NEB), 1 mM each nucleotide triphosphate, 1 U pyrophosphatase (NEB), and 80 U RNAse inhibitor (Roche, Indianapolis, Ind.). This reaction mixture was incubated at 40° C. for 90 min and the resulting transcripts were purified using RNeasy mini kit (Qiagen, Valencia, Calif.).

For transfection of C6/36 cells, RNA transcripts were combined with DOTAP liposomal transfection reagent (Roche) in HEPES-buffered saline (pH 7.6) and added to cell monolayers in 6 well plates. After incubation at 32° C. for 12-18 hours, the cell culture media were removed and replaced with MEM supplemented with 5% FBS, L-glutamine, gentamicin and non-essential amino acids. Cell monolayers were incubated for an additional 5 to 7 days and cell culture media were harvested, clarified by centrifugation, and assayed for the presence of virus by plaque titration in Vero cells. Recovered viruses were terminally diluted twice as described above, and virus suspensions for further analysis were prepared in Vero cells.

In vitro (tissue culture) and in vivo replication of wt DEN4 and DEN4Δ30. The level of replication of both wt DEN4 2A and the vaccine candidate, 2AΔ30, was evaluated in Vero (monkey kidney) and HuH-7 (human hepatoma) cells (FIG. 1), the latter of which has recently been found to efficiently support the replication of DEN2 virus (Lin, Y. L. et al. 2000 *J Med Virol* 60:425-31). The pattern of replication of wt DEN4 2A and 2AΔ30 was similar in both cell lines. Viral titers from cultures infected with 2AΔ30 at an MOI of 0.01 were slightly reduced compared to wt DEN4 2A at 72 hours, but at later time points their level of replication was equivalent. The efficient replication of both DEN4 viruses in each cell line indicated that these continuous lines of cells would be useful for characterization of the ts phenotype of the 1248 potential mutant viruses.

The level of replication of DEN4 virus administered intracerebrally to Swiss Webster mice was first determined to assess whether mice could be used to efficiently evaluate and quantitate the attenuation phenotype of a large set of mutant viruses. Since the susceptibility of mice to DEN infection is age dependent (Cole, G. A. & Wisseman, C. L. Jr. 1969 *Am J Epidemiol* 89:669-80; Cole, G. A. et al. 1973 *J Comp Pathol* 83:243-52), mice aged 7 to 21 days were infected with 2A-13 (a clone of DEN4 wild type virus—see below), rDEN4 or rDEN4Δ30, and after five days the brain of each mouse was removed, and the level of viral replication was quantitated by plaque assay (Table 1). The results indicated that the two wt DEN4 viruses and the rDEN4Δ30 vaccine candidate replicated to high titer (>6.0 $\log_{10}$ PFU/g brain) in 7-day old mice and that the mean viral titers were similar among the three viruses. These results demonstrated the feasibility of using 7-day old mice to screen a large set of mutant viruses, and the high level of replication of wild type and vaccine candidate permits one to quantitate the magnitude of the restriction of replication specified by an attenuating mutation over a 10,000-fold range.

Figure 2:
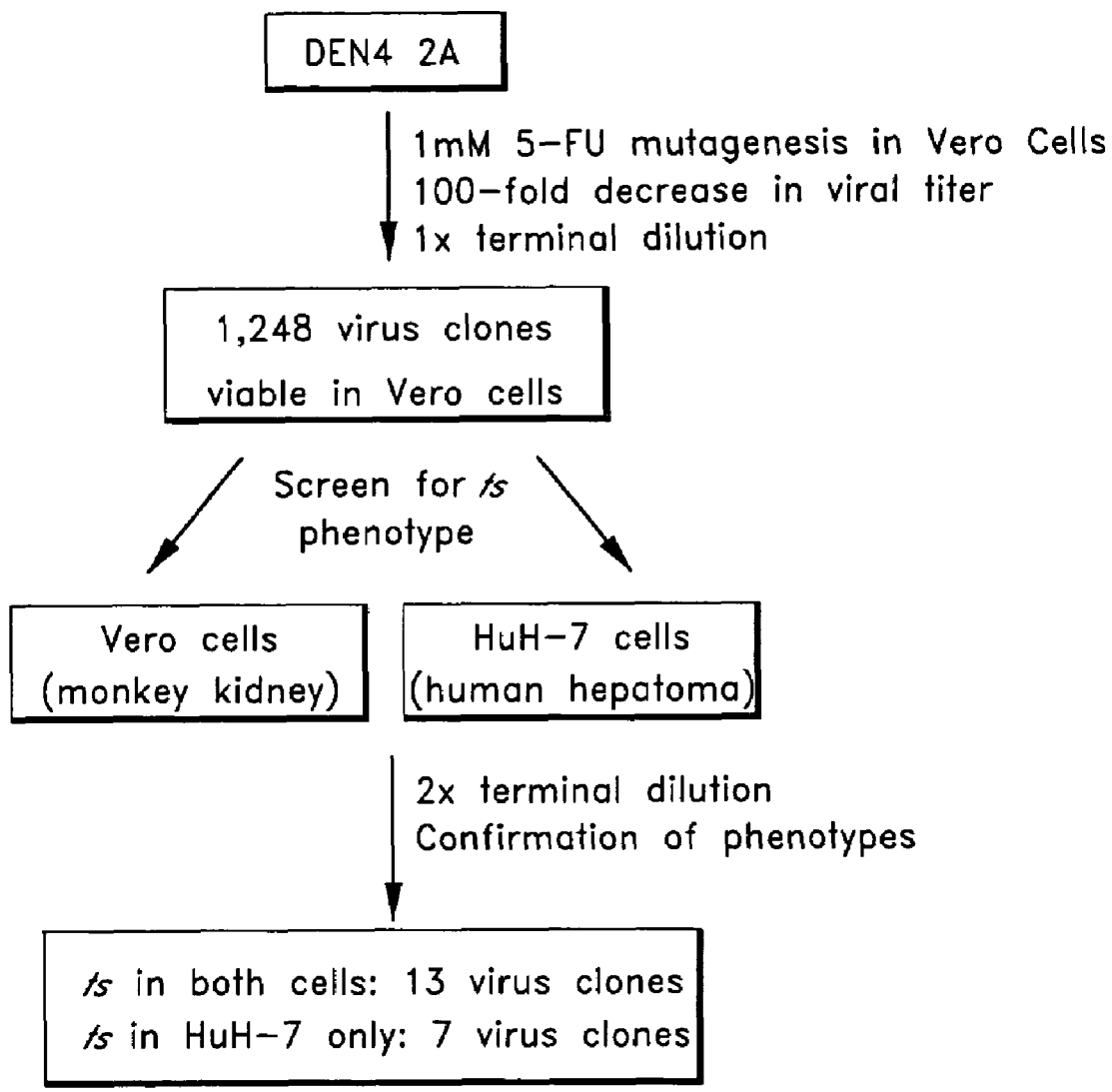
FIG. 2 shows generation of temperature-sensitive (ts) DEN4 viruses by 5-fluorouracil (5-FU) chemical mutagenesis. The wild-type DEN4 2A virus was derived from a cDNA clone of DEN4 strain 814669 (Dominica, 1981). Vero cells were infected with DEN4 2A and overlaid with culture media containing 1 mM 5-fluorouracil (5-FU) which resulted in a reduction of approximately 100-fold in viral replication when compared to untreated controls. Viral progeny from the 1 mM 5-FU-treated cultures were subjected to a single round of terminal dilutions generating 1,248 biologically cloned viruses which were screened for ts phenotypes by assessing virus replication at 35° C. and 39° C. in Vero and HuH-7 cells. Virus clones which demonstrated a 100-fold or greater reduction in titer at 39° C. were terminally diluted an additional two times and amplified in Vero cells. Temperature-sensitive phenotypes of the 3× biologically cloned viruses were confirmed by evaluating efficiency of plaque formation (EOP) in the indicated cells as described in Example 1.

Generation and in vitro characterization of DEN4 5-FU mutant viruses. A panel of 1,248 DEN4 virus clones was generated from a 5-FU-mutagenized suspension of wt DEN4 2A as described above (FIG. 2). Each clone was tested in Vero and HuH-7 cells for the ts phenotype at 39° C., and putative ts mutant viruses were subjected to two additional rounds of biological cloning by terminal dilution, and the ts phenotype of each further cloned virus population was examined in more detail by determining their efficiency of plating (EOP) at permissive temperature (35° C.) and at various restrictive temperatures (Table 2). One virus (clone 2A-13) without a ts phenotype, which was passaged in an identical fashion as the ts mutant viruses, served as the virus to which each of the ts mutant viruses was directly compared for both the ts and att phenotypes.

Thirteen 5-FU mutant viruses were identified which have a ts phenotype in both Vero and HuH-7 cells, and seven mutant viruses were ts only in HuH-7 cells (Table 2). Mutant viruses which were ts in Vero cells but not in HuH-7 cells were not identified. Temperature-sensitivity was defined as a $\geq 2.5$ or $\geq 3.5$ $\log_{10}$ PFU/ml reduction in virus titer in Vero or HuH-7 cells, respectively, at an indicated temperature when compared to the permissive temperature of 35° C. Wild type DEN4 2A was found to have approximately a 0.5 and 1.5 $\log_{10}$ PFU/ml reduction in virus titer in Vero or HuH-7 cells at 39° C., respectively. The Δ30 deletion did not confer a ts phenotype in Vero or HuH-7 cells and exhibited only a slight reduction in virus titer (2.2 $\log_{10}$ PFU/ml) at 39° C. in HuH-7 cells, which was less than 10-fold greater than the reduction of wt DEN4 2A at that temperature. Several 5-FU mutant viruses had a greater than 10,000-fold reduction in virus titer at 39° C. in both Vero and HuH-7 cells. A complete shut-off in viral replication at 39° C. in HuH-7 cells was observed in five virus clones (#571, 605, 631, 967, and 992) which were not ts in Vero cells. Mutations that selectively restrict replication in HuH-7 liver cells may be particularly useful in controlling the replication of dengue virus vaccine candidates in the liver of vaccinees.

Replication of DEN4 5-FU mutant viruses in suckling mice. The level of replication of each of the 20 ts DEN4 mutant viruses in mouse brain was determined (Table 2). The titers obtained were compared to that of the two wt viruses, 2A-13 and rDEN4, which each replicated to a level of greater than $10^6$ PFU/g of brain tissue, and to that of the 2AΔ30 mutant, which conferred only a limited 0.5 $\log_{10}$ PFU/g reduction in mean virus titer compared to the wt controls. The observed reduction in the level of rDEN4Δ30 replication was consistent among 11 separate experiments. Interestingly, the rDEN4Δ30 virus, which was attenuated in both rhesus monkeys and humans (Example 8), was only slightly restricted in replication in mouse brain. Varying levels of restriction of replication were observed among the mutant viruses ranging from a 10-fold (#473) to over 6,000-fold (#686) reduction. Mutant viruses with ts phenotypes in both Vero and HuH-7 cells, as well as in HuH-7 cells alone, were found to have significant att phenotypes. Five of 13 5-FU mutant viruses with ts phenotypes in both Vero and HuH-7 cells and five of seven mutant viruses with ts phenotypes in HuH-7 cells alone had greater than a 100-fold reduction in virus replication. There appeared to be no direct correlation between the magnitude of the reduction in replication at restrictive temperature in tissue culture and the level of attenuation in vivo. The similar level of temperature sensitivity and replication of the rDEN4 wt and clone 2A-13 in mouse brain indicated that observed differences in replication between the ts mutant viruses and clone 2A-13 was not simply a function of passage in Vero cells, but reflects the sequence differences between these viruses.

Sequence analysis of DEN4 5-FU mutant viruses. To determine the genetic basis of the observed ts and att phenotypes, the complete nucleotide sequence of each ts mutant and of clone 2A-13 was determined and summarized in Table 3 (ts in Vero and HuH-7 cells) and Table 4 (ts in only HuH-7 cells).

The only type of mutation identified in the 20 mutant viruses sequenced was a nucleotide substitution (no deletions or insertions occurred), and these were present in each of the coding regions except C and NS4A. Three mutant viruses (#239, 489, and 773) contained only a single missense point mutation in NS3 at nt position 4,995 resulting in a Ser to Pro amino acid (a.a.) change at a.a. position 1,632. For #773, this was the sole mutation present (Table 3). The non-coding mutations in coding regions are not considered to be significant. The 17 additional mutant viruses had multiple mutations (two to five) in a coding region or in an UTR which could potentially confer the observed ts or att phenotypes. Five of the 17 mutant viruses with multiple mutations (#473, 718, 759, 816, and 938) also encoded the point mutation at nt position 4,995. The presence of the 4,995 mutation was found in only DEN4 mutant viruses with ts phenotypes in both Vero and HuH-7 cells.

The sequence analysis indicated that 10 mutant viruses which were ts in Vero and HuH-7 cells and three mutant viruses which were ts in only HuH-7 cells contained mutations in only the 5' and 3' UTR and/or in a nonstructural protein. These mutations are especially suitable for inclusion in chimeric dengue virus vaccine candidates in which the structural genes derive from a DEN1, DEN2, or DEN3 serotype and the remaining coding and non-coding regions come from an attenuated DEN4 vector. Mutations identified in 5-FU DEN4 mutant viruses which were ts in only HuH-7 cells (Table 4) may potentially be utilized in vaccine candidates, such as rDEN4Δ30, to selectively control the replication and pathogenesis of DEN4 in the liver. These combined results from the sequence analysis of 5-FU mutant viruses demonstrate the utility of chemical mutagenesis as a means of introducing attenuating mutations into the dengue virus genome.

The presence of a point mutation at nt position 4,995 in eight separate mutant viruses was described above. Five additional point mutations were also represented in multiple viruses including nt changes at position 1,455 in E, 7,162, 7,163 and 7,564 in NS4B, and 10,275 in the 3' UTR (Table 5). The significance of the occurrence of these "sister" mutations in multiple viruses is discussed in Example 6. Interestingly, the wild-type, parallel-passaged virus, 2A-13, also contained a single mutation at the 7,163 nt position in NS4B.

Introduction of a ts mutation into rDEN4 and rDEN4Δ30. The presence of a single nucleotide substitution (U>C mutation at nt position 4,995 in NS3) in three separate mutant viruses (clones 239, 489, and 773) indicated that this mutation specified the ts and att phenotypes in each of the three mutant viruses. This mutation was cloned into cDNA construct of p4 and p4Δ30 and recombinant viruses were recovered and designated rDEN4-4995 and rDEN4Δ30-4995, respectively. These recombinant viruses were tested for ts and att phenotypes as described above (Table 6). As expected, introduction of mutation 4995 into rDEN4 wt resulted in a significant ts phenotype at 39° C. in both Vero and HuH-7 cells. rDEN4-4995 grew to nearly wild-type levels at the permissive temperature, 35° C., in both cell types, but demonstrated a greater than 10,000-fold reduction at 39° C. (shut-off temperature) in both Vero and HuH-7 cells. The addition of the 4995 mutation to rDEN4Δ30 yields a recombinant virus, rDEN4Δ30-4995, that exhibits the same level of temperature sensitivity as rDEN4-4995 (Table 6).

The rDEN4 viruses encoding the 4995 mutation were next tested for replication in the brains of suckling mice (Table 6). The 4995 mutation conferred an att phenotype upon both rDEN4 and rDEN4Δ30. There was an approximately 1,000-fold reduction in virus replication compared to that of wt virus. The combination of point mutation 4995 and the Δ30 deletion did not appear to result in an additive reduction of virus replication. These results confirmed that the 4995 point mutation indeed specifies the ts and att phenotypes. Importantly, the utility of modifying tissue culture and in vivo phenotypes of the rDEN4Δ30 vaccine candidate by introduction of additional mutations was also demonstrated.

Discussion. Herein we teach how to prepare a tetravalent, live-attenuated dengue virus vaccine using rDEN4Δ30 as the DEN4 component and three antigenic chimeric viruses expressing the structural proteins (C, prM, and E) of DEN1, DEN2, and DEN3 from the attenuated rDEN4Δ30 vector (Example 8). DEN4 virus rDEN4Δ30 containing the Δ30 deletion mutation in the 3' UTR manifests restricted replication in humans while retaining immunogenicity. Since rDEN4Δ30 retains a low level of residual virulence for humans despite this restricted replication, the present study was initiated to generate additional attenuating mutations that are envisioned as being useful to further attenuate rDEN4Δ30 or other dengue viruses and that are envisioned as being incorporated into any of the three antigenic chimeric viruses or other dengue viruses as needed. Temperature-sensitive mutants of dengue viruses (Bhamarapravati, N. & Yoksan, S. 1997 in: *Dengue and Dengue Hemorrhagic Fever* D. J. Gubler & G. Kuno eds. pp. 367-377 CAB International, New York; Eckels, K. H. et al. 1980 *Infect Immun* 27:175-80) as well of other viruses (Skiadopoulos, M. H. et al. 1998 *J Virol* 72:1762-8; Whitehead, S. S. et al. 1999 *J Virol* 73:871-7) manifest restricted replication in vivo. We have generated a panel of 20 ts DEN4 mutant viruses, determined their genomic sequence, and assessed their in vivo attenuation phenotypes. The 20 ts DEN4 mutant viruses were generated by growth in the presence of 5-FU and were first selected for viability in Vero cells, the substrate planned for use in the manufacture of these vaccines, to ensure that the mutant viruses can be grown efficiently in a suitable substrate.

Two classes of mutant viruses were obtained; those ts in both Vero and HuH-7 cells (n=13) or those ts in only HuH-7 cells (n=7). The viruses exhibited a range in their level of temperature sensitivity from a 100- to 1,000,000-fold reduction in replication at the restrictive temperature of 39° C. Since our DEN4 vaccine candidate retains a low level of virulence for the liver and other findings support the ability of dengue viruses to infect hepatocytes (Lin, Y. L. et al. 2000 *J Med Virol* 60:425-31; Marianneau, P. et al. 1997 *J Virol* 71:3244-9) and cause liver pathology (Couvelard, A. et al. 1999 *Hum Pathol* 30:1106-10; Huerre, M. R. et al. 2001 *Virchows Arch* 438:107-15), we sought to develop mutations that would selectively restrict replication of dengue 4 virus in liver cells. Toward this end, we identified seven mutant viruses which have a HuH-7 cell-specific ts phenotype. The mutations present in these viruses are the first reported in DEN viruses that confer restricted replication in liver cells and are envisioned as being useful in limiting virus replication and pathogenesis in the liver of vaccine recipients. The contribution of individual mutations identified in the HuH-7 cell-specific ts viruses to the observed phenotypes is envisioned as being assessed by introduction of the individual mutations into recombinant DEN4 viruses.

Recent evidence has indicated that the magnitude of the viremia in DEN-infected patients positively correlates with disease severity, i.e., the higher the titer of viremia the more severe the disease (Murgue, B. et al. 2000 *J Med Virol* 60:432-8; Vaughn, D. W. et al. 2000 *J Infect Dis* 181:2-9). This indicates that mutations that significantly restrict replication of vaccine candidates in vivo are the foundation of a safe and attenuated vaccine. Evaluation of DEN virus vaccine candidates for in vivo attenuation is complicated by the lack of a suitable animal model which accurately mimics the disease caused by dengue viruses in humans. In the absence of such a model, the replication of the panel of 5-FU mutant viruses in the brains of Swiss Webster suckling mice was assessed as a means to identify an in vivo attenuation phenotype since this animal model is well-suited for the evaluation of a large set of mutant viruses. Each of the 20 ts mutant viruses exhibited an att phenotype manifesting a 10- to 6,000-fold reduction in replication in the brain of mice as compared to wt DEN4 virus (Table 2). This indicates that there is a correlation between the presence of the ts phenotype in tissue culture and attenuation of the mutant in vivo confirming the utility of selecting viruses with this marker as vaccine candidates. However, there was no correlation between the level of temperature sensitivity and the level of restriction in vivo. Furthermore, Sabin observed a dissociation between mouse neurovirulence and attenuation in humans by generating an effective live attenuated virus vaccine against DEN by passage of virus in mouse brain. This research actually resulted in a highly mouse-neurotropic DEN virus which, paradoxically, was significantly attenuated in humans (Sabin, A. B. 1952 *Am J Trop Med Hyg* 1:30-50). Despite this, attenuation for the suckling mouse brain has been reported for other live-attenuated DEN virus vaccine candidates including the DEN2 PDK-53 vaccine strain which is non-lethal in mice and DEN-2 PR-159/S-1 vaccine strain which was significantly attenuated compared to its parental wild-type virus (Bhamarapravati, N. & Yoksan, S. 1997 in: *Dengue and Dengue Hemorrhagic Fever* D. J. Gubler & G. Kuno eds. pp. 367-377 CAB International, New York; Butrapet, S. et al. 2000 *J Virol* 74:3011-9; Eckels, K. H. et al. 1980 *Infect Immun* 27:175-80; Innis, B. L. et al. 1988 *J Infect Dis* 158:876-80). Replication in rhesus monkeys has been reported to be predictive of attenuation for humans (Innis, B. L. et al. 1988 *J Infect Dis* 158:876-80). Recently, murine models of DEN virus infection have been developed using SCID mice transplanted with human macrophage (Lin, Y. L. et al. 1998 *J Virol* 72:9729-37) or liver cell lines (An, J. et al. 1999 *Virology* 263:70-7), but these mice have not as yet been used to assess att phenotypes of candidate vaccine viruses. Mutant viruses or recombinant viruses bearing one or more of these mutations described herein are envisioned as being tested for replication in rhesus monkeys (or other suitable animal model) as predictive for attenuation in humans.

The chemical mutagenesis of DEN4 virus and sequence analysis of resulting viruses described here has resulted in the identification of a large number of point mutations resulting in amino acid substitutions in all genes except C and NS4A as well as point mutations in the 5' and 3' UTR (Tables 3 and 4). This approach of whole-genome mutagenesis has the benefit of identifying mutations dispersed throughout the entire genome which are pre-selected for viability in the Vero cell substrate. Ten 5-FU mutant viruses which were ts in Vero and HuH-7 cells and three viruses which were selectively ts in HuH-7 cells contained only mutations outside of the genes encoding the structural proteins, i.e., in the 5' and 3' UTR or NS genes. These mutations along with the Δ30 deletion in the 3' UTR are particularly suited for inclusion in antigenic, chimeric vaccines which consist of an attenuated DEN4 vector bearing the wild-type structural genes (C, prM, E) of the other DEN virus serotypes. Use of this strategy has several advantages. Each antigenic chimeric virus that possesses structural proteins from a wild-type virus along with attenuating mutations in their UTRs or NS genes should maintain its infectivity for humans, which is mediated largely by the E protein, and, therefore, each vaccine component should be immunogenic (Huang, C. Y. et al. 2000 *J Virol* 74:3020-8). The replicative machinery of the tetravalent vaccine strains would share the same attenuating mutations in the NS genes or in the UTR which should attenuate each vaccine component to a similar degree and thereby minimize interference or complementation among the four vaccine viruses. In addition, wild-type E protein would be expected to most efficiently induce neutralizing antibodies against each individual DEN virus.

Sequence analysis of dengue viruses (Blok, J. et al. 1992 *Virology* 187:573-90; Lee, E. et al. 1997 *Virology* 232:281-90; Puri, B. et al. 1997 *J Gen Virol* 78:2287-91) and yellow fever viruses (Dunster, L. M. et al. 1999 *Virology* 261:309-18; Holbrook, M. R. et al. 2000 *Virus Res* 69:31-9) previously generated by serial passage in tissue culture have mutations throughout much of the genome, a pattern we have observed in the present study. Recent analysis of the DEN2 PDK-53 vaccine strain has identified the important mutations involved in attenuation which were located in non-structural regions including the 5' UTR, NS1 and NS3 (Butrapet, S. et al. 2000 *J Virol* 74:3011-9). This DEN2 vaccine strain has been used to generate a chimeric virus with DEN1 C-prM-E genes (Huang, C. Y. et al. 2000 *J Virol* 74:3020-8). In separate studies, the sequence of the DEN1 vaccine strain 45AZ5 PDK-27 was determined and compared to parental viruses, but the mutations responsible for attenuation have not yet been identified (Puri, B. et al. 1997 *J Gen Virol* 78:2287-91).

Several amino acid substitutions were identified in more than one ts 5-FU mutant virus (Table 5). Lee et al. have previously reported finding repeated mutations in separate DEN3 virus clones after serial passage in Vero cells (Lee, E. et al. 1997 *Virology* 232:281-90). A mutation (K>N) identified in E at a.a. position 202 in a single DEN3 passage series was also found in our 5-FU mutant virus #1012 (K>E). Mutations observed in the 5-FU sister mutant viruses are envisioned as representing adaptive changes that confer an increased efficiency of DEN4 replication in Vero cells. Such mutations are envisioned as being beneficial for inclusion in a live-attenuated DEN virus vaccine by increasing the yield of vaccine virus during manufacture. Interestingly, three distinct amino acid substitutions were found in NS4B of the 5-FU sister mutant viruses. The exact function of this gene is unknown, but previous studies of live-attenuated yellow fever vaccines (Jennings, A. D. et al. 1994 *J Infect Dis* 169:512-8; Wang, E. et al. 1995 *J Gen Virol* 76:2749-55) and Japanese encephalitis vaccines (Ni, H. et al. 1995 *J Gen Virol* 76:409-13) have identified mutations in NS4B associated with attenuation phenotypes.

The mutation at nt position 4995 of NS3 (S1632P) was present as the only significant mutation identified in three 5-FU mutant viruses (#239, #489, and #773). This mutation was introduced into a recombinant DEN4 virus and found to confer a ts and att phenotype (Table 6). These observations clearly identify the 4995 mutation as an attenuating mutation. Analysis of a sequence alignment (Chang, G.-J. 1997 in: *Dengue and Dengue Hemorrhagic Fever* D. J. Gubler & G. Kuno, eds. pp. 175-198 CAB International, New York) of the four dengue viruses indicated that the Ser at a.a. position 1632 is conserved in DEN1 and DEN2, while DEN3 contains an Asn at this position indicating that the mutation is predicted to be useful in modifying the phenotypes of the other DEN virus serotypes. The NS3 protein is 618 a.a. in length and contains both serine protease and helicase activities (Bazan, J. F. & Fletterick, R. J. 1989 *Virology* 171:637-9; Brinkworth, R. I. et al. 1999 *J Gen Virol* 80:1167-77; Valle, R. P. & Falgout, B. 1998 *J Virol* 72:624-32). The 4995 mutation results in a change at a.a. position 158 in NS3 which is located in the N-terminal region containing the protease domain. Amino acid position 158 is located two a.a. residues away from an NS3 conserved region designated homology box four. This domain has been identified in members of the flavivirus family and is believed to be a critical determinant of the NS3 protease substrate specificity (Bazan, J. F. & Fletterick, R. J. 1989 *Virology* 171:637-9; Brinkworth, R. I. et al. 1999 *J Gen Virol* 80:1167-77). However, the exact mechanism which results in the phenotype associated with the 4995 mutation has not yet been identified. The identification of the 4995 mutation as an attenuating mutation permits a prediction of its usefulness for the further attenuation of rDEN4Δ30.

We have determined the contribution of individual 5-FU mutations to the observed phenotypes by introduction of the mutations into recombinant DEN4 viruses as was demonstrated herein for the 4995 mutation (see Example 3). In addition, combination of individual mutations with each other or with the Δ30 mutation is useful to further modify the attenuation phenotype of DEN4 virus candidate vaccines. The introduction of the 4995 mutation into rDEN4Δ30 described herein rendered the rDEN4Δ30-4995 double mutant ts and 1000-fold more attenuated for the mouse brain than rDEN4Δ30. This observation has demonstrated the feasibility of modifying both tissue culture and in vivo phenotypes of this and other dengue virus vaccine candidates. Once the mutations responsible for the HuH-7 cell-specific ts phenotype are identified as described above and introduced into the rDEN4Δ30 vaccine candidate, we envision confirming that these mutations attenuate rDEN4Δ30 vaccine virus for the liver of humans. A menu of attenuating mutations is envisioned as being assembled that is predicted to be useful in generating satisfactorily attenuated recombinant dengue vaccine viruses and in increasing our understanding of the pathogenesis of dengue virus (see Example 7).

EXAMPLE 2

Chemical Mutagenesis of DEN4 Virus Results in Small-Plaque Mutant Viruses with Temperature-Sensitive and Attenuation Phenotypes Mutations that restrict replication of dengue virus have been sought for the generation of recombinant live-attenuated dengue virus vaccines. Dengue virus type 4 (DEN4) was previously grown in Vero cells in the presence of 5-fluorouracil, and the characterization of 1,248 mutagenized, Vero cell-passaged clones identified 20 temperature-sensitive (ts) mutant viruses that were attenuated (att) in suckling mouse brain (Example 1). The present investigation has extended these studies by identifying an additional 22 DEN4 mutant viruses which have a small-plaque size (sp) phenotype in Vero cells and/or the liver cell line, HuH-7. Five mutant viruses have a sp phenotype in both Vero and HuH-7 cells, three of which are also ts. Seventeen mutant viruses have a sp phenotype in only HuH-7 cells, thirteen of which are also ts. Each of the sp viruses was growth restricted in the suckling mouse brain, exhibiting a wide range of reduction in replication (9- to 100,000-fold). Complete nucleotide sequence was determined for the 22 DEN4 sp mutant viruses, and nucleotide substitutions were found in the 3' untranslated region (UTR) as well as in all coding regions except NS4A. Identical mutations have been identified in multiple virus clones indicating that they are involved in the adaptation of DEN4 virus to efficient growth in Vero cells.

The DEN viruses cause more disease and death of humans than any other arbovirus, and more than 2.5 billion people live in regions with endemic dengue infection (Gubler, D. J. 1998 Clin Microbiol Rev 11:480-96). Annually, there are an estimated 50-100 million cases of dengue fever (DF) and 500,000 cases of the more severe and potentially lethal dengue hemorrhagic fever/dengue shock syndrome (DHF/DSS) (Gubler, D. J. & Meltzer, M. 1999 Adv Virus Res 53:35-70). Dengue fever is an acute infection characterized by fever, retro-orbital headache, myalgia, and rash. At the time of defervescence during DF, a more severe complication of DEN virus infection, DHF/DSS, may occur which is characterized by a second febrile period, hemorrhagic manifestations, hepatomegaly, thrombocytopenia, and hemoconcentration, which may lead to potentially life-threatening shock (Gubler, D. J. 1998 Clin Microbiol Rev 11:480-96).

The sites of DEN virus replication in humans and their importance and relationship to the pathogenesis of DF and DHF/DSS are still incompletely understood (Innis, B. L. 1995 in: *Exotic Viral Infections* J. S. Porterfield, ed. pp. 103-146 Chapman and Hall, London). In addition to replication in lymphoid cells, it has become evident that the liver is involved in DEN infection of humans. Transient elevations in serum alanine aminotransferase (ALT) and aspartate aminotransferase (AST) levels are observed in the majority of DEN virus-infected patients and hepatomegaly is observed in some patients (Kalayanarooj, S. et al. 1997 *J Infect Dis* 176:313-21; Kuo, C. H. et al. 1992 *Am J Trop Med Hyg* 47:265-70; Mohan, B. et al. 2000 *J Trop Pediatr* 46:40-3; Wahid, S. F. et al. 2000 *Southeast Asian J Trop Med Public Health* 31:259-63). DEN virus antigen-positive hepatocytes are seen surrounding areas of necrosis in the liver of fatal cases (Couvelard, A. et al. 1999 *Hum Pathol* 30:1106-10; Huerre, M. R. et al. 2001 *Virchows Arch* 438:107-15), from which dengue virus sequences were identified using RT-PCR (Rosen, L. et al. 1999 *Am J Trop Med Hyg* 61:720-4). Of potential importance to the etiology of severe dengue virus infection, three studies have demonstrated that the mean levels of serum ALT and AST were significantly increased in patients with DHF/DSS compared to those with DF (Kalayanarooj, S. et al. 1997 *J Infect Dis* 176:313-21; Mohan, B. et al. 2000 *J Trop Pediatr* 46:40-3; Wahid, S. F. et al. 2000 *Southeast Asian J Trop Med Public Health* 31:259-63). As expected, elevation of serum liver enzymes has previously been observed in clinical trials of DEN virus vaccine candidates (Example 8; Eckels, K. H. et al. 1984 *Am J Trop Med Hyg* 33:684-9; Edelman, R. et al. 1994 *J Infect Dis* 170:1448-55; Kanesa-thasan, N. et al. 2001 *Vaccine* 19:3179-3188; Vaughn, D. W. et al. 1996 *Vaccine* 14:329-36).

Based on the increasing disease burden associated with DEN virus infection over the past several decades, a vaccine which confers protection against the four dengue virus serotypes is needed, but none is presently licensed. Because of the increased risk for severe DHF/DSS associated with secondary infection with a heterologous DEN virus serotype (Burke, D. S. et al. 1988 *Am J Trop Med Hyg* 38:172-80; Halstead, S. B. et al. 1977 *J Exp Med* 146:218-29; Thein, S. et al. 1997 *Am J Trop Med Hyg* 56:566-72), an effective vaccine must confer simultaneous protection against each of the four DEN virus serotypes. Several approaches are presently being pursued to develop a tetravalent vaccine against the dengue viruses (Bancroft, W. H. et al. 1984 *J Infect Dis* 149:1005-10; Bhamarapravati, N. & Sutee, Y. 2000 *Vaccine* 18:44-7; Butrapet, S. et al. 2000 *J Virol* 74:3011-9; Guirakhoo, F. et al. 2000 *J Virol* 74:5477-85; Huang, C. Y. et al. 2000 *J Virol* 74:3020-8; Kanesa-thasan, N. et al. 2001 *Vaccine* 19:3179-3188). One such approach, a live-attenuated DEN4 vaccine candidate, termed 2AΔ30, was both attenuated and immunogenic in a cohort of 20 volunteers (Example 8). The recombinant 2AΔ30 virus contains a 30 nt deletion in the 3' UTR which removes nucleotides 10,478-10,507 and was found to produce a low or undetectable level of viremia in vaccinees at a dose of $10^5$ PFU/vaccinee. An asymptomatic rash was reported in 50% of volunteers, and the only laboratory abnormality observed was an asymptomatic, transient rise in the serum ALT level in 5 of the 20 vaccinees. All 2AΔ30 vaccinees developed serum neutralizing antibodies against DEN4 virus (mean titer: 1:580), and 2AΔ30 was not transmitted to mosquitoes that fed experimentally on vaccinees (Troyer, J. M. et al. 2001 *Am J Trop Med Hyg* 65:414-9). Because of the desirable properties conferred by the Δ30 mutation, chimeric vaccine candidates are being constructed which contain the structural genes of DEN virus type 1, 2, and 3, in the attenuated DEN4 background bearing the genetically stable Δ30 mutation. Attenuating mutations outside of the structural genes are particularly attractive for inclusion in antigenic chimeric vaccine candidates because they will not affect the infectivity or immunogenicity conferred by the major mediator of humoral immunity to DEN viruses, the envelope (E) protein.

The presence of rash and elevated ALT levels suggests that the 2AΔ30 vaccine candidate may be slightly under-attenuated in humans. Similarly, many previous attempts to develop live attenuated dengue virus vaccines have yielded vaccine candidates that were either over- or under-attenuated in humans, some of which also induced elevation of serum ALT and AST levels (Bhamarapravati, N. & Yoksan, S. 1997 in: *Dengue and Dengue Hemorrhagic Fever* D. J. Gubler & G. Kuno eds. pp. 367-377 CAB International, New York; Eckels, K. H. et al. 1984 *Am J Trop Med Hyg* 33:684-9; Innis, B. L. et al. 1988 *J Infect Dis* 158:876-80; Kanesa-thasan, N. et al. 2001 *Vaccine* 19:3179-3188; McKee, K. T., Jr. et al. 1987 *Am J Trop Med Hyg* 36:435-42). Therefore, we have developed a menu of point mutations conferring temperature-sensitive (ts), small-plaque (sp), and attenuation (att) phenotypes capable of attenuating DEN4 viruses to a varying degree (Example 1). We have previously described 20 mutant viruses that exhibit a ts, but not sp, phenotype in Vero cells or HuH-7 liver cells and that show attenuated replication in mouse brain (Example 1). Addition of such mutations to 2AΔ30 or to other dengue virus vaccine candidates is envisioned as yielding vaccine candidates that exhibit a more satisfactory balance between attenuation and immunogenicity.

In the present Example, we have extended our analysis of the panel of 1,248 DEN4 virus clones previously generated by mutagenesis with 5-fluorouracil (5-FU) (Example 1), by identifying a set of 22 sp mutant viruses, some of which also have a ts phenotype. Small plaque mutant viruses were sought since such viruses are often attenuated in humans (Bhamarapravati, N. & Yoksan, S. 1997 in: *Dengue and Dengue Hemorrhagic Fever* D. J. Gubler & G. Kuno eds. pp. 367-377 CAB International, New York; Butrapet, S. et al. 2000 *J Virol* 74:3011-9; Crowe, J. E. Jr. et al. 1994 *Vaccine* 12:783-790; Crowe, J. E. Jr. et al. 1994 *Vaccine* 12:691-699; Eckels, K. H. et al. 1980 *Infect Immun* 27:175-80; Innis, B. L. et al. 1988 *J Infect Dis* 158:876-80; Murphy, B. R. & Chanock, R. M. 2001 in: *Fields Virology* D. M. Knipe, et al. Eds. Vol. 1, pp. 435-468 Lippincott Williams & Wilkins, Philadelphia; Takemoto, K. K. 1966 *Prog Med Virol* 8:314-48). Because natural infection with dengue viruses and vaccination with 2AΔ30 may be associated with liver toxicity in humans, we identified mutant viruses with restricted replication in human liver cells. Accordingly, viruses were screened for plaque size and temperature-sensitivity in the human hepatoma cell line, HuH-7, as well as in Vero cells. Here we describe the ts phenotype, nucleotide sequence, and growth properties in suckling mice of 22 sp DEN4 mutant virus clones.

Cells and viruses. WHO Vero cells (African green monkey kidney cells) and HuH-7 cells (human hepatoma cells) (Nakabayashi, H. et al. 1982 *Cancer Res* 42:3858-63) were maintained as described in Example 1. DEN4 2A virus is a wild type virus derived from a cDNA clone of DEN4 strain 814669 (Dominica, 1981) (Lai, C. J. et al. 1991 *PNAS USA* 88:5139-43; Mackow, E. et al. 1987 *Virology* 159:217-28). The nucleotide sequence of DEN4 2A, the parent of the 5-FU mutant viruses, was previously assigned GenBank accession number AF375822 (Example 1). The DEN4 vaccine candidate, 2AΔ30, (Example 8) contains a 30 nt deletion in the 3' untranslated region (UTR) which removes nucleotides 10,478-10,507 (Men, R. et al. 1996 *J Virol* 70:3930-7). The cDNA clones p4, a modified derivative of the DEN4 2A cDNA clone, and p4Δ30 were used to generate recombinant wild type and attenuated viruses, rDEN4 and rDEN4Δ30, respectively (Example 8). GenBank accession numbers were previously assigned as follows (virus: accession number): DEN4 strain 814669: AF326573; 2AΔ30: AF326826; rDEN4: AF326825; rDEN4Δ30: AF326827.

Generation and biological cloning of mutant viruses with a sp phenotype. The generation of 1,248 virus clones from a pool of 5-fluorouracil-mutagenized DEN4 2A has been previously described (Example 1). Briefly, monolayers of Vero cells were infected with DEN4 2A at a multiplicity of infection (MOI) of 0.01 and overlaid with MEM supplemented with 2% FBS and 1 mM 5-fluorouracil (5-FU) (Sigma, St. Louis, Mo.), which reduced replication of DEN4 2A 100-fold. Vero cells in 96-well plates were inoculated with the 5-FU treated virus suspension, and virus clones were harvested from plates receiving terminally-diluted virus. A total of 1,248 virus clones were generated from the cultures treated with 1 mM 5-FU. Two virus clones, 2A-1 and 2A-13, were generated in the same manner from control cultures not treated with 5-FU and served as parallel-passaged control viruses with a wild type phenotype.

Evaluation of in vitro plaque size and temperature sensitivity. The 1,248 5-FU-mutagenized virus clones were screened for temperature sensitivity by assessing virus replication at 35° C. (permissive temperature) and 39° C. (restrictive temperature) in Vero and HuH-7 cells. Cell monolayers in 96-well plates were inoculated with serial ten-fold dilutions of virus and replicate plates were incubated at 35° C. and 39° C. for five days in temperature-controlled water baths. Virus replication was determined by immunoperoxidase staining as previously described (Example 1). A collection of 193 5-FU virus clones demonstrated a 100-fold or greater reduction in titer at 39° C. in either cell line, and these presumptive ts viruses were further characterized. The efficiency of plaque formation (EOP) at permissive and restrictive temperatures and the plaque size of each of the 193 virus clones were determined as follows. Serial ten-fold dilutions of virus suspension were inoculated onto confluent Vero cell and HuH-7 cell monolayers in replicate 24-well plates. After incubation at 35° C. for two hours, monolayers were overlaid with 0.8% methylcellulose (EM Science, Gibbstown, N.J.) in L-15 medium (Quality Biologicals, Gaithersburg, Md.) supplemented with 2% FBS, gentamicin, and L-glutamine. After incubation of replicate plates for five days at 35, 37, 38, or 39° C. in temperature-controlled water baths, plaques were visualized by immunoperoxidase staining and counted as previously described. Plaque size of each of the 193 viruses was evaluated at the permissive temperature (35° C.) and compared to that of DEN4 2A-13 parallel-passaged control virus with a wild type plaque size. Mutant viruses incubated at the permissive temperature of 35° C. which had a plaque size ≦1 mm or ≦0.4 mm (approximately ≦50% the size of wild type DEN4 2A-13) in Vero or HuH-7 cells, respectively, were designated as having a sp phenotype. The level of temperature sensitivity and plaque size of each virus was confirmed in at least two separate experiments. Seventy-five viruses which were confirmed to have a putative ts and/or sp phenotype were biologically cloned an additional two times and phenotypes were re-assessed. Twenty-two of the 75 terminally diluted viruses were found to have a sp phenotype. Sixteen of the 22 sp mutant viruses were also found to have a ts phenotype as defined by a 2.5 or 3.5 $\log_{10}$ PFU/ml reduction in virus titer in Vero or HuH-7 cells, respectively, at restrictive temperature compared to the permissive temperature of 35° C. as previously described (Example 1). Twenty of the 75 terminally-diluted viruses were found to have a ts phenotype without a sp phenotype and were previously described (Example 1). The remainder of the 75 viruses did not meet either criteria for a ts or sp mutant virus.

Evaluation of sp mutant viruses for restricted replication in suckling mice. Animal experiments were carried out in accordance with the regulations and guidelines of the National Institutes of Health, Bethesda, Md. Growth of DEN4 5-FU mutant viruses was determined in Swiss Webster suckling mice (Taconic Farms, Germantown, N.Y.). Groups of six seven-day-old mice were inoculated intracerebrally with $10^4$ PFU of virus in 30 µl Opti-MEM I (Invitrogen) and the brain of each mouse was removed five days later and individually analyzed as previously described (Example 1). Clarified supernatants of 10% suspensions of mouse brain were frozen at −70° C., and the virus titer was determined by plaque assay in Vero cells.

Determination of the complete genomic sequence of the sp mutant viruses. The nucleotide sequence of the 5-FU-mutagenized DEN4 viruses was determined as described in Example 8. Briefly, genomic RNA was isolated from virus clones and cDNA was prepared by reverse transcription and served as template for the generation of overlapping PCR fragments. A panel of primers was designed to sequence both strands of the PCR product from which consensus sequences were assembled and analyzed. The nucleotide sequence of the 5' and 3' regions of the virus genome was determined after circularization of the RNA genome as described in Example 8.

Figures 3A, 3B, 3C:
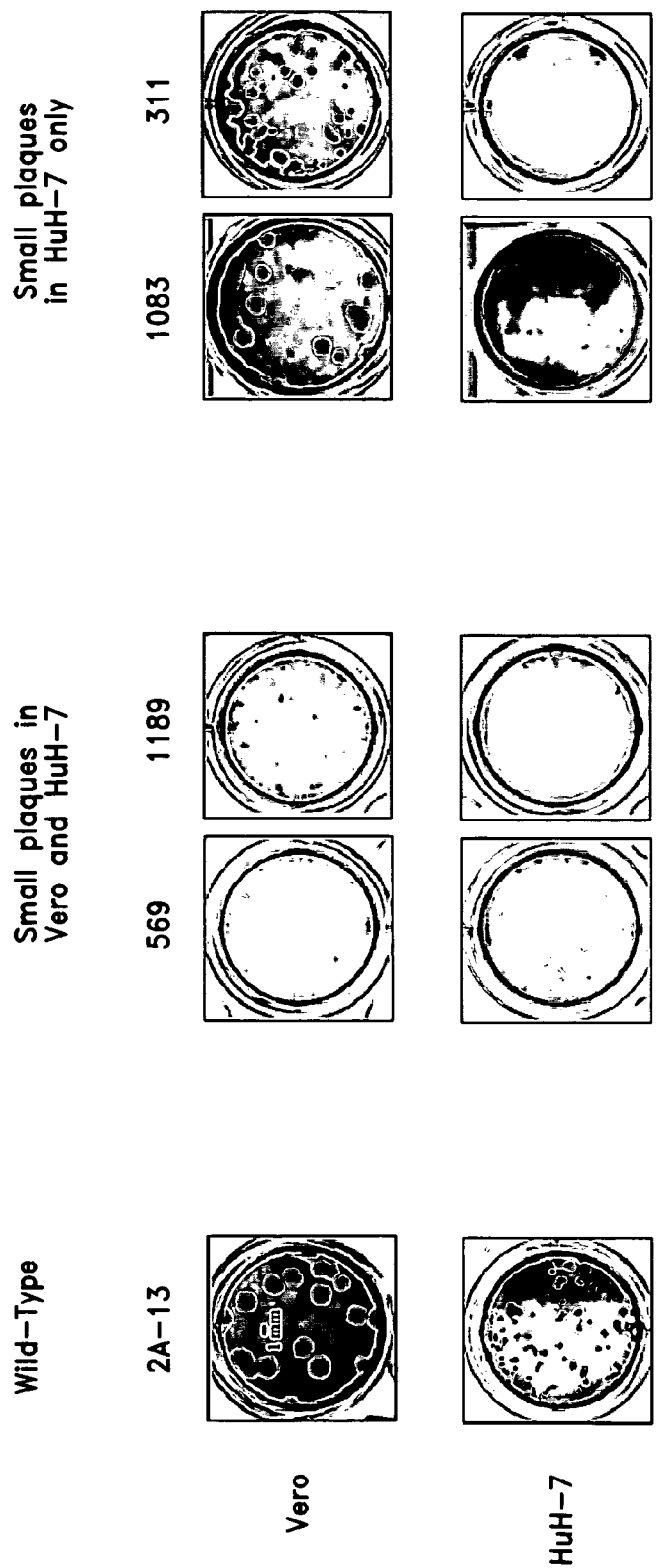
FIG. 3 shows plaque size phenotypes of representative 5-FU mutant DEN4 viruses. Serial ten-fold dilutions of wild-type DEN4 2A-13 (A), 5-FU mutant viruses #569 and #1189 (B), and 5-FU mutant viruses #1083 and #311 (C) were inoculated onto confluent Vero and HuH-7 cell monolayers in 24-well plates. After incubation at 35° C. for two hours, monolayers were overlaid with 0.8% methylcellulose culture media. Following incubation at 35° C. for five days, plaques were visualized by immunoperoxidase staining. Viruses which had a plaque size that was ≦1 mm (approximately ≦50% the size of wt DEN4 2A-13) at the permissive temperature of 35° C. were designated as having the small-plaque (sp) phenotype. Mutant viruses #569 and #1189 (B) were sp in both Vero and HuH-7 cells, and #311 and #1083 (C) were sp in only HuH-7 cells.

Identification of DEN4 5-fluorouracil mutant viruses with a sp phenotype. The generation of a panel of 1,248 virus clones from a wild type DEN4 2A virus suspension mutagenized by 5-FU has been described previously (Example 1). In the present study twenty-two mutant viruses with a sp phenotype were identified. The plaque size of representative mutant viruses is illustrated in FIG. 3. The plaque size of DEN4 2A-13 virus (a parallel-passaged virus with a wild type phenotype derived from control cultures not treated with 5-FU) was consistently smaller in HuH-7 cells than that observed in Vero cells (FIG. 3A). Mutant viruses #569 and #1189 (FIG. 3B) were sp in both Vero and HuH-7 cells. In contrast, 5-FU mutant virus clones #311 and #1083 (FIG. 3C) were sp in only HuH-7 cells, suggesting a liver cell-specific defect in replication within this phenotypic group. As indicated in Table 7, five mutant viruses were found to have a sp phenotype in both Vero and HuH-7 cells while 17 viruses had a sp phenotype in only HuH-7 cells. Each 5-FU mutant virus clone was compared for a sp or ts phenotype with three control viruses, 2A-13, wild type rDEN4, and rDEN4Δ30. The recombinant viruses, rDEN4 and rDEN4Δ30, each had a plaque size in Vero and HuH-7 cells similar to that of DEN4 2A-13 indicating that the Δ30 mutation does not confer a sp phenotype (Table 7).

Most of the sp 5-FU mutant viruses also had a ts phenotype in Vero and/or HuH-7 cells (Table 7) since mutant viruses were initially screened for temperature sensitivity. Temperature-sensitivity was defined as a 2.5 or 3.5 $\log_{10}$ PFU/ml reduction in virus titer in Vero or HuH-7 cells, respectively, at restrictive temperature compared to the permissive temperature of 35° C. as previously defined (Example 1). Three mutant viruses (#574, #1269 and #1189) were sp and ts in both Vero and HuH-7 cells, while nine mutant viruses (#506-326 in Table 7) were found to be ts in both cell types but sp only in HuH-7 cells. Four viruses (#1104, 952, 738, and 1083) were found to have a wild type phenotype in Vero cells but were both sp and ts in HuH-7 cells. These four mutant viruses each had a 6,000- to 600,000-fold reduction in virus titer at 39° C. in HuH-7 cells with only a 6- to 40-fold reduction at 39° C. in Vero cells. Finally, sp mutant viruses were identified which did not have a ts phenotype in either cell line; two of these viruses (#569 and #761) were sp in both Vero and HuH-7 cells and four viruses (#1096-1012) were sp in only HuH-7 cells (Table 7). As described previously, the Δ30 mutation did not confer temperature-sensitivity in either cell line (Example 1).

The sp 5-FU mutant viruses have restricted replication in suckling mouse brain. The 22 sp DEN4 5-FU mutant viruses were evaluated for their ability to replicate in the brain of one-week-old suckling mice. As a marker for in vivo attenuation, their level of replication was compared with that of the parallel-passaged control virus with a wild type phenotype, 2A-13 (Table 7). Nineteen of 22 sp mutant viruses had a greater than 100-fold reduction in virus replication in the brain of suckling mice compared to 2A-13 and nine viruses had a reduction of greater than 10,000-fold.

The five mutant viruses which were sp in both Vero and HuH-7 cells were 5,000-fold to 100,000-fold restricted in replication compared to 2A-13. Two of these mutant viruses, #569 and #761, were not ts in either cell line but had a reduction in virus titer of greater than 10,000-fold in mouse brain, indicating that the sp phenotype in both Vero and HuH-7 cells is an important surrogate marker for attenuated replication in suckling mouse brain. 5-FU mutant viruses which were sp in only HuH-7 cells had a more variable range of replication in mouse brain. Three viruses had a mean reduction in virus titer of less than 10-fold when compared to 2A-13 virus. However, 8 of 13 viruses which were ts in Vero and/or HuH-7 cells but sp in only HuH-7 cells had a greater than 5,000-fold reduction in virus replication. The results of the in vivo replication analysis of the previously described 20 ts 5-FU mutant viruses (Example 1) and the 22 sp mutant viruses are summarized in Table 8. Mutant viruses with both a sp and ts phenotype were found to have a significantly greater level of attenuation in the brain of suckling mice when compared to viruses with only a ts phenotype.

Sequence analysis of the sp 5-FU mutant viruses. To initiate an analysis of the genetic basis of the ts, sp, or att phenotype of the 22 sp mutant viruses, the complete nucleotide sequence of each virus genome was determined and is summarized in Table 9 (sp in Vero and HuH-7 cells) and Table 10 (sp in only HuH-7 cells). All identified mutations were nucleotide substitutions, as deletions or insertions were not observed. Point mutations were distributed throughout the genome, including the 3' UTR as well as in all coding regions. Because all 5-FU mutant viruses were found to have at least two mutations (two to six), the observed phenotypes cannot be directly attributed to a specific mutation. The majority of sp viruses also contained translationally silent point mutations (none to four) in the structural or non-structural coding regions. However, these silent mutations are not expected to contribute to the observed phenotypes. Six of the 22 sp mutant viruses (Tables 9 and 10) were found to have mutations in only the NS genes and/or the 3' UTR, indicating that the sp phenotype can be conferred by mutations outside of the structural genes.

Presence of identical mutations in multiple 5-FU mutant viruses. Analysis of the complete nucleotide sequence data for the 5-FU mutant viruses identified several repeated mutations which were present in two or more viruses. Such mutations were also identified previously during our analysis of twenty 5-FU mutant viruses with a ts but not sp phenotype (Example 1). Because these mutations occurred in viruses together with additional mutations, the contribution of the repeated mutations to the observed sp, ts, and att phenotypes remains empirical. Table 11 lists the repeated mutations found among the 20 ts (not sp) mutant viruses described previously (Example 1) and the 22 sp mutant viruses described here. Repeated mutations were identified in the following genes: two in E, two in NS3, five in NS4B, one in NS5, and two in the 3' UTR. Interestingly, within a thirty nucleotide region of NS4B (nt 7153-7182), there were five different nucleotide substitutions which were found in sixteen viruses. Also at nt 7,546 in NS4B, an amino acid substitution (Ala→Val) was found in 10 different 5-FU mutant viruses. The significance of these repeated mutations in NS4B as well as in other DEN4 genomic regions remains empirical, but a reasonable explanation for this phenomenon is that these mutations are involved in adaptation of DEN4 virus for efficient growth in Vero cells, as further discussed in Example 6.

Discussion. As part of a molecular genetic vaccine strategy, we have developed attenuating mutations that are envisioned as being useful in the development of a live attenuated tetravalent dengue virus vaccine. Specifically, mutations which restrict replication of the vaccine virus in human liver cells were generated since there was some residual virulence of the rDEN4Δ30 vaccine candidate for the liver of humans. Mutant viruses with a sp phenotype were sought in both Vero cells and HuH-7 human liver cells, in order to identify host-range mutant viruses that were specifically restricted in replication in HuH-7 cells (sp in HuH-7 but not in Vero). Such mutations are envisioned as being useful in limiting replication of a candidate vaccine in the liver of vaccinees while preserving both efficient replication in Vero cells and immunogenicity in vivo.

Several observations from the present study indicate that sp mutations confer an att phenotype in vivo. This is not surprising since attenuation in suckling mouse brain has been reported for live DEN virus vaccine candidates possessing sp phenotypes, including the DEN2 PDK-53 and DEN2 PR-159/S-1 vaccine strains (Bhamarapravati, N. & Yoksan, S. 1997 in: *Dengue and Dengue Hemorrhagic Fever* D. J. Gubler & G. Kuno eds. pp. 367-377 CAB International, New York; Butrapet, S. et al. 2000 *J Virol* 74:3011-9; Eckels, K. H. et al. 1980 *Infect Immun* 27:175-80; Innis, B. L. et al. 1988 *J Infect Dis* 158:876-80). Each of 22 DEN4 5-FU mutant viruses with a sp phenotype (some of which were also ts) in either Vero or HuH-7 cells manifested restricted replication in the brains of mice. Six 5-FU mutant viruses with a sp phenotype in the absence of a ts phenotype were more attenuated in the brains of suckling mice than mutant viruses with solely a ts phenotype (Example 1), indicating that the sp phenotype specifies a greater level of attenuation for mouse brain than does the ts phenotype. Mutant viruses with both a ts and sp phenotype had an even greater reduction in replication, further indicating that the attenuation conferred by the ts and sp phenotypes can be additive. Importantly, seventeen of the 22 sp mutant viruses were host-range sp mutant viruses, being sp only in HuH-7 cells. Since such mutations are envisioned as being useful in restricting the replication of a DEN4 virus in human liver cells, we used nucleotide sequence analysis to determine the genetic basis of the sp phenotype.

Analysis of the complete genomic sequence of the 22 sp DEN4 viruses revealed substitutions in the 3' UTR as well as coding mutations in all genes except NS4A. It was first noted that several specific mutations were present in two or more of the 22 sp DEN4 mutant viruses and that many of these same mutations were also previously identified among the set of 20 ts DEN4 mutant viruses (Example 1). Since flaviviruses can rapidly accumulate mutations during passage in tissue culture (Dunster, L. M. et al. 1999 Virology 261:309-18; Mandl, C. W. et al. 2001 J Virol 75:5627-37), many of these over-represented mutations, previously referred to as putative Vero cell adaptation mutations (Example 1), likely promote efficient replication in Vero cells and were selected unintentionally during the biological cloning of the mutant viruses. The effect of these mutations on DEN virus replication in Vero cells, the proposed substrate for vaccine manufacture, is discussed in Example 6.

The sp mutations identified among the 5-FU mutant viruses are envisioned as being useful in several different approaches for the development of DEN virus vaccine strains. As described above for the generation of antigenic chimeric viruses, one or more sp attenuating mutations are envisioned as being added to the attenuated DEN4Δ30 genetic background to supplement the att phenotype of the Δ30 mutation. A second approach is to introduce a sp attenuating mutation, with or without Δ30, into infectious cDNA clones of the other three DEN serotypes. The ability to transfer mutations among genetically-related viruses and maintain similar att phenotypes has been previously demonstrated (Skiadopoulos, M. H. et al. 1999 Virology 260:125-35). These distinct strategies are envisioned as being useful as separate or complementary approaches to the construction of a tetravalent DEN virus vaccine, underlining the importance of the identification of a large panel of att mutations within the DEN viruses.

EXAMPLE 3

Recombinant DEN4 Viruses Containing Mutations Identified in 5-FU Mutant Viruses Show Restricted Replication in Suckling Mouse Brain and in SCID Mice Transplanted with Human Liver Cells Data was presented in Examples 1 and 2 that summarizes the generation, characterization and sequence analysis of 42 attenuated mutant DEN4 viruses. For three of the mutant viruses (#239, 489, and 773) with a single missense mutation at nt position 4995 in NS3, it was clear that the identified mutation specified the ts and att phenotypes. This conclusion was confirmed in Example 1 by tissue culture and in vivo characterization of rDEN4-4995, a recombinant virus into which the 4995 mutation had been introduced by site-directed mutagenesis. In this analysis, rDEN4-4995 exhibited the same level of temperature sensitivity and attenuation as 5-FU mutant viruses #239, 489, and 773. The individual mutation(s) in the remaining 5-FU mutant viruses that specify the observed phenotypes remains to be identified, since most of these viruses possess more than one nucleotide substitution. We have conducted an analysis to identify the mutations in a subset of the other 39 mutant viruses that specify the ts, sp, and att phenotypes by introduction of each mutation into the wt DEN4 cDNA (p4) and evaluation of the phenotypes of the resulting recombinant DEN4 viruses bearing the individual mutations. Previous studies of a DEN2 virus vaccine candidate (Butrapet, S. et al. 2000 J Virol 74:3011-9) as well as other virus vaccines (Whitehead, S. S. et al. 1999 J Virol 73:871-7) have demonstrated the utility of this approach for the identification of the genetic basis of attenuation.

As described in Examples 1 and 2, 19 5-FU mutant viruses were identified which were found to contain coding mutations in only the NS genes and/or nucleotide substitutions in the 5' or 3' UTR which would facilitate the generation of antigenic chimeric viruses. In the present example, the genetic basis of the observed sp, ts, and mouse brain att phenotypes was identified for these 19 viruses using reverse genetics to generate recombinant DEN4 (rDEN4) viruses containing individual mutations identified in the panel of DEN4 mutant viruses. In addition, the 19 5-FU mutant viruses were evaluated for replication in a novel small animal model for DEN4 virus replication, SCID mice transplanted with HuH-7 cells (SCID-HuH-7), and the genetic basis of the att viruses was identified using mutant rDEN4 viruses. Also presented are findings describing the generation and characterization of a recombinant virus containing two of the identified attenuating mutations as well as combination of select 5-FU mutations with the Δ30 mutation.

Generation of rDEN4 viruses containing 5-FU mutations. The methods used for the generation of rDEN4 viruses are outlined in FIG. 4 and are similar to those described in Example 1. Briefly, the p4 cDNA was digested with the appropriate restriction enzymes and the resulting fragments were subcloned into a modified pUC119 vector. For Kunkel mutagenesis, single-stranded DNA preparations of the pUC-NS vectors were made, and primers were designed to individually introduce mutations that were present in the 5-FU mutant viruses. The sequences of the 41 mutagenic oligonucleotides used to generate the single-mutation recombinant viruses are presented in Table 12. Primers were designed to co-introduce or co-ablate a translationally-silent restriction enzyme site in the cDNA, which greatly facilitates the screening and identification of cDNA clones possessing the mutant sequence. Fragments containing the introduced mutations were cloned back into p4, and nucleotide sequence analysis confirmed the presence of the nucleotide changes. A total of 33 rDEN4 viruses was generated which contained each of the individual mutations present in the 19 5-FU mutant viruses containing only coding mutations in the NS genes and/or nucleotide substitutions in the 5' or 3' UTR. An additional 8 rDEN4 viruses were generated from mutations identified in the remaining panel of 42 5-FU mutant viruses.

A cDNA clone was also generated which combined the mutations identified at nt position 4995 in NS3 and 7849 in NS5. The 7849 mutation was introduced into the p4-4995 cDNA clone by replacing the XmaI-PstI fragment with that derived from the p4-7849 cDNA clone. The presence of both mutations was confirmed by sequence analysis. The Δ30 mutation was introduced into the 3' UTR of the individual mutant cDNA clones by replacing the MluI-KpnI fragment with that derived from the p4Δ30 cDNA clone, and the presence of the deletion was confirmed by sequence analysis.

Recombinant viruses were recovered by transfection of Vero or C6/36 cells with RNA transcripts derived from the mutant cDNA clones as described in Example 1. Recovered viruses were terminally diluted twice and working stocks of viruses were prepared in Vero cells. Each of the mutant cDNA clones was recovered after transfection as expected since the 5-FU mutant viruses containing these mutations were viable.

Characterization of ts and att phenotypes of the rDEN4 viruses containing introduced mutations. Of the 19 5-FU mutant viruses with mutations in only NS genes and/or the 5' or 3' UTR, six had an sp phenotype (Table 13), ten had a ts phenotype in Vero and HuH-7 cells (Table 14), and three had a ts phenotype in only HuH-7 cells (Table 15). For the six sp 5-FU mutant viruses, #738, 922, 1081, 1083, 1136, and 1189, seventeen mutations identified by sequence analysis resulted in a coding change or a nucleotide change in the UTR and each was engineered into an individual DEN4 cDNA clone. Virus containing each defined mutation was successfully recovered and propagated and was tested for efficiency of plaque formation in Vero and HuH-7 cells at various temperatures, plaque size phenotype, and growth properties in suckling mice using methods previously described in Examples 1 and 2.

Table 13 lists the phenotypes of the six sp 5-FU mutant parent viruses and those of the 17 rDEN4 viruses encoding single mutations present in the parent virus. For example, 5-FU mutant #1189 (parent), which was ts and sp in both cell lines and had an almost 10,000-fold reduction in replication in suckling mouse brain, contained 4 coding mutations at nt position 3303 in NS1, 4812 and 5097 in NS3, and 7182 in NS4B. Analysis of the four rDEN4 viruses containing each of these mutations indicated that rDEN4-5097 had a ts, sp, and att phenotype while rDEN4-3303, rDEN4-4812, and rDEN4-7182 had no discernible phenotypes, indicating that the mutation at nt 5097 was responsible for the phenotype observed in the 5-FU parent, #1189. Thus, analysis of the relative contributions of the four mutations present in the 5-FU mutant #1189 to its attenuation phenotype provides the framework for a similar analysis of the remaining 5-FU mutant viruses. This analysis specifically demonstrates the methods used to identify mutations contributing to the observed phenotype. The ts, sp, and att phenotypes of 5-FU parent viruses #738, 922, 1081, and 1083, were similarly attributed to single mutations 3540, 4306, 2650, and 10634, respectively. However, two separate mutations (3771 and 4891) contributed to the phenotypes of 5-FU mutant virus #1136.

Table 14 lists the genetic basis of the ts and mouse brain attenuation for the ten 5-FU mutant viruses with ts phenotypes in both Vero and HuH-7 cells. As described in Example 1, the 4995 mutation which is the only mutation present in three 5-FU mutant viruses, #239, #489, and #773, was found to confer a ts and att phenotype, confirming the genetic basis for the phenotypes exhibited by these viruses. In three separate experiments, the rDEN4-4995 virus was found to have an approximately 1,000-fold decrease in replication in the brains of suckling mice when compared to that of wild-type virus (Table 6 and 14). The 4995 mutation is also present in 5-FU mutant viruses #473, #759, and #816, each of which has additional mutations. The ts and att phenotypes observed in these viruses can be attributed to the 4995 mutation since the additional mutations did not show discernible phenotypes. Interestingly, 5-FU mutant virus #938 has the 4995 mutation and an additional mutation at nt 3442 in NS1 with both mutations independently conferring restricted replication in mouse brain. The remaining three 5-FU parent viruses in Table 14, #173, #509, and #1033, were found to each contain a single mutation responsible for the att phenotype: 7849, 8092, and 4907, respectively.

Three 5-FU mutant viruses, #686, #992, and #1175 with HuH-7 cell-specific ts phenotypes are listed in Table 15. Mutations in NS3 (5695) and NS5 (10186) were found to confer the phenotypes observed for parent virus #992 and #1175. Interestingly, two mutations in NS2A, 3575 and 4062, were found to result in a synergistic increase in the level of attenuation. Both individual mutations had an approximately 100-fold decrease in virus replication in the brain while the parent virus with both mutations had an almost 10,000-fold reduction. Table 16 lists two additional mutations with an att phenotype, 4896 and 6259 in NS3.

Replication of DEN4 viruses in SCID mice transplanted with HuH-7 cells. Since DEN viruses replicate poorly in the liver of mice and corresponding studies are impractical to conduct in non-human primates, an animal model that evaluates the in vivo level of replication of DEN virus in liver cells was developed based on a recent report examining the replication of DEN virus in SCID mice transplanted with a continuous cell line of human liver tumor cells (An, J. et al. 1999 *Virology* 263:70-7). SCID mice transplanted with human continuous cell lines, primary cells, or organized tissues have similarly been used to study the replication of other viruses which lack a suitable small animal model (Mosier, D. E. 2000 *Virology* 271:215-9). In our study, SCID mice were transplanted with HuH-7 cells since DEN4 virus replicated efficiently in these cells in tissue culture and since these were the cells used to define the host-range phenotype. These studies are envisioned as addressing the utility of examining DEN virus infection in SCID mouse-xenograft models for vaccine development (An, J. et al. 1999 *Virology* 263:70-7; Lin, Y. L. et al. 1998 *J Virol* 72:9729-37).

To further examine the in vivo growth properties of the 19 5-FU mutant DEN4 viruses with mutations in only the NS genes and/or the 3' UTR and selected corresponding rDEN4 mutant viruses, replication was assessed in SCID mice transplanted with HuH-7 cells (SCID-HuH-7). For analysis of DEN4 virus replication in SCID-HuH-7 mice, four to six week-old SCID mice (Tac:Icr:Ha(ICR)-Prkdc$^{scid}$) (Taconic Farms) were injected intraperitoneally with $10^7$ HuH-7 cells suspended in 200 μl phosphate-buffered saline (PBS). In preparation for transplantation, HuH-7 cells were propagated in cell culture as described above and harvested by trypsinization at approximately 80% confluence. Cells were washed twice in PBS, counted, resuspended in an appropriate volume of PBS, and injected into the peritoneum of mice. Tumors were detected in the peritoneum five to six weeks after transplantation, and only mice with apparent tumors were used for inoculation. Mice were infected by direct inoculation into the tumor with $10^4$ PFU of virus in 50 μl Opti-MEM I. Mice were monitored daily for seven days and serum for virus titration was obtained by tail-nicking on day 6 and 7. Approximately 400 μl blood was collected in a serum separator tube (Sarstedt, Germany), centrifuged, and serum was aliquoted and stored at −70° C. The virus titer was determined by plaque assay in Vero cells. Seven days after infection, most mice developed morbidity and all mice were sacrificed. Tumors were excised and weighed to confirm uniformity of the experimental groups.

Preliminary experiments indicated that SCID-HuH-7 mice inoculated with DEN4 2A-13 directly into the tumor developed viremia with maximum levels (up to 8.0 $\log_{10}$ PFU/ml serum) achieved on day 5 (Table 17). Virus could also be detected in brain, liver, and tumor homogenates.

The level of viremia in SCID-HuH-7 mice infected with parental 5-FU or rDEN4 mutant viruses was compared with that of the parallel-passaged control virus, 2A-13, or rDEN4, respectively. Results of 4 separate experiments indicated that the vaccine candidate, rDEN4Δ30, had an almost 10-fold reduction in virus replication compared to wild type rDEN4

(Table 13) which reflects the apparent attenuation of the rDEN4Δ30 vaccine candidate in humans (Example 8). Results in Tables 13 to 15 indicate that three 5-FU mutant viruses had a greater than 100-fold reduction in viremia in the SCID-HuH-7 mice compared to wild type 2A-13 virus: #1081, #1083, and #1189. The common phenotype among these viruses was a sp phenotype in HuH-7 cells. Analysis of the genetic basis of the att phenotype in these parent 5-FU mutant viruses identified three individual mutations in NS1, NS3, and the 3' UTR which conferred at least a 100-fold reduction in viremia. Specifically, rDEN4-2650 (NS1), rDEN4-5097 (NS3), and rDEN4-10634 (3' UTR) manifested a 2.2, 3.6, and 4.3 $\log_{10}$ PFU/ml reduction in peak titer of viremia compared to rDEN4, respectively. These mutations also conferred the att phenotype in suckling mouse brain. 5-FU mutant virus #738 and #509 had a reduction in viremia in the SCID-HuH-7 mice compared to wild type 2A-13 of 1.9 and 1.5 $\log_{10}$ PFU/ml, respectively, and the genetic basis for these phenotypes is envisioned as being assessed on an empirical basis.

This analysis of the genetic basis of the phenotypes specified by the mutations in the 5-FU mutant viruses that manifested restricted replication in SCID-HuH-7 mice indicated that (1) three separate mutations conferred the att phenotype; (2) these mutations were located in two proteins, NS1 and NS3, and in the 3' UTR; (3) these three mutations were fully responsible for each of the cell culture (ts or sp) and in vivo (attenuation in mouse brain and SCID-HuH-7 mice) phenotypes of the parent viruses; and (4) two of the three mutations specify the host-range sp phenotype (sp on HuH-7 only) and therefore are envisioned as being useful in a vaccine virus. Although the relevance of such SCID-transplant models to virus replication and disease in humans is unknown, the identification of three novel mutations which restrict DEN4 virus replication in SCID-HuH-7 mice is envisioned as facilitating an examination of the correlation between the att phenotype in SCID-HuH-7 mice with that in rhesus monkeys or humans. Such mutations, specifically the host-range sp mutations, are envisioned as being useful in conjunction with the Δ30 or other mutation to decrease the residual virulence of rDEN4Δ30 or other dengue virus for the human liver, and studies are envisioned as being conducted to construct such rDEN4 viruses and evaluate them in monkeys and humans (Example 8).

Combination of two 5-FU mutations results in an additive ts phenotype. The ability to combine individual mutations in rDEN4 virus as a means to modulate the phenotype of the resulting double mutant virus is a major advantage of using recombinant cDNA technology to generate or modify dengue virus vaccine candidates. Addition of multiple ts and att mutations to recombinant vaccine viruses is envisioned as improving the phenotypic stability of the double recombinant due to the decreased possibility of co-reversion of the two mutations to wild-type virulence (Crowe, J. E. Jr. et al. 1994a *Vaccine* 12:783-790; Skiadopoulos, M. H. et al. 1998 *J Virol* 72:1762-8; Subbarao, E. K. et al. 1995 *J Virol* 69:5969-5977; Whitehead, S. S. et al. 1999 *J Virol* 73:871-7). The mutations identified at nt position 4995 in NS3 and 7849 in NS5 were combined in a single p4 cDNA clone and a recombinant virus, designated rDEN4-4995-7849, was recovered and evaluated for its ts and att phenotypes (Table 18). rDEN4-4995-7849 was more ts than either recombinant virus containing the individual mutations (Table 18), indicating the additive effect of the two ts mutations. The rDEN4-4995-7849 virus had a greater than 10,000-fold reduction in replication in the brains of suckling mice. The reduction in replication of the double mutant virus was only slightly increased over that of rDEN4-7849, however, a difference in the level of replication between rDEN4-4995-7849 and rDEN4-7849 would be difficult to detect since the level of replication of both viruses was close to the lower limit of detection (2.0 $\log_{10}$ PFU/g brain).

Combination of selected 5-FU mutations with the Δ30 mutation confers increased attenuation of rDEN4Δ30 for the brains of suckling mice. To define the effect of adding individual mutations to the attenuated rDEN4Δ30 background, five combinations have been constructed: rDEN4Δ30-2650, rDEN4Δ30-4995, rDEN4Δ30-5097, rDEN4Δ30-8092, and rDEN4Δ30-10634. Addition of such missense mutations with various ts, sp, and att phenotypes is envisioned as serving to decrease the reactogenicity of rDEN4Δ30 while maintaining sufficient immunogenicity.

The Δ30 mutation was introduced into the 3' UTR of the individual mutant cDNA clones by replacing the MluI-KpnI fragment with that derived from the p4Δ30 cDNA clone, and the presence of the deletion was confirmed by sequence analysis. Recombinant viruses were recovered by transfection in C6/36 cells for each rDEN4 virus. However, upon terminal dilution and passage, the rDEN4Δ30-5097 virus was found to not grow to a sufficient titer in Vero cells and was not pursued further. This is an example of a cDNA in which the 5-FU mutation and the Δ30 mutation are not compatible for efficient replication in cell culture. To begin the process of evaluating the in vivo phenotypes of the other four viruses which replicated efficiently in cell culture, rDEN4 viruses containing the individual mutations and the corresponding rDEN4Δ30 combinations were tested together for levels of replication in suckling mouse brain. The results in Table 19 indicate that addition of each of the mutations confers an increased level of attenuation in growth upon the rDEN4Δ30 virus, similar to the level conferred by the individual 5-FU mutation. No synergistic effect in attenuation was observed between the missense mutations and Δ30. These results indicate that the missense mutations at nucleotides 2650, 4995, 8092, and 10634 are compatible with Δ30 for growth in cell culture and in vivo and can further attenuate the rDEN4Δ30 virus in mouse brain. Further studies in SCID-HuH-7 mice, rhesus monkeys, and humans are envisioned as establishing the effect of the combination of individual mutations and Δ30 upon attenuation and immunogenicity (Example 8).

By identifying the specific mutations in the 5-FU mutant viruses which confer the observed phenotypes, a menu of defined ts, sp, and att mutations is envisioned as being assembled (see Example 7). Numerous combinations of two or more of these mutations are envisioned as being selected with or without the Δ30 mutation. Such mutations and their combinations are envisioned as being useful for the construction of recombinant viruses with various levels of in vivo attenuation, thus facilitating the generation of candidate vaccines with acceptable levels of attenuation, immunogenicity, and genetic stability.

EXAMPLE 4

Generation of DEN4 Mutant Viruses with Temperature-Sensitive and Mouse Attenuation Phenotypes through Charge-Cluster-to-Alanine Mutagenesis The previous Examples described the creation of a panel of DEN4 mutant viruses with ts, sp, and att phenotypes obtained through 5-FU mutagenesis. As indicated in these Examples, the attenuating mutations identified in the 5-FU mutant viruses are envisioned as having several uses including (1)

fine tuning the level of attenuation of existing dengue virus vaccine candidates and (2) generation of new vaccine candidates by combination of two or more of these attenuating mutations. In the current example, we created a second panel of mutant viruses through charge-cluster-to-alanine mutagenesis of the NS5 gene of DEN4 and examined the resulting mutant viruses for the ts, sp, and att phenotypes as described in Examples 1 and 2. The charge-cluster-to-alanine mutant viruses recovered demonstrated a range of phenotypes including ts in Vero cells alone, ts in HuH-7 cells alone, ts in both cell types, att in suckling mouse brains, and att in SCID-HuH-7 mice.

The usefulness of mutant viruses expressing these phenotypes has already been described, however charge-cluster-to-alanine mutant viruses possess some additional desirable characteristics. First, the relevant mutations are envisioned as being designed for use in the genes encoding the non-structural proteins of DEN4, and therefore are envisioned as being useful to attenuate DEN1, DEN2, and DEN3 antigenic chimeric recombinants possessing a DEN4 vector background. Second, the phenotype is usually specified by three or more nucleotide changes, rendering the likelihood of reversion of the mutant sequence to that of the wild type sequence less than for a single point mutation, such as mutations identified in the panel of 5-FU mutant viruses. Finally, charge-cluster-to-alanine attenuating mutations are envisioned as being easily combinable among themselves or with other attenuating mutations to modify the attenuation phenotype of DEN4 vaccine candidates or of DEN1, DEN2, and DEN3 antigenic chimeric recombinant viruses possessing a DEN4 vector background.

Charge-Cluster-to-Alanine-Mutagenesis. The cDNA p4, from which recombinant wild type and mutant viruses were generated, has been described in Examples 1, 2, and 3 and in FIG. 4. Charge-cluster-to-alanine mutagenesis (Muylaert, I. R. et al. 1997 *J Virol* 71:291-8), in which pairs of charged amino acids are replaced with alanine residues, was used to individually mutagenize the coding sequence for 80 pairs of contiguous charged amino acids in the DEN4 NS5 gene. Subclones suitable for mutagenesis were derived from the full length DEN4 plasmid (p4) by digestion with XmaI/PstI (pNS5A), PstI/SacII (pNS5B) or SacII/MluI (pNS5C) at the nucleotide positions indicated in FIG. 4. These fragments were then subcloned and Kunkel mutagenesis was conducted as described in Examples 1 and 3. To create each mutation, oligonucleotides were designed to change the sequence of individual pairs of codons to GCAGCX (SEQ ID NO: 69), thereby replacing them with two alanine codons (GCX) and also creating a BbvI restriction site (GCAGC) (SEQ ID NO: 70). The BbvI site was added to facilitate screening of cDNAs and recombinant viruses for the presence of the mutant sequence. Restriction enzyme fragments bearing the alanine mutations were cloned back into the full-length p4 plasmid as described in Examples 1 and 3.

Initial evaluation of the phenotype of the 32 charge-cluster-to-alanine mutant viruses revealed a range in restriction of replication in suckling mouse brain and SCID-HuH-7 mice. To determine whether attenuation could be enhanced by combining mutations, double mutant viruses carrying two pairs of charge-cluster-to-alanine mutations were created by swapping appropriate fragments carrying one pair of mutations into a previously-mutagenized p4 cDNA carrying a second pair of mutations in a different fragment using conventional cloning techniques.

Transcription and Transfection. 5'-capped transcripts were synthesized in vitro from mutagenized cDNA templates using AmpliCap SP6 RNA polymerase (Epicentre, Madison, Wis.). Transfection mixtures, consisting of 1 µg of transcript in 60 µl of HEPES/saline plus 12 µl of dioleoyl trimethylammonium propane (DOTAP) (Roche Diagnostics Corp., Indianapolis, Ind.), were added, along with 1 ml Virus production-serum free medium (VP-SFM) to subconfluent monolayers of Vero cells in 6-well plates. Transfected monolayers were incubated at 35° C. for approximately 18 hr, cell culture medium was removed and replaced with 2 ml VP-SFM, and cell monolayers were incubated at 35° C. After 5 to 6 days, cell culture medium was collected, and the presence of virus was determined by titration in Vero cells followed by immunoperoxidase staining as previously described. Recovered virus was amplified by an additional passage in Vero cells, and virus suspensions were combined with SPG (sucrose-phosphate-glutamate) stabilizer (final concentration: 218 mM sucrose, 6 mM L-glutamic acid, 3.8 mM potassium phosphate, monobasic, and 7.2 mM potassium phosphate, dibasic, pH 7.2), aliquoted, frozen on dry ice, and stored at −70° C.

cDNA constructs not yielding virus after transfection of Vero cells were used to transfect C6/36 cells as follows. Transfection mixtures, as described above, were added, along with 1 ml of MEM containing 10% fetal bovine serum (FBS), 2 mM L-glutamine, 2 mM non-essential amino acids, and 0.05 mg/ml gentamicin, to monolayers of C6/36 cells. Transfected cell monolayers were incubated at 32° C. for 18 hr, cell culture medium was removed and replaced with 2 ml fresh medium, and cell monolayers were incubated at 32° C. After 5 to 6 days, cell culture media were then used to infect Vero cells and incubated for 5-6 days, at which time cell culture media were collected, frozen and titered as described above.

Recovered viruses were biologically cloned by two rounds of terminal dilution in Vero cells followed by an additional amplification in Vero cells. Briefly, virus was initially diluted to a concentration of approximately 20 PFU/ml in VP-SFM and then subjected to a series of two-fold dilutions across a 96-well plate. Virus dilutions were used to infect Vero cell monolayers in a 96-well plate and incubated for 5 to 6 days at 35° C. Following incubation, cell culture media were removed and temporarily stored at 4° C., and the virus-positive cell monolayers were identified by immunoperoxidase staining. Terminal dilution was achieved when ≦25% of cell monolayers were positive for virus. Cell culture medium from a positive monolayer at the terminal dilution was subjected to an additional round of terminal dilution. Following the second terminal dilution, virus was amplified in Vero cells (75 cm² flask), collected and frozen as previously described.

Assays for temperature-sensitivity and mouse attenuation. Assay of the level of temperature sensitivity of the charge-cluster-to-alanine mutant viruses in Vero and HuH-7 cells and their level of replication in the brain of suckling mice were conducted as described in Example 1 and assay of the level of replication in SCID-HuH-7 mice was conducted as described in Example 3.

Charge-cluster-to-alanine mutant viruses are viable and show temperature-sensitive and mouse attenuation phenotypes. Of 80 full-length DEN4 cDNA constructs containing a single pair of charge-to-alanine mutations, virus was recovered from 32 in either Vero or C6/36 cells (FIG. 5). The level of temperature sensitivity of wt rDEN4, rDEN4Δ30, and the 32 mutant viruses is summarized in Table 20. One mutant virus (645-646) was ts in Vero but not HuH-7 cells and 7 mutant viruses were ts in HuH-7 but not Vero cells. Such mutants whose temperature sensitivity is host-cell dependent are referred to as temperature-sensitive, host-range (tshr) mutants. Thirteen mutant viruses were ts in both cell types, and 11 mutant viruses were not ts on either cell type. Thus a total of 21 mutant viruses were ts with 8 mutant viruses exhibiting an tshr specificity. None of the mutant viruses showed a small plaque phenotype at permissive temperature. Mutant viruses showed a wide range (0 to 10,000-fold) of restricted replication in suckling mouse brain (Table 20). Fourteen mutant viruses were attenuated in suckling mouse brain, arbitrarily defined as a $\geq 1.5$ $\log_{10}$-unit reduction in virus titer. There was no correlation between attenuation in mouse brain and temperature sensitivity in either Vero cells (Kendall Rank correlation: P=0.77) or HuH-7 cells (Kendall Rank correlation: P=0.06).

Thirteen mutant viruses that either showed an att phenotype in suckling mouse brain or whose unmutated charged amino acid pair was highly conserved among the four DEN serotypes (see Example 7) were assayed for att in SCID-HuH-7 mice (Table 21). Three of these mutant viruses showed >100-fold decrease in replication relative to wild type DEN4. Overall, mean log reduction from wild type in suckling mice did not show significant correlation with mean log reduction in SCID-HuH-7 mice (Spearman rank correlation, N=13, P=0.06). However, mutant virus 200-201 was unusual in that it showed a high level of restriction in SCID-HuH-7 mice but little restriction in suckling mouse brain. When virus 200-201 was removed from the analysis, restriction of replication in suckling and SCID-HuH-7 mice showed a significant correlation (Spearman rank correlation, N=12, P=0.02).

Combining charge-cluster-to-alanine mutations present in two viruses into one virus can enhance its ts and att phenotypes. Six paired mutations were combined into fourteen double-pair mutant viruses, of which six could be recovered in Vero or C6/36 cells (Table 22). All of the individual paired mutations used in double-pair mutant viruses were ts on HuH-7 cells, none was ts in Vero cells, and for all combinations at least one mutation pair conferred an att phenotype in suckling mouse brain. Evaluation of four of the double-pair mutant viruses (Table 23) revealed that combining charge-cluster-to-alanine mutation pairs invariably resulted in the acquisition of a ts phenotype in Vero cells (4 out of 4 viruses) and often resulted in a lowered shutoff temperature in HuH-7 cells (3 out of 4 viruses). In half of the viruses assayed, combination of charge-cluster-to-alanine mutation pairs resulted in enhanced restriction of replication (10-fold greater than either component mutation) in suckling mouse brain (Table 23) and in SCID-HuH-7 mice (Table 24).

Summary. The major usefulness of the charge-cluster-to-alanine mutations stems from their design: they are located in the DEN4 non-structural gene region and therefore are envisioned as being useful to attenuate DEN4 itself as well as antigenic chimeric viruses possessing the DEN4 NS gene region. Furthermore, they are predicted to be phenotypically more stable than the single-nucleotide substitution mutant viruses such as the 5-FU mutant viruses. Finally, combinations of mutations are envisioned as being created in order to fine-tune attenuation and to further stabilize attenuation phenotypes.

EXAMPLE 5

Identification and Characterization of DEN4 Mutant Viruses Restricted in Replication in Mosquitoes Section 1. Identification of Viruses Showing Restriction of Replication in Mosquitoes.

In Examples 1 and 4, DEN4 mutant viruses were generated through 5-FU mutagenesis and charge-cluster-to-alanine mutagenesis, respectively, in order to identify mutations that confer ts, sp and att phenotypes. Another highly desirable phenotype of a dengue virus vaccine is restricted growth in the mosquito host. A dengue virus vaccine candidate should not be transmissible from humans to mosquitoes in order to prevent both the introduction of a dengue virus into an environment in which it is currently not endemic and to prevent the possible loss of the attenuation phenotype during prolonged replication in an individual mosquito host. Loss of the attenuation phenotype could also occur following sustained transmission between humans and mosquitoes. Recently, loss of attenuation of a live attenuated poliovirus vaccine was seen following sustained transmission among humans (CDC 2000 *MMWR* 49:1094).

In the present example, a panel of 1248 DEN4 mutant viruses generated through 5-FU mutagenesis and 32 DEN4 mutant viruses generated through charge-cluster-to-alanine mutagenesis were assayed for restricted growth in mosquito cells. This is a useful preliminary assay for restriction in vivo, since restriction in cultured mosquito cells is often, though not always, associated with poor infectivity for mosquitoes (Huang, C. Y. et al. 2000 *J Virol* 74:3020-8). Mutant viruses that showed restriction in mosquito cells and robust growth in Vero cells (the substrate for vaccine development, as discussed in Example 6) were targeted for further characterization.

Generation and characterization of the 5-1A1 mutant. The generation and isolation of the panel of 1248 5-FU mutant viruses and the panel of 32 charge-cluster-to-alanine mutant viruses have been described in Examples 1, 2, and 4. Vero and C6/36 cells were maintained as described in Example 1.

Figure 10:
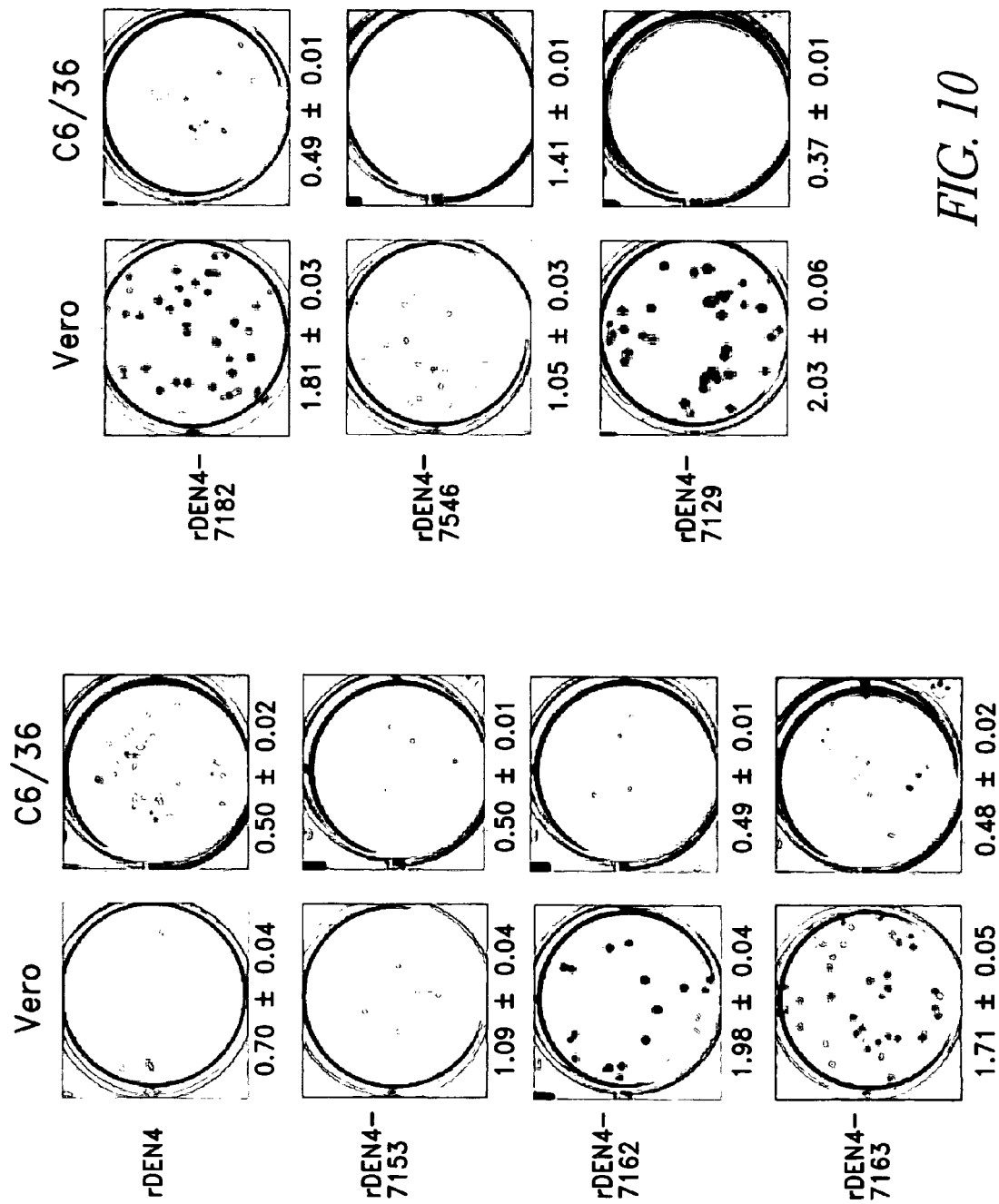
FIG. 10 shows plaque size phenotypes of rDEN4 viruses encoding Vero adaptation mutations. Serial three-fold dilutions of the indicated viruses were inoculated onto confluent Vero and C6/36 cell monolayers in 6-well plates. After incubation at 37° C. (Vero) or 32° C. (C6/36) for two hours, monolayers were overlaid with 0.8% methylcellulose culture media. Following incubation for five days, plaques were visualized by immunoperoxidase staining. Values below each well are the average plaque size in mm±standard error. For each of the virus-infected wells, 36 plaques were measured on the digital image of the 6-well plate on Adobe Photoshop at 300% view.

Each of the 1248 5-FU mutant viruses and 32 charge-cluster-to-alanine mutant viruses was titered in C6/36 cell monolayers in 24-well plates at 32° C. and 5% $CO_2$. After 5 days, plaques were immunostained with anti-DEN4 rabbit polyclonal antibody and counted as described in the preceding Examples. Mutant viruses were assayed for one of two phenotypes indicating restricted growth in mosquito cells: either sp in C6/36 cells relative to Vero cells or a $\geq 3.5$ $\log_{10}$ PFU/ml decrease in titer between Vero and C6/36 cells at the permissive temperature for each cell type. Two mutant viruses, one generated by 5-FU mutagenesis (#5) and one generated by charge-cluster-to-alanine mutagenesis (rDEN4-356,357), showed reduced plaque size in C6/36 cells. After three terminal dilutions, the 5-FU mutant #5, designated 5-1A1, maintained the reduced plaque size phenotype. Additionally, recombinant virus rDEN4-7546, tested for Vero cell adaptation (discussed in detail in Example 6) also showed reduced plaque size in C6/36 (FIG. 10).

The multicycle growth kinetics of both 5-1A1 and the recombinant wild type rDEN4 in C6/36 cells were determined as described in Example 1. Briefly, cells were infected in triplicate at a multiplicity of infection of 0.01 and samples were harvested at 24-hr intervals. Samples were flash frozen and titered in a single assay in Vero cell monolayers.

Oral infection of mosquitoes. *Aedes aegypti* is one of the primary vectors of dengue virus (Gubler, D. J. 1998 *Clin Microbiol Rev* 11:480-96). This species was reared at 26° C. and 80% relative humidity (RH) with a 16 hr daylight cycle. Adults were allowed continuous access to a cotton pad soaked in a 10% sucrose solution. Five to ten day old female *Ae. aegypti* which had been deprived of a sugar source for 48 hr were fed a bloodmeal consisting of equal volumes of washed human red blood cells, 10% sucrose solution, and dengue virus suspension. The infected blood meal was prepared immediately prior to feeding and offered to mosquitoes in a water-jacketed feeder covered in stretched parafilm and preheated to 38° C. (Rutledge, L. C. et al. 1964 *Mosquito News*

24:407-419). Mosquitoes that took a full bloodmeal within 45 min were transferred to a new container by aspirator and maintained as described above. After 21 days, mosquitoes were stored at −20° C. until dissection.

Intrathoracic inoculation of mosquitoes. The large, non-haematophagous mosquito *Toxorhynchites splendens* is a sensitive host for determining the infectivity of dengue virus. This species was reared at 24° C. and 75% RH with a 12 hr daylight cycle. Larvae and pupae were fed on appropriately sized *Aedes* larvae; adults were allowed continuous access to a cotton pad soaked in a 10% sucrose solution. Groups of one to ten day old adult *T. splendens* of both sexes were immobilized by immersion of their container in an icewater bath and inoculated intrathoracically with undiluted virus and serial tenfold dilutions of virus in 1X PBS. Virus was inoculated in a 0.22 µl dose using a Harvard Apparatus microinjector (Medical Systems Corp, Greenvale N.Y.) and a calibrated glass needle (technique is a modification of the method described in Rosen and Gubler, 1974).

Detection of viral antigen in body and head tissues by immunofluorescence assay (IFA). Head and midgut preparations of *Aedes aegypti* and head preparations of *Toxorhynchites splendens* were made on glass slides as described in Sumanochitrapon et al. (Sumanochitrapon, W. et al. 1998 *Am J Trop Med Hyg* 58:283-6). Slides were fixed in acetone for 20 min, and placed at 4° C. until processed by IFA. The primary antibody, hyperimmune mouse ascites fluid specific for DEN-4 (HMAF), was diluted 1/100 in PBS-Tween 20 (0.05%). Slides were incubated at 37° C. in a humid chamber for 30 min, and subsequently rinsed in PBS-Tween 20. The secondary antibody, FITC conjugated goat anti-mouse IgG (KPL, Gaithersburg, Md.), was diluted 1/200 in PBS-Tween 20 with 0.002% Evan's Blue. Slides were viewed on an Olympus BX60 microscope. The infectious dose required to infect 50% of mosquitoes ($ID_{50}$) was determined by the method of Reed and Muench (Reed, L. J. & Muench, H. 1938 *Am J Hyg* 27:493-497). For *Aedes aegypti* infections, two $OID_{50}$ (oral infectious dose 50) values were calculated for each virus: the $OID_{50}$ required to produce an infection in the midgut, with or without dissemination to the head, and the $OID_{50}$ required to produce disseminated infection. For *Tx. splendens* one $MID_{50}$ (mosquito infectious dose 50) value was calculated.

Statistical Analysis. The percentage of mosquitoes infected by different viruses were compared using logistic regression analysis (Statview, Abacus Inc.).

Mutations restricting growth of DEN4 in mosquito cells but not Vero cells are rare. Out of 1280 mutant viruses initially assayed, only two, #5 and rDEN4-356,357, showed reduced plaque size in C6/36 cells and normal plaque size in Vero cells. One additional virus, rDEN4-7546 (described in Example 6), with reduced plaque size in C6/36 was detected in subsequent assays. Mutant virus #5 was cloned by three successive terminal dilutions and designated 5-1A1; rDEN4-7546 and rDEN4-356,357 had already been twice-terminally diluted when they were tested in C6/36 cells. Virus 5-1A1 has been extensively characterized and its phenotypes are described in detail in the following section. rDEN4-356,357 and rDEN4-7546 are envisioned as being characterized in a similar fashion.

Figure 6:
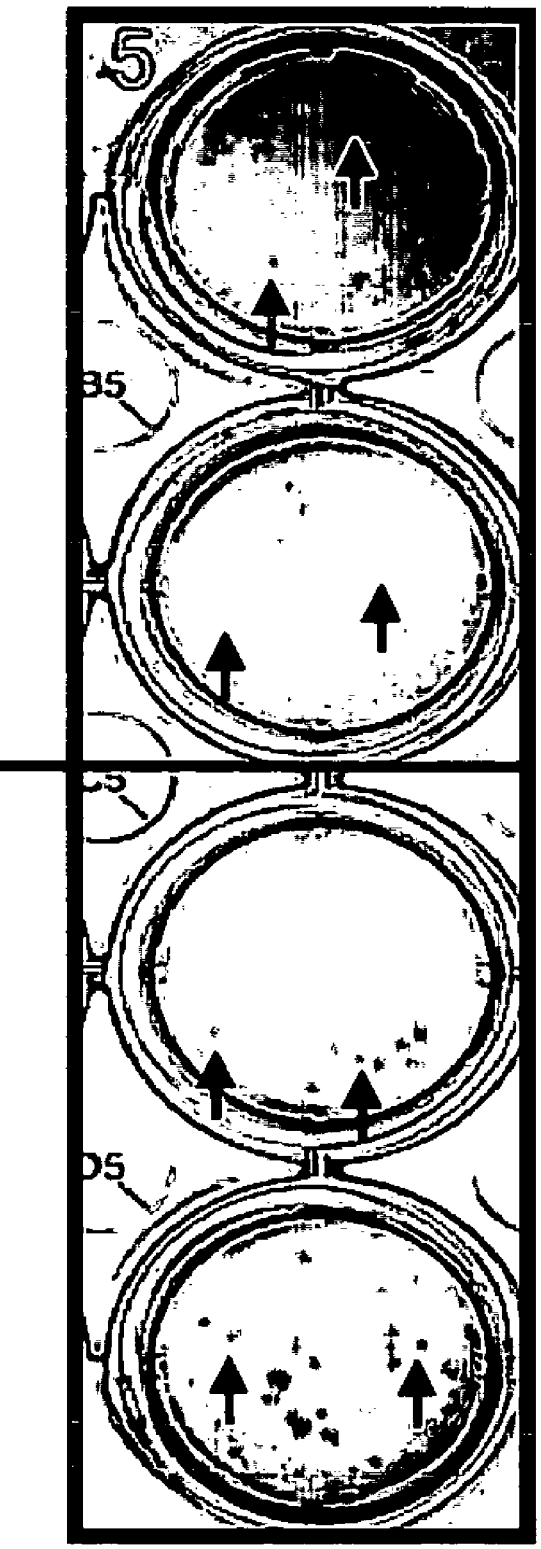
FIG. 6 shows plaque size of mutant 5-1A1 in C6/36 cells. Note that 5-1A1 has a small plaque phenotype in C6/36 cells relative to that of the wild type virus.
Figure 7:
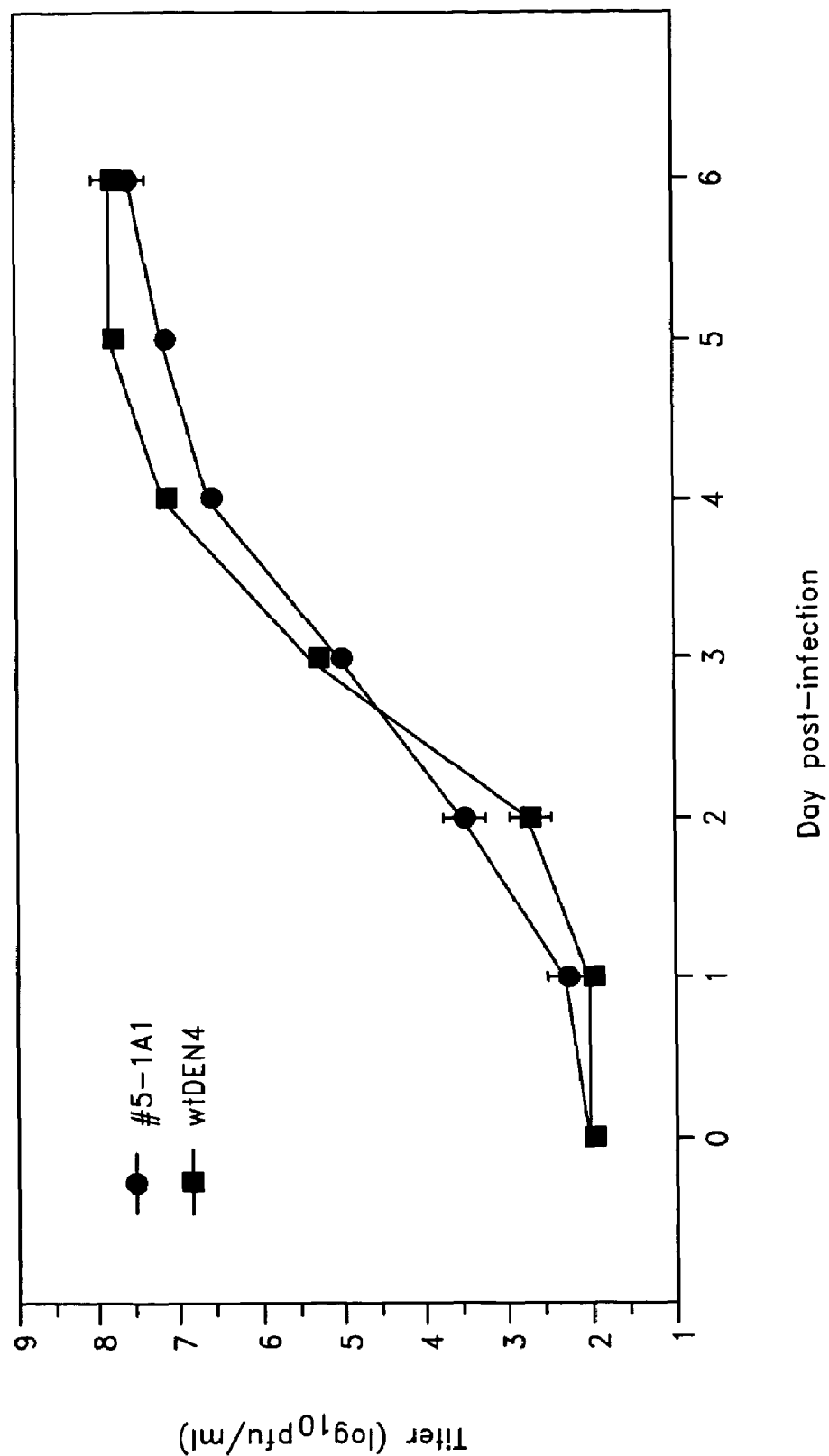
FIG. 7 shows growth of wild type rDEN4 and 5-1A1 in C6/36 cells. Cells were inoculated in triplicate with each virus at an MOI of 0.01, and the amount of virus present in the supernatants that were harvested on the indicated days was determined by plaque enumeration in Vero cells. The titers are expressed as $\log_{10}$ PFU/ml±standard error.

Plaque size and growth kinetics of 5-1A1. 5-1A1 replicated to 6.7 $\log_{10}$ PFU/ml in Vero cells with normal plaque size and replicated to 7.6 $\log_{10}$ PFU/ml in C6/36 cells with small plaque size (FIG. 6, Table 25). In comparison, wild type DEN4 used as a concurrent control replicated to 7.3 $\log_{10}$ PFU/ml in Vero cells, 8.3 $\log_{10}$ PFU/ml in C6/36 cells, and showed normal plaque size in both cell types (FIG. 6, Table 25). The growth kinetics of 5-1A1 was compared to that of wild type DEN4 by infecting C6/36 cells at an MOI of 0.01 and monitoring the production of infectious virus. The kinetics and magnitude of replication of 5-1A1 in C6/36 cells was comparable to that of wild type DEN4 (FIG. 7).

5-1A1 is restricted in its ability to infect mosquitoes. 5-1A1 was evaluated for its ability to infect *Aedes aegypti* mosquitoes through an artificial bloodmeal (Table 26). In this assay the ability to infect the midgut of the mosquito and the ability for a midgut infection to disseminate to the head are measured separately. The oral infectious dose 50 ($OID_{50}$) of wild type DEN4 for the midgut was 3.3 $\log_{10}$ PFU; the $OID_{50}$ of wild type DEN4 for a disseminated infection was 3.9 $\log_{10}$ PFU. In contrast, 5-1A1 never infected 50% of mosquitoes at the doses used. In order to calculate the $OID_{50}$ for midgut infections by 5-1A1, it was assumed that at a 10-fold higher dose, 100% of 25 mosquitoes would have become infected. Using this assumption, the conservative estimate of the $OID_{50}$ for midgut infections by 5-1A1 was $\geq 3.9$ $\log_{10}$ PFU. Because 5-1A1 produced only 3 disseminated infections, we did not attempt to calculate an $OID_{50}$ for this category. 5-1A1 was significantly restricted in its ability to infect the midgut relative to wild type DEN4 (logistic regression, N=150, P<0.001). Additionally, 5-1A1 produced very few disseminated infections, but because of low numbers this result was not amenable to statistical analysis.

5-1A1 was also significantly restricted in its ability to infect *Tx. splendens* mosquitoes following intrathoracic inoculation (Table 27). The $MID_{50}$ of wild type DEN4 was 2.3 $\log_{10}$ PFU whereas the $MID_{50}$ of 5-1A1 was estimated to be >3.0 $\log_{10}$ PFU (logistic regression, N=36, P<0.01).

5-1A1 does not show a ts or an att phenotype. 5-1A1 was tested for temperature sensitivity in Vero and HuH-7 cells and for attenuation in suckling mouse brains as described in Example 1. The mutant virus was not temperature sensitive, as defined in Example 1, and was not attenuated in suckling mouse brain (Table 25).

Identification and confirmation of the mutation responsible for the phenotype of 5-1A1. The nucleotide sequence of the entire genome of 5-1A1 was determined as described in Example 1. Sequencing of 5-1A1 revealed three changes from the wild type sequence: two translationally-silent point mutations at positions 7359 and 9047, and one coding point mutation (C to U) at position 7129 in the NS4B gene which resulted in a proline to leucine substitution.

Figure 4:
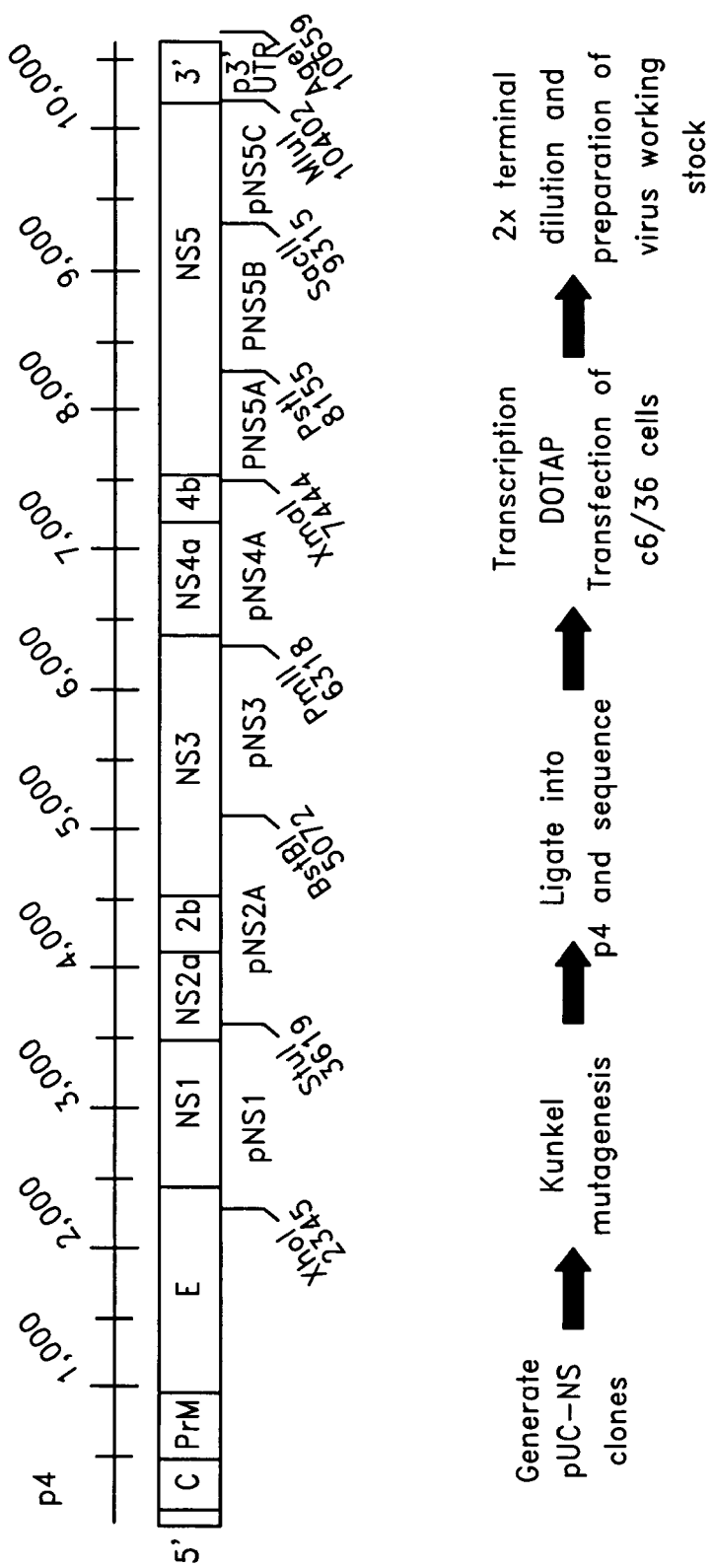
FIG. 4 shows generation of recombinant DEN4 viruses. (A), The p4 cDNA clone is represented which was constructed from the 2A cDNA clone (derived from DEN4 814669) by site-directed mutagenesis. Restriction enzyme sites were introduced or removed to facilitate subsequent cloning of DEN4 recombinants bearing introduced attenuating mutations. Restriction enzyme sites are shown and define fragments of the genome that were sub-cloned into modified pUC-119 vectors for site-directed mutagenesis to introduce mutations identified in the 5-FU mutant viruses. (B), An outline of the methods used to generate rDEN4 viruses is also represented and described in Example 1.

To formally confirm the effect of the C7129U mutation, the mutation was inserted into the cDNA p4, which has been described in Examples 1, 2, and 3 and in FIG. 4, using Kunkel mutagenesis as described in Examples 1 and 3. The mutagenized cDNA was transcribed and transfected as described in Example 3, and the resulting virus, after two terminal dilutions, was designated rDEN4-7129-1A. Like 5-1A1, rDEN4-7129-1A showed normal plaque size and titer in Vero cells and reduced plaque size and normal titer in C6/36 cells (Table 25). rDEN4-7129-1A was not ts on either Vero or HuH-7 cells and was not att in suckling mouse brain. Additionally, rDEN4-7129-1A did not show the SCID-HuH-7 att phenotype described in Example 3 (Table 25). The ability of rDEN4-7129-1A to infect mosquitoes is envisioned as being tested in both *Ae. aegypti* and *Tx. splendens*.

To test the compatibility of the C7129U mutation and the Δ30 deletion, the C7129U mutation was inserted into rDEN4Δ30 using previously described techniques. The resulting virus, designated rDEN4Δ30-7129, is envisioned as being tested for the phenotypes listed in Table 25.

In summary, three mutant viruses, 5-1A1, rDEN4-356,357 and rDEN4-7546, showed a particular combination of phenotypes characterized by normal plaque size and replication to high titers in Vero cells and small plaque size but unrestricted growth in mosquito cells. 5-1A1 was further characterized and lacked temperature sensitivity in either Vero or HuH-7 cells and showed normal levels of replication in mouse brain and in SCID-HuH-7 mice and restricted infectivity for both Ae. aegypti and Tx. splendens mosquitoes. In comparison to wild type rDEN4, the 5-1A1 mutant had one coding mutation: a point mutation (C to U) at nucleotide 7129 in NS4B resulting in a replacement of Pro with Leu. Because 5-1A1 contains only a single missense mutation, the phenotype of this mutant virus can be attributed to the effect of the mutation at position 7129. These results indicate that the 7129 mutation is responsible for the phenotype of decreased infectivity for mosquitoes and is predicted to be useful to restrict replication of vaccine candidates in mosquitoes. To formally confirm this, we have inserted the 7129 mutation into a recombinant DEN4 virus. The resulting virus, designated rDEN4-7129-1A, shows an absence of ts and att phenotypes similar to 5-1A1. It is envisioned as being tested for mosquito infectivity.

The 7129 mutation is a valuable point mutation to include in a DEN4 vaccine candidate and into each of the dengue virus antigenic chimeric vaccine candidates since its biological activity is host specific, i.e., it is restricted in replication in mosquitoes but not in mammals. Moreover, as discussed in Example 6, the 7129 mutation has also been shown to enhance replication in Vero cells. Thus, its insertion into a vaccine candidate is envisioned as enhancing vaccine production in tissue culture without affecting the biological properties specified by other attenuating mutations. It is also envisioned as providing a useful safeguard against mosquito transmission of a dengue virus vaccine.

Section II. Design of Mutations to Restrict Replication in Mosquitoes

In Section 1 of Example 5, we screened a large panel of mutant viruses carrying both random mutations (generated with 5-fluorouracil) and specific mutations (generated through charge-cluster-to-alanine mutagenesis) for restricted growth in C6/36 cells, a proxy measure for restriction in mosquitoes. However, in neither case were mutations designed for the specific purpose of restricting replication in mosquitoes. In this section, we identified nucleotide sequences in the 3' UTR that show conserved differences between the mosquito-transmitted and tick-transmitted flaviviruses. We then altered those sequences in the DEN4 cDNA p4 by either deleting them altogether or exchanging them with the homologous sequence of the tick-transmitted Langat virus. The resulting viruses were assayed for reduced plaque size and titer in both Vero and C6/36 cells and for infectivity for Ae. aegypti and Tx. splendens.

Identification and modification of particular 3' UTR sequences showing conserved differences between vectors. Several studies (Olsthoorn, R. C. & Bol, J. F. 2001 *RNA* 7:1370-7; Proutski, V. et al. 1997 *Nucleic Acids Res* 25:1194-202) have identified conserved differences in the nucleotide sequences of the 3' UTR of mosquito-transmitted and tick-transmitted flaviviruses. Such differences are concentrated in the 3' terminal core region, the approximately 400 3' terminal nucleotides. It has been suggested that these sequences may have a vector-specific function (Proutski, V. et al. 1997 *Nucleic Acids Res* 25:1194-202). While such a function has not been identified, it may nonetheless be possible to disrupt vector infectivity by deleting or otherwise altering these nucleotides.

Figure 8:
FIG. 8 shows nucleotide alignment of the 3' UTR of mosquito-borne and tick-borne flaviviruses. cDNA sequences are shown 5' to 3' and represent a portion of the UTR corresponding to DEN4 nucleotides 10417 to 10649 (3' genome end). Nucleotide numbering represents the position in the alignment. Regions deleted or swapped are indicated using the nucleotide numbering of DEN4. GenBank accession numbers for mosquito-borne viruses: DEN4 (SEQ ID NO: 2): AF326825, DEN1 (SEQ ID NO: 3): U88535, DEN2 (SEQ ID NO: 4): AF038403, DEN3 (SEQ ID NO: 5): M93130, West Nile virus (WN) (SEQ ID NO: 6): M12294, Japanese encephalitis virus (JE) (SEQ ID NO: 7): AF315119, Yellow fever virus (YF) (SEQ ID NO: 8): U17067; GenBank accession numbers for tick-borne viruses: Powassan virus (POW) (SEQ ID NO: 9): L06436, Louping III virus (LI) (SEQ ID NO: 10): Y07863, Tick-borne encephalitis virus (TBE) (SEQ ID NO: 11): U27495, and Langat virus (LGT) (SEQ ID NO: 12): AF253419.

To identify target sequences for this type of alteration, we constructed an alignment of the 3' UTR nucleotide sequences of seven mosquito-transmitted flaviviruses and four tick-transmitted flaviviruses (FIG. 8). From this alignment, we identified several sequences that showed conserved differences between the mosquito-transmitted flaviviruses and tick-transmitted flaviviruses. We then designed primers to alter these sequences in the wt DEN4 cDNA p4 (FIG. 4) in one of two ways: 1) deletion of the nucleotides (Δ) or 2) replacement of the nucleotides with the homologous sequence from the tick-transmitted flavivirus Langat (swap). Langat was chosen as the template for swapped nucleotides because it is naturally attenuated (Pletnev, A. G. 2001 *Virology* 282:288-300), and therefore unlikely to enhance the virulence of rDEN4 virus derived from the modified cDNA. The DEN4 sequences altered and the mutagenesis primers used to do so are listed in Table 28. Nucleotides 10508-10530 correspond to the CS2 region identified in previous studies (Proutski, V. et al. 1997 *Nucleic Acids Res* 25:1194-202).

Mutagenesis of p4, transcription and transfection were conducted as previously described in Section I of this Example. All five of the engineered viruses were recovered, and all were subjected to two rounds of terminal dilution as previously described.

Evaluation of phenotypes: cell culture. Viruses were titered in Vero and C6/36 cells as previously described, and the results are listed in Table 29. All of the viruses replicated to >5.0 $\log_{10}$ PFU/ml; one of them (rDEN4Δ10508-10530) replicated to >8.0 $\log_{10}$ PFU/ml. Only one of the viruses (rDEN4Δ10535-10544) was small plaque in C6/36 cells; this virus showed wild-type plaque size in Vero cells. Interestingly, another virus (rDEN4swap10508-10539) showed wild type plaque size in C6/36 cells but was sp in Vero cells.

Evaluation of phenotypes: mosquito infectivity. To date one of the five viruses has been tested for infectivity via intrathoracic inoculation in Tx. splendens, using previously described methods. Virus rDEN4Δ10508-10530 was dramatically restricted in infectivity relative to the wild type (Table 30). So few mosquitoes were infected that it was not possible to calculate an $MID_{50}$ for this virus.

One of the five viruses has been tested for infectivity of Ae. aegypti fed on an infectious bloodmeal using previously described methods. rDEN4swap10535-10544 (Table 31) caused significantly fewer midgut infections than wild type rDEN4, but the percentage of disseminated infections did not differ between rDEN4swap10535-10544 and wild type rDEN4. All of the viruses are envisioned as being tested for mosquito infectivity using both methods.

Summary. In this example we have outlined two different strategies for preventing mosquito transmission of a dengue vaccine. First, several small substitution mutations, including two point mutations and one paired charge-to-alanine substitution, have been shown to restrict the replication of DEN4 in mosquito C6/36 cells in cell culture, and one of these mutations (C7129U) has been shown to restrict the ability of DEN4 virus to infect mosquitoes. Second, we have created a variety of deletion and substitution mutations in regions of the DEN4 3' UTR that show conserved differences between mosquito-transmitted and tick-transmitted flaviviruses. One of these viruses is sp in C6/36 cells and at least two of these viruses show some degree of restriction of mosquito infectivity. By design, the nucleotide sequences in which these mutations were made are highly conserved among the four dengue serotypes and among mosquito-transmitted flaviviruses in general, indicating that they are portable to other vaccine candidates for mosquito-borne flaviviruses. All of the mutations discussed in this Example lie outside the structural genes and so are envisioned as being useful in constructing antigenic-chimeric vaccine candidates.

EXAMPLE 6

Adaptation Mutations which Enhance the Replication of DEN4 and DEN4 Chimeric Viruses in Vero Cells Vero cells are a highly characterized substrate that should be suitable for the manufacture of live attenuated flavivirus vaccines, such as dengue virus and tick-borne encephalitis virus. In addition, Vero cells can also be used to grow flaviviruses to high titer for the preparation of an inactivated virus vaccine. Optimal sequences for the efficient growth of dengue viruses in Vero cells have not been identified, but it is well known that flaviviruses accumulate mutations during passage in various cell cultures (Dunster, L. M. et al. 1999 *Virology* 261:309-18; Theiler, M. & Smith, H. H. 1937 *J Exp Med* 65:787-800). Inclusion of specific sequences in live attenuated viruses that enhance their replication in Vero cells and increase the number of doses of vaccine produced per unit substrate would greatly facilitate their manufacture. Similarly, inclusion of Vero cell growth-promoting sequences in wild type viruses used for the preparation of an inactivated virus vaccine would also greatly facilitate the manufacture of the vaccine. The present example identifies mutations that occur following passage of DEN4 virus and DEN2/4 chimeric viruses in Vero cells. Data derived from five sources provided information for this analysis making it possible to generate a list of Vero cell growth-promoting sequences.

Presence of identical mutations in multiple 5-FU mutant viruses. First, as described in Examples 1 and 2, the genomes of 42 dengue virus clones isolated from a 5-FU mutagenized stock of virus were completely sequenced. If mutations that enhance replication occurred during the passage of these 42 mutant viruses in Vero cells, then such mutations should reveal themselves by representation in more than one clone. Analysis of the 42 sequences revealed the occurrence of specific missense mutations in coding regions or nucleotide substitutions in UTRs in multiple clones that are not present in the 2A parental virus genome (Tables 11 and 32). These mutations, many of which occur within a 400 nucleotide section of the NS4B coding region, represent Vero cell-adaptation mutations. One mutation, such as the 4995 mutation, present in eight viruses was found to specify both ts and att phenotypes (Examples 1 and 3). In contrast, the 7163 mutation, present in six viruses, does not specify a ts or att phenotype (Table 13) and thus is an example of a specific Vero cell growth-promoting mutation.

Presence of Vero cell adaptation mutations in other DEN4 viruses and DEN2/4 antigenic chimeric viruses. Second, the 2A-13 dengue virus that was used as a parallel passaged wild type control during the 5-FU experiments described in Example 1 was grown and cloned in Vero cells in the absence of 5-FU in a manner identical to that of the 5-FU treated viruses. Sequence analysis of this 5-FU untreated virus, designated 2A-13-1A1, revealed that the virus genome contained a mutation at nucleotide 7163 (Example 1 and Table 32), identical to the missense mutation previously identified in 6 of the 5-FU mutant viruses (Tables 11 and 32). This indicates that growth and passage of DEN4 virus in Vero cells is sufficient to acquire this specific mutation, i.e. mutagenesis with 5-FU is not required. Thus, information from two separate sources indicates that the 7163 mutation appeared in separate Vero cell passaged viruses, thereby strengthening the interpretation that this mutation is growth promoting.

Third, following passage of the 2AΔ30 and rDEN4Δ30 in Vero cells, sequence analysis revealed the presence of a mutation at nucleotides 7153 and 7163, respectively. These two mutations were also previously identified among the 5-FU treated viruses (Table 32). Again, identical mutations appeared following independent passage of virus in Vero cells, corroborating the hypothesis that these mutations confer a growth advantage in Vero cells.

Fourth, an antigenic chimeric dengue virus vaccine candidate was generated that expressed the structural proteins C, prM, and E from DEN2 on a DEN4 wild type genetic background or an attenuated Δ30 genetic background. To construct this virus, the C, prM and E region of wild type cDNA plasmid p4 was replaced with a similar region from DEN2 virus strain NGC (FIG. 10). Specifically, nucleotides between restriction sites BglII (nt 88) and XhoI (nt 2345) of p4 were replaced with those derived from dengue type 2 virus. RNA transcripts synthesized from the resulting p4-D2 plasmid were transfected into Vero cells and rDEN2/4 virus was recovered. A further attenuated version of this chimeric virus containing the Δ30 mutation, rDEN2/4Δ30, was recovered in C6/36 mosquito cells following transfection of cells with RNA transcripts derived p4Δ30-D2. However, rDEN2/4Δ30 could not be recovered directly in Vero cells. The rDEN2/4Δ30 mutant virus recovered in C6/36 cells replicated to very low levels in Vero cells (<1.0 $\log_{10}$ PFU/ml) but grew to high titer in C6/36 cells (>6.0 $\log_{10}$ PFU/ml). Genomic sequence of the C6/36-derived virus matched the predicted cDNA sequence and is shown in Appendix 3. Nevertheless, when C6/36-derived rDEN2/4Δ30 was serially passaged 3 to 4 times in Vero cells, a virus population adapted for growth in Vero cells emerged. Virus from this Vero cell-adapted preparation was cloned and amplified in Vero cells to a titer >6.0 $\log_{10}$ PFU/ml. The genomic sequence was determined for 2 independent virus clones and compared to the predicted cDNA sequence (Table 33 and 34). Each cloned virus contains a mutation in a non-structural gene which coincides closely in location or sequence with a mutation previously identified among the panel of 5-FU mutagenized viruses. The other mutations in these two clones also might confer a growth advantage in Vero cells. Importantly, the mutations identified in Tables 33 and 34 are absolutely required for replication in Vero cells, and it would not be possible to produce the rDEN2/4Δ30 vaccine candidate in Vero cells without the growth-promoting mutations identified in Tables 33 and 34.

Fifth, sequence analysis of the dengue 4 wild-type virus strain 814669 (GenBank accession no. AF326573) following passage in Vero cells identified a mutation in the NS5 region at nucleotide 7630 which had previously been identified among the panel of 5-FU mutagenized viruses (Table 32). This mutation at nucleotide 7630 was introduced into recombinant virus rDEN4 by site-directed mutagenesis as described in Table 16. The resulting virus, rDEN4-7630, was not temperature sensitive when tested at 39° C., indicating that mutation 7630 does not contribute to temperature sensitivity.

Characterization of rDEN2/4Δ30 chimeric viruses containing single and multiple Vero cell adaptation mutations. The generation of chimeric virus rDEN2/4Δ30 provided a unique opportunity for evaluating the capacity of individual mutations to promote increased growth in Vero cells. Because rDEN2/4Δ30 replicates to very low titer in Vero cells, yet can be efficiently generated in C6/36 mosquito cells, recombinant virus bearing putative Vero-cell adapting mutations were first generated in C6/36 cells and then virus titers were determined in both C6/36 and Vero cells. As shown in Table 35, addition of a single mutation to rDEN2/4Δ30 resulted in a greater than 1000-fold increase in titer in Vero cells, confirming the Vero cell adaptation phenotype conferred by these mutations. However, the combination of two separate mutations into a single virus did not increase the titer in Vero cells beyond the level observed for viruses bearing a single adaptation mutation. Inclusion of either the 7182 or 7630 mutation in the cDNA of rDEN2/4Δ30 allowed the virus to be recovered directly in Vero cells, circumventing the need to recover the virus in C6/36 cells.

Characterization of the growth properties of rDEN4 viruses containing single and multiple defined Vero cell adaptation mutations. To confirm the ability of Vero cell adaptation mutations to enhance growth of DEN4 viruses, site-directed mutagenesis was used to generate rDEN4 viruses encoding selected individual mutations as described in Examples 1 and 3. Five mutations in NS4B (7153, 7162, 7163, 7182, and 7546) from the list of repeated mutations in the 5-FU mutant viruses (Table 32) were introduced singly into the p4 cDNA clone. In addition, the mosquito-restricted, rDEN4-7129 virus was evaluated for enhanced growth in Vero cells since the location of this mutation is in the same region of NS4B. Each virus, including wild-type rDEN4, was recovered, terminally diluted, and propagated in C6/36 cells to prevent introduction of additional Vero cell adaptation mutations, however, because of its restricted growth in C6/36 cells, rDEN4-7129 was propagated only in Vero cells.

Plaque size was evaluated for each mutant rDEN4 virus in Vero cells and C6/36 cells and compared to wild-type rDEN4. Six-well plates of each cell were inoculated with dilutions of virus and plaques were visualized five days later. Representative plaques are illustrated in FIG. 10 and demonstrate that the presence of a Vero cell adaptation mutation does indeed confer increased virus cell to cell spread and growth specifically in Vero cells. In C6/36 cells, average plaque size was approximately 0.50 mm for both wild-type rDEN4 and each mutant virus (except for rDEN4-7546 and rDEN4-7129 which were smaller than wild-type; see Example 5). However, rDEN4 viruses expressing mutation 7162, 7163, 7182, and 7129 had a greater than two-fold increase in plaque size in Vero cells compared to wild-type rDEN4 virus. A smaller but consistent increase in plaque size was observed for rDEN4-7153 and rDEN4-7546.

Figure 11:
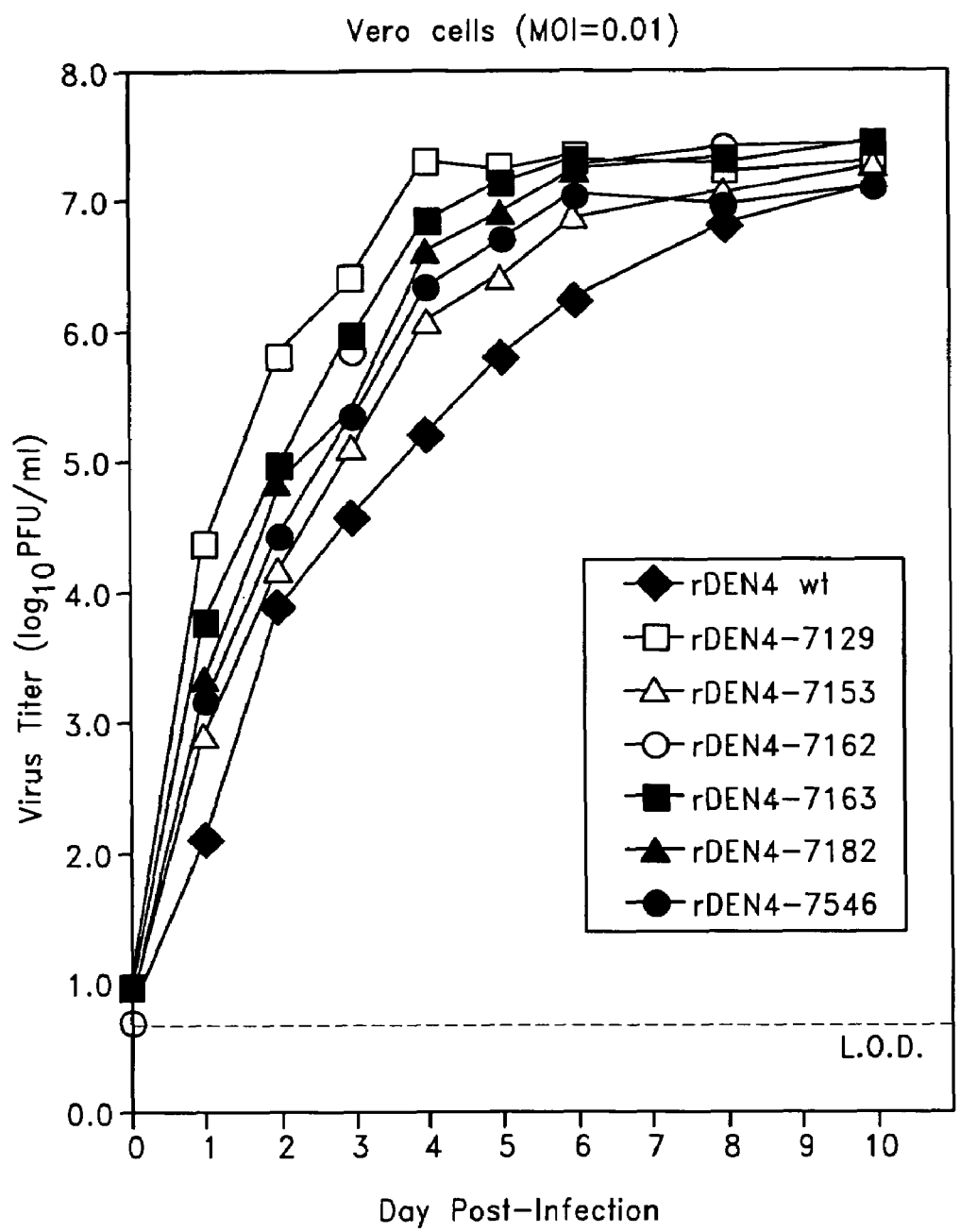
FIG. 11 shows growth curve in Vero cells of rDEN4 viruses encoding single Vero adaptation mutations. Vero cells were infected with the indicated viruses at an MOI of 0.01. Confluent cell monolayers in 25-cm$^2$ tissue culture flasks were washed and overlaid with a 1.5 ml inoculum containing the indicated virus. After a two hour incubation at 37° C., cells were washed three times in PBS and 5 ml of culture medium supplemented with 2% FBS was added. A 1 ml aliquot of tissue culture medium was removed, replaced with fresh medium, and designated the 0 hour time-point. At the indicated time points post-infection, samples of tissue culture medium were removed, clarified, and frozen at −70° C. The level of virus replication was assayed by plaque titration in Vero cells. Briefly, serial ten-fold dilutions of cell culture media samples were inoculated onto confluent Vero cell monolayers in 24-well plates in duplicate and overlaid with Opti-MEM containing 0.8% methylcellulose. After five days, plaques were visualized by immunoperoxidase staining as described in Example 1. Limit of detection (L.O.D.) is ≧0.7 $\log_{10}$ PFU/ml.

Growth kinetics and virus yield in Vero cells was assessed for the same panel of rDEN4 viruses. Vero cells were infected at an MOI of 0.01 and samples were removed daily for 10 days, titered on Vero cells, and plaques were visualized. The results in FIG. 11 indicate that the presence of a Vero cell adaptation mutation increased the kinetics of virus growth, but had only a marginal effect on the peak virus yield. At day four post-infection, wild-type rDEN4 grew to 5.2 $\log_{10}$ PFU/ml while the level of replication in rDEN4-7129-infected cells was 100-fold higher. The rest of the mutant rDEN4 viruses had an increased yield at day four ranging from 0.9 (rDEN4-7153) to 1.6 (rDEN4-7162 and -7163) $\log_{10}$ PFU/ml. Interestingly, enhanced kinetics of virus growth correlated with increased plaque size in Vero cells. The peak virus yield was reached by day 6 post-infection for rDEN4-7129, -7162, -7163, and -7182 while wild-type rDEN4 did not reach peak titer until day 10. However, the peak virus yield was only slightly higher in rDEN4 viruses expressing Vero cell adaptation mutations.

Figure 12:
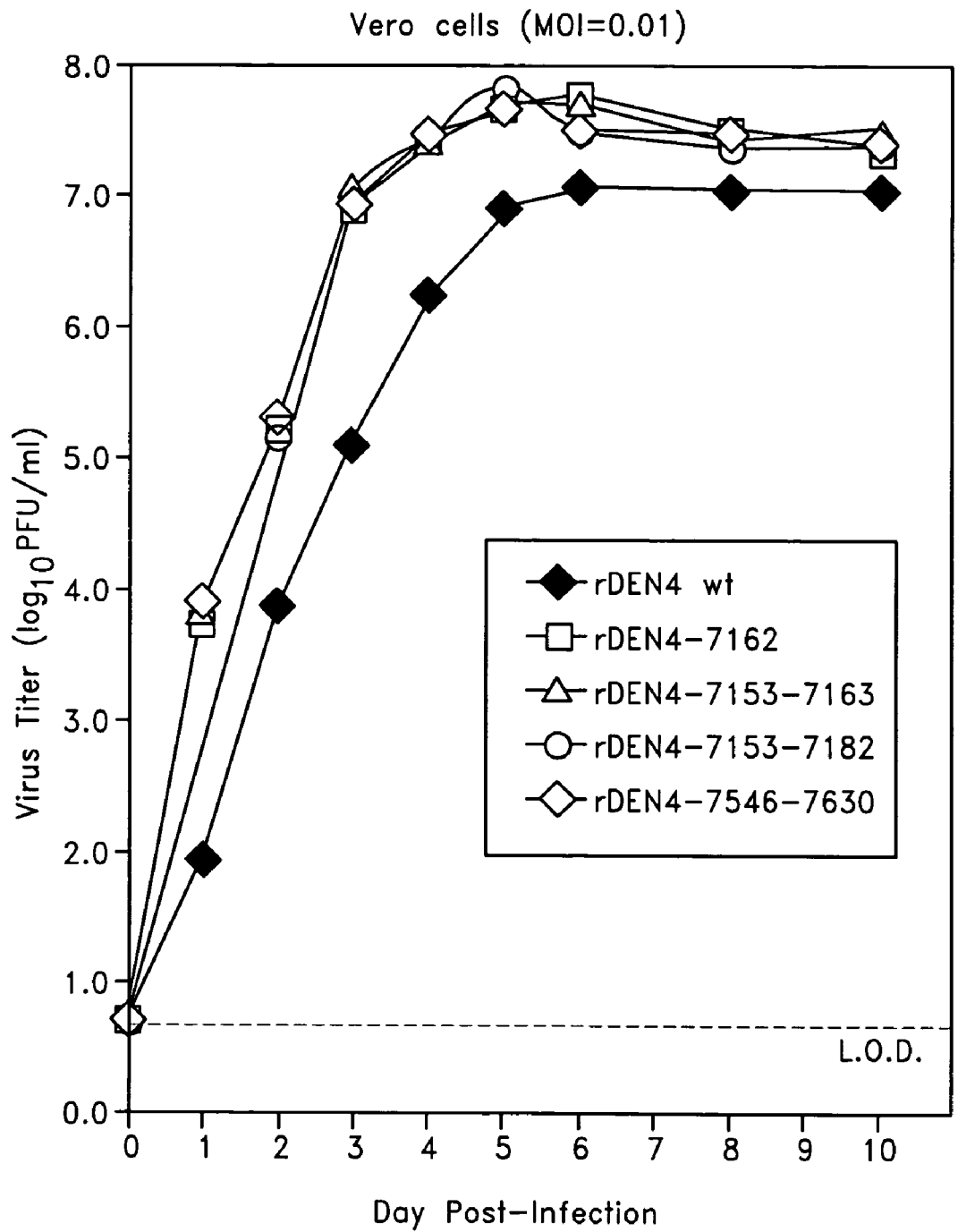
FIG. 12 shows growth curve in Vero cells of rDEN4 viruses encoding combined Vero cell adaptation mutations. Vero cells were infected with the indicated viruses at an MOI of 0.01. Confluent cell monolayers in 25-cm² tissue culture flasks were washed and overlaid with a 1.5 ml inoculum containing the indicated virus. After a two hour incubation at 37° C., cells were washed three times in PBS and 5 ml of culture medium supplemented with 2% FBS was added. A 1 ml aliquot of tissue culture medium was removed, replaced with fresh medium, and designated the 0 hour time-point. At the indicated time points post-infection, samples of tissue culture medium were removed, clarified, and frozen at −70° C. The level of virus replication was assayed by plaque titration in Vero cells. Limit of detection (L.O.D.) is $\geq 0.7 \log_{10}$ PFU/ml.

In an effort to further enhance rDEN4 replication, especially the peak virus yield, combinations of selected Vero cell adaptation mutations were introduced into the rDEN4 background. Three viruses with dual mutations were generated: rDEN4-7153-7163, rDEN4-7153-7182, and rDEN4-7546-7630 and tested in a Vero cell time course infection as described above along with rDEN4 and rDEN4-7162 as a positive control (FIG. 12). The viruses expressing combined mutations grew in a nearly identical manner to rDEN4-7162 indicating that these selected combinations did not enhance the kinetics or peak virus yield. Additional combinations of these and other Vero cell adaptation mutations are envisioned as increasing peak virus yield.

Discussion. Some of the growth promoting mutations listed in Table 32 are also found in homologous regions of DEN1, DEN2, and DEN3 and are envisioned as serving to promote the replication of these viruses in Vero cells. Specifically, the growth promoting mutations indicated in Table 32 that are present in a DEN4 virus are envisioned as being useful for importation into homologous regions of other flaviviruses, such as DEN1, DEN2 and DEN3. Examples of such conserved regions are shown in Appendix 4 and are listed in Table 36. The nucleotides for both mutation 7129 and 7182 are conserved in all four dengue virus serotypes. It is also interesting to note that mutation 7129 not only increases growth in Vero cells (FIG. 10), but it also forms small plaques in mosquito cells (FIG. 6, Table 25). Lee et al. previously passaged DEN3 virus in Vero cells and performed limited sequence analysis of only the structural gene regions of the resulting viruses (Lee, E. et al. 1997 Virology 232:281-90). From this analysis a menu of Vero adaptation mutations was assembled. Although none of these mutations correspond to the Vero adaptation mutations identified in this Example, a single mutation at amino acid position 202 in DEN3 corresponds to mutation 1542 identified in 5-FU mutant virus #1012. The current Example emphasizes the importance in this type of study of determining the sequence of the entire viral genome.

Vero cell growth optimized viruses are envisioned as having usefulness in the following areas. First, the yield of a live attenuated vaccine virus in Vero cells is predicted to be augmented. The live attenuated vaccine candidate is conveniently a DEN4 or other dengue virus or a DEN1/4, DEN2/4, or DEN3/4 antigenic chimeric virus, or a chimeric virus of another flavivirus based on the DEN4 background. The increased yield of vaccine virus is envisioned as decreasing the cost of vaccine manufacture. Second, Vero cell adaptation mutations that are attenuating mutations, such as the 4995 mutation, are envisioned as being stable during the multiple passage and amplification of virus in Vero cell cultures that is required for production of a large number of vaccine doses. Third, Vero cell adaptation mutations are actually required for the growth of the rDEN2/4Δ30 vaccine candidate in Vero cells. Fourth, the increase in yield of a DEN wild type or an attenuated virus is envisioned as making it economically feasible to manufacture an inactivated virus vaccine. Fifth, the presence of the Vero cell growth promoting mutations in the DEN4 vector of the rDEN1/4, rDEN2/4, and rDEN3/4 antigenic chimeric viruses or other flavivirus chimeric viruses based on DEN4 is envisioned as permitting the viruses to grow to a high titer and as thereby being useful in the manufacture of a inactivated virus vaccine. Sixth, the insertion of Vero cell growth promoting mutations into cDNAs such as rDEN2/4Δ30 is envisioned as permitting recovery of virus directly in Vero cells, for which there are qualified master cell banks for manufacture, rather than in C6/36 cells for which qualified cell banks are not available. And seventh, insertion of the 7129 and 7182 mutations into DEN1, DEN2, or DEN3 wt viruses is envisioned as increasing their ability to replicate efficiently and be recovered from cDNA in Vero cells.

EXAMPLE 7

Assembly of a List of Attenuating Mutations

The data presented in these examples permits the assembly of a list of attenuating mutations that is summarized in Table 37. This list contains individual mutations identified in Tables 13-16, 20, and 21 that are known to independently specify an attenuation phenotype. Mutation 7129 is also included since it is derived from virus 5-1A1 shown to be attenuated in mosquitoes. We envision using various combinations of mutations from this list to generate viruses with sets of desirable properties such as restricted growth in the liver or in the brain as taught in Example 3 (Table 18) and Example 4 (Tables 23 and 24). These mutations are also combinable with other previously described attenuating mutations such as the Δ30 mutation, as taught in Example 1 (Table 6) and Example 3 (Table 19) to produce recombinant viruses that are satisfactorily attenuated and immunogenic. Mutations listed in Table 37 are also envisioned as being combined with other previously described attenuating mutations such as other deletion mutations or other point mutations (Blok, J. et al. 1992 *Virology* 187:573-90; Butrapet, S. et al. 2000 *J Virol* 74:3011-9; Men, R. et al. 1996 *J Virol* 70:3930-7; Puri, B. et al. 1997 *J Gen Virol* 78:2287-91).

The possibility of importing an attenuating mutation present in one paramyxovirus into a homologous region of a second paramyxovirus has recently been described (Durbin, A. P. et al. 1999 *Virology* 261:319-30; Skiadopoulos, M. H. et al. 1999 *Virology* 260:125-35). Such an importation confers an att phenotype to the second virus or, alternatively, further attenuates the virus for growth in vivo. Similarly we envision importing an attenuating mutation present in one flavivirus to a homologous region of a second flavivirus which would confer an att phenotype to the second flavivirus or, alternatively, would further attenuate the virus for growth in vivo. Specifically, the attenuating mutations indicated in Table 37 are envisioned as being useful for importation into homologous regions of other flaviviruses. Examples of such homologous regions are indicated in Appendix 4 for the mutations listed in Table 37.

EXAMPLE 8

Evaluation of Dengue Virus Vaccine in Humans and Rhesus Monkeys

The present example evaluates the attenuation for humans and rhesus monkeys (as an animal model) of a DEN-4 mutant bearing a 30 nucleotide deletion (Δ30) that was introduced into its 3' untranslated region by site-directed mutagenesis and that was found previously to be attenuated for rhesus monkeys (Men, R. et al. 1996 *J Virol* 70:3930-7), as representative of the evaluation of any dengue virus vaccine for attenuation in humans and rhesus monkeys (as an animal model).

Viruses and cells. The wild type (wt) DEN-4 virus strain 814669 (Dominica, 1981), originally isolated in *Aedes pseudoscutellaris* (AP61) cells, was previously plaque-purified in LLC-MK2 cells and amplified in C6/36 cells as described (Mackow, E. et al. 1987 *Virology* 159:217-28). For further amplification, the C6/36 suspension was passaged 2 times in Vero (WHO) cells maintained in MEM-E (Life Technologies, Grand Island, N.Y.) supplemented with 10% FBS. Viruses derived from RNA transfection or used for clinical lot development were grown in Vero (WHO) cells maintained in serum-free media, VP-SFM (Life Technologies).

Construction of DEN-4 deletion mutants. A 30 nucleotide (nt) deletion was previously introduced into the 3' untranslated region of the 2A cDNA clone of wt DEN-4 strain 814669 as described (Men, R. et al. 1996 *J Virol* 70:3930-7). This deletion removes nucleotides 10478-10507, and was originally designated 3'd 172-143, signifying the location of the deletion relative to the 3' end of the viral genome. In the current example, this deletion is referred to as Δ30. The full-length 2A cDNA clone has undergone several subsequent modifications to improve its ability to be genetically manipulated. As previously described, a translationally-silent XhoI restriction enzyme site was engineered near the end of the E region at nucleotide 2348 to create clone 2A-XhoI (Bray, M. & Lai, C. J. 1991 *PNAS USA* 88:10342-6). In this example, the viral coding sequence of the 2A-XhoI cDNA clone was further modified using site-directed mutagenesis to create clone p4: a unique BbvCI restriction site was introduced near the C-prM junction (nucleotides 447-452); an extra XbaI restriction site was ablated by mutation of nucleotide 7730; and a unique SacII restriction site was created in the NS5 region (nucleotides 9318-9320). Each of these engineered mutations is translationally silent and does not change the amino acid sequence of the viral polypeptide. Also, several mutations were made in the vector region of clone p4 to introduce or ablate additional restriction sites. The cDNA clone p4Δ30 was generated by introducing the Δ30 mutation into clone p4. This was accomplished by replacing the MluI-KpnI fragment of p4 (nucleotides 10403-10654) with that derived from plasmid 2AΔ30 containing the 30 nucleotide deletion. The cDNA clones p4 and p4Δ30 were subsequently used to generate recombinant viruses rDEN4 and rDEN4Δ30, respectively.

Generation of viruses. Full-length RNA transcripts were synthesized from cDNA clones 2A and 2AΔ30 using SP6 RNA polymerase as previously described (Lai, C. J. et al. 1991 *PNAS USA* 88:5139-43; Men, R. et al. 1996 *J Virol* 70:3930-7). The reaction to generate full-length RNA transcripts from cDNA clones p4 and p4Δ30 was modified and consisted of a 50 µl reaction mixture containing 1 µg linearized plasmid, 60 U SP6 polymerase (New England Biolabs (NEB), Beverly, Mass.), 1X RNA polymerase buffer (40 mM Tris-HCl, pH 7.9, 6 mM $MgCl_2$, 2 mM spermidine, 10 mM dithiothreitol), 0.5 mM m7G(5')ppp(5')G cap analog (NEB), 1 mM each nucleotide triphosphate, 1 U pyrophosphatase (NEB), and 80 U RNAse inhibitor (Roche, Indianapolis, Ind.). This reaction mixture was incubated at 40° C. for 90 min and the resulting transcripts were purified using RNeasy mini kit (Qiagen, Valencia, Calif.). For transfection of Vero cells, purified transcripts (1 µg) were mixed with 12 µl DOTAP liposome reagent (Roche) in saline containing 20 mM HEPES buffer (pH 7.6) and added to cell monolayer cultures in a 6-well plate. After 5-17 days, tissue culture medium was harvested, clarified by centrifugation, and virus was amplified in Vero cells. The presence of virus was confirmed by plaque titration. It should be noted that during the course of transfection and amplification of 2AΔ30 to create the vaccine lot, the virus underwent a total of 6 passages entirely in Vero cells. The remaining viruses, rDEN4 and rDEN4Δ30 were passaged 5 times in Vero cells to generate the virus suspension used for sequence analysis and studies in rhesus monkeys.

Vaccine Production. An aliquot of clarified tissue culture fluid containing vaccine candidate 2AΔ30 was submitted to DynCorp (Rockville, Md.) for amplification of virus in Vero cells and production of a vaccine lot. For vaccine production, 2AΔ30 infected tissue culture supernatant was harvested, SPG buffer added (final concentration: 218 mM sucrose, 6 mM L-glutamic acid, 3.8 mM potassium phosphate, monobasic, and 7.2 mM potassium phosphate, dibasic, pH 7.2), and the virus suspension was clarified by low speed centrifugation. To degrade residual Vero cell DNA, the vaccine suspension was treated with Benzonase endonuclease (American International Chemical, Natick, Mass.), 100 U/ml and incubated for 1 hr at 37° C., followed by high-speed centrifugation (17,000×g, 16 hr). The resulting virus pellet was gently rinsed with MEM-E, resuspended in MEM-E containing SPG, sonicated, distributed into heat-sealed ampoules, and stored frozen at −70° C. Final container safety testing confirmed microbial sterility, tissue culture purity, and animal safety. The 2AΔ30 vaccine lot (designated DEN4-9) has a titer of 7.48 log 10 PFU/ml, with a single dose of 5.0 log 10 PFU/ml containing <1 pg/ml Vero cell DNA and <0.001 U/ml Benzonase endonuclease.

Sequence of cDNA clones and viral genomes. The nucleotide sequence of the viral genome region of cDNA plasmids 2A and p4 was determined on a 310 genetic analyzer (Applied Biosystems, Foster City, Calif.) using vector-specific and DEN-4-specific primers in BigDye terminator cycle sequencing reactions (Applied Biosystems). The nucleotide sequence of the genomes of the parental wt DEN-4 strain 814669 and of recombinant viruses 2A wt, 2AΔ30 (vaccine lot), rDEN4, and rDEN4Δ30 was also determined. Viral RNA was extracted from virus preparations and serum samples using the QIAamp Viral RNA mini kit (Qiagen). Reverse transcription (RT) was performed using random hexamers and the SuperScript First-Strand Synthesis System for RT-PCR (Life Technologies). Overlapping PCR fragments of approximately 2000 base pairs were generated using optimized DEN-4 specific primers and Advantage cDNA polymerase (ClonTech, Palo Alto, Calif.). Both strands of purified PCR fragments were sequenced directly using dye-terminator reactions as described above and results were assembled into a consensus sequence. To determine the nucleotide sequence of the viral RNA 5' and 3' regions, the 5' cap nucleoside of the viral RNA was removed with tobacco acid pyrophosphatase (Epicentre, Madison, Wis.) followed by circularization of the RNA using RNA ligase (Epicentre). RT-PCR was performed as described and a cDNA fragment spanning the ligation junction was sequenced using DEN-4 specific primers. GenBank accession numbers have been assigned as follows (virus: accession number): 814669: AF326573, 2AΔ30: AF326826, rDEN4: AF326825, and rDEN4Δ30: AF326827.

Human Vaccine Recipients. 20 normal healthy adult volunteers were recruited by the Johns Hopkins School of Hygiene and Public Health Center for Immunization Research (CIR) located in Baltimore, Md. The clinical protocol was reviewed and approved by the Joint Committee for Clinical Investigation of the Johns Hopkins University School of Medicine and informed consent was obtained from each volunteer. Volunteers were enrolled in the study if they met the following inclusion criteria: 18-45 years of age; no history of chronic illness; a normal physical examination; human immunodeficiency virus antibody negative, hepatitis B surface antigen negative, and hepatitis C antibody negative; no stool occult blood; and normal values for complete blood cell count (CBC) with differential, hematocrit, platelet count, serum creatinine, serum aspartate amino transferase (AST), alanine amino transferase (ALT), alkaline phosphatase, bilirubin, prothrombin time (PT), partial thromboplastin time (PTT), and urinalysis. Female volunteers were required to have a negative urine pregnancy test prior to vaccination and on the day of vaccination and to agree to use contraception or abstain from sexual intercourse for the duration of the study. Volunteers also lacked serological evidence of prior flavivirus infection as defined by hemagglutination-inhibition antibody titer <1:10 to DEN-1, DEN-2, DEN-3, DEN-4, St. Louis encephalitis virus, Japanese encephalitis virus, or yellow fever virus and a plaque-reduction neutralization titer <1:10 to DEN-4 and yellow fever virus.

Studies in Humans. Volunteers were immunized in three successive cohorts of four, six, and ten volunteers to assess the safety of the vaccine. In this study, an illness was defined as the following: dengue virus infection associated with a platelet count of <90,000/mm$^3$; serum ALT >4 times normal; oral temperature >38° C. for >2 successive days; or headache and/or myalgia lasting >2 successive days. Systemic illness was defined as the occurrence of fever >38° C. for >2 consecutive days, or any 2 of the following for at least two consecutive study days: headache, malaise, anorexia, and myalgia/arthralgia. The trials were conducted between October and April, a time of low mosquito prevalence, to reduce the risk of transmission of vaccine virus from the volunteers to the community.

On the day of vaccination, vaccine candidate 2AΔ30 was diluted to 5.3 $log_{10}$ PFU/ml in sterile saline for injection, USP, and each volunteer was injected subcutaneously with a 0.5 ml containing 5.0 $log_{10}$ PFU of vaccine into the left deltoid region. Volunteers were given a home diary card on which they were to record their temperature twice daily for days 0-5 post-vaccination. The volunteers returned to the clinic each day for examination by a physician and their diary cards were reviewed. The injection site was evaluated for erythema, induration, and tenderness. Clinical signs and symptoms such as headache, rash, petechiae, lymphadenopathy, hepatomegaly, abdominal tenderness, anorexia, nausea, fatigue, myalgia, arthralgia, eye pain, and photophobia were assessed daily. Symptoms were graded as mild (no need for treatment or a change in activity), moderate (treatment needed or change in activity noted, yet still able to continue daily activity) or severe (confined to bed). Blood was drawn for CBC with differential and for virus quantitation on days 0, 2 and 4. Volunteers were admitted to the inpatient unit at the CIR on the sixth day after immunization. The study physician evaluated all volunteers each day by physical examination and interview. The volunteers had their blood pressure, pulse, and temperature recorded four times a day. Blood was drawn each day for CBC with differential and for virus quantitation and every other day for ALT measurement. Volunteers were confined to the inpatient unit until discharge on study day 15. On study days 28 and 42, volunteers returned for physical examination and blood was drawn for virus quantitation (day 28) and for serum antibody measurement (day 28 and 42).

Virus quantitation and amplification. Serum was obtained for detection of viremia and titration of virus in positive specimens. For these purposes 8.5 ml of blood was collected in a serum separator tube and incubated at room temperature for less than 30 min. Serum was decanted into 0.5 ml aliquots, rapidly frozen in a dry ice/ethanol bath and stored at −70° C. Serum aliquots were thawed and serial 10-fold dilutions were inoculated onto Vero cell monolayer cultures in 24-well plates. After one hour incubation at room temperature, the monolayers were overlaid with 0.8% methylcellulose in Opti-MEM (Life Technologies) supplemented with 5% fetal bovine serum (FBS). Following incubation at 37° C. for four days, virus plaques were visualized by immunoperoxidase staining. Briefly, cell monolayers were fixed in 80% methanol for 30 min and rinsed with antibody buffer (5% nonfat milk in phosphate buffered saline). Rabbit polyclonal DEN-4 antibodies were diluted 1:1000 in antibody buffer and added to each well followed by a one hr incubation at 37° C. Primary antibody was removed and the cell monolayers were washed twice with antibody buffer. Peroxidase-labelled goat-anti-rabbit IgG (KPL, Gaithersburg, Md.) was diluted 1:500 in antibody buffer and added to each well followed by a one hr incubation at 37° C. Secondary antibody was removed and the wells were washed twice with phosphate buffered saline. Peroxidase substrate (4 chloro-1-napthol in $H_2O_2$) was added to each well and visible plaques were counted.

For amplification of virus in serum samples, a 0.3 ml aliquot of serum was inoculated directly onto a single well of a 6-well plate of Vero cell monolayers and incubated at 37° C. for 7 days. Cell culture fluid was then assayed for virus by plaque assay as described above.

Serology. Hemagglutination-inhibition (HAI) assays were performed as previously described (Clarke, D. H. & Casals, J. 1958 *Am J Trop Med Hyg* 7:561-73). Plaque-reduction neutralization titers (PRNT) were determined by a modification of the technique described by Russell (Russell, P. K. et al. 1967 *J Immunol* 99:285-90). Briefly, test sera were heat inactivated (56° C. for 30 min) and serial 2-fold dilutions beginning at 1:10 were made in OptiMEM supplemented with 0.25% human serum albumin. rDEN4Δ30 virus, diluted to a final concentration of 1000 PFU/ml in the same diluent, was added to equal volumes of the diluted serum and mixed well. The virus/serum mixture was incubated at 37° C. for 30 min. Cell culture medium was removed from 90% confluent monolayer cultures of Vero cells on 24-well plates and 50 μl of virus/serum mixture was transferred onto duplicate cell monolayers. Cell monolayers were incubated for 60 min at 37° C. and overlaid with 0.8% methylcellulose in OptiMEM supplemented with 2% FBS. Samples were incubated at 37° C. for 4 days after which plaques were visualized by immunoperoxidase staining as described above, and a 60% plaque-reduction neutralization titer was calculated.

Studies in rhesus monkeys. Evaluation of the replication and immunogenicity of wt virus 814669, and recombinant viruses 2A wt, 2AΔ30 (vaccine lot), rDEN4, and rDEN4Δ30 in juvenile rhesus monkeys was performed as previously described (Men R. et al. 1996 *J Virol* 70:3930-7). Briefly, dengue virus seronegative monkeys were injected subcutaneously with 5.0 $\log_{10}$ PFU of virus diluted in L-15 medium (Quality Biological, Gaithersburg, Md.) containing SPG buffer. A dose of 1 ml was divided between two injections in each side of the upper shoulder area. Monkeys were observed daily and blood was collected on days 0-10 and 28, and processed for serum, which was stored frozen at −70° C. Titer of virus in serum samples was determined by plaque assay on Vero cells as described above. Neutralizing antibody titers were determined for the day 28 serum samples as described above. A group of monkeys inoculated with either 2AΔ30 (n=4) or wt virus 814669 (n=8) were challenged on day 42 with a single dose of 5.0 $\log_{10}$ PFU/ml wt virus 814669 and blood was collected for 10 days. Husbandry and care of rhesus monkeys was in accordance with the National Institutes of Health guidelines for the humane use of laboratory animals.

Construction and characterization of DEN-4 wild type and deletion mutant viruses. The nucleotide and deduced amino acid sequences of the previously described wt 814669 virus, the DEN-4 2A wt virus derived from it (designated 2A wt), and the 2AΔ30 vaccine candidate derived from 2A wt virus were first determined. Sequence analysis showed that the wt 814669 virus used in this study had apparently accumulated 2 missense mutations (nucleotides 5826 and 7630) and 3 silent mutations during its passage and amplification since these mutations were not described in previously published reports of the viral sequence (GenBank accession number M14931) and were not present in the 2A cDNA derived from the virus. Sequence comparison between viruses 2A wt and vaccine lot 2AΔ30 revealed that 2AΔ30 accumulated 2 missense mutations (nucleotides 7153 and 8308) and also confirmed the presence of the Δ30 mutation (nucleotides 10478-10507) as well as an additional deletion of nucleotide 10475, which occurred during the original construction of the Δ30 mutation (Men, R. et al. 1996 *J Virol* 70:3930-7). This sequence analysis revealed significant sequence divergence between the biologically-derived wt 814669 virus and its recombinant 2A wt derivative and between the 2A wt and 2AΔ30 virus. Since the 2A wt and 2AΔ30 viruses differed at nucleotides other than the deletion mutation, the attenuation phenotype previously reported for 2AΔ30 (Men, R. et al. 1996 *J Virol* 70:3930-7) could not be formally ascribed solely to the Δ30 mutation and may have been specified by the mutations at nucleotides 7153, 8308, 10475, or the Δ30 deletion.

To determine whether the Δ30 mutation was responsible for the observed attenuation of 2AΔ30, a second pair of viruses, one with and one without the Δ30 mutation, were produced for evaluation in monkeys. A new DEN-4 cDNA vector construct, designated p4, was derived from the 2A-XhoI cDNA clone and translationally-silent mutations were introduced to add or ablate several restriction enzyme sites. These sites were added to facilitate the future genetic manipulation of this DEN-4 wt cDNA by the introduction of other attenuating mutations if needed. The sequence of the genomic region of the p4 cDNA plasmid was identical to that of the 2A wt virus except for the engineered restriction site changes and a point mutation at nucleotide 2440 which was introduced during the original mutagenesis of the 2A cDNA plasmid to create the XhoI site (Bray, M. & Lai, C. J. 1991 *PNAS USA* 88:10342-6). The Δ30 mutation and the neighboring deletion at nucleotide 10475 were co-introduced into the p4 plasmid by replacing a short restriction fragment with one derived from the cDNA clone of 2AΔ30. RNA transcripts derived from the p4 cDNA clone and from its Δ30 derivative each yielded virus (designated rDEN4 wt and rDEN4Δ30, respectively) following transfection of Vero cells. Sequence analysis of the rDEN4 virus revealed that during its passage and amplification in Vero cells it accumulated 2 missense mutations (nucleotides 4353 and 6195), a silent mutation (nucleotide 10157), and a point mutation in the 3' untranslated region (nucleotide 10452). In addition to containing the Δ30 and the accompanying deletion at nucleotide 10475, rDEN4Δ30 had also accumulated a missense mutation (nucleotide 7163) and a silent mutation (nucleotide 7295).

Parental wt 814669 virus and recombinant viruses 2A wt, 2AΔ30, rDEN4, and rDEN4Δ30 each replicate in Vero cells to a titer exceeding 7.0 $\log_{10}$ PFU/ml, and their replication is not temperature sensitive at 39° C.

Virus replication, immunogenicity, and efficacy in monkeys. Groups of rhesus monkeys were inoculated with wt DEN-4 814669, 2A wt, rDEN4, 2AΔ30 and rDEN4Δ30 to assess the level of restriction of replication specified by the Δ30 mutation. Serum samples were collected daily and titer of virus present in the serum was determined by plaque enumeration on Vero cell monolayer cultures. Monkeys inoculated with wt 814669 virus or its recombinant counterparts, 2A wt or rDEN4, were viremic for 3 to 4 days with a mean peak virus titer of nearly 2 $\log_{10}$ PFU/ml. Monkeys inoculated with virus 2AΔ30 or rDEN4Δ30 had a lower frequency of viremia (83% and 50%, respectively), were viremic for only about 1 day, and the mean peak titer was 10-fold lower. Monkeys inoculated with DEN-4 814669, 2A wt, or rDEN4 viruses developed high levels of neutralizing antibody, with mean titers between 442 and 532, consistent with their presumed wild type phenotype. Monkeys inoculated with 2AΔ30 or rDEN4Δ30 developed a lower level of neutralizing antibody, with mean titers of 198 and 223, respectively. The decrease in neutralizing antibody titer in response to 2AΔ30 and rDEN4Δ30 is consistent with the attenuation phenotype of these viruses. Monkeys inoculated with either 2AΔ30 (n=4) or wt 814669 virus (n=8) were challenged after 42 days with wt virus 814669. Dengue virus was not detected in any serum sample collected for up to 10 days following virus challenge, indicating that these monkeys were completely protected following immunization with either wt virus or vaccine candidate 2AΔ30.

Since DEN-4 814669, 2A wt, and rDEN4 each manifest the same level of replication and immunogenicity in rhesus monkeys, it is reasonable to conclude that the identified sequence differences between these presumptive wild type viruses that arose during passage in tissue culture or during plasmid construction do not significantly affect their level of replication in vivo. Similarly, the comparable level of attenuation of 2AΔ30 and rDEN4Δ30 indicates that the mutations shared by these viruses, namely, the Δ30 mutation and its accompanying 10475 deletion mutation, are probably responsible for the attenuation of these viruses rather than their incidental sequence differences.

Clinical Response to immunization with 2AΔ30. The 2AΔ30 vaccine candidate was administered subcutaneously at a dose of $10^5$ PFU to 20 seronegative volunteers. Each of the vaccinees was infected and the virus was well tolerated by all vaccinees. Viremia was detected in 70% of the vaccinees, was present only at low titer, and did not extend beyond day 11.

None of the 20 vaccinees reported soreness or swelling at the injection site. Mild erythema (1-3 mm) around the injection site was noted on examination of 8 volunteers 30 minutes post-vaccination which resolved by the next day in 7 of those volunteers and by the third day in the remaining volunteer. Mild tenderness to pressure at the vaccination site was noted in 2 volunteers and lasted a maximum of 48 hours. During physical examination, ten volunteers (50%) were noted to a have a very mild dengue-like erythematous macular rash (truncal distribution) which occurred with greatest frequency on day 10. None of the volunteers noted the rash themselves, and it was asymptomatic in each instance. Rash was seen only in vaccinees with detectable viremia. Volunteers did not develop systemic illness. Seven volunteers noted an occasional headache that was described as mild, lasting less than 2 hours, and was not present in any volunteer on two consecutive days. One volunteer reported fever of 38.6° C. and 38.2° C. without accompanying headache, chills, eye pain, photophobia, anorexia, myalgia, or arthralgia as an outpatient the evening of day 3 and day 5, respectively. However, this volunteer was afebrile when evaluated by the study staff on the morning of days 3, 4, 5 and 6. All other temperature measurements recorded by the volunteer or study staff were normal. Although tourniquet tests were not performed, two volunteers were noted to have petechiae at the site of the blood pressure cuff after a blood pressure measurement was performed (one on day 6, the other on days 7 and 10). Both of these volunteers had normal platelet counts at that time and throughout the study.

Significant hematological abnormalities were not seen in any vaccinee. Three vaccinees with presumed benign ethnic neutropenia manifested an absolute neutrophil count (ANC) below $1500/mm^3$. These three volunteers had baseline ANCs which were significantly lower than the remaining 17 volunteers and which did not decrease disproportionately to the other volunteers. Two of the three volunteers who became neutropenic never had detectable viremia. A mild increase in ALT levels was noted in 4 volunteers, and a more significant increase in ALT level (up to 238 IU/L) was noted in one volunteer. These ALT elevations were transient, were not associated with hepatomegaly, and were completely asymptomatic in each of the 5 volunteers. Elevated ALT values returned to normal by day 26 post-vaccination. The volunteer with the high ALT value was also noted to have an accompanying mild elevation in AST on day 14 ($10^4$ IU/L) which also returned to baseline by day 26 post-vaccination. This volunteer did not have an associated increase in LDH, bilirubin, or alkaline phosphatase levels.

Serologic response of humans to immunization with 2AΔ30. Each of the twenty vaccinees developed a significant rise in serum neutralizing antibody titer against DEN-4 by day 28. The level of serum neutralizing antibody was similar in viremic (1:662) and non-viremic vaccinees (1:426). The DEN-4 neutralizing antibody titers of both groups had not changed significantly by day 42.

Genetic stability of the Δ30 mutation. RT-PCR and sequence analysis of viral RNA isolated from serum samples (n=6) collected from volunteers 6 to 10 days post-vaccination confirmed the presence of the Δ30 mutation and neighboring deletion at nucleotide 10475.

EXAMPLE 9

Pharmaceutical Compositions

Live attenuated dengue virus vaccines, using replicated virus of the invention, are used for preventing or treating dengue virus infection. Additionally, inactivated dengue virus vaccines are provided by inactivating virus of the invention using known methods, such as, but not limited to, formalin or β-propiolactone treatment. Live attenuated or inactivated viruses containing the mutations described above form the basis of an improved vaccine for the prevention or treatment of dengue infection in humans.

Pharmaceutical compositions of the present invention comprise live attenuated or inactivated dengue viruses, optionally further comprising sterile aqueous or non-aqueous solutions, suspensions, and emulsions. The composition can further comprise auxiliary agents or excipients, as known in the art. See, e.g., Berkow et al. eds. 1987 *The Merck Manual*, 15th edition, Merck and Co., Rahway, N.J.; Goodman et al. eds. 1990 Goodman and Gilman's *The Pharmacological Basis of Therapeutics*, 8th edition, Pergamon Press, Inc., Elmsford, N.Y.; *Avery's Drug Treatment: Principles and Practice of Clinical Pharmacology and Therapeutics*, 3rd edition, ADIS Press, LTD., Williams and Wilkins, Baltimore, Md. 1987; Osol, A. ed. 1980 *Remington's Pharmaceutical Sciences* Mack Publishing Co, Easton, Pa. pp. 1324-1341; Katzung, ed. 1992 *Basic and Clinical Pharmacology* Fifth Edition, Appleton and Lange, Norwalk, Conn.

A virus vaccine composition of the present invention can comprise from about $10^2$-$10^9$ plaque forming units (PFU)/ml, or any range or value therein, where the virus is attenuated. A vaccine composition comprising an inactivated virus can comprise an amount of virus corresponding to about 0.1 to 50 μg of E protein/ml, or any range or value therein.

The agents may be administered using techniques well known to those in the art. Preferably, agents are formulated and administered systemically. Suitable routes may include oral, rectal, transmucosal, or intestinal administration; parenteral delivery, including intramuscular, subcutaneous, intramedullary injections, as well as intrathecal, direct intraventricular, intravenous, intraperitoneal, intradermal, intranasal, or intraocular injections, just to name a few. For injection, the agents of the invention may be formulated in aqueous solutions, preferably in physiologically compatible buffers such as saline, phosphate buffered saline, Tris buffered saline, Hank's buffered saline, growth media such as Eagle's Minimum Essential Medium (MEM), and the like.

When a vaccine composition of the present invention is used for administration to an individual, it can further comprise salts, buffers, adjuvants, or other substances which are desirable for improving the efficacy of the composition. Adjuvants useful with the invention include, but are not limited to: (1) aluminum salts (alum), such as aluminum hydroxide, aluminum phosphate, aluminum sulfate, etc.; (2) oil-in-water emulsion formulations (with or without other specific immunostimulating agents such as muramyl peptides or bacterial cell wall components), such as for example (a) MF59 (International Publication No. WO 90/14837), containing 5% Squalene, 0.5% Tween 80, and 0.5% Span 85 (optionally containing various amounts of MTP-PE, although not required) formulated into submicron particles using a microfluidizer such as Model 110Y microfluidizer (Microfluidics, Newton, Mass.), (b) SAF, containing 10% Squalene, 0.4% Tween 80, 5% pluronic-blocked polymer L121, and thr-MDP either microfluidized into a submicron emulsion or vortexed to generate a larger particle size emulsion, and (c) Ribi™ adjuvant system (RAS), (Ribi Immunochem, Hamilton, Mont.) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); (3) saponin adjuvants, such as Stimulon™ (Cambridge Bioscience, Worcester, Mass.) may be used or particle generated therefrom such as ISCOMs (immunostimulating complexes); (4) Complete Freunds Adjuvant (CFA) and Incomplete Freunds Adjuvant (IFA); (5) cytokines, such as interleukins (IL-1, IL-2, etc.), macrophage colony stimulating factor (M-CSF), tumor necrosis factor (TNF), etc.; (6) mucosal adjuvants such as those derived from cholera toxin (CT), pertussis toxin (PT), *E. coli* heat labile toxin (LT), and mutants thereof (see, e.g., International Publication Nos. WO 95/17211, WO 93/13202, and WO 97/02348); and (7) other substances that act as immunostimulating agents to enhance the effectiveness of the composition.

The pharmacologically active compounds of this invention can be processed in accordance with conventional methods of galenic pharmacy to produce medicinal agents for administration to patients, e.g., mammals including humans.

The compounds of this invention can be employed in admixture with conventional excipients, i.e., pharmaceutically acceptable organic or inorganic carrier substances suitable for parenteral, enteral (e.g., oral) or topical application, which do not deleteriously react with the active compounds. Suitable pharmaceutically acceptable carriers include but are not limited to water, salt solutions, alcohols, gum arabic, vegetable oils, benzyl alcohols, polyethylene glycols, gelatin, carbohydrates such as lactose, amylose or starch, magnesium stearate, talc, silicic acid, viscous paraffin, perfume oil, fatty acid monoglycerides and diglycerides, pentaerythritol fatty acid esters, hydroxy methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds. They can also be combined where desired with other active agents, e.g., vitamins.

For parenteral application, particularly suitable are injectable, sterile solutions, preferably oily or aqueous solutions, as well as suspensions, emulsions, or implants, including suppositories. Ampoules are convenient unit dosages.

For enteral application, particularly suitable are tablets, dragees, liquids, drops, suppositories, or capsules. A syrup, elixir, or the like can be used wherein a sweetened vehicle is employed.

For topical application, there are employed as non-sprayable forms, viscous to semi-solid or solid forms comprising a carrier compatible with topical application and having a dynamic viscosity preferably greater than water. Suitable formulations include but are not limited to solutions, suspensions, emulsions, creams, ointments, powders, liniments, salves, aerosols, etc., which are, if desired, sterilized or mixed with auxiliary agents, e.g., preservatives, stabilizers, wetting agents, buffers or salts for influencing osmotic pressure, etc. For topical application, also suitable are sprayable aerosol preparations wherein the active ingredient, preferably in combination with a solid or liquid inert carrier material, is packaged in a squeeze bottle or in admixture with a pressurized volatile, normally gaseous propellant, e.g., a freon.

The vaccine can also contain variable but small quantities of endotoxin, free formaldehyde, and preservative, which have been found safe and not contributing to the reactogenicity of the vaccines for humans.

EXAMPLE 10

Pharmaceutical Purposes

The administration of the vaccine composition may be for either a "prophylactic" or "therapeutic" purpose. When provided prophylactically, the compositions are provided before any symptom of dengue viral infection becomes manifest. The prophylactic administration of the composition serves to prevent or attenuate any subsequent infection. When provided therapeutically, the live attenuated or inactivated viral vaccine is provided upon the detection of a symptom of actual infection. The therapeutic administration of the compound(s) serves to attenuate any actual infection. See, e.g., Berkow et al. eds. 1987 *The Merck Manual,* 15th edition, Merck and Co., Rahway, N.J.; Goodman et al. eds. 1990 *Goodman and Gilman's The Pharmacological Basis of Therapeutics,* 8th edition, Pergamon Press, Inc., Elmsford, N.Y.; *Avery's Drug Treatment: Principles and Practice of Clinical Pharmacology and Therapeutics,* 3rd edition, ADIS Press, LTD., Williams and Wilkins, Baltimore, Md. 1987; Katzung, ed. 1992 *Basic and Clinical Pharmacology,* Fifth Edition, Appleton and Lange, Norwalk, Conn.

A live attenuated or inactivated vaccine composition of the present invention may thus be provided either before the onset of infection (so as to prevent or attenuate an anticipated infection) or after the initiation of an actual infection.

The vaccines of the invention can be formulated according to known methods to prepare pharmaceutically useful compositions, whereby live attenuated or inactivated viruses are combined in a mixture with a pharmaceutically acceptable vehicle. A composition is said to be a "pharmacologically acceptable vehicle" if its administration can be tolerated by a recipient patient. Suitable vehicles are well known to those in the art, e.g., in Osol, A. ed. 1980 *Remington's Pharmaceutical Sciences* Mack Publishing Co, Easton, Pa. pp. 1324-1341.

For purposes of administration, a vaccine composition of the present invention is administered to a human recipient in a therapeutically effective amount. Such an agent is said to be administered in a "therapeutically effective amount" if the amount administered is physiologically significant. A vaccine composition of the present invention is physiologically significant if its presence results in a detectable change in the physiology of a recipient patient that generates a host immune response against at least one dengue serotype, stimulates the production of neutralizing antibodies, or leads to protection against challenge.

The "protection" provided need not be absolute, i.e., the dengue infection need not be totally prevented or eradicated, if there is a statistically significant improvement compared with a control population or set of patients. Protection may be limited to mitigating the severity or rapidity of onset of symptoms of the dengue virus infection.

EXAMPLE 11

Pharmaceutical Administration

A vaccine of the present invention may confer resistance to one or more dengue serotypes by immunization. In immunization, an live attenuated or inactivated vaccine composition is administered prophylactically, according to a method of the present invention. In another embodiment a live attenuated or inactivated vaccine composition is administered therapeutically, according to a different method of the present invention.

The present invention thus includes methods for preventing or attenuating infection by at least one dengue serotype. As used herein, a vaccine is said to prevent or attenuate a disease if its administration results either in the total or partial attenuation (i.e., suppression) of a symptom or condition of the disease, or in the total or partial immunity of the individual to the disease.

At least one live attenuated or inactivated dengue virus, or composition thereof, of the present invention may be administered by any means that achieve the intended purpose, using a pharmaceutical composition as previously described.

For example, administration of such a composition may be by various parenteral routes such as subcutaneous, intravenous, intradermal, intramuscular, intraperitoneal, intranasal, oral or transdermal routes. Parenteral administration can be by bolus injection or by gradual perfusion over time. A preferred mode of using a pharmaceutical composition of the present invention is by intramuscular, intradermal or subcutaneous application. See, e.g., Berkow et al. eds. 1987 *The Merck Manual* 15th edition, Merck and Co., Rahway, N.J.; Goodman et al. eds. 1990 *Goodman and Gilman's The Pharmacological Basis of Therapeutics,* 8th edition, Pergamon Press, Inc., Elmsford, N.Y.; *Avery's Drug Treatment: Principles and Practice of Clinical Pharmacology and Therapeutics,* 3rd edition, ADIS Press, LTD., Williams and Wilkins, Baltimore, Md. 1987; Osol, A. ed. 1980 *Remington's Pharmaceutical Sciences*, Mack Publishing Co, Easton, Pa. pp. 1324-1341; Katzung, ed. 192 *Basic and Clinical Pharmacology*, Fifth Edition, Appleton and Lange, Norwalk, Conn.

A typical regimen for preventing, suppressing, or treating a dengue virus related pathology, comprises administration of an effective amount of a vaccine composition as described herein, administered as a single treatment, or repeated as enhancing or booster dosages, over a period up to and including between one week and about 24 months, or any range or value therein.

It will be appreciated that the actual preferred amounts of active compound in a specific case will vary according to the specific compound being utilized, the compositions formulated, the mode of application, and the particular situs and organism being treated. Dosages for a given host can be determined using conventional considerations, e.g., by customary comparison of the differential activities of the subject compounds and of a known agent, e.g., by means of an appropriate, conventional pharmacological protocol.

The dosage of a live attenuated virus vaccine for a mammalian (e.g., human) subject can be from about $10^3$-$10^7$ plaque forming units (PFU)/kg, or any range or value therein. The dose of inactivated vaccine can range from about 0.1 to 50 μg of E protein. However, the dosage should be a safe and effective amount as determined by conventional methods, using existing vaccines as a starting point.

The compositions may, if desired, be presented in a pack or dispenser device which may contain one or more unit dosage forms containing the active ingredient. The pack may for example comprise met al or plastic foil, such as a blister pack. The pack or dispenser device may be accompanied by instructions for administration.

TABLE 1

Susceptibility of mice to intracerebral DEN4 infection is age-dependent[a]

| Virus | Mean virus titer ($log_{10}$ PFU/g brain) ± SE following inoculation at indicated age (days) 7 | 14 | 21 |
|---|---|---|---|
| 2A-13 | >6.0 | 4.0 ± 0.2 | 3.1 ± 0.2 |
| rDEN4 | >6.0 | 3.3 ± 0.4 | 3.3 ± 0.2 |
| rDEN4Δ30 | >6.0 | 3.6 ± 0.2 | 2.8 ± 0.3 |

[a]Groups of 4 or 5 Swiss Webster mice were inoculated intracerebrally with $10^5$ PFU virus in a 30 μl inoculum. After 5 days, brains were removed, homogenized and titered in Vero cells.
SE = Standard error.

TABLE 2

Temperature-sensitive (ts) and mouse brain attenuation (att) phenotypes of 5-FU mutant DEN4 viruses.

| | | Mean virus titer ($log_{10}$ PFU/ml) at indicated temp. (° C.) | | | | | | | | | | Virus replication in suckling mice[b] | | |
|---|---|---|---|---|---|---|---|---|---|---|---|---|---|---|
| | | Vero cells | | | | | HuH-7 cells | | | | | | Mean titer ± SE ($log_{10}$ PFU/g brain) | Mean $log_{10}$ reduction from wt[d] |
| Phenotype | Virus | 35 | 37 | 38 | 39 | Δ[a] | 35 | 37 | 38 | 39 | Δ | n | | |
| wt (not ts) | 2A-13 | 7.8 | 7.7 | 7.6 | 7.3 | 0.5 | 7.8 | 7.7 | 7.4 | 6.4 | 1.4 | 66 | 6.6 ± 0.1[c] | — |
| | rDEN4 | 6.5 | 6.4 | 6.4 | 6.0 | 0.5 | 7.1 | 6.7 | 6.0 | 5.5 | 1.6 | 66 | 6.1 ± 0.1[c] | — |
| | rDEN4Δ30 | 6.3 | 6.1 | 6.1 | 5.7 | 0.6 | 6.9 | 6.3 | 5.9 | 4.7 | 2.2 | 64 | 5.6 ± 0.1[c] | 0.5 |

TABLE 2-continued Temperature-sensitive (ts) and mouse brain attenuation (att) phenotypes of 5-FU mutant DEN4 viruses.

| | | Mean virus titer ($\log_{10}$ PFU/ml) at indicated temp. (° C.) | | | | | | | | | | Virus replication in suckling mice[b] | |
|---|---|---|---|---|---|---|---|---|---|---|---|---|---|
| | | Vero cells | | | | | HuH-7 cells | | | | | Mean titer ± SE | Mean $\log_{10}$ |
| Phenotype | Virus | 35 | 37 | 38 | 39 | Δ[a] | 35 | 37 | 38 | 39 | Δ | n | ($\log_{10}$ PFU/g brain) | reduction from wt[d] |
| ts in Vero and | 695 | 6.2 | 6.0 | 5.2 | 2.6[e] | 3.6 | 6.5 | 5.5 | 3.8 | ≤1.6 | >4.9 | 6 | 3.0 ± 0.2 | 3.2 |
| HuH-7 cells | 816 | 6.8 | 6.4 | 5.8 | 3.9 | 2.9 | 7.5 | 6.2 | 5.5 | 3.1 | 4.4 | 6 | 3.3 ± 0.4 | 2.9 |
| | 773 | 7.4 | 6.6 | 6.0 | 3.1 | 4.3 | 7.7 | 6.1 | 5.2 | 3.1 | 4.6 | 12 | 3.7 ± 0.1 | 2.6 |
| | 489 | 7.3 | 6.6 | 6.1 | 3.3 | 4.0 | 7.3 | 6.7 | 5.4 | 3.0 | 4.3 | 6 | 4.5 ± 0.5 | 2.3 |
| | 173 | 7.0 | 6.1 | 3.2 | 2.9 | 4.1 | 7.0 | 3.2 | 3.0 | 2.1 | 4.9 | 18 | 4.7 ± 0.4 | 2.2 |
| | 509 | 6.2 | 5.8 | 5.5 | 3.4 | 2.8 | 6.5 | 6.1 | 4.5 | ≤1.6 | >4.9 | 6 | 4.9 ± 0.3 | 1.9 |
| | 938 | 7.1 | 6.5 | 5.6 | 3.1 | 4.0 | 7.2 | 6.4 | 5.6 | 3.1 | 4.1 | 6 | 5.1 ± 0.2 | 1.7 |
| | 1033 | 6.7 | 6.0 | 5.9 | 4.1 | 2.6 | 6.9 | 5.6 | 4.7 | ≤1.6 | >5.3 | 12 | 4.7 ± 0.2 | 1.7 |
| | 239 | 7.6 | 6.8 | 5.6 | 3.3 | 4.3 | 7.6 | 6.7 | 4.7 | 2.5 | 5.1 | 12 | 4.7 ± 0.3 | 1.5 |
| | 793 | 6.5 | 5.8 | 5.3 | 4.0 | 2.5 | 7.2 | 6.8 | 5.6 | ≤1.6 | >5.6 | 6 | 5.4 ± 0.3 | 1.4 |
| | 759 | 7.2 | 6.9 | 6.4 | 4.7 | 2.5 | 7.5 | 6.8 | 6.3 | 3.1 | 4.4 | 12 | 5.1 ± 0.1 | 1.4 |
| | 718 | 6.1 | 5.9 | 5.3 | 3.5 | 2.6 | 7.0 | 6.5 | 5.7 | 1.7 | 5.3 | 12 | 5.0 ± 0.3 | 1.4 |
| | 473 | 6.7 | 6.3 | 5.4 | 2.0 | 4.7 | 7.2 | 6.7 | 3.7 | 1.9 | 5.3 | 12 | 5.1 ± 0.3 | 1.2 |
| ts in only | 686 | 7.0 | 6.7 | 6.7 | 6.4 | 0.6 | 7.3 | 6.8 | 6.4 | 2.2 | 5.1 | 12 | 2.7 ± 0.2 | 3.8 |
| HuH-7 cells | 967 | 6.8 | 6.4 | 6.4 | 5.1 | 1.7 | 6.8 | 6.4 | 5.4 | ≤1.6 | >5.2 | 6 | 3.6 ± 0.2 | 2.9 |
| | 992 | 7.3 | 7.1 | 6.8 | 5.9 | 1.4 | 7.4 | 6.9 | 5.0 | ≤1.6 | >5.8 | 6 | 3.8 ± 0.1 | 2.7 |
| | 571 | 6.9 | 7.0 | 6.4 | 4.6 | 2.3 | 7.0 | 6.3 | 5.2 | ≤1.6 | >5.4 | 6 | 4.4 ± 0.4 | 2.4 |
| | 605 | 7.6 | 7.5 | 7.1 | 6.9 | 0.7 | 7.8 | 7.2 | 6.8 | ≤1.6 | >6.2 | 12 | 4.5 ± 0.4 | 2.1 |
| | 631 | 7.1 | 6.9 | 6.8 | 5.0 | 2.1 | 7.3 | 7.1 | 6.5 | ≤1.6 | >5.7 | 12 | 4.8 ± 0.3 | 1.9 |
| | 1175 | 7.4 | 7.1 | 6.9 | 5.3 | 2.1 | 7.6 | 6.5 | 4.7 | 3.3 | 4.3 | 12 | 4.7 ± 0.2 | 1.7 |

[a]Reduction in titer ($\log_{10}$ PFU/ml) at 39° C. compared to titer at permissive temperature (35° C.).
[b]Groups of 6 suckling mice were inoculated i.c. with $10^4$ PFU virus in a 30 μl inoculum. Brains were removed 5 days later, homogenized, and titered in Vero cells.
[c]Average of 11 experiments with a total of 64 to 66 mice per group.
[d]Determined by comparing mean viral titers of mice inoculated with mutant virus and the 2A-13 wt control in the same experiment (n = 6 or 12).
[e]Underlined values indicate a 2.5 or 3.5 $\log_{10}$ PFU/ml reduction in titer in Vero cells or HuH-7 cells, respectively, at indicated temp when compared to titer at permissive temp (35° C.).

TABLE 3

Nucleotide and amino acid differences of the 5-FU mutant viruses which are ts in both Vero and HuH-7 cells.

| Virus | Mutations in UTR or coding region that result in an amino acid substitution | | | | Mutations in coding region that do not result in an amino acid substitution | | |
|---|---|---|---|---|---|---|---|
| | Nucleotide position | Gene/ region | Nucleotide change | Amino Acid change[b] | Nucleotide position | Gene | Nucleotide change |
| 173[a] | 7163 | NS4B | A > C | L2354F | 10217 | NS5 | A > U |
| | 7849 | NS5 | A > U | N2583I | | | |
| | 8872 | NS5 | A > G | K2924R | | | |
| 239[a] | 4995 | NS3 | U > C | S1632P | 7511 | NS4B | G > A |
| | | | | | 10070 | NS5 | U > C |
| 473[a] | 4480 | NS2B | U > C | V1460A | 7589 | NS5 | G > A |
| | 4995 | NS3 | U > C | S1632P | 10070 | NS5 | U > C |
| 489[a] | 4995 | NS3 | U > C | S1632P | 2232 | E | U > C |
| | | | | | 3737 | NS2A | C > U |
| 509[a] | 4266 | NS2B | A > G | S1389G | none | | |
| | 8092 | NS5 | A > G | E2664G | | | |
| 695 | 40 | 5' UTR | U > C | n/a | 1391 | E | A > G |
| | 1455 | E | G > U | V452F | | | |
| | 6106 | NS3 | A > G | E2002G | | | |
| | 7546 | NS4B | C > U | A2482V | | | |
| 718 | 2280 | E | U > C | F727L | none | | |
| | 4059 | NS2A | A > G | I1320V | | | |
| | 4995 | NS3 | U > C | S1632P | | | |
| | 7630 | NS5 | A > G | K2510R | | | |
| | 8281 | NS5 | U > C | L2727S | | | |
| 759[a] | 4995 | NS3 | U > C | S1632P | none | | |
| | 8020 | NS5 | A > U | N2640I | | | |
| 773[a] | 4995 | NS3 | U > C | S1632P | none | | |
| 793 | 1776 | E | G > A | A559T | 5771 | NS3 | U > C |
| | 2596 | NS1 | G > A | R832K | 7793 | NS5 | U > A |

TABLE 3-continued

Nucleotide and amino acid differences of the 5-FU mutant viruses which are ts in both Vero and HuH-7 cells.

| | Mutations in UTR or coding region that result in an amino acid substitution | | | | Mutations in coding region that do not result in an amino acid substitution | | |
|---|---|---|---|---|---|---|---|
| Virus | Nucleotide position | Gene/ region | Nucleotide change | Amino Acid change[b] | Nucleotide position | Gene | Nucleotide change |
| | 2677 | NS1 | A > G | D859G | | | |
| | 4387 | NS2B | C > U | S1429F | | | |
| 816[a] | 4995 | NS3 | U > C | S1632P | 6632 | NS4A | G > A |
| | 7174 | NS4B | C > U | A2358V | 6695 | NS4A | G > A |
| 938[a] | 3442 | NS1 | A > G | E1114G | 747 | prM | U > C |
| | 4995 | NS3 | U > C | S1632P | 4196 | NS2b | U > C |
| | 10275 | 3' UTR | A > U | n/a | 6155 | NS3 | G > A |
| 1033[a] | 4907 | NS3 | A > U | L1602F | 548 | prM | C > U |
| | 8730 | NS5 | A > C | N2877H | | | |
| | 9977 | NS5 | G > A | M3292I | | | |

[a]Viruses that contain mutation(s) resulting in an a.a. substitution in only a NS gene(s) and/or nucleotide substitutions in the UTRs are indicated; i.e. no a.a. substitutions are present in the structural proteins (C-prM-E).
[b]Amino acid position in DEN4 polyprotein beginning with the methionine residue of the C protein (nt 102-104) as residue #1. Wild-type amino acid on left of amino acid position; mutant amino acid on right.

TABLE 4

Nucleotide and amino acid differences of the 5-FU mutant viruses which are ts in only HuH-7 cells.

| | Mutations in UTR or coding region that result in an amino acid substitution | | | | Mutations in coding region that do not result in an amino acid substitution | | |
|---|---|---|---|---|---|---|---|
| Virus | Nucleotide position | Gene/ region | Nucleotide change | Amino Acid change[b] | Nucleotide position | Gene | Nucleotide change |
| 571 | 586 | prM | U > C | V162A | 6413 | NS4A | U > C |
| | 7163 | NS4B | A > U | L2354F | | | |
| | 7947 | NS5 | G > A | G2616R | | | |
| 605 | 1455 | E | G > U | V452F | none | | |
| | 7546 | NS4B | C > U | A2482V | | | |
| 631 | 595 | prM | A > G | K165R | 1175 | E | G > A |
| | 6259 | NS3 | U > C | V2053A | 5174 | NS3 | A > G |
| | 7546 | NS4B | C > U | A2482V | | | |
| 686[a] | 3575 | NS2A | G > A | M1158I | 4604 | NS3 | A > G |
| | 4062 | NS2A | A > G | T1321A | 7937 | NS5 | A > G |
| | 7163 | NS4B | A > U | L2354F | | | |
| 967 | 2094 | E | G > C | A665P | 4616 | NS3 | C > U |
| | 2416 | E | U > C | V772A | | | |
| | 7162 | NS4B | U > C | L2354S | | | |
| | 7881 | NS5 | G > A | G2594S | | | |
| 992[a] | 5695 | NS3 | A > G | D1865G | 3542 | NS2A | A > G |
| | 7162 | NS4B | U > C | L2354S | | | |
| 1175[a] | 7153 | NS4B | U > C | V2351A | 6167 | NS3 | U > C |
| | 10186 | NS5 | U > C | I3362T | 10184 | NS5 | G > A |
| | 10275 | 3' UTR | A > U | n/a | | | |

[a]Viruses that contain mutation(s) resulting in an a.a. substitution in only a NS gene(s) and/or nucleotide substitutions in the UTRs are indicated; i.e. no a.a. substitutions are present in the structural proteins.
[b]Amino acid position in DEN4 polyprotein beginning with the methionine residue of the C protein (nt 102-104) as residue #1. Wild-type amino acid on left of amino acid position; mutant amino acid on right.

TABLE 5

Mutations which are represented in multiple 5-FU mutant DEN4 viruses.

| Nucleotide position | Gene/region | Nucleotide change | Amino acid change | Number of viruses with "sister" mutations |
|---|---|---|---|---|
| 1455 | E | G > U | val > phe | 2 |
| 4995 | NS3 | U > C | ser > pro | 8 |
| 7162 | NS4B | U > C | leu > ser | 2 |
| 7163 | NS4B | A > U or C | leu > phe | 3 |
| 7546 | NS4B | C > U | ala > val | 3 |
| 10275 | 3' UTR | A > U | n/a[a] | 2 |

[a] not applicable

TABLE 6

Addition of ts mutation 4995 to rDEN4Δ30 confers a ts phenotype and further attenuates its replication in suckling mouse brain.

| | Mean virus titer ($\log_{10}$ PFU/ml) at indicated temp (° C.) | | | | | | | | | | Replication in suckling mice[b] | |
|---|---|---|---|---|---|---|---|---|---|---|---|---|
| | Vero cells | | | | | HuH-7 cells | | | | | Mean virus titer ± SE | Mean $\log_{10}$ reduction from |
| Virus | 35 | 37 | 38 | 39 | Δ[a] | 35 | 37 | 38 | 39 | Δ | ($\log_{10}$ PFU/g brain) | wt[c] |
| 2A-13 | 7.1 | 7.1 | 6.9 | 6.8 | 0.3 | 7.4 | 7.3 | 6.7 | 6.4 | 1.0 | 6.5 ± 0.1 | — |
| rDEN4 | 7.0 | 6.8 | 6.6 | 6.4 | 0.6 | 7.5 | 7.3 | 6.7 | 6.4 | 1.1 | 6.1 ± 0.2 | — |
| rDEN4Δ30 | 7.0 | 6.7 | 6.2 | 6.2 | 0.8 | 7.5 | 7.0 | 6.5 | 5.1 | 2.4 | 5.9 ± 0.1 | 0.2 |
| rDEN4-4995 | 5.7 | 4.9 | 3.6 | <u>≤1.6</u> | >4.1 | 6.4 | 5.7 | 4.0 | <u>≤1.6</u> | >4.8 | 3.2 ± 0.2 | 2.9 |
| rDEN4Δ30-4995 | 5.9 | 4.9 | 3.9 | <u>≤1.6</u>[d] | >4.3 | 6.4 | 5.6 | 4.4 | <u>≤1.6</u> | >4.8 | 3.0 ± 0.3 | 3.1 |

[a] Reduction in titer ($\log_{10}$ PFU/ml) at 39° C. compared to titer at permissive temperature (35° C.).
[b] Groups of 6 suckling mice were inoculated i.c. with $10^4$ PFU virus in a 30 μl inoculum. Brains were removed 5 days later, homogenized, and titered in Vero cells. The limit of detection is 2.0 $\log_{10}$ PFU/g brain.
[c] Determined by comparing mean viral titers of mice inoculated with sample virus and rDEN4 control.
[d] Underlined values indicate a 2.5 or 3.5 $\log_{10}$ PFU/ml reduction in titer in Vero cells or HuH-7 cells, respectively, at indicated temperature when compared to permissive temperature.

TABLE 7

Temperature-sensitive (ts) and mouse brain attenuation (att) phenotypes of 5-FU DEN4 mutant viruses which exhibit a small plaque (sp) phenotype.

| Phenotype | | | | | Mean virus titer ($\log_{10}$ PFU/ml) at indicated temp (° C.) | | | | | | | | | | Replication in suckling mice[b] | | |
|---|---|---|---|---|---|---|---|---|---|---|---|---|---|---|---|---|---|
| sp | | ts | | | Vero cells | | | | | HuH-7 cells | | | | | | Mean virus titer ± SE | Mean $\log_{10}$ |
| Vero | HuH-7 | Vero | HuH-7 | Virus | 35 | 37 | 38 | 39 | Δ[a] | 35 | 37 | 38 | 39 | Δ | n | ($\log_{10}$ PFU/g brain) | reduction from wt[d] |
| − | − | − | − | 2A-13 | 7.9 | 7.5 | 7.7 | 7.2 | 0.7 | 7.9 | 7.7 | 7.3 | 6.9 | 1.0 | 66 | 6.6 ± 0.1[e] | — |
| − | − | − | − | rDEN4 | 7.9 | 7.6 | 7.7 | 7.3 | 0.6 | 8.1 | 7.6 | 7.5 | 6.7 | 1.4 | 66 | 6.1 ± 0.1[e] | — |
| − | − | − | − | rDEN4Δ30 | 7.3 | 6.6 | 6.6 | 6.1 | 1.2 | 7.3 | 7.2 | 6.9 | 5.9 | 1.4 | 64 | 5.6 ± 0.1[e] | 0.5 |
| + | + | + | + | 574 | 6.6[x] | 5.5 | <u>3.8</u> | <u>≤1.6</u>[e] | ≥5.0 | 6.6[x] | 4.9 | 5.0 | <u>≤1.6</u> | ≥5.0 | 6 | 2.1 ± 0.1 | 5.1 |
| + | + | + | + | 1,269 | 5.3[x] | 4.8 | 3.9 | <u>≤1.6</u> | ≥3.7 | 4.0[x] | 2.4 | 2.0 | <u>≤1.6</u> | ≥2.4 | 6 | 2.7 ± 0.2 | 4.1 |
| + | + | + | + | 1,189 | 6.3[x] | 5.2 | 4.5 | <u>3.8</u> | 2.5 | 5.5[x] | 3.7 | 2.3 | <u>≤1.6</u> | ≥3.9 | 12 | 3.2 ± 0.4 | 3.7 |
| + | + | − | − | 569 | 5.8[x] | 5.6 | 5.6 | 3.7 | 2.1 | 6.2[x] | 6.0 | 5.7 | 5.0 | 1.2 | 12 | 1.9 ± 0.1 | 4.6 |
| + | + | − | − | 761 | 5.0[x] | 4.7 | 4.2 | 2.7 | 2.3 | 5.6[x] | 5.3 | 4.5 | 2.6 | 3.0 | 12 | 2.0 ± 0.1 | 4.2 |
| − | + | + | + | 506 | 7.0 | 6.8 | 5.6 | <u>2.6</u> | 4.4 | 6.7[x] | 4.3 | <u>≤1.6</u> | <u>2.0</u> | 4.7 | 6 | 2.2 ± 0.1 | 4.7 |
| − | + | + | + | 1,136 | 5.1 | 4.2 | <u>2.6</u> | <u>≤1.6</u> | ≥3.5 | 5.7[x] | 3.0 | 3.0 | <u>≤1.6</u> | ≥4.1 | 6 | 2.9 ± 0.3 | 4.5 |
| − | + | + | + | 1,029 | 6.9 | 5.8 | 5.8 | <u>2.9</u> | 4.0 | 7.0[x] | 5.8 | 5.2 | <u>2.5</u> | 4.5 | 6 | 2.2 ± 0.1 | 4.2 |
| − | + | + | + | 1,081 | 6.9 | 5.8 | 4.7 | <u>3.9</u> | 3.0 | 5.8[x] | 4.1 | 3.3 | <u>1.9</u> | 3.9 | 12 | 2.6 ± 0.2 | 3.9 |
| − | + | + | + | 529 | 6.9 | 6.5 | 5.9 | <u>4.0</u> | 2.9 | 7.1[x] | 5.3 | 4.4 | <u>≤1.6</u> | ≥5.5 | 6 | 3.1 ± 0.7 | 3.8 |
| − | + | + | + | 1,114 | 6.7 | 6.4 | 6.2 | <u>2.5</u> | 4.2 | 5.7[x] | 3.0 | 2.9 | <u>1.9</u> | 3.8 | 6 | 2.7 ± 0.3 | 3.7 |
| − | + | + | + | 922 | 7.3 | 7.2 | 6.8 | <u>3.8</u> | 3.5 | 7.4[x] | 5.3 | 4.4 | <u>3.0</u> | 4.4 | 12 | 3.5 ± 0.1 | 2.9 |
| − | + | + | + | 311 | 6.9 | 5.9 | <u>4.3</u> | <u>1.5</u> | 5.4 | 7.1[x] | 5.4 | <u>3.6</u> | <u>≤1.6</u> | ≥5.5 | 12 | 6.1 ± 0.3 | 0.9 |
| − | + | + | + | 326 | 6.6 | 5.7 | 4.5 | <u>3.1</u> | 3.5 | 7.0[x] | 5.5 | 4.1 | <u>2.0</u> | 5.0 | 6 | 6.0 ± 0.1 | 0.9 |
| − | + | − | + | 1,104 | 7.1 | 6.8 | 6.8 | 6.1 | 1.0 | 7.2[x] | 6.4 | 5.8 | <u>2.8</u> | 4.4 | 6 | 2.2 ± 0.1 | 4.7 |
| − | + | − | + | 952 | 7.1 | 7.0 | 6.7 | 5.6 | 1.5 | 7.3[x] | 6.3 | 5.6 | <u>3.0</u> | 4.3 | 6 | 2.4 ± 0.3 | 4.5 |
| − | + | − | + | 738 | 6.5 | 6.0 | 5.9 | 5.7 | 0.8 | 6.9[x] | 6.1 | 5.0 | <u>3.1</u> | 3.8 | 12 | 4.4 ± 0.4 | 2.3 |

TABLE 7-continued

Temperature-sensitive (ts) and mouse brain attenuation (att) phenotypes of 5-FU DEN4 mutant viruses which exhibit a small plaque (sp) phenotype.

| Phenotype | | | | | Mean virus titer ($\log_{10}$ PFU/ml) at indicated temp (° C.) | | | | | | | | | | Replication in suckling mice[b] | |
|---|---|---|---|---|---|---|---|---|---|---|---|---|---|---|---|---|
| sp | | ts | | | Vero cells | | | | | HuH-7 cells | | | | | Mean virus titer ± SE | Mean $\log_{10}$ reduction |
| Vero | HuH-7 | Vero | HuH-7 | Virus | 35 | 37 | 38 | 39 | Δ[a] | 35 | 37 | 38 | 39 | Δ | n | ($\log_{10}$ PFU/g brain) | from wt[d] |
| − | + | − | + | 1,083 | 7.4 | 7.3 | 7.4 | 5.8 | 1.6 | 7.4[x] | 6.6 | 4.5 | ≤1.6 | ≥5.8 | 12 | 4.5 ± 0.4 | 2.0 |
| − | + | − | − | 1,096 | 7.5 | 7.1 | 6.9 | 5.5 | 2.0 | 7.5[x] | 6.6 | 5.6 | 4.8 | 2.7 | 6 | 2.9 ± 0.2 | 3.5 |
| − | + | − | − | 1,021 | 7.0 | 6.9 | 6.6 | 6.3 | 0.7 | 6.9[x] | 5.7 | 4.4 | 4.0 | 2.9 | 6 | 3.9 ± 0.6 | 2.6 |
| − | + | − | − | 1,023 | 6.6 | 6.4 | 6.0 | 5.8 | 0.8 | 6.1[x] | 5.6 | 4.7 | 3.3 | 2.8 | 12 | 4.2 ± 0.3 | 2.3 |
| − | + | − | − | 1,012 | 7.5 | 7.1 | 7.0 | 5.7 | 1.8 | 7.4[x] | 6.8 | 6.8 | 5.6 | 1.8 | 6 | 6.1 ± 0.1 | 0.8 |

[a] Reduction in mean virus titer ($\log_{10}$ PFU/ml) at 39° C. compared to permissive temperature (35° C.).
[b] Groups of 6 suckling mice were inoculated i.c. with $10^4$ PFU virus. Brains were removed 5 days later, homogenized, and titered in Vero cells.
[c] Average of 11 experiments with a total of 64 to 66 mice per group.
[d] Determined by comparing mean viral titers of mice inoculated with mutant virus and concurrent 2A-13 wild type (wt) virus control (n = 6 or 12).
[e] Underlined values indicate a 2.5 or 3.5 $\log_{10}$ PFU/ml reduction in titer in Vero cells or HuH-7 cells, respectively, at indicated temperature when compared to permissive temperature (35° C.).
[x] Small plaque size at 35° C.; small plaques have a diameter of <1.0 mm compared to wild type plaque diameter of 1.5-2.0 mm in Vero cells, or a diameter of <0.4 mm compared to wild type plaque diameter of 0.75 to 1.0 mm in HuH-7 cells.

TABLE 8

Viruses with both ts and sp phenotypes are more restricted in replication in mouse brain than those with only a ts phenotype.

| Cell culture phenotype | Number of viruses | Mean $\log_{10}$ reduction in virus titer from control[b,c] |
|---|---|---|
| ts[a] | 20 | 2.1 ± 0.2 |
| sp | 6 | 3.0 ± 0.6 |
| ts/sp | 16 | 3.5 ± 0.3 |

[a] 20 ts mutant viruses without an sp phenotype were previously described (Example 1).
[b] Determined by comparing mean viral titers of groups of mice inoculated with mutant virus and concurrent 2A-13 parallel-passaged control virus.
[c] Significant difference between ts group and ts/sp group, Tukey-Kramer test (P < 0.05)

TABLE 9

Nucleotide and amino acid differences of the 5-FU mutant DEN4 viruses which produce small plaques in both Vero and HuH-7 cells.

| Virus | Mutations in UTR or in coding regions that result in an amino acid substitution | | | | Mutations in coding regions that do not result in an amino acid substitution | | |
|---|---|---|---|---|---|---|---|
| | Nucleotide position | Gene/ region | Nucleotide change | Amino acid change[b] | Nucleotide position | Gene | Nucleotide change |
| 569 | 826 | prM | G > A | R242K | 1946 | E | C > U |
| | 832 | prM | C > U | P244L | | | |
| | 7546 | NS4B | C > U | A2482V | | | |
| | 10275 | 3' UTR | A > U | n/a | | | |
| | 10279 | 3' UTR | A > U | n/a | | | |
| 574 | 1455 | E | G > U | V452F | 1349 | E | C > U |
| | 1963 | E | U > C | V621A | | | |
| | 3880 | NS2A | A > G | K1260R | | | |
| | 7546 | NS4B | C > U | A2482V | | | |
| | 7615 | NS5 | A > G | N2505S | | | |
| | 10413 | 3' UTR | A > G | n/a | | | |
| 761 | 424 | C | U > C | I108T | none | | |
| | 2280 | E | U > C | F727L | | | |
| | 7131 | NS4B | A > G | T2344A | | | |
| | 7486 | NS4B | A > G | N2462S | | | |
| 1189a | 3303 | NS1 | A > G | R1068G | 6719 | NS4A | U > C |
| | 4812 | NS3 | G > A | V1571I | | | |

TABLE 9-continued

Nucleotide and amino acid differences of the 5-FU mutant DEN4 viruses which produce small plaques in both Vero and HuH-7 cells.

| | Mutations in UTR or in coding regions that result in an amino acid substitution | | | | Mutations in coding regions that do not result in an amino acid substitution | | |
|---|---|---|---|---|---|---|---|
| Virus | Nucleotide position | Gene/ region | Nucleotide change | Amino acid change[b] | Nucleotide position | Gene | Nucleotide change |
| 1269 | 5097 | NS3 | G > A | D1666N | | | |
| | 7182 | NS4B | G > A | G2361S | | | |
| | 2112 | E | U > C | F671L | 542 | prM | C > U |
| | 3256 | NS1 | G > A | G1052E | | | |
| | 3993 | NS2A | U > C | F1298L | | | |
| | 7183 | NS4B | G > U | G2361V | | | |

[a]Virus contains missense mutations in only the non-structural genes.
[b]Amino acid position in DEN4 polyprotein beginning with the methionine residue of the C protein (nt 102-104).
Wild type amino acid on left of amino acid position; mutant amino acid on right.

TABLE 10

Nucleotide and amino acid differences of the 5-FU mutant DEN4 viruses which produce small plaques in only HuH-7 cells.

| | Mutations in UTR or in coding regions that result in an amino acid substitution | | | | Mutations in coding regions that do not result in an amino acid substitution | | |
|---|---|---|---|---|---|---|---|
| Virus | Nucleotide position | Gene/ region | Nucleotide change | Amino acid change[b] | Nucleotide position | Gene | Nucleotide change |
| 311 | 1519 | E | A > G | N473S | 6761 | NS4A | C > U |
| | 2305 | E | G > A | R735K | 10070 | NS5 | U > C |
| | 4896 | NS3 | G > U | A1599S | | | |
| 326 | 1587 | E | C > U | P496S | 1523 | E | G > A |
| | 7546 | NS4B | C > U | A2482V | 6080 | NS3 | U > C |
| | | | | | 10070 | NS5 | U > C |
| 506 | 1455 | E | G > U | V452F | 3887 | NS2A | A > G |
| | 1902 | E | G > A | V601M | 5789 | NS3 | G > C |
| | 7546 | NS4B | C > U | A2482V | | | |
| | 10275 | 3' UTR | A > U | n/a | | | |
| 529 | 777 | prM | U > C | S226P | none | | |
| | 4641 | NS3 | A > G | I1514V | | | |
| | 7153 | NS4B | U > C | V2351A | | | |
| | 8245 | NS5 | U > C | I2715T | | | |
| | 10279 | 3' UTR | A > C | n/a | | | |
| 738[a] | 3540 | NS2A | G > A | E1147K | none | | |
| | 7162 | NS4B | U > C | L2354S | | | |
| 922[a] | 4306 | NS2B | A > G | N1402S | 7736 | NS5 | G > A |
| | 5872 | NS3 | C > U | T1924I | | | |
| | 7163 | NS4B | A > U | L2354F | | | |
| | 10279 | 3' UTR | A > C | n/a | | | |
| 952 | 1449 | E | G > U | V450L | none | | |
| | 1455 | E | G > U | V452F | | | |
| | 7546 | NS4B | C > U | A2482V | | | |
| | 7957 | NS5 | U > C | V2619A | | | |
| | 9543 | NS5 | A > G | I3148V | | | |
| 1012 | 1542 | E | A > G | K481E | 953 | E | A > G |
| | 7162 | NS4B | U > C | L2354S | 1205 | E | G > A |
| | 10542 | 3' UTR | A > G | n/a | 4425 | NS2B | U > C |
| 1021 | 2314 | E | U > C | I738T | 665 | prM | C > A |
| | 3205 | NS1 | C > U | A1035V | 5750 | NS3 | C > U |
| | 4029 | NS2A | U > C | C1310R | 9959 | NS5 | C > U |
| | 7163 | NS4B | A > C | L2354F | | | |
| | 10275 | 3' UTR | A > U | n/a | | | |
| | 10279 | 3' UTR | A > U | n/a | | | |
| 1023 | 2283 | E | G > A | G728R | 1001 | E | C > U |
| | 7182 | NS4B | G > A | G2361S | 1958 | E | A > G |
| | | | | | 3873 | NS2a | U > C |
| | | | | | 8486 | NS5 | C > U |
| 1029 | 850 | prM | C > U | A250V | 3867 | NS2a | C > U |
| | 3087 | NS1 | A > G | T996A | | | |
| | 4891 | NS3 | U > C | I1597T | | | |

TABLE 10-continued

Nucleotide and amino acid differences of the 5-FU mutant DEN4 viruses which produce small plaques in only HuH-7 cells.

| | Mutations in UTR or in coding regions that result in an amino acid substitution | | | | Mutations in coding regions that do not result in an amino acid substitution | | |
|---|---|---|---|---|---|---|---|
| Virus | Nucleotide position | Gene/region | Nucleotide change | Amino acid change[b] | Nucleotide position | Gene | Nucleotide change |
| 1081[a] | 2650 | NS1 | A > G | N850S | 6326 | NS3 | C > U |
| | 7163 | NS4B | A > U | L2354F | 9146 | NS5 | C > U |
| 1083[a] | 3702 | NS2A | G > A | A1201T | 3353 | NS1 | A > G |
| | 7153 | NS4B | U > C | V2351A | 6155 | NS3 | G > A |
| | 10634 | 3' UTR | U > C | n/a | | | |
| 1096 | 892 | prM | G > A | R264Q | 665 | prM | C > A |
| | 7163 | NS4B | A > C | L2354F | 4427 | NS2b | G > A |
| | 8659 | NS5 | C > U | P2853L | | | |
| 1104 | 1692 | E | G > A | V531M | none | | |
| | 5779 | NS3 | C > U | A1893V | | | |
| | 7546 | NS4B | C > U | A2482V | | | |
| 1114 | 709 | prM | A > G | K203R | 1076 | E | U > C |
| | 3693 | NS2A | A > G | I1198V | 1182 | E | C > U |
| | 4614 | NS3 | U > C | F1505L | 5690 | NS3 | C > U |
| | 7546 | NS4B | C > U | A2482V | | | |
| | 9942 | NS5 | A > G | T3281A | | | |
| 1136[a] | 3771 | NS2A | A > G | R1224G | 5621 | NS3 | A > G |
| | 4891 | NS3 | U > C | I1597T | | | |
| | 10275 | 3' UTR | A > U | n/a | | | |

[a]Viruses that contain missense mutations in only the non-structural genes and/or mutations in the UTRs.
[b]Amino acid position in DEN4 polyprotein beginning with the methionine residue of the C protein (nt 102-104).
Wild type amino acid on left of amino acid position; mutant amino acid on right.

TABLE 11

Putative Vero cell adaptation mutations derived from the full set of 5-FU mutant viruses.

| | | 5-FU mutant viruses | | |
|---|---|---|---|---|
| Nucleotide position | Gene/region (a.a. #)[b] | Nucleotide change | Amino acid change | No. of viruses with the mutation |
| 1455 | E (452) | G > U | Val > Phe | 5 |
| 2280 | E (727) | U > C | Phe > Leu | 2 |
| 4891 | NS3 (1597) | U > C | Ile > Thr | 2 |
| 4995 | NS3 (1599) | U > C | Ser > Pro | 8 |
| 7153 | NS4B (2351) | U > C | Val > Ala | 3 |
| 7162 | NS4B (2354) | U > C | Leu > Ser | 4 |
| 7163 | NS4B (2354) | A > U or C | Leu > Phe | 7 |
| 7182 | NS4B (2361) | G > A | Gly > Ser | 2 |
| 7546 | NS4B (2482) | C > U | Ala > Val | 10 |
| 7630 | NS5 (2510) | A > G | Lys > Arg | 1 |
| 10275 | 3' UTR | A > U | n/a[a] | 6 |
| 10279 | 3' UTR | A > C | n/a | 4 |

[a]not applicable
[b]Amino acid position in DEN4 polyprotein beginning with the methionine residue of the C protein (nt 102-104) as residue #1.

TABLE 12

Mutagenic oligonucleotides used to generate recombinant DEN4 viruses containing single 5-FU mutations.

| SEQ ID NO. | Recombinant virus (rDEN4-) | Nucleotide change | Amino acid change | Gene | pUC clone | RE site[a] | Oligonucleotide[b] |
|---|---|---|---|---|---|---|---|
| 23 | 40 | U > C | n/a | 5' UTR | pUC-NheI | BsaWI | CAGTTCCAAAcCGGAAGCTTG |
| 24 | 2650 | A > G | Asn > Ser | NS1 | pUC-NS1 | BsiWI | CCAACGAGCTAtcgTAcGTTCTCTGGG |
| 25 | 3303 | A > G | Arg > Gly | NS1 | pUC-NS1 | StyI | GATTGTGACCATgGcGGCCCATCTTTG |
| 26 | 3442 | A > G | Glu > Gly | NS1 | pUC-NS1 | BlpI | GGAGATTAGGCCgcTGAGcGgtAAAGAAGAG |
| 27 | 3540 | G > A | Glu > Lys | NS2A | pUC-NS1 | BsmI | GTTTGTGGAAaAATGtcTGAGGAGAA |

TABLE 12-continued

Mutagenic oligonucleotides used to generate recombinant DEN4 viruses containing single 5-FU mutations.

| SEQ ID NO. | Recombinant virus (rDEN4-) | Nucleotide change | Amino acid change | Gene | pUC clone | RE site[a] | Oligonucleotide[b] |
|---|---|---|---|---|---|---|---|
| 28 | 3575 | G > A | Met > Ile | NS2A | pUC-NS1 | SspI | CTAGGAAACACATaATATTAGTTGTGG |
| 29 | 3702 | G > A | Ala > Thr | NS2A | pUC-NS2A | BglI | CAGATCCACCTAaCCATAaTGGCAGTG |
| 30 | 3771 | A > G | Arg > Gly | NS2A | pUC-NS2A | AvaI | GGAAACTCACcTCggGAGAGACAGC |
| 31 | 4059 | A > G | Ile > Val | NS2A | pUC-NS2A | BstEII | TTGGGTAGAggTcAccGCACTCATCC |
| 32 | 4062 | A > G | Thr > Ala | NS2A | pUC-NS2A | BsrBI | GTAGAAATAgCcGCtCTCATCCTAG |
| 33 | 4266 | A > G | Ser > Gly | NS2B | pUC-NS2A | SnaBI | GGCGGCTTACGTaATGgGaGGTAGCTCAGC |
| 34 | 4306 | A > G | Asn > Ser | NS2B | pUC-NS2A | AlwNI | CTAGAGAAGGCaGCttctGTGCAGTGG |
| 35 | 4480 | U > C | Val > Ala | NS2B | pUC-NS2A | MscI | CCTTGGcATTCCAGcaACAATGAC |
| 36 | 4812 | G > A | Val > Ile | NS3 | pUC-NS2A | ApoI | GACGTTCAaaTttTaGCCATAGAACC |
| 37 | 4891 | U > C | Ile > Thr | NS3 | pUC-NS2A | KasI | CTGGAGAAAcgGGcGCcGTAACATTAG |
| 38 | 4896 | G > U | Ala > Ser | NS3 | pUC-NS2A | BstEII | GAAATTGGAtCgGTAACcTTAGATTTC |
| 39 | 4907 | A > U | Leu > Phe | NS3 | pUC-NS2A | AclI | GGAGCAGTAACgTTtGATTTCAAACCC |
| 40 | 4995 | U > C | Ser > Pro | NS3 | pUC-NS2A | BsaJI | GTTACCAAAcCtGGgGATTACGTC |
| 41 | 5097 | G > A | Asp > Asn | NS3 | pUC-NS3 | BspHI | GATTAACTATcATGaACTTACACCC |
| 42 | 5695 | A > G | Asp > Gly | NS3 | pUC-NS3 | BanI | GGAAAACCTTTGgcACc**GAGTATCC |
| 43 | 5872 | C > U | Thr > Ile | NS3 | pUC-NS3 | BsrFI | TCCAGTGAtaCCgGCtAGCGCTGCTC |
| 44 | 6106 | A > G | Glu > Gly | NS3 | pUC-NS3 | MscI | GCCTCAGAGGtGgcCAAAGGAAG |
| 45 | 6259 | U > C | Val > Ala | NS3 | pUC-NS3 | BglII | ACATGGAGGcaGAqAg**ATcTGGACTAGA |
| 46 | 7153 | U > C | Val > Ala | NS4B | pUC-NS4A | MscI | AAAGCATGgCc**AAGGATGCTGTC |
| 47 | 7162 | U > C | Leu > Ser | NS4B | pUC-NS4A | BlpI | GCATAATGGACgctAAGCATGACTAAGG |
| 48 | 7163 | A > C | Leu > Phe | NS4B | pUC-NS4A | ApaLI | TTATTGCATAgTGCACg**AAAAGCATG |
| 49 | 7174 | C > U | Ala > Val | NS4B | pUC-NS4A | BsaAI | GGGCCTATTATTTaCg**TAATGGAC |
| 50 | 7182 | G > A | Gly > Ser | NS4B | pUC-NS4A | n/a | CTGCGAATCCTGGtgaTATTATTGC |
| 51 | 7546 | C > U | Ala > Val | NS4B | pUC-NS5A | AclI | CTCATAAAGAAcGttCAAACCCT |
| 52 | 7630 | A > G | Lys > Arg | NS5 | pUC-NS5A | HgaI | CATTAGACAGAcgc**GAGTTTGAAG |
| 53 | 7849 | A > U | Asn > Ile | NS5 | pUC-NS5A | HgaI | TGGCGACgCTCAAGAtaGTGACTGAAG |
| 54 | 8020 | A > U | Asn > Ile | NS5 | pUC-NS5A | ClaI | GAGTCATCaTCgAtaCCAACAATAG |
| 55 | 8092 | A > G | Glu > Gly | NS5 | pUC-NS5A | EcoRI | CTTCAAAACCTGgcTTCTGCATCAAAG |
| 56 | 8281 | U > C | Leu > Ser | NS5 | pUC-NS5B | XmnI | CAAAGATGTTagcAACAGGTTCACAAC |
| 57 | 8730 | A > C | Asn > His | NS5 | pUC-NS5B | AvaI | GGAAAGAAGAAAcAcCCgAGACTGTGC |
| 58 | 8872 | A > G | Lys > Arg | NS5 | pUC-NS5B | PvuI | GGGAACTGGTcGAtcgAGAAAGGGC |
| 59 | 9977 | G > A | Met > Ile | NS5 | pUC-NS5C | SfcI | CCAGTGGATtACtACaGAAGATATGCTC |
| 60 | 10186 | U > C | Ile > Thr | NS5 | pUC-NS5C | AgeI | CAGGAACCTGAcCGGtAAAGAGGAATACG |

TABLE 12-continued

Mutagenic oligonucleotides used to generate recombinant DEN4 viruses containing single 5-FU mutations.

| SEQ ID NO. | Recombinant virus (rDEN4-) | Nucleotide change | Amino acid change | Gene | pUC clone | RE site[a] | Oligonucleotide[b] |
|---|---|---|---|---|---|---|---|
| 61 | 10275 | A > U | n/a | 3' UTR | pUC-NS5C | n/a | CTGTAATTACCAACAtCAAACACCAAAG |
| 62 | 10279 | A > C | n/a | 3' UTR | pUC-NS5C | n/a | CCAACAACAAcCACCAAAGGCTATTG |
| 63 | 10634 | U > C | n/a | 3' UTR | pUC-3'UTR | n/a | GGATTGGTGTTGTcGATCCAACAGG |

[a]Primers were engineered which introduced (underline) or ablated (hatched line) translationally-silent restriction enzyme sites.
[b]Lowercase letters indicate nt changes and bold letters indicate the site of the 5-FU mutation, which in some oligonucleotides differs from the original nucleotide substitution change in order to create a unique restriction enzyme site. The change preserves the codon for the amino acid substitution.

TABLE 13 sp, ts and mouse attenuation phenotypes of rDEN4 mutant viruses encoding single mutations identified in six sp 5-FU mutant viruses.

| 5-FU mutant virus | Virus | Gene/region containing mutation | Mean virus titer ($log_{10}$ PFU/ml) at indicated temp (° C.) Vero cells 35 | Vero cells 39 | Vero cells Δ[a] | HuH-7 cells 35 | HuH-7 cells 39 | HuH-7 cells Δ | Replication in suckling mice[b] n | Mean virus titer ± SE ($log_{10}$ PFU/g brain) | Mean $log_{10}$-unit reduction from value for wt[c] | Replication in HuH-7-SCID mice[d] n | Mean peak virus titer ± SE ($log_{10}$ PFU/ml serum) | Mean $log_{10}$-unit reduction from value for wt[c] |
|---|---|---|---|---|---|---|---|---|---|---|---|---|---|---|
| | 2A-13 | | 7.6 | 7.1 | 0.5 | 7.8 | 6.6 | 1.2 | 30 | 6.5 ± 0.1 | — | 29 | 6.8 ± 0.2 | — |
| | rDEN4 | | 7.6 | 6.8 | 0.8 | 8.0 | 6.7 | 1.3 | 54 | 5.8 ± 0.1 | — | 32 | 6.3 ± 0.2 | — |
| | rDEN4Δ30 | | 7.6 | 6.9 | 0.7 | 7.7 | 5.6 | 2.1 | 30 | 5.6 ± 0.1 | 0.2 | 18 | 5.4 ± 0.2 | 0.9 |
| 738 | parent | | 6.5 | 5.7 | 0.8 | $^{x}$6.9 | 3.1$^{e}$ | 3.8 | 12 | 4.4 ± 0.4 | 2.3 | 9 | 5.4 ± 0.7 | 1.9 |
| | rDEN4-3540 | NS2A | 6.9 | 5.1 | 1.8 | 7.4 | 3.7 | 3.7 | 12 | 4.1 ± 0.3 | 1.7 | 5 | 6.1 ± 0.3 | (+)0.1 |
| | rDEN4-7162 | NS4B | 7.2 | 6.8 | 0.4 | 7.4 | 6.6 | 0.8 | 8 | 5.6 ± 0.3 | 0.3 | 5 | 6.8 ± 0.6 | 0.3 |
| 922 | parent | | 7.3 | 3.8 | 3.5 | $^{x}$7.4 | 3.0 | 4.4 | 12 | 3.5 ± 0.1 | 2.9 | 6 | 6.2 ± 0.2 | 0.4 |
| | rDEN4-4306 | NS2B | $^{x}$5.0 | 2.2 | 2.8 | $^{x}$5.6 | <1.6 | >4.0 | 12 | 1.7 ± 0.1 | 4.1 | 5 | 5.2 ± 0.6 | 1.1 |
| | rDEN4-5872 | NS3 | 5.7 | 2.5 | 3.2 | $^{x}$6.5 | <1.6 | >4.9 | 12 | 4.5 ± 0.3 | 1.3 | 5 | 6.2 ± 0.5 | 0.1 |
| | rDEN4-7163 | NS4B | 7.8 | 7.2 | 0.6 | 8.0 | 7.4 | 0.6 | 6 | 6.2 ± 0.2 | (+)0.1 | 6 | 5.8 ± 0.6 | (+)0.2 |
| | rDEN4-10279 | 3' UTR | 6.9 | 5.7 | 1.2 | 7.7 | 5.7 | 2.0 | 6 | 4.8 ± 0.2 | 0.7 | 4 | 6.7 ± 0.2 | 0.4 |
| 1081 | parent | | 6.9 | 3.9 | 3.0 | $^{x}$5.8 | 1.9 | 3.9 | 12 | 2.6 ± 0.2 | 3.9 | 4 | 4.2 ± 0.5 | 2.4 |
| | rDEN4-2650 | NS1 | 5.1 | 3.0 | 2.1 | $^{x}$5.5 | 2.8 | 2.7 | 12 | 3.0 ± 0.3 | 2.8 | 6 | 4.7 ± 0.5 | 2.2 |
| | rDEN4-7163 | NS4B | 7.8 | 7.2 | 0.6 | 8.0 | 7.4 | 0.6 | 6 | 6.2 ± 0.2 | (+)0.1 | 6 | 5.8 ± 0.6 | (+)0.2 |
| 1083 | parent | | 7.4 | 5.8 | 1.6 | $^{x}$7.4 | <1.6 | ≧5.8 | 12 | 4.5 ± 0.4 | 2.0 | 9 | 4.4 ± 0.3 | 2.9 |
| | rDEN4-3702 | NS2A | 6.8 | 5.6 | 1.2 | 7.6 | 4.7 | 2.9 | 18 | 4.9 ± 0.3 | 0.9 | 7 | 6.3 ± 0.3 | 0.2 |
| | rDEN4-7153 | NS4B | 7.7 | 7.2 | 0.5 | 8.0 | 6.9 | 1.1 | 6 | 5.7 ± 0.1 | 0.2 | 4 | 5.9 ± 0.7 | 0.1 |
| | rDEN4-10634 | 3' UTR | 4.9 | 1.6 | 3.3 | $^{x}$5.7 | <1.6 | ≧4.1 | 12 | 2.4 ± 0.3 | 3.4 | 7 | 3.3 ± 0.4 | 3.6 |
| 1136 | parent | | 5.1 | <1.6 | ≧3.5 | $^{x}$5.7 | <1.6 | ≧4.1 | 6 | 2.9 ± 0.3 | 4.5 | 7 | 4.5 ± 0.4 | 1.2 |
| | rDEN4-3771 | NS2A | 7.0 | 4.6 | 2.4 | $^{x}$7.6 | 3.7 | 3.9 | 12 | 2.6 ± 0.4 | 3.2 | 4 | 6.4 ± 0.2 | (+)0.1 |
| | rDEN4-4891 | NS3 | 7.1 | <1.6 | >5.5 | $^{x}$7.4 | <1.6 | >5.8 | 12 | 2.5 ± 0.3 | 3.5 | 6 | 6.0 ± 0.5 | 0.3 |
| | rDEN4-10275 | 3' UTR | 6.9 | 5.8 | 1.1 | 7.1 | 5.2 | 1.9 | 6 | 5.0 ± 0.3 | 0.5 | 4 | 6.7 ± 0.3 | 0.4 |
| 1189 | parent | | $^{x}$6.3 | 3.8 | 2.5 | $^{x}$5.5 | <1.6 | ≧3.9 | 12 | 3.2 ± 0.4 | 3.7 | 13 | 2.3 ± 0.3 | 3.8 |
| | rDEN4-3303 | NS1 | 6.1 | 4.8 | 1.3 | 6.6 | 3.9 | 2.7 | 8 | 5.7 ± 0.4 | 0.2 | 4 | 6.3 ± 0.3 | 0.8 |
| | rDEN4-4812 | NS3 | 7.0 | 6.3 | 0.7 | 7.1 | 6.3 | 0.8 | 12 | 4.8 ± 0.2 | 1.0 | 5 | 6.1 ± 0.5 | (+)0.5 |
| | rDEN4-5097 | NS3 | $^{x}$5.0 | <1.6 | >3.4 | $^{x}$4.6 | <1.6 | >3.0 | 12 | 1.8 ± 0.1 | 4.0 | 8 | 1.9 ± 0.1 | 4.3 |
| | rDEN4-7182 | NS4B | 7.7 | 6.9 | 0.8 | 7.8 | 6.8 | 1.0 | 6 | 6.2 ± 0.1 | (+)0.1 | 6 | 6.3 ± 0.3 | (+)0.7 |

[a]Reduction in mean virus titer ($log_{10}$ PFU/ml) at 39° C. compared to permissive temperature (35° C.).
[b]Groups of 6 suckling mice were inoculated i.c. with $10^4$ PFU of virus. Brains were removed 5 days later, homogenized, and titered in Vero cells.
[c]Comparison of mean virus titers of mice inoculated with mutant virus and concurrent DEN4 control. Bold denotes ≧50- or ≧100- fold decrease in replication in suckling or SCID-HuH-7 mice, respectively.
[d]Groups of HuH-7-SCID mice were inoculated directly into the tumor with $10^4$ PFU virus. Serum was collected on day 6 and 7 and titered in Vero cells.
[e]Underlined values indicate a 2.5 or 3.5 $log_{10}$ PFU/ml reduction in titer in Vero cells or HuH-7 cells, respectively, at indicated temp when compared to permissive temp (35° C.).
[x]Small plaque size at 35° C.; small plaques have a diameter of <1.0 mm compared to wild type plaque diameter of 1.5-2.0 mm in Vero cells, or a diameter of <0.4 mm compared to wild type plaque diameter of 0.75 to 1.0 mm in HuH-7 cells.

TABLE 14

Phenotypes of rDEN4 mutant viruses encoding single mutations identified in 10 5-FU mutant viruses that are ts in both Vero and HuH-7 cells.

| 5-FU mutant viruses | rDEN4-Mutation (nt position) | Gene/region | Mean virus titer (log₁₀ PFU/ml) at indicated temp (° C.) Vero cells 35 | 37 | 39 | 39 | Δ$^a$ | HuH-7 cells 35 | 37 | 38 | 39 | Δ | n | Replication in 7-day mice$^b$ Mean log₁₀ reduction from wt$^c$ (log₁₀ PFU/g brain) | n | Replication in HuH-7-SCID mice$^d$ Mean log₁₀ reduction from wt$^c$ (log₁₀ PFU/ml serum) |
|---|---|---|---|---|---|---|---|---|---|---|---|---|---|---|---|---|
| 239, 489 | parent | | 7.6 | 6.8 | 5.6 | 3.3$^e$ | 4.3 | 7.6 | 6.7 | 4.7 | 2.5 | 5.1 | 30 | 2.1 | 6 | 0.3 |
| 773 | 4995$^f$ | NS3 | 5.7 | 4.9 | 3.6 | ≤1.6 | >4.1 | 6.4 | 5.7 | 4.0 | ≤1.6 | >4.8 | 6 | 2.9 | | |
| 473 | parent | | 6.7 | 6.3 | 5.4 | 2.0 | 4.7 | 7.2 | 6.7 | 3.7 | 1.9 | 5.3 | 12 | 1.2 | 8 | (+)0.3 |
| | 4480 | NS2B | 6.7 | 6.3 | 6.0 | 5.7 | 1.0 | 7.6 | 7.2 | 6.0 | 5.2 | 2.4 | 6 | 0.7 | | |
| | 4995$^f$ | NS3 | 5.7 | 4.9 | 3.6 | ≤1.6 | >4.1 | 6.4 | 5.7 | 4.0 | ≤1.6 | >4.8 | 6 | 2.9 | | |
| 759 | parent | | 7.2 | 6.9 | 6.4 | 4.7 | 2.5 | 7.5 | 6.8 | 6.3 | 3.1 | 4.4 | 12 | 1.4 | 5 | (+)0.4 |
| | 4995$^f$ | NS3 | 5.7 | 4.9 | 3.6 | ≤1.6 | >4.1 | 6.4 | 5.7 | 4.0 | ≤1.6 | >4.8 | 6 | 2.9 | | |
| | 8020 | NS5 | 7.1 | 6.6 | 6.7 | 5.9 | 1.2 | 7.4 | 7.1 | 6.1 | 5.4 | 2.0 | 6 | 0.5 | | |
| 816 | parent | | 6.8 | 6.4 | 5.8 | 3.9 | 2.9 | 7.5 | 6.2 | 5.5 | 3.1 | 4.4 | 6 | 2.9 | 6 | 0.4 |
| | 4995$^f$ | NS3 | 5.7 | 4.9 | 3.6 | ≤1.6 | >4.1 | 6.4 | 5.7 | 4.0 | ≤1.6 | >4.8 | 6 | 2.9 | | |
| | 7174 | NS4B | 6.9 | 7.1 | 6.9 | 6.1 | 0.8 | 7.5 | 7.2 | 7.1 | 5.6 | 1.9 | 6 | 0.6 | | |
| 938 | parent | | 7.1 | 6.5 | 5.6 | 3.1 | 4.0 | 7.2 | 6.4 | 5.6 | 3.1 | 4.1 | 6 | 1.7 | 6 | 0.5 |
| | 3442 | NS1 | 5.1 | 3.6 | 4.3 | 2.1 | 3.0 | 5.9 | 4.9 | 3.9 | ≤1.6 | 4.3 | 6 | 4.1 | | |
| | 4995$^f$ | NS3 | 5.7 | 4.9 | 3.6 | ≤1.6 | >4.1 | 6.4 | 5.7 | 4.0 | ≤1.6 | >4.8 | 6 | 2.9 | | |
| | 10275 | 3' UTR | 6.9 | 6.4 | 6.4 | 5.8 | 1.1 | 7.1 | 6.8 | 7.1 | 5.2 | 1.9 | 6 | 0.5 | | |
| 173 | parent | | 7.0 | 6.1 | 3.2 | 2.9 | 4.1 | 7.0 | 3.2 | 3.0 | 2.1 | 4.9 | 18 | 2.2 | 6 | 1.1 |
| | 7163 | NS4B | 7.8 | 7.7 | 7.6 | 7.2 | 0.6 | 8.0 | 7.7 | 7.5 | 7.4 | 0.6 | 6 | (+)0.1 | | |
| | 7849 | NS5 | 7.0 | 6.7 | 3.7 | 2.1 | 4.9 | 7.7 | 5.5 | 3.6 | 2.4 | 5.3 | 6 | 3.1 | | |
| | 8872 | NS5 | 7.0 | 6.3 | 6.4 | 4.4 | 2.6 | 7.4 | 6.4 | 5.1 | 2.9 | 4.5 | 6 | 0.1 | | |
| 509 | parent | | 6.2 | 5.8 | 5.5 | 3.4 | 2.8 | 6.5 | 6.1 | 4.5 | ≤1.6 | >4.9 | 6 | 1.9 | 6 | 1.5 |
| | 4266 | NS2B | 5.9 | 6.1 | 6.1 | 5.2 | 0.7 | 6.7 | 6.1 | 5.7 | 5.3 | 1.4 | 6 | 1.0 | | |
| | 8092 | NS5 | 5.0$^x$ | 4.6 | 4.6 | ≤1.6 | >3.4 | 5.6$^x$ | 4.8 | 4.4 | ≤1.6 | >4.0 | 12 | 4.0 | | |
| 1033 | parent | | 6.7 | 6.0 | 5.9 | 4.1 | 2.6 | 6.9 | 5.6 | 4.7 | ≤1.6 | >5.3 | 12 | 1.7 | 5 | 0.7 |
| | 4907 | NS3 | 6.7 | 6.0 | 5.8 | 4.0 | 2.7 | 7.1 | 6.1 | 6.8 | 2.3 | 4.8 | 12 | 1.8 | | |
| | 8730 | NS5 | 7.0 | 6.7 | 6.6 | 6.7 | 0.3 | 7.6 | 7.0 | 7.2 | 6.6 | 1.0 | 12 | 0.6 | | |
| | 9977 | NS5 | 5.6 | 5.5 | 4.6 | 4.1 | 1.5 | 6.4 | 6.1 | 6.2 | 4.6 | 1.8 | 6 | 0.7 | | |

$^a$Reduction in mean virus titer (log₁₀ PFU/ml) at 39° C. compared to permissive temperature (35° C.).
$^b$Groups of 6 suckling mice were inoculated i.c. with 10⁴ PFU of virus. Brains were removed 5 days later, homogenized, and titered in Vero cells.
$^c$Comparison of mean virus titers of mice inoculated with mutant virus and concurrent DEN4 control. Bold denotes ≧50- or ≧100- fold decrease in replication in suckling or SCID-HuH-7 mice, respectively.
$^d$Groups of HuH-7-SCID mice were inoculated directly into the tumor with 10⁴ PFU virus. Serum was collected on day 6 and 7 and titered in Vero cells.
$^e$Underlined values indicate a 2.5 or 3.5 log₁₀ PFU/ml reduction in titer in Vero cells or HuH-7 cells, respectively, at indicated temp when compared to permissive temp (35° C.).
$^f$Data represents the results from a single rDEN4-4995 virus.
$^x$Small plaque size at 35° C.; small plaques have a diameter of <1.0 mm compared to wild type plaque diameter of 1.5-2.0 mm in Vero cells, or a diameter of <0.4 mm compared to wild type plaque diameter of 0.75 to 1.0 mm in HuH-7 cells.

TABLE 15 sp, ts and mouse attenuation phenotypes of rDEN4 mutant viruses encoding single mutations identified in 3 HuH-7 cell-specific ts 5-FU mutant viruses.

| 5-FU mutant viruses | rDEN4-Mutation (nt position) | Gene/region | Mean virus titer (log₁₀ PFU/ml) at indicated temp (° C.) Vero cells 35 | 37 | 39 | 39 | Δ$^a$ | HuH-7 cells 35 | 37 | 38 | 39 | Δ | n | Replication in 7-day mice$^b$ Mean log₁₀ reduction from wt$^c$ (log₁₀ PFU/g brain)₁₀ | n | Replication in HuH-7-SCID mice$^b$ Mean log₁₀ reduction from wt$^c$ (log₁₀ PFU/ml serum) |
|---|---|---|---|---|---|---|---|---|---|---|---|---|---|---|---|---|
| 686 | parent | | 7.0 | 6.7 | 6.7 | 6.4 | 0.6 | 7.3 | 6.8 | 6.4 | 2.2 | 5.1 | 12 | 3.8 | 6 | 1.2 |
| | 3575 | NS2A | 6.9 | 6.9 | 7.1 | 7.0 | 0.0 | 7.9 | 6.8 | 6.9 | 4.9 | 3.0 | 12 | 2.3 | | nd$^e$ |
| | 4062 | NS2A | 6.8 | 6.6 | 6.3 | 4.7 | 2.1 | 6.9 | 6.8 | 7.0 | ≤1.6 | >5.3 | 12 | 2.2 | | nd |
| | 7163 | NS4B | 7.8 | 7.7 | 7.6 | 7.2 | 0.6 | 8.0 | 7.7 | 7.5 | 7.4 | 0.6 | 6 | (+)0.1 | | nd |
| 992 | parent | | 7.3 | 7.1 | 6.8 | 5.9 | 1.4 | 7.4 | 6.9 | 5.0 | ≤1.6 | >5.8 | 6 | 2.7 | 7 | 1.3 |
| | 5695 | NS3 | 5.6 | 4.7 | 4.7 | 3.8 | 1.8 | 6.3 | 5.1 | 3.7 | ≤1.6 | >4.7 | 6 | 2.8 | | nd |
| | 7162 | NS4B | 7.2 | 7.3 | 6.6 | 6.8 | 0.4 | 7.4 | 7.3 | 7.3 | 6.6 | 0.8 | 8 | 0.3 | | nd |

TABLE 15-continued sp, ts and mouse attenuation phenotypes of rDEN4 mutant viruses encoding single mutations identified in 3 HuH-7 cell-specific ts 5-FU mutant viruses.

| 5-FU mutant viruses | rDEN4-Mutation (nt position) | Gene/ region | Mean virus titer ($log_{10}$ PFU/ml) at indicated temp (° C.) Vero cells 35 | 37 | 39 | 39 | Δ[a] | HuH-7 cells 35 | 37 | 38 | 39 | Δ | Replication in 7-day mice[b] n | Mean $log_{10}$ reduction from wt[c] ($log_{10}$ PFU/g brain)$_{10}$ | Replication in HuH-7-SCID mice[b] n | Mean $log_{10}$ reduction from wt[c] ($log_{10}$ PFU/ml serum) |
|---|---|---|---|---|---|---|---|---|---|---|---|---|---|---|---|---|
| 1175 | parent | | 7.4 | 7.1 | 6.9 | 5.3 | 2.1 | 7.6 | 6.5 | 4.7 | 3.3 | 4.3 | 12 | 1.7 | 5 | 1.0 |
| | 7153 | NS4B | 7.7 | 7.7 | 7.6 | 7.2 | 0.5 | 8.0 | 7.8 | 7.5 | 6.9 | 1.1 | 6 | 0.2 | | nd |
| | 10186 | NS5 | 4.3 | 3.7 | 2.4 | <1.6 | >2.7 | 5.1 | <1.6 | <1.6 | <1.6 | >3.5 | 6 | 3.4 | | nd |
| | 10275 | 3' UTR | 6.9 | 6.4 | 6.4 | 5.8 | 1.1 | 7.1 | 6.8 | 7.1 | 5.2 | 1.9 | 6 | 0.5 | | nd |

[a]Reduction in titer ($log_{10}$ PFU/ml) at 39° C. compared to permissive temperature (35° C.).
[b]Groups of 6 suckling mice were inoculated i.c. with $10^4$ PFU virus. Brains were removed 5 days later, homogenized, and titered in Vero cells.
[c]Determined by comparing mean viral titers of mice inoculated with mutant virus and concurrent 2A-13 or rDEN4 wt control.
[d]Underlined values indicate a 2.5 or 3.5 $log_{10}$ PFU/ml reduction in titer in Vero cells or HuH-7 cells, respectively, at indicated temp when compared to permissive temp (35° C.).

TABLE 16

Temperature-sensitive (ts) and mouse brain attenuation (att) phenotypes of additional rDEN4 viruses encoding single 5-FU mutations.

| 5-FU mutant virus | Virus | Gene/ region containing mutation | Mean virus titer ($log_{10}$ PFU/ml) at indicated temp (° C.) Vero cells 35 | 37 | 38 | 39 | Δ[a] | HuH-7 cells 35 | 37 | 38 | 39 | Δ | Replication in suckling mice[b] n | Mean virus titer ± SE ($log_{10}$ PFU/g brain) | Mean $log_{10}$-unit reduction from value for wt[c] |
|---|---|---|---|---|---|---|---|---|---|---|---|---|---|---|---|
| 695 | rDEN4-40 | 5' UTR | 7.4 | 7.2 | 6.7 | 6.2 | 1.2 | 7.6 | 7.5 | 7.1 | 5.8 | 1.8 | | nd[f] | nd |
| 718 | rDEN4-4059 | NS2A | 7.0 | 6.7 | 6.4 | 6.2 | 0.8 | 7.7 | 7.1 | 7.0 | 6.6 | 1.1 | | nd | nd |
| 311 | rDEN4-4896 | NS3 | 7.0 | 6.1 | 5.9 | 4.2 | 2.8 | 6.9[x] | 6.0 | 5.6 | 3.3 | 3.6 | 6 | 4.1 ± 0.4 | 2.0** |
| 695 | rDEN4-6106 | NS3 | 6.8 | 6.3 | 5.9 | 3.9 | 2.9 | 7.1 | 6.0 | 5.2 | 3.4 | 3.7 | | nd | nd |
| 631 | rDEN4-6259 | NS3 | 7.0 | 6.1 | 5.8 | 5.0 | 2.0 | 7.5 | 6.6 | 5.7 | 4.2 | 3.3 | 6 | 2.2 ± 0.2 | 3.9** |
| 695[e] | rDEN4-7546 | NS4B | 7.5 | 7.6 | 7.4 | 6.6 | 0.9 | 7.7 | 7.6 | 7.3 | 5.7 | 2.0 | | nd | nd |
| 718 | rDEN4-7630 | NS5 | 7.0 | 6.9 | 6.9 | 6.4 | 0.6 | 7.4 | 7.4 | 7.2 | 6.8 | 0.6 | 6 | 5.0 ± 0.3 | 0.5 |
| 718 | rDEN4-8281 | NS5 | 6.4 | 6.6 | 6.7 | 5.4 | 1.0 | 7.6 | 7.6 | 7.0 | 5.1 | 2.5 | 6 | 5.0 ± 0.5 | 1.1 |

[a]Reduction in titer ($log_{10}$ PFU/ml) at 39° C. compared to titer at permissive temperature (35° C.).
[b]6 mice were inoculated i.c. with $10^4$ PFU virus in 30 μl inoculum. Brains were removed 5 days later, homogenized, and titered on Vero cells. Limit of detection is 2.0 $log_{10}$ PFU/g.
[c]Determined by comparing mean viral titers of mice inoculated with sample virus and wt rDEN4 control.
[d]Underlined values indicate a 2.5 or 3.5 $log_{10}$ PFU/ml reduction in titer in Vero cells or HuH-7 cells, respectively, at indicated temperature when compared to permissive temperature (35° C.).
[e]The 7546 mutation is also present in nine other 5-FU mutant viruses.
[x]Small plaque size at 35° C.; small plaques have a diameter of <0.4 mm compared to wt plaque diameter of 0.75 to 1.0 mm in HuH-7 cells.
[f]not determined
**The att phenotype is defined as a reduction of >1.5 $log_{10}$ PFU/g compared to wt virus.

TABLE 17

Growth of wt DEN-4 2A-13 in SCID mice transplanted with HuH-7 cells.[a]

| Dose ($log_{10}$ PFU/ml) | Mouse # | Virus titer $log_{10}$ PFU/ml serum day 3 | day 5 | $log_{10}$ PFU/g tissue Brain | Liver | Tumor |
|---|---|---|---|---|---|---|
| 4 | 87 | 2.7 | 5.9 | 2.0 | 6.9 | 8.0 |
| | 88 | 2.0 | 5.9 | 3.8 | 3.3 | 8.0 |
| | 89 | <1.7 | 6.2 | 2.7 | 3.6 | 8.0 |
| | 90 | 1.7 | 3.5 | 3.2 | 3.0 | 7.0 |
| 5 | 84 | <1.7 | 7.2 | 3.2 | 4.0 | 7.0 |
| | 85 | 1.7 | 6.6 | 3.6 | 6.3 | 5.8 |
| 6 | 91 | 4.4 | 8.3 | 6.0 | 7.3 | 8.0 |
| | 92 | 4.2 | 7.7 | 3.3 | 6.9 | 7.3 |
| | 93 | 4.0 | 6.6 | 3.3 | 5.7 | 8.4 |
| | 94 | 4.3 | 8.1 | 5.8 | 7.8 | 7.5 |

[a]SCID mice were injected i.p. with $10^7$ HuH-7 human hepatoma cells. Approximately 8 weeks later, groups of tumor-bearing SCID-HuH-7 mice were inoculated with virus directly into the tumor. Serum and tissues were collected on day 5, processed, and titered in Vero cells.

TABLE 18

Combination of ts mutations, NS3 4995 and NS5 7849, in rDEN4 results in an additive ts phenotype.

| Virus | Mean virus titer ($log_{10}$ PFU/ml) at indicated temp (° C.) | | | | | | | | | | Replication in suckling mice[b] | |
|---|---|---|---|---|---|---|---|---|---|---|---|---|
| | Vero cells | | | | | HuH-7 cells | | | | | Mean virus titer ± SE | Mean $log_{10}$ |
| | 35 | 37 | 38 | 39 | Δ[a] | 35 | 37 | 38 | 39 | Δ | ($log_{10}$ PFU/g brain) | reduction from wt[c] |
| 2A-13 wt | 7.1 | 7.1 | 6.9 | 6.8 | 0.3 | 7.4 | 7.3 | 6.7 | 6.4 | 1.0 | 6.9 ± 0.09 | — |
| rDEN4 wt | 7.0 | 6.8 | 6.6 | 6.4 | 0.6 | 7.5 | 7.3 | 6.7 | 6.4 | 1.1 | 6.5 ± 0.11 | — |
| rDEN4Δ30 | 7.0 | 6.7 | 6.2 | 6.2 | 0.8 | 7.5 | 7.0 | 6.5 | 5.1 | 2.4 | 5.9 ± 0.21 | 0.6 |
| rDEN4-4995 | 5.7 | 4.9 | 3.6 | <u><1.6</u>[d] | >4.1 | 6.4 | 5.7 | 4.0 | <u><1.6</u> | >4.8 | 3.4 ± 0.10 | 3.1 |
| rDEN4-7849 | 7.0 | 6.7 | <u>3.7</u> | <u>2.1</u> | 4.9 | 7.7 | 5.5 | <u>3.6</u> | <u>2.4</u> | 5.3 | 2.6 ± 0.29 | 3.9 |
| rDEN4-4995-7849 | 5.9 | <u>2.8</u> | <u><1.6</u> | <u><1.6</u> | >4.3 | 5.6 | 2.4 | <u><1.6</u> | <u><1.6</u> | >4.0 | 2.3 ± 0.20 | 4.2 |

[a]Reduction in titer ($log_{10}$ PFU/ml) at 39° C. compared to titer at permissive temperature (35° C.).
[b]Groups of 6 suckling mice were inoculated i.c. with $10^4$ PFU virus. Brains were removed 5 days later, homogenized, and titered in Vero cells. The limit of detection is 2.0 $log_{10}$ PFU/g.
[c]Determined by comparing mean viral titers of mice inoculated with sample virus and rDEN4 wt control.
[d]Underlined values indicate a 2.5 or 3.5 $log_{10}$ PFU/ml reduction in titer in Vero cells or HuH-7 cells, respectively, at indicated temperature when compared to permissive temperature.

TABLE 19

The 5-FU mutations are compatible with the Δ30 mutation for replication in the brain of suckling mice.

| Virus | No. of mice/group | Mean virus titer ± SE ($log_{10}$ PFU/g brain)[a] | Mean $log_{10}$-unit reduction from wt[b] |
|---|---|---|---|
| rDEN4 | 12 | 6.0 ± 0.1 | — |
| rDEN4Δ30 | 12 | 5.3 ± 0.1 | 0.7 |
| rDEN4-2650[c] | 12 | 3.7 ± 0.2 | 2.3 |
| rDEN4Δ30-2650 | 12 | 3.9 ± 0.1 | 2.1 |
| rDEN4-4995[d] | 6 | 3.5 ± 0.2 | 2.5 |
| rDEN4Δ30-4995 | 6 | 2.7 ± 0.4 | 3.3 |
| rDEN4-8092[d] | 12 | 2.0 ± 0.1 | 4.0 |
| rDEN4Δ30-8092 | 6 | 3.2 ± 0.2 | 2.8 |
| rDEN4-10634[c] | 12 | 3.8 ± 0.1 | 2.2 |
| rDEN4Δ30-10634 | 12 | 3.6 ± 0.1 | 2.4 |

[a]Groups of 6 suckling mice were inoculated i.c. with $10^4$ PFU of virus. Brains were removed 5 days later, homogenized, and titered in Vero cells.
[b]Comparison of mean virus titers of mice inoculated with mutant virus and rDEN4 control.
[c]Mutation restricts growth in both mouse brain and HuH-7-SCID mice.
[d]Mutation restricts growth in mouse brain only. The 8092 mutation has not been tested in SCID-HuH7 mice.

TABLE 20

Temperature-sensitive and mouse brain attenuation phenotypes of viruses bearing charge-cluster-to-alanine mutations in the NS5 gene of DEN4.

| Mutation[a] | Changed AA Pair | # nt changed | Mean virus titer ($log_{10}$ PFU/ml at indicated temperature (° C.)[b] | | | | | | | | | | Replication in suckling mice[d] | |
|---|---|---|---|---|---|---|---|---|---|---|---|---|---|---|
| | | | Vero Cells | | | | | HuH-7 Cells | | | | | | Mean titer ± SE ($log_{10}$ PFU/g brain) | Mean log reduction from wt[e] |
| | | | 35 | 37 | 38 | 39 | Δ[c] | 35 | 37 | 38 | 39 | Δ | n | | |
| wt (rDEN4) | n/a | 0 | 8.1 | 8.1 | 7.9 | 7.6 | 0.5 | 8.3 | 8.0 | 7.5 | 7.5 | 0.8 | 48 | 6.0 ± 0.16 | — |
| deletion (rDEN4Δ30) | n/a | 30 | 6.3 | 6.1 | 6.1 | 5.7 | 0.6 | 6.9 | 6.3 | 5.9 | 4.7 | 2.2 | 42 | 5.4 ± 0.22 | 0.6 |
| 21-22 | DR | 4 | 7.2 | 6.8 | 6.7 | 6.1 | 1.1 | 7.6 | 7.1 | 7.0 | 4.7 | 2.9 | 6 | 5.0 ± 0.50 | 0.6 |
| 22-23 | RK | 4 | 7.0 | 7.8 | 6.9 | <u>3.7</u> | 3.3 | 7.6 | 7.6 | 6.5 | <u><1.7</u> | >5.9 | 6 | 2.6 ± 0.19 | 2.9 |
| 23-24 | KE | 3 | 6.7 | 6.6 | 6.0 | 6.5 | 0.2 | 7.1 | 7.3 | 5.6 | <u><1.7</u> | >5.4 | 18 | 4.7 ± 0.09 | 1.5 |
| 26-27 | EE | 3 | 7.8 | 7.6 | 6.8 | <u>4.0</u> | 3.8 | 8.4 | 8.2 | 7.3 | <u>4.9</u> | 3.5 | 6 | 5.7 ± 0.30 | +0.1 |
| 46-47 | KD | 3 | 7.4 | 7.4 | 7.3 | 7.0 | 0.4 | 7.8 | 7.8 | 7.3 | 6.8 | 1.0 | 6 | 5.4 ± 0.42 | 0.5 |
| 157-158 | EE | 3 | 6.5 | 7.2 | 5.1 | 5.1 | 1.4 | 7.6 | 7.4 | 5.9 | <u><1.7</u> | >5.9 | 6 | 2.8 ± 0.31 | 2.7 |
| 200-201 | KH | 4 | 5.3 | 4.6 | 5.3 | 4.1 | 1.2 | 5.6 | 4.9 | 3.7 | <u><1.7</u> | >3.9 | 12 | 5.5 ± 0.45 | 0.8 |
| 246-247 | RH | 5 | 6.9 | 5.8 | 5.7 | 5.4 | 1.5 | 6.4 | 6.1 | 6.1 | 5.5 | 0.9 | 6 | 6.1 ± 0.17 | +0.5 |
| 253-254 | EK | 4 | 7.1 | 6.9 | 6.8 | 7.0 | 0.1 | 7.9 | 7.5 | 7.6 | 6.8 | 1.1 | 6 | 6.2 ± 0.13 | +0.6 |
| 356-357 | KE | 3 | 7.7 | 7.6 | 7.0 | 7.0 | 0.7 | 8.0 | 7.3 | 6.4 | <u><1.7</u> | >6.3 | 6 | 3.5 ± 0.58 | 2.0 |
| 387-388 | KK | 5 | 7.7 | 6.1 | 7.0 | <u><1.7</u> | >6.0 | 7.0 | 6.3 | 7.0 | <u><1.7</u> | >5.3 | 6 | 3.1 ± 0.33 | 2.4 |
| 388-389 | KK | 5 | 5.1 | 4.5 | <u><1.7</u> | <u><1.7</u> | >3.4 | 6.1 | 5.0 | <u><1.7</u> | <u><1.7</u> | >4.4 | 6 | 5.0 ± 0.23 | 1.4 |
| 396-397 | RE | 4 | 7.0 | 7.3 | 6.5 | 5.5 | 1.5 | 7.5 | 7.6 | 7.5 | <u><1.7</u> | >5.8 | 18 | 5.4 ± 0.35 | 1.1 |
| 397-398 | EE | 2 | 7.0 | 7.1 | 7.0 | <u>3.0</u> | 4.0 | 8.0 | 7.6 | 7.0 | <u><1.7</u> | >6.3 | 6 | 6.0 ± 0.22 | 0.8 |
| 436-437 | DK | 4 | 4.5 | 3.3 | 3.0 | <u>2.0</u> | 2.5 | 5.7 | 4.5 | <u><1.7</u> | <u><1.7</u> | >4.0 | 12 | 2.3 ± 0.14 | 3.9 |
| 500-501 | RE | 3 | 6.6 | 6.3 | 5.7 | <u>2.3</u> | 4.3 | 7.1 | 6.5 | <u><1.7</u> | <u><1.7</u> | >5.4 | 6 | 6.9 ± 0.49 | +0.7 |

TABLE 20-continued

Temperature-sensitive and mouse brain attenuation phenotypes of viruses bearing charge-cluster-to-alanine mutations in the NS5 gene of DEN4.

| Mutation[a] | Changed AA Pair | # nt changed | Mean virus titer ($\log_{10}$ PFU/ml at indicated temperature (° C.)[b]) | | | | | | | | | | Replication in suckling mice[d] | |
|---|---|---|---|---|---|---|---|---|---|---|---|---|---|---|
| | | | Vero Cells | | | | | HuH-7 Cells | | | | | Mean titer ± SE ($\log_{10}$ PFU/ g brain) | Mean log reduction from wt[e] |
| | | | 35 | 37 | 38 | 39 | Δ[c] | 35 | 37 | 38 | 39 | Δ | n | | |
| 520-521 | EE | 3 | 5.6 | 4.7 | 4.3 | <1.7 | >3.9 | 6.7 | 5.7 | <1.7 | <1.7 | >5.0 | 6 | 5.2 ± 0.48 | 0.2 |
| 523-524 | DK | 4 | 6.6 | 6.3 | 6.3 | 5.8 | 0.8 | 7.1 | 6.6 | <1.7 | <1.7 | >5.4 | 6 | 4.2 ± 0.47 | 1.3 |
| 524-525 | KK | 5 | 7.1 | 6.9 | 6.9 | 6.6 | 0.5 | 7.8 | 7.4 | 7.0 | 5.3 | 2.5 | 6 | 3.4 ± 0.54 | 2.1 |
| 525-526 | KD | 4 | 7.8 | 7.1 | 7.6 | 6.8 | 1.0 | 7.9 | 7.7 | 8.0 | 6.9 | 1.0 | 6 | 3.7 ± 0.64 | 1.8 |
| 596-597 | KD | 3 | 4.6 | 4.0 | 2.6 | <1.7 | >2.9 | 5.7 | 4.9 | 4.0 | <1.7 | >4.0 | 6 | 5.9 ± 0.14 | 0.5 |
| 641-642 | KE | 4 | 7.3 | 6.9 | 6.9 | 5.2 | 2.1 | 7.8 | 7.5 | 7.2 | 6.9 | 0.9 | 6 | 4.7 ± 0.45 | 1.2 |
| 642-643 | ER | 3 | 6.8 | 6.1 | 4.0 | 3.3 | 3.5 | 7.5 | 7.1 | 6.6 | 3.0 | 4.5 | 12 | 2.6 ± 0.15 | 3.6 |
| 645-646 | EK | 4 | 6.3 | 5.3 | 5.9 | 3.1 | 3.2 | 6.4 | 5.8 | 5.5 | 4.5 | 1.9 | 6 | 5.4 ± 0.51 | 0.2 |
| 649-650 | KE | 3 | 6.9 | 6.8 | 6.9 | 6.3 | 0.6 | 7.1 | 7.3 | 7.5 | 7.0 | 0.1 | 12 | 6.4 ± 0.20 | +0.2 |
| 654-655 | DR | 4 | 6.3 | 5.7 | <1.7 | <1.7 | >4.6 | 7.0 | 7.1 | 4.6 | <1.7 | >5.3 | 12 | 1.8 ± 0.10 | 4.0 |
| 750-751 | RE | 3 | 7.1 | 7.1 | 6.9 | 5.7 | 1.4 | 7.8 | 6.9 | 6.5 | 5.6 | 2.2 | 6 | 6.0 ± 0.18 | 0.7 |
| 808-809 | ED | 3 | 4.6 | 4.1 | <1.7 | <1.7 | >2.9 | 5.2 | <1.7 | <1.7 | <1.7 | >3.5 | 6 | 1.8 ± 0.05 | 3.1 |
| 820-821 | ED | 2 | 6.3 | 6.3 | 5.6 | <1.7 | >4.6 | 6.9 | 6.0 | 5.7 | <1.7 | >5.2 | 6 | 5n5 ± 0.33 | 1.2 |
| 827-828 | DK | 4 | 6.9 | 6.3 | 6.3 | 5.9 | 1.0 | 7.5 | 6.9 | 5.0 | <1.7 | >5.8 | 6 | 3.6 ± 0.76 | 2.3 |
| 877-878 | KE | 3 | 7.6 | 7.3 | 7.0 | 7.0 | 0.6 | 7.9 | 7.9 | 7.3 | 5.8 | 2.1 | 12 | 4.4 ± 0.65 | 1.8 |
| 878-879 | EE | 3 | 7.6 | 7.3 | 7.3 | 7.1 | 0.5 | 8.1 | 8.1 | 7.9 | 6.6 | 1.5 | 12 | 2.4 ± 0.10 | 3.8 |

[a]Positions of the amino acid pair mutated to an alanine pair; numbering starts at the amino terminus of the NS5 protein.
[b]Underlined values indicate a 2.5 or 3.5 log10 PFU/ml reduction in titer in Vero or HuH-7 cells, respectively, at the indicated temperatures when compared to permissive temperature (35° C.).
[c]Reduction in titer (log10 PFU/ml) at 39° C. compared to permissive temperature (35° C.).
[d]Groups of six mice were inoculated i.c. with 4.0 log10 PFU virus in a 30 µl inoculum. The brain was removed 5 days later, homogenized, and titered in Vero cells.
[e]Determined by comparing mean viral titers in mice inoculated with sample virus and concurrent wt controls (n = 6). The attenuation phenotype is defined as a reduction of ≧1.5 log10 PFU/g compared to wt virus; reductions of ≧1.5 are listed in boldface.

TABLE 21

SCID-HuH-7 attenuation phenotypes of viruses bearing charge-cluster-to-alanine mutations in the NS5 gene of DEN4.

| Mutation[a] | AA changed | n | Replication in SCID-HuH-7 mice[b] | |
|---|---|---|---|---|
| | | | Mean peak virus titer ± SE ($\log_{10}$ PFU/ml serum) | Mean log reduction from wt[c] |
| wt | na | 21 | 5.4 ± 0.4 | — |
| Δ30 | na | 4 | 3.7 ± 0.6 | 2.5 |
| 23-24 | KE | 19 | 4.7 ± 0.5 | 1.3 |
| 157-158 | EE | 6 | 4.6 ± 0.6 | 1.3 |
| 200-201 | KH | 12 | 3.7 ± 0.2 | 2.6 |
| 356-357 | KE | 10 | 6.3 ± 0.7 | (−) 1.1 |
| 396-397 | RE | 12 | 4.4 ± 1.3 | 1.2 |
| 397-398 | EE | 6 | 6.0 ± 0.5 | (−) 0.1 |
| 436-437 | DK | 6 | 3.6 ± 0.2 | 2.6 |
| 500-501 | RE | 8 | 5.1 ± 0.4 | 1.1 |
| 523-524 | DK | 5 | 5.3 ± 0.7 | 0.6 |
| 750-751 | RE | 8 | 5.1 ± 0.4 | 1.1 |
| 808-809 | ED | 8 | 3.2 ± 0.4 | 3.0 |
| 827-828 | DK | 5 | 2.9 ± 0.2 | 1.6 |
| 878-879 | EE | 5 | 4.4 ± 0.7 | 1.5 |

[a]Positions of the amino acid pair changed to a pair of alanines; numbering starts at the amino terminus of the NS5 protein.
[b]Groups of SCID-HuH-7 mice were inoculated directly into the tumor with $10^4$ PFU virus. Serum was collected on days 6 and 7 and titered in Vero cells.
[c]Comparison of mean virus titers of mice inoculated with mutant virus and concurrent DEN4 control. Bold denotes a ≧100-fold decrease in replication. A (−) sign indicates an increase in replication relative to wt.

TABLE 22

Combination of paired charge-cluster-to-alanine mutations into double-pair mutant viruses.

| Mutation Pair 1 | Mutation Pair 2 | Recovered |
|---|---|---|
| 23-24 | 200-201 | Yes |
| 23-24 | 356-357 | Yes |
| 23-24 | 396-397 | Yes |
| 23-24 | 523-524 | Yes |
| 23-24 | 827-828 | No |
| 157-158 | 200-201 | No |
| 157-158 | 356-357 | No |
| 157-158 | 396-397 | No |
| 157-158 | 523-524 | Yes |
| 157-158 | 827-828 | No |
| 827-828 | 200-201 | No |
| 827-828 | 356-357 | No |
| 827-828 | 396-397 | Yes |
| 827-828 | 523-524 | No |

TABLE 23

Temperature-sensitive and mouse brain attenuation phenotypes of double charge-cluster-to-alanine mutants of the NS5 gene of rDEN4.

| Mutation[a] | Charged AA Pair | # nt changed | Mean virus titer (log10 PFU/ml) at indicated temperature (° C.)[b] | | | | | | | | | | Replication in suckling mice[d] | | |
|---|---|---|---|---|---|---|---|---|---|---|---|---|---|---|---|
| | | | Vero Cells | | | | | HuH-7 cells | | | | | Mean virus titer ± SE | Mean log reduction |
| | | | 35 | 37 | 38 | 39 | Δ[c] | 35 | 37 | 38 | 39 | Δ | n | (log$_{10}$ PFU/g brain) | from wt[e] |
| wt | n/a | 0 | 8.1 | 8.1 | 7.9 | 7.6 | 0.5 | 8.3 | 8.0 | 7.5 | 7.5 | 0.8 | 48 | 6.0 ± 0.16 | — |
| Δ30 | n/a | 30 | 6.3 | 6.1 | 6.1 | 5.7 | 0.6 | 6.9 | 6.3 | 5.9 | 4.7 | 2.2 | 42 | 5.4 ± 0.22 | 0.6 |
| 23-24 | KE | 3 | 6.7 | 6.6 | 6.0 | 6.5 | 0.2 | 7.1 | 7.3 | 5.6 | <1.7 | >5.4 | 18 | 4.7 ± 0.09 | 1.5 |
| 200-201 | KH | 4 | 5.3 | 4.6 | 5.3 | 4.1 | 1.2 | 5.6 | 4.9 | 3.7 | <1.7 | >3.9 | 12 | 5.5 ± 0.45 | 0.8 |
| 23-24; 200-201 | KE, KH | 7 | 7.1 | 6.5 | 6.6 | <1.7 | >5.4 | 7.8 | 7.3 | <1.7 | <1.7 | >6.1 | 6 | 5.8 ± 0.16 | 0.6 |
| 23-24 | KE | 3 | 6.7 | 6.6 | 6.0 | 6.5 | 0.2 | 7.1 | 7.3 | 5.6 | <1.7 | >5.4 | 18 | 4.7 ± 0.09 | 1.5 |
| 356-357 | KE | 3 | 7.7 | 7.6 | 7.0 | 7.0 | 0.7 | 8.0 | 7.3 | 6.4 | <1.7 | >6.3 | 6 | 3.5 ± 0.58 | 2.0 |
| 23-24; 356-357 | KE, KE | 6 | | | | | | | | | | | | | |
| 23-24 | KE | 3 | 6.7 | 6.6 | 6.0 | 6.5 | 0.2 | 7.1 | 7.3 | 5.6 | <1.7 | >5.4 | 18 | 4.7 ± 0.09 | 1.5 |
| 396-397 | RE | 4 | 7.0 | 7.3 | 6.5 | 5.5 | 1.5 | 7.5 | 7.6 | 7.5 | <1.7 | >5.8 | 18 | 5.4 ± 0.35 | 1.1 |
| 23-24; 396-397 | KE, RE | 7 | 6.3 | 4.9 | <1.7 | <1.7 | >4.6 | 7.1 | 6.0 | 5.6 | <1.7 | >5.4 | 6 | 3.7 ± 0.44 | 2.7 |
| 157-158 | EE | 3 | 6.5 | 7.2 | 5.1 | 5.1 | 1.4 | 7.6 | 7.4 | 5.9 | <1.7 | >5.9 | 6 | 2.8 ± 0.31 | 2.7 |
| 396-397 | RE | 4 | 7.0 | 7.3 | 6.5 | 5.5 | 1.5 | 7.5 | 7.6 | 7.5 | <1.7 | >5.8 | 18 | 5.4 ± 0.35 | 1.1 |
| 157-158; 396-397 | EE, RE | 7 | | | | | | | | | | | 6 | 2.0 ± 0.12 | 4.8 |
| 157-158 | EE | 3 | 6.5 | 7.2 | 5.1 | 5.1 | 1.4 | 7.6 | 7.4 | 5.9 | <1.7 | >5.9 | 6 | 2.8 ± 0.31 | 2.7 |
| 523-524 | DK | 4 | 6.6 | 6.3 | 6.3 | 5.8 | 0.8 | 7.1 | 6.6 | <1.7 | <1.7 | >5.4 | 6 | 4.2 ± 0.47 | 1.3 |
| 157-158; 523-524 | EE, DK | 7 | 5.6 | 3.9 | <1.7 | <1.7 | >3.9 | 6.3 | 4.1 | <1.7 | <1.7 | >4.6 | | | |
| 396-397 | RE | 4 | 7.0 | 7.3 | 6.5 | 5.5 | 1.5 | 7.5 | 7.6 | 7.5 | <1.7 | >5.8 | 6 | 4.8 ± 0.54 | 1.6 |
| 827-828 | DK | 4 | 6.9 | 6.3 | 6.3 | 5.9 | 1.0 | 7.5 | 6.9 | 5.0 | <1.7 | >5.8 | 6 | 3.6 ± 0.76 | 2.3 |
| 396-397; 827-828 | RE, DK | 8 | 7.0 | 6.5 | 6.0 | <1.7 | 5.3 | >6.7 | 5.7 | <1.7 | <1.7 | >5.0 | 6 | 4.7 ± 0.10 | 1.2 |

[a]Positions of the amino acid pair mutated to an alanine pair; numbering starts at the amino terminus of the NS5 protein.
[b]Underlined values indicate a 2.5 or 3.5 log$_{10}$ PFU/ml reduction in titer in Vero or HuH-7 cells respectively, at the indicated temperatures when compared to permissive temperature (35° C.).
[c]Reduction in titer (log$_{10}$ PFU/ml) at 39° C. compared to permissive temperature (35° C.).
[d]Groups of six suckling mice were inoculated i.c. with 4.0 log$_{10}$ PFU virus in a 30 μl inoculum. Brains were removed 5 days later, homogenized, and titered in Vero cells.
[e]Determined by comparing mean viral titers in mice inoculated with sample virus and concurrent wt controls (n = 6); reductions ≧ 1.5 are listed in boldface.

TABLE 24

SCID-HuH-7 attenuation phenotypes of double charge-cluster-to-alanine mutants of the NS5 gene of rDEN4.

| Mutation[a] | Charged AA Pair | n | Replication in SCID-HuH-7 mice[b] | |
|---|---|---|---|---|
| | | | Mean peak virus titer ± SE (log$_{10}$ PFU/ml serum) | Mean log reduction from wt[c] |
| wt | n/a | 21 | 5.4 ± 0.4 | — |
| Δ30 | n/a | 4 | 3.7 ± 0.6 | 2.5 |
| 23-24 | KE | 19 | 4.7 ± 0.5 | 1.3 |
| 200-201 | KH | 12 | 3.7 ± 0.2 | 2.6 |
| 23-24; 200-201 | KE, KH | 13 | 3.4 ± 0.1 | 2.9 |
| 23-24 | KE | 19 | 4.7 ± 0.5 | 1.3 |
| 356-357 | KE | 10 | 6.3 ± 0.7 | (+) 1.1 |
| 23-24; 356-357 | KE, KE | 4 | 3.6 ± 0.3 | 2.3 |
| 23-24 | KE | 19 | 4.7 ± 0.5 | 1.3 |
| 396-397 | RE | 12 | 4.4 ± 1.3 | 1.2 |
| 23-24; 396-397 | KE, RE | 10 | 3.4 ± 0.5 | 3.3 |
| 157-158 | EE | 6 | 4.6 ± 0.6 | 1.3 |
| 396-397 | RE | 12 | 4.4 ± 1.3 | 1.2 |
| 157-158; 396-397 | EE, RE | 6 | 2.2 ± 0.2 | 3.6 |
| 157-158 | EE | 6 | 4.6 ± 0.6 | 1.3 |
| 523-524 | DK | 5 | 5.3 ± 0.7 | 0.6 |
| 157-158; 523-524 | EE, DK | 3 | 5.1 ± 0.6 | 0.8 |
| 396-397 | RE | 12 | 4.4 ± 1.3 | 1.2 |
| 827-828 | DK | 5 | 2.9 ± 0.2 | 1.6 |
| 396-397; 827-828 | RE, DK | 4 | 4.1 ± 0.7 | 0.4 |

[a]Positions of the amino acid pair mutated to an alanine pair; numbering starts at the amino terminus of the NS5 protein.
[b]Groups of SCID-HuH-7 mice were inoculated directly into the tumor with 10$^4$ PFU of virus. Serum was collected on days 6 and 7 and titered in Vero cells.
[c]Comparison of mean virus titers of mice inoculated with mutant virus and concurrent DEN4 control. Bold denotes a ≧100-fold decrease in replication. A (+) sign indicates an increase in replication relative to wt.

TABLE 25

Phenotypes (temperature sensitivity, plaque size and replication in mouse brain and SCID-HuH-7 mice) of wt DEN4 and viruses containing the Δ30 and 7129 mutations.

| | | Mean virus titer ($log_{10}$ PFU/ml) at indicated temperature (° C.) | | | | | | | Replication in suckling mouse brain[c] | | | Replication in SCID-HuH-7 mice[e] | | |
|---|---|---|---|---|---|---|---|---|---|---|---|---|---|---|
| | | VERO | | | HUH7 | | | C6/36 | | Mean virus titer ± SE ($log_{10}$ PFU/g brain) | Mean log reduction from wt[d] | | Mean peak virus titer ± SE ($log_{10}$ PFU/ml serum)[f] | Mean log reduction from wt[d] |
| Virus ID | Mutation[a] | 35 | 39 | Δ[b] | 35 | 39 | Δ | 32 | n | | | n | | |
| 1-TD-1A | wt | 7.3 | 6.8 | 0.5 | 8 | 6.8 | 1.2 | 8.3 | 36 | 6.1 ± 0.21 | — | 21 | 5.4 ± 0.4 | — |
| p4Δ30 | Δ30 | 6.6 | 6.5 | 0.1 | 7.4 | 6.4 | 1.0 | | 42 | 5.4 ± 0.22 | 0.6 | 4 | 3.7 ± 0.6 | 2.5 |
| 5-1A1 | C7129U | 6.7 | 6.5 | 0.2 | 7.5 | 6 | 1.5 | 7.6* | 6 | 6.2 ± 0.30 | 0.0 | | | |
| rDEN4-7129-1A | C7129U | 7.3 | 7.0 | 0.3 | 7.6 | 6.3 | 1.3 | 7.5* | 6 | 7.2 ± 0.12 | (−) 0.4 | 4 | 5.4 ± 0.8 | (−) 0.8 |
| rDEN4Δ30-7129 | C7129U + Δ30 | 7.0 | | | | | | 7.1* | | | | | | |

[a]Position and identity of the mutated nucleotides.

[b]Reduction in titer ($log_{10}$ PFU/ml) at 39° C. compared to permissive temperature (35° C.).

[c]Groups of six suckling mice were inoculated i.c. with 4.0 $log_{10}$ PFU virus in a 30 μl inoculum. The brain was removed 5 days later, homogenized, and titered in Vero cells.

[d]Determined by comparing mean viral titers in mice inoculated with sample virus and concurrent wt controls (n = 6). The attenuation phenotype is defined as a ≧50- or ≧100-fold decrease in replication in suckling or SCID-HuH-7 mice, respectively. A (−) sign indicates an increase in replication relative to the wt control.
[e]Groups of SCID-HuH-7 mice were inoculated directly into the tumor with $10^4$ PFU virus. Serum was collected on days 6 and 7 and titered in Vero cells.
*Small plaque size.

TABLE 26

The 5-fluorouracil 5-1A1 small plaque mutant demonstrates a restriction of midgut infection following oral infection of *Aedes aegytpi* mosquitoes:

| Virus tested | Dose ingested ($log_{10}$ PFU)[a] | No. mosquitoes tested | Midgut-only infection[b] | Disseminated infection[c] | Total no. infected[d,e] |
|---|---|---|---|---|---|
| wtDEN4 | 4.5 | 19 | 1 (5%) | 17 (89%) | 18 (95%) |
| (2A-13) | 3.5 | 26 | 9 (35%) | 7 (27%) | 16 (62%) |
| | 2.5 | 28 | 1 (4%) | 0 | 1 (4%) |
| | | | | $OID_{50}$ = 3.9 | $OID_{50}$ = 3.3 |
| 5-1A1 | 3.5 | 34 | 4 (12%) | 2 (6%) | 6 (18%) |
| | 2.5 | 9 | 0 | 1 (11%) | 1 (11%) |
| | 1.5 | 23 | 0 | 0 | 0 |
| | | | | | $OID_{50}$ ≧ 3.9 |

[a]Amount of virus ingested, assuming a 2 μl bloodmeal.

[b]Number (percentage) of mosquitoes with detectable dengue virus antigen in midgut tissue, but no detectable dengue virus antigen in head; mosquitoes were assayed 21 days post-feed, and dengue virus antigen was identified by IFA.

[c]Number (percentage) of mosquitoes with detectable dengue virus antigen in both midgut and head tissue.

[d]Total number (percentage) of mosquitoes with detectable dengue virus antigen.

[e]The proportion of total infections caused by wild type DEN4 was significantly higher than the proportion caused by 5-1A1 (logistic regression, N = 426, P < 0.0001). There were too few disseminated infection caused by 5-1A1 to permit statistical analysis.

TABLE 27

The 5-fluorouracil 5-1A1 small plaque mutant demonstrates a restriction of infection following intrathoracic inoculation of *Toxorhynchites splendens* mosquitoes.

| Virus tested | Dose ingested ($\log_{10}$ PFU)[a] | No. mosquitoes tested | No (%) infected[c] |
|---|---|---|---|
| wtDEN4 | 4.0 | 5 | 5 (100) |
| (2A-13) | 3.0 | 4 | 4 (100) |
|  | 2.0 | 4 | 1 (25) |
|  |  |  | $MID_{50}$ = 2.3 $\log_{10}$ PFU |
| 5-1A1 | 3.0 | 9 | 0 |
|  | 2.0 | 7 | 1 (14) |
|  | 1.0 | 7 | 0 |
|  |  |  | $MID_{50}$ > 3.0 $\log_{10}$ PFU |

[a]Amount of virus inoculated in a 0.22 μl inoculum.
[b]Number (percentage) of mosquitoes with detectable dengue virus antigen in head tissue; mosquitoes were assayed 14 days post-inoculation, and dengue virus antigen was identified by IFA.
[c]The proportion of infections caused by wild type DEN4 was significantly higher than the proportion caused by 5-1A1 (logistic regression, N = 36, P < 0.01).

TABLE 28

Mutagenesis primers for the deletion or swap of sequences in DEN4 showing conserved differences from tick-borne flaviviruses.

| DEN4 nucleotides[1] | Type of mutation[2] | Mutagenesis Primer[3] | SEQ ID NO |
|---|---|---|---|
| 10508-10530 | Δ | CTGGTGGAAGCCCAACACAAAAAC | 64 |
| 10508-10530 | swap | CTGGTGGAAGGAAGAGAGAAATTG GCAACTCCCCAACACAAAAAC | 65 |
| 10535-10544 | Δ | AGACCCCCCCAAGCATATTGAC | 66 |
| 10535-10544 | swap | AGACCCCCCCAATATTTCCTCCTC CTATAGCATATTGAC | 67 |
| 10541-10544 | Δ | CCCAACACAAAGCATATTGAC | 68 |

[1]Nucleotides numbered 5' to 3', in the opposite direction from FIG. 5.3
[2]Δ: deletion of specified DEN4 nucleotides; swap: exhange of specified DEN4 nucleotides with homologous sequence from Langat
[3]no swap mutation was made for nucleotides 10541-10544

TABLE 29

Virus titer and plaque size of 3' UTR mutant viruses in Vero and C6/36 cells.

| | Vero | | C6/36 | |
|---|---|---|---|---|
| Virus | Titer ($\log_{10}$ PFU/ml) | Plaque size[1] | Titer ($\log_{10}$ PFU/ml) | Plaque size |
| rDEN4Δ10508-10530 | 8.1 | wt | 7.5 | wt |
| rDEN4swap10508-10530 | 5.4 | sp | 6.6 | wt |
| rDEN4Δ10535-10544 | 5.8 | wt | 7.0 | sp |
| rDEN4swap10535-10544 | 7.0 | wt | 7.3 | wt |
| rDEN4Δ10541-10544 | 6.4 | wt | >7.0 | wt |

[1]Plaque size is designated as equivalent to wild type (wt) or ≦50% of wild type (sp) on the designated cell type.

TABLE 30

Infectivity of wt DEN4 and 3' UTR mutants for *Toxorhynchites splendens* via intrathoracic inoculation.

| Virus | Dose ($\log_{10}$ PFU)[a] | No. mosquitoes tested | % Infected[b] | $MID_{50}$ ($\log_{10}$ PFU) |
|---|---|---|---|---|
| rDEN4 wt | 3.3 | 6 | 83 | 2.3 |
|  | 2.3 | 7 | 57 |  |
|  | 1.3 | 6 | 0 |  |
|  | 0.3 | 6 | 0 |  |
| rDEN4Δ10508-10530 | 4.4 | 8 | 0 |  |
|  | 3.4 | 9 | 11 |  |
|  | 2.4 | 4 | 0 |  |

[a]Amount of virus inoculated in a 0.22 μl inoculum.
[b]Percentage of mosquitoes with detectable dengue virus antigen in head tissue; mosquitoes were assayed 14 days post-inoculation, and dengue virus antigen was identified by IFA

TABLE 31

Infectivity of 3' UTR swap mutant viruses for *Aedes aegypti* fed on an infectious bloodmeal.

| Virus Tested | Dose ingested ($\log_{10}$ PFU)[a] | No. Mosquitoes Tested | Total No. Infected[b,c] | Disseminated Infections[c,d] |
|---|---|---|---|---|
| rDEN4 | 3.8 | 18 | 11 (61%) | 4 (22%) |
|  | 2.8 | 15 | 5 (33%) | 1 (6%) |
|  | 1.8 | 15 | 0 | 0 |
|  |  |  | $OID_{50}$ = 3.4 | $OID_{50}$ = ≧4.2 |
| rDEN4swap 10535-10544 | 3.8 | 25 | 5 (20%) | 2 (8%) |
|  | 2.8 | 25 | 0 | 0 |
|  | 1.8 | 20 | 0 | 0 |
|  |  |  | $OID_{50}$ = ≧4.2 |  |

[a]Amount of virus ingested, assuming a 2 μl bloodmeal.
[b]Number (%) of mosquitoes with detectable dengue virus antigen in the midgut tissue; mosquitoes were assayed either 14 d post-feed and dengue virus antigen was identified by IFA.
[c]At a dose of 3.8 $\log_{10}$ PFU, rDEN4swap10535-10544 infected significantly fewer mosquitoes at the midgut than wt rDEN4 (Fisher's exact test, N = 43, P < 0.01), although disseminated infections were not significantly different (Fisher's exact test, N = 43, P = 0.38).
[d]Number (%) of mosquitoes with detectable dengue virus antigen in the head tissue.

TABLE 32

Putative Vero cell adaptation mutations derived from the set of 5-FU mutant viruses and other DEN4 viruses passaged in Vero cells.

| | | 5-FU mutant viruses | | | Other DEN viruses passaged in Vero cells | | |
|---|---|---|---|---|---|---|---|
| Nucleotide position | Gene/region (a.a. #)[b] | Nucleotide change | Amino acid change | No. of viruses with the mutation | Virus | Nucleotide change | Amino acid change |
| 1455 | E (452) | G > U | val > phe | 5 | | | |
| 2280[1,2,3] | E (727) | U > C | phe > leu | 2 | | | |
| 4891[2,3] | NS3 (1597) | U > C | ile > thr | 2 | | | |
| 4995[1,2] | NS3 (1599) | U > C | ser > pro | 8 | | | |
| 7153 | NS4B (2351) | U > C | val > ala | 3 | 2AΔ30 | U > C | val > ala |
| 7162 | NS4B (2354) | U > C | leu > ser | 4 | 2A-1 | U > C | leu > ser |
| 7163 | NS4B (2354) | A > U or C | leu > phe | 7 | rDEN4Δ30 | A > U | leu > phe |
| | | | | | 2A-13-1A1 | A > U | leu > phe |
| 7182[1,2,3] | NS4B (2361) | G > A | gly > ser | 2 | | | |
| 7546 | NS4B (2482) | C > U | ala > val | 10 | | | |
| 7630[3] | NS5 (2510) | A > G | lys > arg | 1 | 814669 | A > G | lys > arg |
| 10275 | 3' UTR | A > U | n/a[c] | 6 | | | |
| 10279 | 3' UTR | A > C | n/a | 4 | | | |

[a]Conservation with DEN1, DEN2, or DEN3 is designated by superscript. Lack of conservation is designated by no superscript.
[b]Amino acid position in DEN4 polyprotein beginning with the methionine residue of the C protein (nt 102-104) as residue #1.
[c]not applicable

TABLE 33

Sequence analysis of rDEN2/4Δ30 clone 27(p4)-2-2A2.

| | | Mutation | |
|---|---|---|---|
| Nucleotide | Gene | Nucleotide | Amino acid |
| 743 | M anchor | G > A | Gly > Glu |
| 1493 | E | C > U | Ser > Phe |
| 7544* | NS4B | C > U | Ala > Val |

*Same as DEN4 nucleotide position 7546

TABLE 34

Sequence analysis of rDEN2/4Δ30 clone 27(p3)-2-1A1.

| | | Mutation | |
|---|---|---|---|
| Nucleotide | Gene | Nucleotide | Amino acid |
| 1345 | E | U > C | Tyr > His |
| 4885* | NS3 | G > A | Glu > Lys |
| 8297 | NS5 | G > A | Arg > Lys |

*Codon adjacent to 5-FU mutation 4891

TABLE 35

Recombinant virus rDEN2/4Δ30 bearing Vero adaptation mutations can be recovery and titered on Vero cells.

| | Virus titer in indicated cell line[1] ($\log_{10}$ PFU/ml) | | Virus titer following recovery in Vero cells ($\log_{10}$ PFU/ml) |
|---|---|---|---|
| Virus | C6/36 | Vero | |
| rDEN2/4Δ30 wt | 5.2 | 1.7 | <0.7 |
| rDEN2/4Δ30-7153 | 5.4 | 5.2 | <0.7 |
| rDEN2/4Δ30-7162 | 5.4 | 5.3 | nd[2] |
| rDEN2/4Δ30-7182 | 4.7 | 4.9 | 2.3 |
| rDEN2/4Δ30-7630 | 5.3 | 4.8 | 1.3 |
| rDEN2/4Δ30-7153-7163 | 5.1 | 4.7 | nd |
| rDEN2/4Δ30-7153-7182 | 4.1 | 3.2 | nd |
| rDEN2/4Δ30-7546-7630 | 5.2 | 5.2 | nd |

[1]Virus recovered following transfection of C6/36 mosquito cells was terminally diluted once in C6/36 cells and titered simultaneously in C6/36 cells and Vero cells.
[2]not determined

TABLE 36

Putative Vero cell adaptation mutations of dengue type 4 virus and the corresponding wildtype amino acid residue in other dengue viruses.

| | | | Amino acid in indicated wt dengue virus[b] | | | |
|---|---|---|---|---|---|---|
| Mutation | Amino acid position[a] | Mutant residue | DEN4 | DEN1 | DEN2 | DEN3 |
| 1455 | 452 | F | V | I | A | A |
| 2280 | 727 | L | F[c] | F | F | F |
| 4891 | 1597 | T | I | V | I | I |
| 4995 | 1632 | P | S | S | S | N |
| 7129 | 2343 | L | P | P | P | P |
| 7153 | 2351 | A | V | F | F | L |
| 7162 | 2354 | S | L | V | V | V |
| 7163 | 2354 | F | L | V | V | V |
| 7182 | 2361 | S | G | G | G | G |
| 7546 | 2482 | V | A | L | T | V |
| 7630 | 2510 | R | K | S | S | K |

[a]Amino acid position is given for the polyprotein of DEN4
[b]DEN4 = rDEN4 (GenBank AF326825); DEN1 = Western pacific (GenBank DVU88535); DEN2 = New Guinea C (GenBank AF038403); DEN3 = H87 (GenBank M93130)
[c]Underlined nucleotides are shared between DEN4 and one or more additional DEN types.

TABLE 37

Mutations known to attenuate dengue type 4 virus and the corresponding wildtype amino acid residue in other dengue virus.

| | Mutation | Amino acid position[a] | Mutant residue | Amino acid in indicated wt dengue virus[b] | | | |
|---|---|---|---|---|---|---|---|
| | | | | DEN4 | DEN1 | DEN2 | DEN3 |
| 5-FU mutations | 2650 | 850 | S | N[d] | N | N | N |
| | 3442 | 1114 | G | E | E | E | E |
| | 3540 | 1147 | K | E | E | E | E |
| | 3575 | 1158 | I | M | L | A | M |
| | 3771 | 1224 | G | R | R | K | R |
| | 4062 | 1321 | A | T | L | A | T |
| | 4306 | 1402 | S | N | E | D | D |
| | 4891 | 1597 | T | I | V | I | I |
| | 4896 | 1599 | S | A | A | A | A |
| | 4907 | 1602 | F | L | L | L | L |
| | 4995 | 1632 | P | S | S | S | N |
| | 5097 | 1666 | N | D | D | D | D |
| | 5695 | 1865 | G | D | D | D | D |
| | 6259 | 2053 | A | V | V | V | V |
| | 7129[c] | 2343 | L | P | P | P | P |
| | 7849 | 2583 | I | N | K | N | K |
| | 8092 | 2664 | G | E | Q | Q | Q |
| | 10186 | 3362 | T | I | I | I | I |
| | 10634 | 3′ UTR | — | — | — | — | — |
| Charge-cluster-to-alanine mutations | 22, 23 | 2509, 2510 | AA | RK | KS | KS | RK |
| | 23, 24 | 2510, 2511 | AA | KE | SE | SE | KE |
| | 157, 158 | 2644, 2645 | AA | EE | EE | EA | EE |
| | 200, 201 | 2687, 2688 | AA | KH | KH | KY | KH |
| | 356, 357 | 2843, 2844 | AA | KE | KE | KE | KE |
| | 387, 388 | 2874, 2875 | AA | KK | RN | KK | RN |
| | 436, 437 | 2923, 2924 | AA | DK | HR | DK | DK |
| | 524, 525 | 3011, 3012 | AA | KK | KI | KK | KI |
| | 525, 526 | 3012, 3013 | AA | KD | IP | KE | IP |
| | 642, 643 | 3129, 3130 | AA | ER | ER | IA | KK |
| | 654, 655 | 3141, 3142 | AA | DR | ER | ER | ER |
| | 808, 809 | 3295, 3296 | AA | ED | ED | ED | ED |
| | 827, 828 | 3314, 3315 | AA | DK | DK | DK | DK |
| | 877, 878 | 3364, 3365 | AA | KE | NE | NE | NE |
| | 878, 879 | 3365, 3366 | AA | EE | EN | EE | EE |

[a]Amino acid position is given for the polyprotein of DEN4
[b]DEN4 = rDEN4 (GenBank AF326825); DEN1 = Western pacific (GenBank U88535); DEN2 = New Guinea C (GenBank AF038403); DEN3 = H87 (GenBank M93130)
[c]This mutation results in decreased replication of DEN4 in mosquitoes.
[d]Underlined nucleotides are shared between DEN4 and one or more additional DEN types.

APPENDIX 1

Sequence of recombinant dengue type 4 virus strain 2A

| | |
|---|---|
| LOCUS | AF375822 10649 bp ss-RNA linear VRL 19-SEP-2001 |
| DEFINITION | Dengue virus type 4 recombinant clone 2A, complete genome. |
| ACCESSION | AF375822 |
| VERSION | AF375822.1 GI:14269097 |
| KEYWORDS | . |
| SOURCE | Dengue virus type 4. |
| ORGANISM | Dengue virus type 4 Viruses; ssRNA positive-strand viruses, no DNA stage; Flaviviridae; Flavivirus; Dengue virus group. |
| REFERENCE | 1 (bases 1 to 10649) |
| AUTHORS | Blaney, J. E. Jr., Johnson, D. H., Firestone, C. Y., Hanson, C. T., Murphy, B. R. and Whitehead, S. S. |
| TITLE | Chemical Mutagenesis of Dengue Virus Type 4 Yields Mutant Viruses Which Are Temperature Sensitive in Vero Cells or Human Liver Cells and Attenuated in Mice |
| JOURNAL | J. Virol. 75 (20), 9731-9740 (2001) |
| MEDLINE | 21443968 |
| PUBMED | 11559806 |
| REFERENCE | 2 (bases 1 to 10649) |
| AUTHORS | Blaney, J. E. Jr., Johnson, D. H., Firestone, C. Y., Hanson, C. T., Murphy, B. R. and Whitehead, S. S. |
| TITLE | Direct Submission |

APPENDIX 1-continued

Sequence of recombinant dengue type 4 virus strain 2A

| | |
|---|---|
| JOURNAL | Submitted (02-MAY-2001) LID, NIAID, 7 Center Drive, Bethesda, MD 20892, USA |
| FEATURES | Location/Qualifiers |
| source | 1 . . . 10649<br>/organism = "Dengue virus type 4"<br>/virion<br>/db_xref = "taxon:11070" |
| mat_peptide | 102 . . . 440<br>/note = "anchC"<br>/product = "anchored capsid protein" |
| mat_peptide | 102 . . . 398<br>/note = "virC"<br>/product = "virion capsid protein" |
| CDS | 102 . . . 10265<br>/codon_start = 1<br>/product = "polyprotein precursor"<br>/protein_id = "AAK58017.1"<br>/db_xref = "GI:14269098" |

/translation = "MNQRKKVVRPPFNMLKRERNRVSTPQGLVKRFST
GLFSGKGPLRMVLAFITFLRVLSIPPTAGILKRWGQLKKNKAIKILIGFR
KEIGRMLNILNGRKRSTITLLCLIPTVMAFSLSTRDGEPLMIVAKHERGR
PLLFKTTEGINKCTLIAMDLGEMCEDTVTYKCPLLVNTEPEDIDCWCNLT
STWVMYGTCTQSGERRREKRSVALTPHSGMGLETRAETWMSSEGAWKHAQ
RVESWILRNPGFALLAGFMAYMIGQTGIQRTVFFVLMMLVAPSYGMRCVG
VGNRDFVEGVSGGAWVDLVLEHGGCVTTMAQGKPTLDFELTKTTAKEVAL
LRTYCIEASISNITTATRCPTQGEPYLKEEQDQQYICRRDVVDRGWGNGC
GLFGKGGVVTCAKFSCSGKITGNLVQIENLEYTVVVTVHNGDTHAVGNDT
SNHGVTAMITPRSPSVEVKLPDYGELTLDCEPRSGIDFNEMILMKMKKKT
WLVHKQWFLDLPLPWTAGADTSEVHWNYKERMVTFKVPHAKRQDVTVLGS
QEGAMHSALAGATEVDSGDGNHMFAGHLKCKVRMEKLRIKGMSYTMCSGK
FSIDKEMAETQHGTTVVKVKYEGAGAPCKVPIEIRDVNKEKVVGRIISST
PLAENTNSVTNIELEPPFGDSYIVIGVGNSALTLHWFRKGSSIGKMFEST
YRGAKRMAILGETAWDFGSVGGLFTSLGKAVHQVFGSVYTTMFGGVSWMI
RILIGFLVLWIGTNSRNTSMAMTCIAVGGITLFLGFTVQADMGCVVSWSG
KELKCGSGIFVVDNVHTWTEQYKFQPESPARLASAILNAHKDGVCGIRST
TRLENVMWKQITNELNYVLWEGGHDLTVVAGDVKGVLTKGKRALTPPVSD
LKYSWKTWGKAKIFTPEARNSTFLIDGPDTSECPNERRAWNSLEVEDYGF
GMFTTNIWMKFREGSSEVCDHRLMSAAIKDQKAVHADMGYWIESSKNQTW
QIEKASLIEVKTCLWPKTHTLWSNGVLESQMLIPKSYAGPFSQHNYRQGY
ATQTVGPWHLGKLEIDFGECPGTTVTIQEDCDHRGPSLRTTTASGKLVTQ
WCCRSCTMPPLRFLGEDGCWYGMEIRPLSEKEENMVKSQVTAGQGTSETF
SMGLLCLTLFVEECLRRRVTRKHMILVVVITLCAIILGGLTWMDLLRALI
MLGDTMSGRIGGQIHLAIMAVFKMSPGYVLGVFLRKLTSRETALMVIGMA
MTTVLSIPHDLMELIDGISLGLILLKIVTQPFDNTQVGTLALSLTFIRSTM
PLVMAWRTIMAVLFVVTLIPLCRTSCLQKQSHWVEITALILGAQALPVYL
MTLMKGASRRSWPLNEGIMAVGLVSLLGSALLKNDVPLAGPMVAGGLLLA
AYVMSGSSADLSLEKAANVQWDEMADITGSSPIIEVKQDEDGSFSIRDVE
ETMMITLLVKLALITVSGLYPLAIPVTMTLWYMWQVKTQRSGALWDVPSP
AATKKAALSEGVYRIMQRGLFGKTQVGVGIHMEGVFHTMWHVTRGSVICH
ETGRLEPSWADVRNDMISYGGGWRLGDKWKEEDVQVLAIEPGKNPKHVQ
TKPGLFKTLTGEIGAVTLDFKPGTSGSPIINRKGKVIGLYGNGVVTKSGD
YVSAITQAERIGEPDYEVDEDIFRKKRLTIMDLHPGAGKTKRILPSIVRE
ALKRRLRTLILAPTRVVAAEMEEALRGLPIRYQTPAVKSEHTGREIVDLM
CHATFTTRLLSSTRVPNYNLIVMDEAHFTDPSSVAARGYISTRVEMGEAA
AIFMTATPPGATDPFPQSNSPIEDIEREIPERSWNTGFDWITDYQGKTVW
FVPSIKAGNDIANCLRKSGKKVIQLSRKTFDTEYPKTKLTDWDFVVTTDI
SEMGANFRAGRVIDPRRCLKPVILPDGPERVILAGPIPVTPASAAQRRGR
IGRNPAQEDDQVFSGDPLKNDEDHAHWTEAKMLLDNIYTPEGIIPTLFG
PEREKTQAIDGEFRLRGEQRKTFVELMRRGDLPVWLSYKVASAGISYKDR
EWCFTGERNNQILEEMMEVEIWTREGEKKKLRPRWLDARVYAGPMALKDF
KEFASGRKSITLDILTEIASLPTYLSSRAKLALDNIVMLHTTERGGRAYQ
HALNELPESLETLMLVALLGAMTAGIFLFFMQGKGIGKLSMGLITIAVAS
GLLWVAEIQPQWIAASIILEFFLMVLLIPEPEKQRTPQDNQLIYVILTIL
TIIGLIAANEMGLIEKTKTDFGFYQVANQAAVLMGLKGWPLHRMDLGVPLLA
MGCYSQVNPTTLTASLVMLLVHYAIIGPGLQAKATREAQKRTAAGIMKNP
TVDGITVIDLEPISYDPKFEKQLGQVMLLVLCAGQLLMRTTWAFCEVLT
LATGPILTLWEGNPGRFWNTTIAVSTANIFRGSYLAGAGLAFSLIKNAQT
PRRGTGTTGETLGEKWKRQLNSLDRKEFEEYKRSGILEVDRTEAKSALKD

APPENDIX 1-continued

Sequence of recombinant dengue type 4 virus strain 2A

GSKIKHAVSRGSSKIRWIVERGMVKPKGKVVDLGCGRGGWSYYMATLKNV
TEVKGYTKGGPGHEEPIPMATYGWNLVKLHSGVDVFYKPTEQVDTLLCDI
GESSSNPTIEEGRTLRVLKMVEPWLSSKPEFCIKVLNPYMPTVIEELEKL
QRKHGGNLVRCPLSRNSTHEMYWVSGASGNIVSSVNTTSKMLLNRFTTRH
RKPTYEKDVDLGAGTRSVSTETEKPDMTIIGRRLQRLQEEHKETWHYDQE
NPYRTWAYHGSYEAPSTGSASSMVNGVVKLLTKPWDVIPMVTQLAMTDTT
PFGQQRVFKEKVDTRTPQPKPGTRMVMTTTANWLWALLGKKKNPRLCTRE
EFISKVRSNAAIGAVFQEEQGWTSASEAVNDSRFWELVDKERALHQEGKC
ESCVYNMMGKREKKLGEFGRAKGSRAIWYMWLGARFLEFEALGFLNEDHW
FGRENSWSGVEGEGLHRLGYILEEIDKKDGDLMYADDTAGWDTRITEDDL
QNEELITEQMAPHHKILAKAIFKLTYQNKVVKVLRPTPRGAVMDIISRKD
QRGSGQVGTYGLNTFTNMEVQLIRQMEAEGVITQDDMQNPKGLKERVEKW
LKECGVDRLKRMAISGDDCVVKPLDERFGTSLLFLNDMGKVRKDIPQWEP
SKGWKNWQEVPFCSHHFHKIFMKDGRSLVVPCRNQDELIGRARISQGAGW
SLRETACLGKAYAQMWSLMYFHRRDLRLASMAICSAVPTEWFPTSRTTWS
IHAHHQWMTTEDMLKVWNRVWIEDNPNMTDKTPVHSWEDIPYLGKREDLW
CGSLIGLSSRATWAKNIHTAITQVRNLIGKEEYVDYMPVMKRYSAPSESE
GVL"

| | |
|---|---|
| mat_peptide | 441 . . . 938<br>/note = "prM"<br>/product = "membrane precursor protein" |
| mat_peptide | 714 . . . 938<br>/note = "M"<br>/product = "membrane protein" |
| mat_peptide | 939 . . . 2423<br>/note = "E"<br>/product = "envelope protein" |
| mat_peptide | 2424 . . . 3479<br>/product = "NS1 protein" |
| mat_peptide | 3480 . . . 4133<br>/product = "NS2A protein" |
| mat_peptide | 4134 . . . 4523<br>/product = "NS2B protein" |
| mat_peptide | 4524 . . . 6377<br>/product = "NS3 protein" |
| mat_peptide | 6378 . . . 6758<br>/product = "NS4A protein" |
| mat_peptide | 6759 . . . 6827<br>/product = "2K protein" |
| mat_peptide | 6828 . . . 7562<br>/product = "NS4B protein" |
| mat_peptide | 7563 . . . 10262<br>/product = "NS5 protein" |

BASE COUNT  3302 a  2212 c  2800 g  2335 t
ORIGIN

```
  1 agttgttagt ctgtgtggac cgacaaggac agttccaaat
    cggaagcttg cttaacacag
 61 ttctaacagt ttgtttgaat agagagcaga tctctggaaa
    aatgaaccaa cgaaaaaagg
121 tggttagacc cccttcaat atgctgaaac gcgagagaaa
    ccgcgtatca acccctcaag
181 ggttggtgaa gagattctca accggacttt tttctgggaa
    aggacccta cggatggtgc
241 tagcattcat cacgttttg cgagtccttt ccatcccacc
    aacagcaggg attctgaaga
301 gatgggaca gttgaagaaa aataaggcca tcaagatact
    gattggattc aggaaggaga
```

APPENDIX 1-continued

Sequence of recombinant dengue type 4 virus strain 2A

```
 361 taggccgcat gctgaacatc ttgaacggga gaaaaaggtc
     aacgataaca ttgctgtgct
 421 tgattcccac cgtaatggcg ttttccttgt caacaagaga
     tggcgaaccc ctcatgatag
 481 tggcaaaaca tgaaaggggg agacctctct tgtttaagac
     aacagagggg atcaacaaat
 541 gcactctcat tgccatggac ttgggtgaaa tgtgtgagga
     cactgtcacg tataaatgcc
 601 ccctactggt caataccgaa cctgaagaca ttgattgctg
     gtgcaacctc acgtctacct
 661 gggtcatgta tgggacatgc acccagagcg agaacggag
     acgagagaag cgctcagtag
 721 ctttaacacc acattcagga atgggattgg aaacaagagc
     tgagacatgg atgtcatcgg
 781 aaggggcttg gaagcatgct cagagagtag agagctggat
     actcagaaac ccaggattcg
 841 cgctcttggc aggatttatg gcttatatga ttgggcaaac
     aggaatccag cgaactgtct
 901 tctttgtcct aatgatgctg gtcgcccat cctacggaat
     gcgatgcgta ggagtaggaa
 961 acagagactt tgtggaagga gtctcaggtg gagcatgggt
     cgacctggtg ctagaacatg
1021 gaggatgcgt cacaaccatg gcccagggaa aaccaacctt
     ggatttttgaa ctgactaaga
1081 caacagccaa ggaagtggct ctgttaagaa cctattgcat
     tgaagcctca atatcaaaca
1141 taactacggc aacaagatgt ccaacgcaag agagccttta
     tctgaaagag gaacaggacc
1201 aacagtacat ttgccggaga gatgtggtag acagagggtg
     gggcaatggc tgtggcttgt
1261 ttggaaaagg aggagttgtg acatgtgcga agttttcatg
     ttcggggaag ataacaggca
1321 atttggtcca aattgagaac cttgaataca cagtggttgt
     aacagtccac aatgagaca
1381 cccatgcagt aggaaatgac acatccaatc atggagttac
     agccatgata actcccaggt
1441 caccatcggt ggaagtcaaa ttgccggact atggagaact
     aacactcgat tgtgaaccca
1501 ggtctggaat tgactttaat gagatgattc tgatgaaaat
     gaaaaagaaa acatggctcg
1561 tgcataagca atggttttg gatctgcctc ttccatggac
     agcaggagca gacacatcag
1621 aggttcactg gaattacaaa agagagaatgg tgacattaa
     ggttcctcat gccaagagac
1681 aggatgtgac agtgctggga tctcaggaag gagccatgca
     ttctgccctc gctgagcca
1741 cagaagtgga ctccggtgat ggaaatcaca tgtttgcagg
     acatcttaag tgcaaagtcc
1801 gtatggagaa attgagaatc aagggaatgt catacacgat
     gtgttcagga aagttttcaa
```

```
1861 ttgacaaaga gatggcagaa acacagcatg ggacaacagt
     ggtgaaagtc aagtatgaag
1921 gtgctggagc tccgtgtaaa gtccccatag agataagaga
     tgtaaacaag gaaaaagtgg
1981 ttgggcgtat catctcatcc accccctttgg ctgagaatac
     caacagtgta accaacatag
2041 aattagaacc ccccttttggg gacagctaca tagtgatagg
     tgttggaaac agcgcattaa
2101 cactccattg gttcaggaaa gggagttcca ttggcaagat
     gtttgagtcc acatacagag
2161 gtgcaaaacg aatggccatt ctaggtgaaa cagcttggga
     ttttggttcc gttggtggac
2221 tgttcacatc attgggaaag gctgtgcacc aggttttgg
     aagtgtgtat acaaccatgt
2281 ttggaggagt ctcatggatg attagaatcc taattgggtt
     cttagtgttg tggattggca
2341 cgaactcaag gaacacttca atggctatga cgtgcatagc
     tgttggagga atcactctgt
2401 ttctgggctt cacagttcaa gcagacatgg ttgtgtggt
     gtcatggagt gggaaagaat
2461 tgaagtgtgg aagcggaatt tttgtggttg acaacgtgca
     cacttggaca gaacagtaca
2521 aatttcaacc agagtccccca gcgagactag cgtctgcaat
     attaaatgcc cacaaagatg
2581 gggtctgtgt aattagatca accacgaggc tggaaaatgt
     catgtggaag caaataacca
2641 acgagctaaa ctatgttctc tgggaaggag acatgacct
     cactgtagtg gctggggatg
2701 tgaaggggt gttgaccaaa ggcaagagag cactcacacc
     cccagtgagt gatctgaaat
2761 attcatggaa gacatgggga aaagcaaaaa tcttcacccc
     agaagcaaga aatagcacat
2821 ttttaataga cggaccagac acctctgaat gccccaatga
     acgaagagca tggaactctc
2881 ttgaggtgga agactatgga tttggcatgt tcacgaccaa
     catatggatg aaattccgag
2941 aaggaagttc agaagtgtgt gaccacaggt taatgtcagc
     tgcaattaaa gatcagaaag
3001 ctgtgcatgc tgacatgggt tattggatag agagctcaaa
     aaaccagacc tggcagatag
3061 agaaagcatc tctattgaa gtgaaaacat gtctgtggcc
     caagacccac acactgtgga
3121 gcaatgagt gctggaaagc cagatgctca ttccaaaatc
     atatgcgggc cttttttcac
3181 agcacaatta ccgccagggc tatgccacgc aaaccgtggg
     cccatggcac ttaggcaaat
3241 tagagataga ctttggagaa tgccccggaa caacagtcac
     aattcaggag gattgtgacc
3301 atagaggccc atctttgagg accaccactg catctggaaa
     actagtcacg caatggtgct
```

APPENDIX 1-continued

Sequence of recombinant dengue type 4 virus strain 2A

```
3361 gccgctcctg cacgatgcct cccttaaggt tcttgggaga
     agatgggtgc tggtatggga
3421 tggagattag gcccttgagt gaaaaagaag agaacatggt
     caaatcacag gtgacggccg
3481 gacagggcac atcagaaact ttttctatgg gtctgttgtg
     cctgaccttg tttgtggaag
3541 aatgcttgag gagaagagtc actaggaaac acatgatatt
     agttgtggtg atcactcttt
3601 gtgctatcat cctgggaggc ctcacatgga tggacttact
     acgagccctc atcatgttgg
3661 gggacactat gtctggtaga ataggaggac agatccacct
     agccatcatg gcagtgttca
3721 agatgtcacc aggatacgtg ctgggtgtgt ttttaaggaa
     actcacttca agagagacag
3781 cactaatggt aataggaatg gccatgacaa cggtgctttc
     aattccacat gaccttatgg
3841 aactcattga tggaatatca ctgggactaa ttttgctaaa
     aatagtaaca cagtttgaca
3901 acacccaagt gggaaccttca gctcttttcct tgactttcat
     aagatcaaca atgccattgg
3961 tcatggcttg gaggaccatt atggctgtgt tgtttgtggt
     cacactcatt cctttgtgca
4021 ggacaagctg tcttcaaaaa cagtctcatt gggtagaaat
     aacagcactc atcctaggag
4081 cccaagctct gccagtgtac ctaatgactc ttatgaaagg
     agcctcaaga agatcttggc
4141 ctcttaacga gggcataatg gctgtgggtt tggttagtct
     cttaggaagc gctcttttaa
4201 agaatgatgt ccctttagct ggcccaatgg tggcaggagg
     cttacttctg gcggcttacg
4261 tgatgagtgg tagctcagca gatctgtcac tagagaaggc
     cgccaacgtg cagtgggatg
4321 aaatggcaga cataacaggc tcaagcccaa tcatagaagt
     gaagcaggat gaagatggct
4381 ctttctccat acgggacgtc gaggaaacca atatgataac
     ccttttggtg aaactggcac
4441 tgataacagt gtcaggtctc taccccttgg caattccagt
     cacaatgacc ttatggtaca
4501 tgtggcaagt gaaaacacaa agatcaggag ccctgtggga
     cgtcccctca cccgctgcca
4561 ctaaaaagc cgcactgtct gaaggagtgt acaggatcat
     gcaaagaggg ttattcggga
4621 aaactcaggt tggagtaggg atacacatgg aagtgtatt
     tcacacaatg tggcatgtaa
4681 caagaggatc agtgatctgc cacgagactg ggagattgga
     gccatcttgg ctgacgtca
4741 ggaatgacat gatatcatac ggtgggggat ggaggcttgg
     agacaaatgg gacaaagaag
4801 aagacgttca ggtcctcgcc atagaaccag gaaaaaatcc
     taaacatgtc caaacgaaac
```

```
4861 ctggcctttt caagaccta actggagaaa ttggagcagt
     aacattagat ttcaaacccg
4921 gaacgtctgg ttctcccatc atcaacagga aggaaaagt
     catcggactc tatggaaatg
4981 gagtagttac caaatcaggt gattacgtca gtgccataac
     gcaagccgaa agaattggag
5041 agccagatta tgaagtggat gaggacattt ttcgaaagaa
     aagattaact ataatggact
5101 tacaccccgg agctggaaag acaaaaagaa ttcttccatc
     aatagtgaga gaagccttaa
5161 aaaggaggct acgaacttttg attttagctc ccacgagagt
     ggtggcggcc gagatggaag
5221 aggccctacg tggactgcca atccgttatc agaccccagc
     tgtgaaatca gaacacacag
5281 gaagagagat tgtagacctc atgtgtcatg caaccttcac
     aacaagactt ttgtcatcaa
5341 ccagggttcc aaattacaac cttatagtga tggatgaagc
     acatttcacc gatcccttcta
5401 gtgtcgcggc tagaggatac atctcgacca gggtggaaat
     gggagaggca gcagccatct
5461 tcatgaccgc aaccccctcc ggagcgacag atccctttcc
     ccagagcaac agcccaatag
5521 aagacatcga gagggaaatt ccggaaggt catggaacac
     agggttcgac tggataacag
5581 actaccaagg gaaaactgtg tggtttgttc ccagcataaa
     agctggaaat gacattgcaa
5641 attgtttgag aaagtcggga aagaaagtta ccagttgag
     tagaaaaacc tttgatacag
5701 agtatccaaa aacgaaactc acggactggg actttgtggt
     cactacagac atatctgaaa
5761 tggggggccaa ttttagagcc gggagagtga tagaccctag
     aagatgcctc aagccagtta
5821 tcctaccaga tgggccagag agagtcattt tagcaggtcc
     tattccagtg actccagcaa
5881 gcgctgctca gagaagaggg cgaataggaa ggaacccagc
     acaagaagac gaccaatacg
5941 ttttctccgg agaccactta aaaaatgatg aagatcatgc
     ccactggaca gaagcaaaga
6001 tgctgcttga caatatctac acccccagaag ggatcattcc
     aacattgttt ggtccggaaa
6061 gggaaaaaac ccaagccatt gatggagagt ttcgcctcag
     aggggaacaa aggaagactt
6121 ttgtggaatt aatgaggaga ggagaccttc cggtgtggct
     gagctataag gtagcttctg
6181 ctggcattc ttacaaagat cgggaatggt gcttcacagg
     ggaaagaaat aaccaaattt
6241 tagaagaaaa catggaggtt gaaatttgga ctagagaggg
     agaaagaaa aagctaaggc
6301 caagatggtt agatgcacgt gtatacgctg accccatggc
     tttgaaggat ttcaaggagt
```

APPENDIX 1-continued

Sequence of recombinant dengue type 4 virus strain 2A

```
6361 ttgccagtgg aaggaagagt ataactctcg acatcctaac
     agagattgcc agtttgccaa 6421 cttacctttc ctctagggcc aagctcgccc ttgataacat
     agtcatgctc cacacaacag 6481 aaagaggagg gagggcctat caacacgccc tgaacgaact
     tccggagtca ctggaaacac 6541 tcatgcttgt agctttacta ggtgctatga cagcaggcat
     cttcctgttt ttcatgcaag 6601 ggaaaggaat agggaaattg tcaatgggtt tgataaccat
     tgcggtggct agtggcttgc 6661 tctgggtagc agaaattcaa ccccagtgga tagcggcctc
     aatcatacta gagttttttc 6721 tcatggtact gttgataccg gaaccagaaa aacaaaggac
     cccacaagac aatcaattga 6781 tctacgtcat attgaccatt ctcaccatca ttggtctaat
     agcagccaac agatggggc 6841 tgattgaaaa acaaaaacg gattttgggt tttaccaggt
     aaaaacgaaa accaccatcc 6901 tcgatgtgga cttgagacca gcttcagcat ggacgctcta
     tgcagtagcc accacaattc 6961 tgactcccat gctgagacac accatagaaa acacgtcggc
     caacctatct ctagcagcca 7021 ttgccaacca ggcagccgtc ctaatggggc ttggaaaagg
     atggccgctc cacagaatgg 7081 acctcggtgt gccgctgtta gcaatgggat gctattctca
     agtgaaccca acaaccttga 7141 cagcatcctt agtcatgctt ttagtccatt atgcaataat
     aggcccagga ttgcaggcaa 7201 aagccacaag agaggcccag aaaaggacag ctgctgggat
     catgaaaaat cccacagtgg 7261 acgggataac agtaatagat ctagaaccaa tatcctatga
     cccaaaattt gaaaagcaat 7321 tagggcaggt catgctacta gtcttgtgtg ctggacaact
     actcttgatg agaacaacat 7381 gggctttctg tgaagtcttg actttggcca caggaccaat
     cttgaccttg tgggagggca 7441 acccgggaag gttttgaac acgaccatag ccgtatccac
     cgccaacatt ttcaggggaa 7501 gttacttggc gggagctgga ctggcttttt cactcataaa
     gaatgcacaa acccctagga 7561 ggggaactgg gaccacagga gagacactgg agagaagtg
     gaagagacag ctaaactcat 7621 tagacagaaa agagtttgaa gagtataaaa gaagtggaat
     actagaagtg gacaggactg 7681 aagccaagtc tgccctgaaa gatgggtcta aaatcaagca
     tgcagtatct agagggtcca 7741 gtaagatcag atggattgtt gagagaggga tggtaaagcc
     aaaagggaaa gttgtagatc 7801 ttggctgtgg gagaggagga tggtcttatt acatggcgac
     actcaagaac gtgactgaag
```

APPENDIX 1-continued

Sequence of recombinant dengue type 4 virus strain 2A

```
7861 tgaaagggta tacaaaagga ggtccaggac atgaagaacc
     gattcccatg gctacttatg 7921 gttggaattt ggtcaaactc cattcagggg ttgacgtgtt
     ctacaaaccc acagagcaag 7981 tggacacccct gctctgtgat attggggagt catcttctaa
     tccaacaata gaggaaggaa 8041 gaacattaag agttttgaag atggtggagc catggctctc
     ttcaaaacct gaattctgca 8101 tcaaagtcct taccccctac atgccaacag tcatagaaga
     gctggagaaa ctgcagagaa 8161 aacatggtgg gaaccttgtc agatgcccgc tgtccaggaa
     ctccacccat gagatgtatt 8221 gggtgtcagg agcgtcggga acattgtga gctctgtgaa
     cacaacatca aagatgttgt 8281 tgaacaggtt cacaacaagg cataggaaac ccacttatga
     gaaggacgta gatcttgggg 8341 caggaacgag aagtgtctcc actgaaacag aaaaaccaga
     catgacaatc attgggagaa 8401 ggcttcagcg attgcaagaa gagcacaaag aaacctggca
     ttatgatcag gaaaacccat 8461 acagaacctg ggcgtatcat ggaagctatg aagctccttc
     gacaggctct gcatcctcca 8521 tggtgaacgg ggtggtaaaa ctgctaacaa aaccctggga
     tgtgattcca atggtgactc 8581 agttagccat gacagataca ccccttttg gcaacaaag
     agtgttcaaa gagaaggtgg 8641 ataccagaac accacaacca aaaccccggta cacgaatggt
     tatgaccacg acagccaatt 8701 ggctgtgggc cctccttgga aagaagaaaa atcccagact
     gtgcacaagg gaagagttca 8761 tctcaaaagt tagatcaaac gcagccatag cgcagtcttt
     tcaggaagaa cagggatgga 8821 catcagccag tgaagctgtg aatgacagcc ggttttggga
     actggttgac aaagaaaggg 8881 ccctacacca ggaagggaaa tgtgaatcgt gtgtctataa
     catgatggga aaacgtgaga 8941 aaaagttagg agagtttggc agagccaagg gaagccgagc
     aatctggtac atgtggctgg 9001 gagcgcggtt tctggaattt gaagccctgg gttttttgaa
     tgaagatcac tggtttggca 9061 gagaaaattc atggagtgga gtggaagggg aaggtctgca
     cagattggga tatatcctgg 9121 aggagataga caagaaggat ggagacctaa tgtatgctga
     tgacacagca ggctgggaca 9181 caagaatcac tgaggatgac cttcaaaatg aggaactgat
     cacggaacag atggctcccc 9241 accacaagat cctagccaaa gccattttca aactaaccta
     tcaaacaaa gtggtgaaag 9301 tcctcagacc cacaccgaga ggagcggtga tggatatcat
     atccaggaaa gaccaaagag
```

APPENDIX 1-continued

Sequence of recombinant dengue type 4 virus strain 2A

```
 9361 gtagtggaca agttggaaca tatggtttga acacattcac
      caacatgaa gttcaactca 9421 tccgccaaat ggaagctgaa ggagtcatca cacaagatga
      catgcagaac ccaaaagggt 9481 tgaaagaaag agttgagaaa tggctgaaag agtgtggtgt
      cgacaggtta aagaggatgg 9541 caatcagtgg agacgattgc gtggtgaagc ccctagatga
      gaggtttggc acttccctcc 9601 tcttcttgaa cgacatggga aaggtgagga aagacattcc
      gcagtgggaa ccatctaagg 9661 gatggaaaaa ctggcaagag gttccttttt gctcccacca
      ctttcacaag atctttatga 9721 aggatggccg ctcactagtt gttccatgta gaaaccagga
      tgaactgata gggagagcca 9781 gaatctcgca gggagctgga tggagcttaa gagaaacagc
      ctgcctgggc aaagcttacg 9841 cccagatgtg gtcgcttatg tacttccaca gaagggatct
      gcgtttagcc tccatggcca 9901 tatgctcagc agttccaacg gaatggtttc caacaagcag
      aacaacatgg tcaatccacg 9961 ctcatcacca gtggatgacc actgaagata tgctcaaagt
      gtggaacaga gtgtggatag 10021 aagacaaccc taatatgact gacaagactc cagtccattc
      gtgggaagat ataccttacc 10081 tagggaaaag agaggatttg tggtgtggat ccctgattgg
      actttcttcc agagccacct 10141 gggcgaagaa cattcacacg gccataaccc aggtcaggaa
      cctgatcgga aaagaggaat 10201 acgtggatta catgccagta atgaaaagat acagtgctcc
      ttcagagagt gaaggagttc 10261 tgtaattacc aacaacaaac accaaaggct attgaagtca
      ggccacttgt gccacggttt 10321 gagcaaaccg tgctgcctgt agctccgcca ataatgggag
      gcgtaataat ccccagggag 10381 gccatgcgcc acggaagctg tacgcgtggc atattggact
      agcggttaga ggagacccct 10441 cccatcactg acaaaacgca gcaaaagggg gcccgaagcc
      aggaggaagc tgtactcctg 10501 gtggaaggac tagaggttag aggagacccc cccaacacaa
      aaacagcata ttgacgctgg 10561 gaaagaccag agatcctgct gtctctgcaa catcaatcca
      ggcacagagc gccgcaagat 10621 ggattggtgt tgttgatcca acaggttct
```

APPENDIX 2

Sequence of recombinant dengue type 4 virus strain rDEN4

```
LOCUS       AF326825 10649 bp RNA VRL 03-JAN-2001
DEFINITION  Dengue virus type 4 recombinant clone
            rDEN4, complete sequence.
ACCESSION   AF326825
VERSION     AF326825.1 GI:12018169
KEYWORDS    .
SOURCE      Dengue virus type 4.
ORGANISM    Dengue virus type 4 Viruses; ssRNA
            positive-strand viruses, no DNA stage;
            Flaviviridae; Flavivirus; Dengue virus
            group.
REFERENCE   1 (bases 1 to 10649)
AUTHORS     Durbin, A. P., Karron, R. A., Sun, W.,
            Vaughn, D. W., Reynolds, M. J.,
            Perreault, J. R., Men, R. H.,
            Lai, C. J., Elkins, W. R.,
            Chanock, R. M., Murphy, B. R. and
            Whitehead, S. S.
TITLE       A live attenuated dengue virus type 4
            vaccine candidate with a 30 nucleotide
            deletion in the 3' untranslated region
            is highly attenuated and immunogenic in
            humans
JOURNAL     Unpublished
REFERENCE   2 (bases 1 to 10649)
AUTHORS     Whitehead, S. S.
TITLE       Direct Submission
JOURNAL     Submitted (08-DEC-2000) LID, NIAID,
            7 Center Drive, Bethesda,
            MD 20892, USA MITTS
FEATURES    Location/Qualifiers
source      1 . . . 10649
            /organism = "Dengue virus type 4"
            /db_xref = "taxon:11070"
            /clone = "rDEN4"
mat_peptide 102 . . . 440
            /product = "anchored capsid (anchC)
            protein"
mat_peptide 102 . . . 398
            /product = "virion capsid (virC)
            protein"
CDS         102 . . . 10265
            /codon_start = 1
            /product = "polyprotein precursor"
            /protein_id = "AAG45435.1"
            /db_xref = "GI:12018170"
/translation = "MNQRKKVVRPPFNMLKRERNRVSTPQGLVKRFST
GLFSGKGPLRMVLAFITFLRVLSIPPTAGILKRWGQLKKNKAIKILIGFR
KEIGRMLNILNGRKRSTITLLCLIPTVMAFSLSTRDGEPLMIVAKHERGR
PLLFKTTEGINKCTLIAMDLGEMCEDTVTYKCPLLVNTEPEDIDCWCNLT
STWVMYGTCTQSGERRREKRSVALTPHSGMGLETRAETWMSSEGAWKHAQ
RVESWILRNPGFALLAGFMAYMIGQTGIQRTVFFVLMMLVAPSYGMRCVG
VGNRDFVEGVSGGAWVDLVLEHGCVTTMAQGKPTLDFELTKTTAKEVAL
LRTYCIEASISNITTATRCPTQGEPYLKEEQDQQYICRRDVVDRGWGNGC
GLFGKGGVVTCAKFSCSGKITGNLVQIENLEYTVVVTVHNGDTHAVGNDT
SNHGVTAMITPRSPSVEVKLPDYGELTLDCEPRSGIDFNEMILMKMKKKT
```

APPENDIX 2-continued

Sequence of recombinant dengue type 4 virus strain rDEN4

```
WLVHKQWFLDLPLPWTAGADTSEVHWNYKERMVTFKVPHAKRQDVTVLGS
QEGANHSALAGATEVDSGDGNHMFAGHLKCKVRMEKLRIKGMSYTMCSGK
FSIDKEMAETQHGTTVVKVKYEGAGAPCKVPIEIRDVNKEKVVGRIISST
PLAENTNSVTNIELEPPFGDSYIVIGVGNSALTLHWFRKGSSIGKMFEST
YRGAKRMAILGETAWDFGSVGGLFTSLGKAVHQVFGSVYTTMFGGVSWMI
RILIGFLVLWIGTNSRNTSMAMTCIAVGGITLFLGFTVQADMGCVASWSG
KELKCGSGIFVVDNVHTWTEQYKFQPESPARLASAILNAHKDGVCGIRST
TRLENVMWKQITNELNYVLWEGGHDLTVVAGDVKGVLTKGKRALTPPVSD
LKYSWKTWGKAKIFTPEARNSTFLIDGPDTSECPNERRAWNSLEVEDYGF
GMFTTNIWMKFREGSSEVCDHRLMSAAIKDQKAVHADMGYWIESSKNQTW
QIEKASLIEVKTCLWPKTHTLWSNGVLESQMLIPKSYAGPFSQHNYRQGY
ATQTVGPWHLGKLEIDFGECPGTTVTIQEDCDHRGPSLRTTTASGKLVTQ
WCCRSCTMPPLRFLGEDGCWYGMEIRPLSEKEENMVKSQVTAGQGTSETF
SMGLLCLTLFVEECLRRRVTRKHMILVVVITLCAIILGGLTWMDLLRALI
MLGDTMSGRIGGQIHLAIMAVFKMSPGYVLGVFLRKLTSRETALMVIGMA
MTTVLSIPHDLMELIDGISLGLILLKIVTQFDNTQVGTLALSLTFIRSTM
PLVMAWRTIMAVLFVVTLIPLCRTSCLQKQSHWVEITALILGAQALPVYL
MTLMKGASRRSWPLNEGIMAVGLVSLLGSALLKNDVPLAGPMVAGGLLLA
AYVMSGSSADLSLEKAANVQWDEMADITGSSPIVEVKQDEDGSFSIRDVE
ETNMITLLVKLALITVSGLYPLAIPVTMTLWYMWQVKTQRSGALWDVPSP
AATKKAALSEGVYRIMQRGLFGKTQVGVGIHMEGVFHTMWHVTRGSVICH
ETGRLEPSWADVRNDMISYGGGWRLGDKWDKEEDVQVLAIEPGKNPKHVQ
TKPGLFKTLTGEIGAVTLDFKPGTSGSPIINRKGKVIGLYGNGVVTKSGD
YVSAITQAERIGEPDYEVDEDIFRKKRLTIMDLHPGAGKTKRILPSIVRE
ALKRRLRTLILAPTRVVAAEMEEALRGLPIRYQTPAVKSEHTGREIVDLM
CHATFTTRLLSSTRVPNYNLIVMDEAHFTDPSSVAARGYISTRVEMGEAA
AIFMTATPPGATDPFPQSNSPIEDIEREIPERSWNTGFDWITDYQGKTVW
FVPSIKAGNDIANCLRKSGKKVIQLSRKTFDTEYPKTKLTDWDFVVTTDI
SEMGANFRAGRVIDPRRCLKPVILPDGPERVILAGPIPVTPASAAQRRGR
IGRNPAQEDDQYVFSGDPLKNDEDHAHWTEAKMLLDNIYTPEGIIPTLFG
PEREKTQAIDGEFRLRGEQRKTFVELMRRGDLPVWLSYKVASAGISYEDR
EWCFTGERNNQILEENMEVEIWTREGEKKKLPRWLDARVYADPMALKDF
KEFASGRKSITLDILTEIASLPTYLSSRAKLALDNIVMLHTTERGGRAYQ
HALNELPESLETLMLVALLGAMTAGIFLFFMQGKGIGKLSMGLITIAVAS
GLLWVAEIQPQWIAASIILEFFLMVLLIPEPEKQRTPQDNQLIYVILTIL
TIIGLIAANEMGLIEKTKTDFGFYQVKTETTILDVDLRPASAWTLYAVAT
TILTPMLRHTIENTSANLSLAAIANQAAVLMGLGKGWPLHRMDLGVPLLA
MGCYSQVNPTTLTASLVMLLVHYAIIGPGLQAKATREAQKRTAAGIMKNP
TVDGITVIDLEPISYDPKFEKQLGQVMLLVLCAGQLLLMRTTWAFCEVLT
LATGPILTLWEGNPGRFWNTTIAVSTANIFRGSYLAGAGLAFSLIKNAQT
PRRGTGTTGETLGEKWKRQLNSLDRKEFEEYKRSGILEVDRTEAKSALKD
GSKIKHAVSRGSSKIRWIVERGMVKPKGKVVDLGCGRGGWSYYMATLKNV
TEVKGYTKGGPGHEEPIPMATYGWNLVKLHSGVDVFYKPTEQVDTLLCDI
GESSSNPTIEEGRTLRVLKMVEPWLSSKPEFCIKVLNPYMPTVIEELEKL
QRKHGGNLVRCPLSRNSTHEMYWVSGASGNIVSSVNTTSKMLLNRFTTRH
RKPTYEKDVDLGAGTRSVSTETEKPDMTIIGRRLQRLQEEHKETWHYDQE
NPYRTWAYHGSYEAPSTGSASSMVNGVVKLLTKPWDVIPMVTQLAMTDTT
PFGQQRVFKEKVDTRTPQPKPGTRMVMTTTANWLWALLGKKKNPRLCTRE
EFISKVRSNAAIGAVFQEEQGWTSASEAVNDSRFWELVDKERALHQEGKC
ESCVYNMMGKREKKLGEFGRAKGSRAIWYMWLGARFLEFEALGFLNEDHW
FGRENSWSGVEGEGLHRLGYILEEIDKKDGDLMYADDTAGWDTRITEDDL
QNEELITEQMAPHHKILAKAIFKLTYQNKVVKVLRPTPRGAVMDIISRKD
QRGSGQVGTYGLNTFTNMEVQLIRQMEAEGVITQDDMQNPKGLKERVEKW
LKECGVDRLKRMAISGDDCVVKPLDERFGTSLLFLNDMGKVRKDIPWEP
SKGWNWQEGWPCSHHFHKIFMKDGRSLVVPCRNQDELIGRARISQGAGW
SLRETACLGKAYAQMWSLMYFHRRDLRLASMAICSAVPTEWFPTSRTTWS
IHAHHQWMTTEDMLKVWNRVWIEDNPNMTDKTPVHSWEDIPYLGKREDLW
CGSLIGLSSRATWAKNIHTAITQVRNLIGKEEYVDYMPVMKRYSAPSESE
GVL"

mat_peptide    441 . . . 938
               /product = "membrane precursor (prM)
               protein"

mat_peptide    714 . . . 938
               /product = "membrane (M) protein"

mat_peptide    939 . . . 2423
               /product = "envelope (E) protein"

mat_peptide    2424 . . . 3479
               /product = "NS1 protein"

mat_peptide    3480 . . . 4133
               /product = "NS2A protein"

mat_peptide    4134 . . . 4523
               /product = "NS2B protein"

mat_peptide    4524 . . . 6377
               /product = "NS3 protein"

mat_peptide    6378 . . . 6758
               /product = "NS4A protein"

mat_peptide    6759 . . . 6827
               /product = "2K protein"

mat_peptide    6828 . . . 7562
               /product = "NS4B protein"

mat_peptide    7563 . . . 10262
               /product = "NS5 protein"

rDEN4 sequence 1 agttgttagt ctgtgtggac cgacaaggac agttccaaat
      cggaagcttg cttaacacag 61 ttctaacagt ttgtttgaat agagagcaga tctctggaaa
      aatgaaccaa cgaaaaaagg 121 tggttagacc acctttcaat atgctgaaac gcgagagaaa
      ccgcgtatca accctcaag 181 ggttggtgaa gagattctca accggacttt ttctggaa
      aggacccta cggatggtgc 241 tagcattcat cacgttttg cgagtccttt ccatcccacc
      aacagcaggg attctgaaga 301 gatgggaca gttgaagaaa aataaggcca tcaagatact
      gattggattc aggaaggaga 361 taggccgcat gctgaacatc ttgaacggga gaaaaaggtc
      aacgataaca ttgctgtgct 421 tgattcccac cgtaatggcg ttttccctca gcacaagaga
      tggcgaaccc ctcatgatag 481 tggcaaaaca tgaaaggggg agacctctct tgtttaagac
      aacagagggg atcaacaaat 541 gcactctcat tgccatggac ttgggtgaaa tgtgtgagga
      cactgtcacg tataaatgcc 601 ccctactggt caataccgaa cctgaagaca ttgattgctg
      gtgcaacctc acgtctacct 661 gggtcatgta tgggacatgc acccagagcg agaacggaa
      acgagagaag cgctcagtag 721 ctttaacacc acattcagga atgggattgg aaacaagagc
      tgagacatgg atgtcatcgg 781 aaggggcttg gaagcatgct cagagagtag agagctggat
      actcagaaac ccaggattcg 841 cgctcttggc aggatttatg cttatatga ttgggcaaac
      aggaatccag cgaactgtct 901 tctttgtcct aatgatgctg gtcgcccat cctacggaat
      gcgatgcgta ggagtaggaa 961 acagagactt tgtggaagga gtctcaggtg gagcatgggt
      cgacctggtg ctagaacatg 1021 gaggatgcgt cacaaccatg gcccaggaa aaccaaacctt
      ggattttgaa ctgactaaga 1081 caacagccaa ggaagtggct ctgttaagaa cctattgcat
      tgaagcctca atatcaaaca
```

APPENDIX 2-continued

Sequence of recombinant dengue type 4 virus strain rDEN4

```
1141 taactacggc aacaagatgt ccaacgcaag gagagcctta
     tctgaaagag aacaggacc 1201 aacagtacat ttgccggaga gatgtggtag acagagggtg
     gggcaatggc tgtggcttgt 1261 ttggaaaagg aggagttgtg acatgtgcga agttttcatg
     ttcggggaag ataacaggca 1321 atttggtcca aattgagaac cttgaataca cagtggttgt
     aacagtccac aatggagaca 1381 cccatgcagt aggaaatgac acatccaatc atggagttac
     agccatgata actcccaggt 1441 caccatcggt ggaagtcaaa ttgccggact atggagaact
     aacactcgat tgtgaaccca 1501 ggtctggaat tgactttaat gagatgattc tgatgaaaat
     gaaaaagaaa acatggctcg 1561 tgcataagca atggttttg gatctgccct cttccatggac
     agcaggagca gacacatcag 1621 aggttcactg gaattacaaa gagagaatgg tgacatttaa
     ggttcctcat gccaagagac 1681 aggatgtgac agtgctggga tctcaggaag gagccatgca
     ttctgccctc gctggagcca 1741 cagaagtgga ctccggtgat ggaaatcaca tgtttgcagg
     acatcttaag tgcaaagtcc 1801 gtatggagaa attgagaatc aagggaatgt catacacgat
     gtgttcagga aagttttcaa 1861 ttgacaaaga gatggcagaa acacagcatg ggacaacagt
     ggtgaaagtc aagtatgaag 1921 gtgctggagc tccgtgtaaa gtccccatag agataagaga
     tgtaaacaag gaaaaagtgg 1981 ttgggcgtat catctcatcc accccttttgg ctgagaatac
     caacagtgta accaacatag 2041 aattagaacc ccccttttggg gacagctaca tagtgatagg
     tgttggaaac agcgcattaa 2101 cactccattg gttcaggaaa gggagttcca ttggcaagat
     gttttgagtcc acatacagag 2161 gtgcaaaacg aatggccatt ctaggtgaaa cagcttggga
     ttttggttcc gttggtggac 2221 tgttcacatc attgggaaag gctgtgcacc aggttttttgg
     aagtgtgtat acaaccatgt 2281 ttggaggagt ctcatggatg attagaatcc taattgggtt
     cttagtgttg tggattggca 2341 cgaactcgag gaacacttca atggctatga cgtgcatagc
     tgttggagga atcactctgt 2401 ttctgggctt cacagttcaa gcagacatgg gttgtgtggc
     gtcatggagt gggaaagaat 2461 tgaagtgtgg aagcggaatt tttgtggttg acaacgtgca
     cacttggaca gaacagtaca 2521 aatttcaacc agagtcccca gcgagactag cgtctgcaat
     attaaatgcc cacaaagatg 2581 gggtctgtgg aattagatca accacgaggc tggaaaatgt
     catgtggaag caaataacca
```

```
2641 acgagctaaa ctatgttctc tgggaaggag acatgacct
     cactgtagtg gctggggatg 2701 tgaaggggg gttgaccaaa ggcaagagag cactcacacc
     cccagtgagt gatctgaaat 2761 attcatggaa gacatgggga aaagcaaaaa tcttcacccc
     agaagcaaga aatagcacat 2821 ttttaataga cggaccagac acctctgaat gccccaatga
     acgaagagca tggaactctc 2881 ttgaggtgga agactatgga tttggcatgt tcacgaccaa
     catatggatg aaattccgag 2941 aaggaagttc agaagtgtgt gaccacaggt taatgtcagc
     tgcaattaaa gatcagaaag 3001 ctgtgcatgc tgacatgggt tattggatag agagctcaaa
     aaaccagacc tggcagatag 3061 agaaagcatc tcttattgaa gtgaaaacat gtctgtggcc
     caagacccac acactgtgga 3121 gcaatggagt gctggaaagc cagatgctca ttccaaaatc
     atatgcgggc ccttttttcac 3181 agcacaatta ccgccaggc tatgccacgc aaaccgtggg
     cccatggcac ttaggcaaat 3241 tagagataga ctttgagaa tgccccggaa caacagtcac
     aattcaggag gattgtgacc 3301 atagaggccc atctttgagg accaccactg catctggaaa
     actagtcacg caatggtgct 3361 gccgctcctg cacgatgcct cccttaaggt tcttgggaga
     agatgggtgc tggtatggga 3421 tggagattag gccccttgagt gaaaaagaag gaaacatggt
     caaatcacag gtgacggccg 3481 gacagggcac atcagaaact tttttctatgg gtctgttgtg
     cctgaccttg tttgtggaag 3541 aatgcttgag gagaagagtc actaggaaac acatgatatt
     agttgtggtg atcactcttt 3601 gtgctatcat cctgggaggc ctcacatgga tggacttact
     acgagccctc atcatgttgg 3661 gggacactat gtctggtaga ataggaggac agatccacct
     agccatcatg gcagtgttca 3721 agatgtcacc aggatacgtg ctgggtgtgt ttttaaggaa
     actcacttca agagagacag 3781 cactaatggt aataggaatg gccatgacaa cggtgctttc
     aattccacat gaccttatgg 3841 aactcattga tggaatatca ctgggactaa ttttgctaaa
     aatagtaaca cagtttgaca 3901 acacccaagt gggaaccta gctctttcct tgactttcat
     aagatcaaca atgccattgg 3961 tcatggcttg gaggaccatt atggctgtgt tgtttgtggt
     cacactcatt cctttgtgca 4021 ggacaagctg tcttcaaaaa cagtctcatt gggtagaaat
     aacagcactc atcctaggag 4081 cccaagctct gccagtgtac ctaatgactc ttatgaaagg
     agcctcaaga agatcttggc
```

APPENDIX 2-continued

Sequence of recombinant dengue type 4 virus strain rDEN4

```
4141 ctcttaacga gggcataatg gctgtgggtt tggttagtct
     cttaggaagc gctctttaa
4201 agaatgatgt cccttagct ggcccaatgg tggcaggagg
     cttacttctg gcggcttacg
4261 tgatgagtgg tagctcagca gatctgtcac tagagaaggc
     cgccaacgtg cagtgggatg
4321 aaatggcaga cataacaggc tcaagcccaa tcgtagaagt
     gaagcaggat gaagatggct
4381 cttctccat acgggacgtc gaggaaacca atatgataac
     ccttttggtg aaactggcac
4441 tgataacagt gtcaggtctc taccccttgg caattccagt
     cacaatgacc ttatggtaca
4501 tgtggcaagt gaaaacacaa agatcaggag ccctgtggga
     cgtcccctca cccgctgcca
4561 ctaaaaagc cgcactgtct gaaggagtgt acaggatcat
     gcaaagaggg ttattcggga
4621 aaactcaggt tggagtaggg atacacatgg aaggtgtatt
     tcacacaatg tggcatgtaa
4681 caagaggatc agtgatctgc cacgagactg ggagattgga
     gccatcttgg ctgacgtca
4741 ggaatgacat gatatcatac ggtgggggat ggaggcttgg
     agacaaatgg gacaaagaag
4801 aagacgttca ggtcctcgcc atagaaccag gaaaaaatcc
     taaacatgtc caaacgaaac
4861 ctggccttt caagaccta actggagaaa ttggagcagt
     aacattagat ttcaaacccg
4921 gaacgtctgg ttctcccatc atcaacagga aggaaaagt
     catcggactc tatggaaatg
4981 gagtagttac caaatcaggt gattacgtca gtgccataac
     gcaagccgaa agaattggag
5041 agccagatta tgaagtggat gaggacattt ttcgaaagaa
     aagattaact ataatggact
5101 tacaccccgg agctggaaag acaaaaagaa ttcttccatc
     aatagtgaga gaagccttaa
5161 aaaggaggct acgaactttg attttagctc ccacgagagt
     ggtggcggcc gagatgaag
5221 aggccctacg tggactgcca atccgttatc agaccccagc
     tgtgaaatca gaacacacag
5281 gaagagagat tgtagacctc atgtgtcatg caaccttcac
     aacaagactt ttgtcatcaa
5341 ccaggtcc aaattacaac cttatagtga tggatgaagc
     acatttcacc gatcttcta
5401 gtgtcgcggc tagaggatac atctcgacca gggtggaaat
     gggagaggca gcagccatct
5461 tcatgaccgc aaccccctcc ggagcgacag atccctttcc
     ccagagcaac agcccaatag
5521 aagacatcga gagggaaatt ccggaaaggt catggaacac
     agggttcgac tggataacag
5581 actaccaagg gaaaactgtg tggtttgttc ccagcataaa
     agctggaaat gacattgcaa
```

```
5641 attgtttgag aaagtcggga aagaaagtta ccagttgag
     taggaaaacc tttgatacag
5701 agtatccaaa aacgaaactc acggactggg actttgtggt
     cactacagac atatctgaaa
5761 tgggggccaa ttttagagcc gggagagtga tagaccctag
     aagatgcctc aagccagtta
5821 tcctaccaga tggggcagag agagtcattt tagcaggtcc
     tattccagtg actccagcaa
5881 gcgctgctca gagaagaggg cgaataggaa ggaacccagc
     acaagaagac gaccaatacg
5941 ttttctccgg agacccacta aaaatgatg aagatcatgc
     ccactggaca gaagcaaaga
6001 tgctgcttga caatatctac acccccagaag ggatcattcc
     aacattgttt ggtccggaaa
6061 gggaaaaac ccaagccatt gatggagagt tcgcctcag
     aggggaacaa aggaagactt
6121 ttgtggaatt aatgaggaga ggagaccttc cggtgtggct
     gagctataag gtagcttctg
6181 ctggcatttc ttacgaagat cgggaatggt gcttcacagg
     ggaaagaaat aaccaaattt
6241 tagaagaaaa catggaggtt gaaatttgga ctagagaggg
     agaaagaaa aagctaaggc
6301 caagatggtt agatgcacgt gtatacgctg accccatggc
     tttgaaggat ttcaaggagt
6361 ttgccagtgg aaggaagagt ataactctcg acatcctaac
     agagattgcc agtttgccaa
6421 cttacctttc ctctagggcc aagctcgccc ttgataacat
     agtcatgctc cacacaacag
6481 aaagaggagg gagggcctat caacacgccc tgaacgaact
     tccggagtca ctggaaacac
6541 tcatgcttgt agctttacta ggtgctatga cagcaggcat
     cttcctgttt ttcatgcaag
6601 ggaaggaat agggaaattg tcaatggatt tgataaccat
     tgcggtggct agtggcttgc
6661 tctgggtagc agaaattcaa ccccagtgga tagcggcctc
     aatcatacta gagttttttc
6721 tcatggtact gttgataccg gaaccagaaa acaaaggac
     cccacaagac aatcaattga
6781 tctacgtcat attgaccatt ctcaccatca ttggtctaat
     agcagccaac gagatggggc
6841 tgattgaaaa aacaaaaacg gattttgggt tttaccaggt
     aaaaacagaa accaccatcc
6901 tcgatgtgga cttgagacca gcttcagcat ggacgctcta
     tgcagtagcc accacaattc
6961 tgactcccat gctgagacac accatagaaa acacgtcggc
     caacctatct ctagcagcca
7021 ttgccaacca ggcagccgtc ctaatggggc ttggaaaagg
     atggccgctc acagaatgg
7081 acctcggtgt gccgctgtta gcaatgggat gctattctca
     agtgaaccca acaaccttga
```

APPENDIX 2-continued

Sequence of recombinant dengue type 4 virus strain rDEN4

```
7141  cagcatcctt agtcatgctt ttagtccatt atgcaataat
      aggcccagga ttgcaggcaa 7201  aagccacaag agaggcccag aaaaggacag ctgctgggat
      catgaaaaat cccacagtgg 7261  acgggataac agtaatagat ctagaaccaa tatcctatga
      cccaaaattt gaaaagcaat 7321  tagggcaggt catgctacta gtcttgtgtg ctggacaact
      actcttgatg agaacaacat 7381  gggctttctg tgaagtcttg actttggcca caggaccaat
      cttgaccttg tgggagggca 7441  acccgggaag gttttggaac acgaccatag ccgtatccac
      cgccaacatt ttcaggggaa 7501  gttacttggc gggagctgga ctggcttttt cactcataaa
      gaatgcacaa acccctagga 7561  ggggaactgg gaccacagga gagacactgg gagagaagtg
      gaagagacag ctaaactcat 7621  tagacagaaa agagtttgaa gagtataaaa gaagtggaat
      actagaagtg gacaggactg 7681  aagccaagtc tgccctgaaa gatgggtcta aaatcaagca
      tgcagtatca agagggtcca 7741  gtaagatcag atggattgtt gagagaggga tggtaaagcc
      aaaagggaaa gttgtagatc 7801  ttggctgtgg gagaggagga tggtcttatt acatggcgac
      actcaagaac gtgactgaag 7861  tgaaagggta tacaaaagga ggtccaggac atgaagaacc
      gattcccatg gctacttatg 7921  gttggaattt ggtcaaactc cattcagggg ttgacgtgtt
      ctacaaaccc acagagcaag 7981  tggacaccct gctctgtgat attggggagt catcttctaa
      tccaacaata gaggaaggaa 8041  gaacattaag agttttgaag atggtggagc catggctctc
      ttcaaaacct gaattctgca 8101  tcaaagtcct taaccctac atgccaacag tcatagaaga
      gctggagaaa ctgcagagaa 8161  aacatggtgg gaaccttgtc agatgcccgc tgtccaggaa
      ctccacccat gagatgtatt 8221  gggtgtcagg agcgtcggga acattgtga gctctgtgaa
      cacaacatca aagatgttgt 8281  tgaacaggtt cacaacaagg cataggaaac ccacttatga
      gaaggacgta gatcttgggg 8341  caggaacgag aagtgtctcc actgaaacag aaaaaccaga
      catgacaatc attgggagaa 8401  ggcttcagcg attgcaagaa gagcacaaag aaacctggca
      ttatgatcag gaaaacccat 8461  acagaacctg ggcgtatcat ggaagctatg aagctccttc
      gacaggctct gcatcctcca 8521  tggtgaacgg ggtggtaaaa ctgctaacaa acccctggga
      tgtgattcca atggtgactc 8581  agttagccat gacagataca accccttttg gcaacaaag
      agtgttcaaa gagaaggtg
```

```
8641  ataccagaac accacaacca aaacccggta cacgaatggt
      tatgaccacg acagccaatt 8701  ggctgtgggc cctccttgga aagaagaaaa atcccagact
      gtgcacaagg gaagagttca 8761  tctcaaaagt tagatcaaac gcagccatag gcgcagtctt
      tcaggaagaa cagggatgga 8821  catcagccag tgaagctgtg aatgacagcc ggttttggga
      actggttgac aaagaaaggg 8881  ccctacacca ggaagggaaa tgtgaatcgt gtgtctataa
      catgatggga aaacgtgaga 8941  aaagttagg agagtttggc agagccaagg gaagccgagc
      aatctggtac atgtggctgg 9001  gagcgcggtt tctggaattt gaagccctgg ttttttgaa
      tgaagatcac tggtttggca 9061  gagaaaattc atggagtgga gtggaagggg aaggtctgca
      cagattggga tatatcctgg 9121  aggagataga caagaaggat ggagacctaa tgtatgctga
      tgacacagca ggctgggaca 9181  caagaatcac tgaggatgac cttcaaaatg aggaactgat
      cacggaacag atggctcccc 9241  accacaagat cctagccaaa gccattttca aactaaccta
      tcaaaacaaa gtggtgaaag 9301  tcctcagacc cacaccgcgg ggagcggtga tggatatcat
      atccaggaaa gaccaaagag 9361  gtagtggaca agttggaaca tatggtttga acacattcac
      caacatggaa gttcaactca 9421  tccgccaaat ggaagctgaa ggagtcatca cacaagatga
      catgcagaac ccaaaagggt 9481  tgaaagaaag agttgagaaa tggctgaaag agtgtggtgt
      cgacaggtta aagaggatgg 9541  caatcagtgg agacgattgc gtggtgaagc ccctagatga
      gaggtttgc acttccctcc 9601  tcttcttgaa cgacatggga aaggtgagga aagacattcc
      gcagtgggaa ccatctaagg 9661  gatggaaaaa ctggcaagag gttccttttt gctcccacca
      cttttcacaag atctttatga 9721  aggatggccg ctcactagtt gttccatgta gaaaccagga
      tgaactgata gggagagcca 9781  gaatctcgca gggagctgga tggagcttaa gagaaacagc
      ctgcctgggc aaagcttacg 9841  cccagatgtg gtcgcttatg tacttccaca gaagggatct
      gcgtttagcc tccatggcca 9901  tatgctcagc agttccaacg gaatggtttc caacaagcag
      aacaacatgg tcaatccacg 9961  ctcatcacca gtggatgacc actgaagata tgctcaaagt
      gtggaacaga gtgtggatag 10021 aagacaaccc taatatgact gacaagactc cagtccattc
      gtgggaagat ataccttacc 10081 tagggaaaag agaggatttg tggtgtggat ccctgattgg
      actttcttcc agagccacct
```

APPENDIX 2-continued

Sequence of recombinant dengue type 4 virus strain rDEN4

```
10141 gggcgaagaa cattcat

APPENDIX 3-continued

Sequence of recombinant dengue type 2 chimeric virus strain rDEN2/4Δ30

```
mat_peptide 712 . . . 936
            /product = "membrane (M) protein"

mat_peptide 937 . . . 2421
            /product = "envelope (E) protein"

mat_peptide 2422 . . . 3477
            /product = "NS1 protein"

mat_peptide 3478 . . . 4131
            /product = "NS2A protein"

mat_peptide 4132 . . . 4521
            /product = "NS2B protein"

mat_peptide 4522 . . . 6375
            /product = "NS3 protein"

mat_peptide 6376 . . . 6756
            /product = "NS4A protein"

mat_peptide 6757 . . . 6825
            /product = "2K protein"

mat_peptide 6826 . . . 7560
            /product = "NS4B protein"
mat_peptide 7561 . . . 10260
            /product = "NS5 protein"

rDEN2/4Δ30 sequence 1 agttgttagt ctgtgtggac cgacaaggac agttccaaat
      cggaagcttg
   51 cttaacacag ttctaacagt ttgtttgaat agagagcaga
      tctctgatga
  101 ataaccaacg aaaaaaggcg agaaatacgc ctttcaatat
      gctgaaacgc
  151 gagagaaacc gcgtgtcgac tgtacaacag ctgacaaaga
      gattctcact
  201 tggaatgctg cagggacgag gaccattaaa actgttcatg
      gccctggtgg
  251 cgttccttcg tttcctaaca atcccaccaa cagcagggat
      actgaagaga
  301 tggggaacaa ttaaaaaatc aaaagccatt aatgttttga
      gagggttcag
  351 gaaagagatt ggaaggatgc tgaacatctt gaacaggaga
      cgcagaactg
  401 caggcatgat cattatgctg attccaacag tgatggcgtt
      ccatttaacc
  451 acacgtaacg gagaaccaca catgatcgtc agtagacaag
      agaaagggaa
  501 aagtcttctg tttaaaacag aggatggtgt gaacatgtgt
      accctcatgg
  551 ccatggacct tggtgaattg tgtgaagata caatcacgta
      caagtgtcct
  601 cttctcaggc agaatgaacc agaagacata gattgttggt
      gcaactctac
  651 gtccacatgg gtaacttatg gacgtgtac caccacagga
      gaacacagaa
  701 gagaaaaaag atcagtggca ctcgttccac atgtgggaat
      gggactggag
```

APPENDIX 3-continued

Sequence of recombinant dengue type 2 chimeric virus strain rDEN2/4Δ30

```
  751 acacgaactg aaacatggat gtcatcagaa ggggcctgga
      aacatgccca
  801 gagaattgaa acttggatct tgagacatcc aggctttacc
      ataatggcag
  851 caatcctggc ataccacata ggaacgacac atttccaaag
      agccctgatt
  901 ttcatcttac tgacagctgt cgctccttca atgacaatgc
      gttgcatagg
  951 aatatcaaat agagactttg tagaagggt ttcaggagga
      agctgggttg
 1001 acatagtctt agaacatgga agctgtgtga cgacgatggc
      aaaaaacaaa
 1051 ccaacattgg attttgaact gataaaaaca gaagccaaac
      aacctgccac
 1101 tctaaggaag tactgtatag aggcaaagct gaccaacaca
      acaacagaat
 1151 ctcgctgccc aacacaagga gaacctagcc taatgaagaa
      gcaggacaaa
 1201 aggttcgtct gcaaacactc catggtggac agaggatggg
      gaaatgatg
 1251 tggattattt ggaaaaggag gcattgtgac ctgtgctatg
      ttcacatgca
 1301 aaaagaacat ggaaggaaaa gtcgtgcaac cagaaaactt
      ggaatacacc
 1351 attgtgataa caccctcactc aggggaagag catgcagtcg
      gaaatgacac
 1401 aggaaaacat ggcaaggaaa tcaaaataac accacagagt
      tccatcacag
 1451 aagcagagtt gacaggctat ggcactgtca cgatggagtg
      ctctccagag
 1501 acgggcctcg acttcaatga gatggtgttg ctgcaaatgg
      aaaataaagc
 1551 ttggctggtg cacaggcaat ggttcctaga cctgccgttg
      ccatggctgc
 1601 ccggagcgga cacacaagga tcaaattgga tacagaaaga
      gacattggtc
 1651 actttcaaaa atccccatgc gaagaaacag gatgttgttg
      ttttgggatc
 1701 ccaagaaggg gccatgcaca cagcactcac aggggccaca
      gaaatccaga
 1751 tgtcatcagg aaacttactg ttcacaggac atctcaagtg
      caggctgagg
 1801 atggacaaac tacagctcaa aggaatgtca tactctatgt
      gcacaggaaa
 1851 gtttaaagtt gtgaaggaaa tagcagaaac acaacatgga
      acaatagtta
 1901 tcagagtaca atatgaaggg gacggttctc catgtaagat
      cccttttgag
 1951 ataatggatt tggaaaaaag acatgtttta ggtcgcctga
      ttacagtcaa
```

APPENDIX 3-continued

Sequence of recombinant dengue type 2 chimeric virus strain rDEN2/4Δ30

```
2001 cccaatcgta acagaaaaag atagcccagt caacatagaa
     gcagaacctc 2051 cattcggaga cagctacatc atcataggag tagagccggg
     acaattgaag 2101 ctcaactggt ttaagaaagg aagttctatc ggccaaatgt
     ttgagacaac 2151 aatgagggga gcgaagagaa tggccatttt aggtgacaca
     gcttgggatt 2201 ttggatccct gggaggagtg tttacatcta taggaaaggc
     tctccaccaa 2251 gttttcggag caatctatgg ggctgccttc agtggggtct
     catggactat 2301 gaaaatcctc ataggagtca ttatcacatg gataggaatg
     aactcgagga 2351 acacttcaat ggctatgacg tgcatagctg ttggaggaat
     cactctgttt 2401 ctgggcttca cagttcaagc agacatgggt tgtgtggcgt
     catggagtgg 2451 gaaagaattg aagtgtggaa gcggaatttt tgtggttgac
     aacgtgcaca 2501 cttggacaga acagtacaaa tttcaaccag agtccccagc
     gagactagcg 2551 tctgcaatat taaatgccca caagatggg tgctgtggaa
     ttagatcaac 2601 cacgaggctg aaaatgtca tgtggaagca ataaccaac
     gagctaaact 2651 atgttctctg ggaaggagga catgacctca ctgtagtggc
     tggggatgtg 2701 aaggggtgt tgaccaaagg caagagagca ctcacacccc
     cagtgagtga 2751 tctgaaatat tcatggaaga catgggaaa agcaaaaatc
     ttcacccag 2801 aagcaagaaa tagcacattt ttaatagacg gaccagacac
     tctgaatgc 2851 cccaatgaac gaagagcatg gaactctctt gaggtggaag
     actatggatt 2901 tggcatgttc acgaccaaca tatggatgaa attccgagaa
     ggaagttcag 2951 aagtgtgtga ccacaggtta atgtcagctg caattaaaga
     tcagaaagct 3001 gtgcatgctg acatgggtta ttggatagag agctcaaaaa
     accagacctg 3051 gcagatagag aaagcatctc ttattgaagt gaaaacatgt
     ctgtggccca 3101 agaccacac actgtggagc aatggagtgc tggaaagcca
     gatgctcatt 3151 ccaaaatcat atgcgggccc ttttttcacag cacaattacc
     gccagggcta 3201 tgccacgcaa accgtgggcc catggcactt aggcaaatta
     gagatagact
```

```
3251 ttggagaatg ccccggaaca acagtcacaa ttcaggagga
     ttgtgaccat 3301 agaggcccat ctttgaggac caccactgca tctggaaaac
     tagtcacgca 3351 atggtgctgc cgctcctgca cgatgcctcc cttaaggttc
     ttgggagaag 3401 atgggtgctg gtatgggatg gagattaggc ccttgagtga
     aaaagaagag 3451 aacatggtca aatcacaggt gacggccgga cagggcacat
     cagaaacttt 3501 ttctatgggt ctgttgtgcc tgaccttgtt tgtggaagaa
     tgcttgagga 3551 gaagagtcac taggaaacac atgatattag ttgtggtgat
     cactctttgt 3601 gctatcatcc tgggaggcct cacatggatg tacttactac
     gagccctcat 3651 catgttgggg gacactatgt ctggtagaat aggaggacag
     atccacctag 3701 ccatcatggc agtgttcaag atgtcaccag gatacgtgct
     gggtgtgttt 3751 ttaaggaaac tcacttcaag agagacagca ctaatggtaa
     taggaatggc 3801 catgacaacg gtgctttcaa ttccacatga ccttatgaa
     ctcattgatg 3851 gaatatcact gggactaatt ttgctaaaaa tagtaacaca
     gtttgacaac 3901 acccaagtgg gaaccttagc tctttccttg actttcataa
     gatcaacaat 3951 gccattggtc atggcttgga ggaccattat ggctgtgttg
     tttgtggtca 4001 cactcattcc tttgtgcagg acaagctgtc ttcaaaaaca
     gtctcattgg 4051 gtagaaataa cagcactcat cctaggagcc aagctctgc
     cagtgtacct 4101 aatgactctt atgaaaggag cctcaagaag atcttggcct
     cttaacgagg 4151 gcataatggc tgtgggtttg gttagtctct taggaagcgc
     tcttttaaag 4201 aatgatgtcc ctttagctgg cccaatggtg gcaggaggct
     tacttctggc 4251 ggcttacgtg atgagtggta gctcagcaga tctgtcacta
     gagaaggccg 4301 ccaacgtgca gtgggatgaa atggcagaca taacaggctc
     aagcccaatc 4351 atagaagtga agcaggatga agatggctct ttctccatac
     gggacgtcga 4401 ggaaccaat atgataaccc ttttggtgaa actggcactg
     ataacagtgt 4451 caggtctcta ccccttggca attccagtca caatgaccgt
     atggtacatg
```

APPENDIX 3-continued

Sequence of recombinant dengue type 2 chimeric virus strain rDEN2/4Δ30

| | |
|---|---|
| 4501 | tggcaagtga aaacacaaag atcaggagcc ctgtgggacg tcccctcacc |
| 4551 | cgctgccact aaaaaagccg cactgtctga aggagtgtac aggatcatgc |
| 4601 | aaagagggtt attcgggaaa actcaggttg gagtagggat acacatggaa |
| 4651 | ggtgtatttc acacaatgtg gcatgtaaca gaggatcagt gatctgcca |
| 4701 | cgagactggg agattggagc catcttgggc tgacgtcagg aatgacatga |
| 4751 | tatcatacgg tggggatgg aggcttggag acaaatggga caaagaagaa |
| 4801 | gacgttcagg tcctcgccat agaaccagga aaaaatccta aacatgtcca |
| 4851 | aacgaaacct ggccttttca gaccctaac tggagaaatt ggagcagtaa |
| 4901 | cattagattt caaacccgga acgtctggtt ctcccatcat caacaggaaa |
| 4951 | ggaaaagtca tcggactcta tggaaatgga gtagttacca aatcaggtga |
| 5001 | ttacgtcagt gccataacgc aagccgaaag aattggagag ccagattatg |
| 5051 | aagtggatga ggacattttt cgaaagaaaa tttagctccc aatggactta |
| 5101 | caccccggag ctggaaagac aaaaagaatt gactgccaat tagtgagaga |
| 5151 | agccttaaaa aggaggctac gaactttgat agagagattg acgagagtgg |
| 5201 | tggcggccga gatggaagag gccctacgtg gactgccaat ccgttatcag |
| 5251 | accccagctg tgaaatcaga acacacagga agagagattg tagacctcat |
| 5301 | gtgtcatgca accttcacaa caagactttt gtcatcaacc agggttccaa |
| 5351 | attacaacct tatagtgatg gatgaagcac atttcaccga tccttctagt |
| 5401 | gtcgcggcta gaggatacat ctcgaccagg gtggaaatgg gagaggcagc |
| 5451 | agccatcttc atgaccgcaa ccctcccgg agcgacagat cccttcccc |
| 5501 | agagcaacag cccaatagaa gacatcgaga gggaaattcc ggaaaggtca |
| 5551 | tggaacacag ggttcgactg gataacagac taccaaggga aaactgtgtg |
| 5601 | gtttgttccc agcataaag ctggaaatga cattgcaaat tgtttgagaa |
| 5651 | agtcgggaaa gaaagttatc cagttgagta ggaaaacctt tgatacagag |
| 5701 | tatccaaaaa cgaaactcac ggactgggac tttgtggtca ctacagacat |
| 5751 | atctgaaatg ggggccaatt ttagagccgg gagagtgata gaccctagaa |
| 5801 | gatgcctcaa gccagttatc ctaccagatg ggccagagag agtcatttta |
| 5851 | gcaggtccta ttccagtgac tccagcaagc gctgctcaga aagagggcg |
| 5901 | aataggaagg aacccagcac aagaagacga ccaatacgtt ttctccggag |
| 5951 | acccactaaa aaatgatgaa gatcatgccc actggacaga agcaaagatg |
| 6001 | ctgcttgaca atatctacac cccagaaggg atcattccaa cattgtttgg |
| 6051 | tccggaaagg gaaaaaaccc aagccattga tggagagttt cgcctcagag |
| 6101 | gggaacaaag gaagactttt gtggaattaa tgaggagagg agaccttccg |
| 6151 | gtgtggctga gctataaggt agcttctgct ggcatttctt acaaagatcg |
| 6201 | ggaatggtgc ttcacagggg aaagaaataa ccaaattta gaagaaaaca |
| 6251 | tggaggttga aatttggact agagagggag aaaagaaaaa gctaaggcca |
| 6301 | agatggttag atgcacgtgt atacgctgac cccatggctt tgaaggattt |
| 6351 | caaggagttt gccagtggaa ggaagagtat aactctcgac atcctaacag |
| 6401 | agattgccga tttgccaact tacctttcct ctagggccaa gctcgccctt |
| 6451 | gataacatag tcatgctcca cacaacagaa agaggaggga gggcctatca |
| 6501 | acacgccctg aacgaacttc cggagtcact ggaaacactc atgcttgtag |
| 6551 | ctttactagg tgctatgaca gcaggcatct tcctgttttt catgcaaggg |
| 6601 | aaaggaatag ggaaattgtc aatgggtttg ataaccattg cggtggctag |
| 6651 | tggcttgctc tgggtagcag aaattcaacc ccagtggata gcggcctcaa |
| 6701 | tcatactaga gttttttctc atggtactgt tgataccgga accagaaaaa |
| 6751 | caaaggaccc cacaagacaa tcaattgatc tacgtcatat tgaccatttct |
| 6801 | caccatcatt ggtctaatag cagccaacga tggggctg attgaaaaaa |
| 6851 | caaaaacgga ttttggttt taccaggtaa aaacagaaac caccatcctc |
| 6901 | gatgtggact tgagaccagc ttcagcatgg acgctctatg cagtagccac |
| 6951 | cacaattctg actcccatgc tgagacacac catagaaaac acgtcggcca |

APPENDIX 3-continued

Sequence of recombinant dengue type 2 chimeric
virus strain rDEN2/4Δ30

| | |
|---|---|
| 7001 | acctatctct agcagccatt gccaaccagg cagccgtcct aatgggcttt |
| 7051 | ggaaaaggat ggccgctcca cagaatggac ctcggtgtgc cgctgttagc |
| 7101 | aatgggatgc tattctcaag tgaacccaac aaccttgaca gcatccttag |
| 7151 | tcatgctttt agtccattat gcaataatag gcccaggatt gcaggcaaaa |
| 7201 | gccacaagag aggcccagaa aaggacagct gctgggatca tgaaaaatcc |
| 7251 | cacagtggac gggataacag taatagatct agaaccaata tcctatgacc |
| 7301 | caaaatttga aaagcaatta gggcaggtca tgctactagt cttgtgtgct |
| 7351 | ggacaactac tcttgatgag aacaacatgg gctttctgtg aagtcttgac |
| 7401 | tttggccaca ggaccaatct tgaccttgtg ggagggcaac ccgggaaggt |
| 7451 | tttggaacac gaccatagcc gtatccaccg ccaacatttt cagggaagt |
| 7501 | tacttggcgg gagctggact ggcttttttca ctcataaaga atgcacaaac |
| 7551 | ccctaggagg ggaactggga ccacaggaga gacactggga gagaagtgga |
| 7601 | agagacagct aaactcatta gacagaaaag agtttgaaga gtataaaaga |
| 7651 | agtggaatac tagaagtgga caggactgaa gccaagtctg ccctgaaaga |
| 7701 | tgggtctaaa atcaagcatg cagtatcaag agggtccagt aagatcagat |
| 7751 | ggattgttga gagagggatg gtaaagccaa aagggaaagt tgtagatctt |
| 7801 | ggctgtggga gaggaggatg gtcttattac atggcgacac tcaagaacgt |
| 7851 | gactgaagtg aaagggtata caaaaggagg tccaggacat gaagaaccga |
| 7901 | ttcccatggc tacttatggt tggaatttgg tcaaactcca ttcagggggtt |
| 7951 | gacgtgttct acaaacccac agagcaagtg gacaccctgc tctgtgatat |
| 8001 | tggggagtca tcttctaatc caacaataga ggaaggaaga acattaagag |
| 8051 | ttttgaagat ggtggagcca tggctctctt caaaacctga attctgcatc |
| 8101 | aaagtcctta acccctacat gccaacagtc atagaagagc tggagaaact |
| 8151 | gcagagaaaa catggtggga accttgtcag atgcccgctg tccaggaact |
| 8201 | ccacccatga gatgtattgg gtgtcaggag cgtcgggaaa cattgtgagc |
| 8251 | tctgtgaaca caacatcaaa gatgttgttg aacaggttca acaaggca |
| 8301 | taggaaaccc acttatgaga aggacgtaga tcttggggca ggaacgagaa |
| 8351 | gtgtctccac tgaaacagaa aaaccagaca tgacaatcat tgggagaagg |
| 8401 | cttcagcgat gcaagaaga gcacaaagaa acctggcatt atgatcagga |
| 8451 | aaacccatac agaacctggg cgtatcatgg aagctatgaa gctccttcga |
| 8501 | caggctctgc atcctccatg gtgaacgggg tggtaaaact gctaacaaaa |
| 8551 | ccctgggatg tgattccaat ggtgactcag ttagccatga cagatacaac |
| 8601 | cccttttggg caacaaagag tgttcaaaga aaggtggat accagaacac |
| 8651 | cacaaccaaa acccggtaca cgaatggtta tgaccacgac agccaattgg |
| 8701 | ctgtgggccc tccttggaaa gagaaaaat cccagactgt gcacaaggga |
| 8751 | agagttcatc tcaaaagtta gatcaaacgc agccataggc gcagtctttc |
| 8801 | aggaagaaca gggatggaca tcagccagtg aagctgtgaa tgacagccgg |
| 8851 | ttttgggaac tggttacaa agaaagggcc ctacaccagg aagggaaatg |
| 8901 | tgaatcgtgt gtctataaca tgatgggaaa acgtgagaaa aagttaggag |
| 8951 | agtttggcag agccaaggga agccgagcaa tctggtacat gtggctggga |
| 9001 | gcgcggtttc tggaatttga agccctgggt ttttttgaatg aagatcactg |
| 9051 | gtttggcaga gaaaattcat ggagtggagt ggaaggggaa ggtctgcaca |
| 9101 | gattgggata tatcctggag gagatagaca agaaggatgg agacctaatg |
| 9151 | tatgctgatg acacagcagg ctgggacaca agaatcactg aggatgacct |
| 9201 | tcaaaatgag gaactgatca cggaacagat ggctccccac cacaagatcc |
| 9251 | tagccaaagc catttttcaaa ctaacctatc aaaacaaagt ggtgaaagtc |
| 9301 | ctcagaccca caccgcgggg agcggtgatg gatatcatat ccaggaaaga |
| 9351 | ccaaagaggt agtggacaag ttggaacata tggtttgaac acattccaca |
| 9401 | acatggaagt tcaactcatc cgccaaatgg aagctgaagg agtcatcaca |
| 9451 | caagatgaca tgcagaaccc aaaagggttg aaagaaagag ttgagaaatg |

APPENDIX 3-continued

Sequence of recombinant dengue type 2 chimeric virus strain rDEN2/4Δ30

```
 9501 gctgaaagag tgtggtgtcg acaggttaaa gaggatggca
      atcagtggag 9551 acgattgcgt ggtgaagccc ctagatgaga ggtttggcac
      ttccctcctc 9601 ttcttgaacg acatgggaaa ggtgaggaaa gacattccgc
      agtgggaacc 9651 atctaaggga tggaaaaact ggcaagaggt tccttttgc
      tcccaccact 9701 ttcacaagat ctttatgaag gatggccgct cactagttgt
      tccatgtaga 9751 aaccaggatg aactgatagg gagagccaga atctcgcagg
      gagctggatg 9801 gagcttaaga gaaacagcct gcctgggcaa agcttacgcc
      cagatgtggt 9851 cgcttatgta cttccacaga agggatctgc gtttagcctc
      catggccata 9901 tgctcagcag ttccaacgga atggtttcca acaagcagaa
      caacatggtc 9951 aatccacgct catcaccagt ggatgaccac tgaagatatg
      ctcaaagtgt 10001 ggaacagagt gtggatagaa gacaaccct atatgactga
      caagactcca
```

Sequence of recombinant dengue type 2 chimeric virus strain rDEN2/4Δ30

```
10051 gtccattcgt gggaagatat accttaccta gggaaaagag
      aggatttgtg 10101 gtgtggatcc ctgattggac tttcttccag agccacctgg
      gcgaagaaca 10151 ttcacacggc cataacccag gtcaggaacc tgatcggaaa
      agaggaatac 10201 gtggattaca tgccagtaat gaaaagatac agtgctcctt
      cagagagtga 10251 aggagttctg taattaccaa caacaaacac caaaggctat
      tgaagtcagg 10301 ccacttgtgc cacggtttga gcaaaccgtg ctgcctgtag
      ctccgccaat 10351 aatgggaggc gtaataatcc caggaggc catgcgccac
      ggaagctgta 10401 cgcgtggcat attggactag cggttagagg agacccctcc
      catcactgac 10451 aaaacgcagc aaaaggggc ccaagactag aggttagagg
      agacccccccc 10501 aacacaaaaa cagcatattg acgctgggaa agaccagaga
      tcctgctgtc 10551 tctgcaacat caatccaggc acagagcgcc gcaagatgga
      ttggtgttgt 10601 tgatccaaca ggttct
```

APPENDIX 4

Alignment of dengue virus polyproteins

```
DEN4      1 MNQRKKVVRPPFNMLKRERNRVSTPQGLVKRFSTGLFSGKGPLRMVLAF  49
DEN1-WP   1 MNNQRKKTGRPSFNMLKRARNRVSTVSQLAKRFSKGLLSGQGPMKLVMAF  50
DEN2-NGC  1 MNNQRKKARNTPFNMLKRERNRVSTVQQLTKRFSLGMLQGRGPLKLFMAL  50
DEN3-H87  1 MNNQRKKTGKPSINMLKRVRNRVSTGSQLAKRFSRGLLNGQGPMKLVMAF  50
            *****     ***** ****** *  **** *.  *.**.... *

DEN4     50 ITFLRVLSIPPTAGILKRWGQLKKNKAIKILIGFRKEIGRMLNILNGRKR  99
DEN1-WP  51 IAFLRFLAIPPTAGILARWGSFKKNGAIKVLRGFKKEISNMLNIMNRRKR 100
DEN2-NGC 51 VAFLRFLTIPPTAGILKRWGTIKKSKAINVLRGFRKEIGRMLNILNRRRR 100
DEN3-H87 51 IAFLRFLAIPPTAGVLARWGTFKKSGAIKVLKGFKKEISNMLSIINKRKK 100
            ..*** *.******.*  ***   **   * **.***  **  *.*  ..

DEN4    100 STITLLCLIPTVMAFSLSTRDGEPLMIVAKHERGRPLLFKTTEGINKCTL 149
DEN1-WP 101 SVTMLLMLLPTALAFHLTTRGGEPHMIVSKQERGKSLLFKTSAGVNMCTL 150
DEN2-NGC 101 TAGMIIMLIPTVMAFHLTTRNGEPHMIVSRQEKGKSLLFKTEDGVNMCTL 150
DEN3-H87 101 TSLCLMMMLPATLAFHLTSRDGEPRMIVGKNERGKSLLFKTASGINMCTL 150
            .   ..  .*. .**  *.* *** *** .. **.*  ***** *.* ***

DEN4    150 IANDLGEMCEDTVTYKCPLLVNTEPEDIDCWCNLTSTWVMYGTCTQSGER 199
DEN1-WP 151 IAMDLGELCEDTMTYKCPRITETEPDDVDCWCNATETWVTYGTCSQTGEH 200
DEN2-NGC 151 MAMDLGELCEDTITYKCPFLRQNEPEDIDCWCNSTSTWVTYGTCTTTGEH 200
```

APPENDIX 4-continued

Alignment of dengue virus polyproteins

```
DEN3-H87  151  IAMDLGEMCDDTVTYKCPHITEVEPEDIDCWCNLTSTWVTYGTCNQAGEH  200
               .******.*.**.*****  .   **.*.***** * *** ****  .**.

DEN4      200  RREKRSVALTPHSGMGLETRAETWMSSEGAWKHAQRVESWILRNPGFALL  249

DEN1-WP   201  RRDKRSVALAPHVGLGLETRTETWMSSEGAWKQIQKVETWALRHPGFTVI  250

DEN2-NGC  201  RREKRSVALVPGVGMGLETRTETWMSSEGAWKHAQRIETWILRHPGFTIM  250

DEN3-H87  201  RRDKRSVALAPHVGMGLDTRTQTWMSAEGAWRQVEKVETWALRHPGFTIL  250
               **.******.** **.**.**..****.****.. ...*.* **.***...

DEN4      250  AGFMAYMIGQTGIQRTVFFVLMMLVAPSYGMRCVGVGNRDFVEGVSGGAW  299

DEN1-WP   251  ALFLAHAIGTSITQKGIIFILLMLVTPSMAMRCVGIGNRDFVEGLSGATW  300

DEN2-NGC  251  AAILAYTIGTTHFQRALIFILLTAVAPSMTMRCIGISNRDFVEGVSGGSW  300

DEN3-H87  251  ALFLAHYIGTSLTQKVVIFILLMLVTPSMTMRCVGVGNRDFVEGLSGATW  300
                *  .*  **  .   *. .  *.**    ***.*.******.** .*

DEN4      300  VDLVLEHGGCVTTMAQGKPTLDFELTKTTAKEVALLRTYCIEASISNITT  349

DEN1-WP   301  VDVVLEHGSCVTTMAKDKPTLDIELLKTEVTNPAVLRKLCIEAKISNTTT  350

DEN2-NGC  301  VDIVLEHGSCVTTMAKNKPTLDFELIKTEAKQPATLRKYCIEAKLTNTTT  350

DEN3-H87  301  VDVVLEHGGCVTTMAKNKPTLDIELQKTEATQLATLRKLCIEGKITNITT  350
               **.****** ******. ***** ** **      * **  ***  ..* **

DEN4      350  ATRCPTQGEPYLKEEQDQQYICRRDVVDRGWGNGCGLFGKGGVVTCAKFS  399

DEN1-WP   351  DSRCPTQGEATLVEEQDTNFVCRRTFVDRGWGNGCGLFGKGSLITCAKFK  400

DEN2-NGC  351  DSRCPTQGEPSLNEEQDKRFVCKHSMVDRGWGNGCGLFGKGGIVTCAMFT  400

DEN3-H87  351  DSRCPTQGEAILPEEQDQNYVCKHTYVDRGWGNGCGLFGKGSLVTCAKFQ  400
                .*******  * ****   .*..  *************** ..*** *

DEN4      400  CSGKITGNLVQIENLEYTVVVTVHNGDTHAVGNDTSNHGVTAMITPRSPS  449

DEN1-WP   401  CVTKLEGKIVQYENLKYSVIVTVHTGDQHQVGNETTEHGTTATITPQAPT  450

DEN2-NGC  401  CKKNMKGKVVQPENLEYTIVITPHSGEEHAVGNDTGKHGKEIKITPQSSI  450

DEN3-H87  401  CLESIEGKVVQHENLKYTVIITVHTGDQHQVGNET--QGVTAEITSQAST  448
               *    .  *  .**  ***  .... *  *  *.  *  ***.*  .*         **  ..

DEN4      450  VEVKLPDYGELTLDCEPRSGIDFNEMILMKMKKKTWLVHKQWFLDLPLPW  499

DEN1-WP   451  SEIQLTDYGALTLDCSPRTGLDFNEMVLLTMEKKSWLVHKQWFLDLPLPW  500

DEN2-NGC  451  TEAELTGYGTVTMECSPRTGLDFNEMVLLQMENKAWLVHRQWFLDLPLPW  500

DEN3-H87  449  AEAILPEYGTLGLECSPRTGLDFNEMILLTMKNKAWMVHRQWFFDLPLPW  498
                *   *  **   ..*  **.*.*****.*.  *  *.*.**.***  ******

DEN4      500  TAGADTSEVHWNYKERMVTFKVPHAKRQDVTVLGSQEGAMHSALAGATEV  549

DEN1-WP   501  TSGASTSQETWNRQDLLVTFKTAHAKKQEVVVLGSQEGAMHTALTGATEI  550

DEN2-NGC  501  LPGADTQGSNWIQKETLVTFKNPHAKKQDVVVLGSQEGAMHTALTGATEI  550

DEN3-H87  499  TSGATTKTPTWNRKELLVTFKNAHAKKQEVVVLGSQEGAMHTALTGATEI  548
                ** *     *   .. .****  ***.*.*  **********.**.****.

DEN4      550  DSGDGNHMFAGHLKCKVRMEKLRIKGMSYTMCSGKFSIDKEMAETQHGTT  599

DEN1-WP   551  QTSGTTTIFAGHLKCRLKMDKLTLKGMSYVMCTGSFKLEKEVAETQHGTV  600

DEN2-NGC  551  QMSSGNLLFTGHLKCRLRMDKLQLKGMSYSMCTGKFKVVKEIAETQHGTI  600

DEN3-H87  549  QTSGGTSIFAGHLKCRLKMDKLKLKGMSYAMCLNTFVLKKEVSETQHGTI  598
                . .*.*****...*.** ***** **  .*  . **..******

DEN4      600  VVKVKYEGAGAPCKVPIEIRDVNKEKVVGRIISSTPLAENTNSVTNIELE  649
```

APPENDIX 4-continued

Alignment of dengue virus polyproteins

```
DEN1-WP   601 LVQVKYEGTDAPCKIPFSSQDEKGVTQNGRLITANPIVTDKEKPVNIEAE   650

DEN2-NGC  601 VIRVQYEGDGSPCKIPFEIMDLEKRHVLGRLITVNPIVTEKDSPVNIEAE   650

DEN3-H87  599 LIKVEYKGEDAPCKIPFSTEDGQGKAHNGRLITANPVVTKKEEPVNIEAE   648
              ...* * *  .***.*     *       **.*. .*.         *** *

DEN4      650 PPFGDSYIVIGVGNSALTLHWFRKGSSIGKMFESTYRGAKRMAILGETAW   699

DEN1-WP   651 PPFGESYIVVGAGEKALKLSWFKKGSSIGKMFEATARGARRMAILGDTAW   700

DEN2-NGC  651 PPFGDSYIIIGVEPGQLKLNWFKKGSSIGQMIETTMRGAKRMAILGDTAW   700

DEN3-H87  649 PPFGESNIVIGIGDKALKINWYRKGSSIGKMFEATARGARRMAILGDTAW   698
              ****.* *..*        *  . *.******.*  *.* ***.******.***

DEN4      700 DFGSVGGLFTSLGKAVHQVFGSVYTTMFGGVSWMIRILIGFLVLWIGTNS   749

DEN1-WP   701 DFGSIGGVFTSVGKLIHQIFGTAYGVLFSGVSWTMKIGIGILLTWLGLNS   750

DEN2-NGC  701 DFGSLGGVFTSIGKALHQVFGAIYGAAFSGVSWTMKILIGVIITWIGMNS   750

DEN3-H87  699 DFGSVGGVLNSLGKMVHQIFGSAYTALFSGVSWIMKIGIGVLLTWIGLNS   748
              ****.**. .*.**  .**.**. *    * ****  .* **  ..*.* **

DEN4      750 RNTSMAMTCIAVGGITLFLGFTVQADMGCVASWSGKELKCGSGIFVVDNV   799

DEN1-WP   751 RSTSLSMTCIAVGMVTLYLGVMVQADSGCVINWKGRELKCGSGIFVTNEV   800

DEN2-NGC  751 RSTSLSVSLVLVGVVTLYLGVMVQADSGCVVSWKNKELKCGSGIFITDNV   800

DEN3-H87  749 KNTSMSFSCIAIGIITLYLGVVVQADMGCVINWKGKELKCGSGIFVTNEV   798
              . **..  . .* .**.**  **** ***   *  .*********.    *

DEN4      800 HTWTEQYKFQPESPARLASAILNAHKDGVCGIRSTTRLENVMWKQITNEL   849

DEN1-WP   801 HTWTEQYKFQADSPKRLSAAIGKAWEEGVCGIRSATRLENIMWKQISNEL   850

DEN2-NGC  801 HTWTEQYKFQPESPSKLASAIQKAHEEGICGIRSVTRLENLMWKQITPEL   850

DEN3-H87  799 HTWTEQYKFQADSPKRVATAIAGAWENGVCGIRSTTRMENLLWKQIANEL   848
              **********  .**   ...  **   * *.***** **.**..****. **

DEN4      850 NYVLWEGGHDLTVVAGDVKGVLTKGKRALTPPVSDLKYSWKTWGKAKIFT   899

DEN1-WP   851 NHILLENDMKFTVVVGDVSGILAQGKKMIRPQPMEHKYSWKSWGKAKIIG   900

DEN2-NGC  851 NHILSENEVKLTIMTGDIKGIMQAGKRSLQPQPTELKYSWKTWGKAKMLS   900

DEN3-H87  849 NYILWENDIKLTVVVGDITGVLEQGKRTLTPQPMELKYSWKTWGLAKIVT   898
              * .* *.    *.. **. *.. **. * .    . ****.** **.

DEN4      900 PEARNSTFLIDGPDTSECPNERRAWNSLEVEDYGFGMFTTNIWMKFREGS   949

DEN1-WP   901 ADVQNTTFIIDGPNTPECPDNQRAWNIWEVEDYGFGIFTTNIWLKLRDSY   950

DEN2-NGC  901 TESHNQTFLIDGPETAECPNTNRAWNSLEVEDYGFGVFTTNIWLKLREKQ   950

DEN3-H87  899 AETQNSSFIIDGPSTPECPSASRAWNVWEVEDYGFGVFTTNIWLKLREVY   948
               . .* .****.* ***    ****  ********.******.* *.

DEN4      950 SEVCDHRLMSAAIKDQKAVHADMGYWIESSKNQTWQIEKASLIEVKTCLW   999

DEN1-WP   951 TQVCDHRLMSAAIKDSKAVHADMGYWIESEKNETWKLARASFIEVKTCIW   1000

DEN2-NGC  951 DVFCDSKLMSAAIKDNRAVHADMGYWIESALNDTWKIEKASFIEVKSCHW   1000

DEN3-H87  949 TQLCDHRLMSAAVKDERAVHADMGYWIESQKNGSWKLEKASLIEVKTCTW   998
              **.*****.** .*************   *. *.. .** ****.* *

DEN4      1000 PKTHTLWSNGVLESQMLIPKSYAGPFSQHNYRQGYATQTVGPWHLGKLEI  1049

DEN1-WP   1001 PKSHTLWSNGVLESEMIIPKIYGGPISQHNYRPGYFTQTAGPWHLGKLEL  1050

DEN2-NGC  1001 PKSHTLWSNGVLESEMIIPKNFAGPVSQHNYRPGYHTQTAGPWHLGKLEM  1050
```

APPENDIX 4-continued

Alignment of dengue virus polyproteins

```
DEN3-H87   999 PKSHTLWSNGVLESDMIIPKSLAGPISQHNHRPGYHTQTAGPWHLGKLEL 1048
               **.***********.****   **.****.*.**.***.**********.

DEN4      1050 DFGECPGTTVTIQEDCDHRGPSLRTTTASGKLVTQWCCRSCTMPPLRFLG 1099

DEN1-WP   1051 DFDLCEGTTVVVDEHCGNRGPSLRTTTVTGKTIHEWCCRSCTLPPLRFKG 1100

DEN2-NGC  1051 DFDFCEGTTVVVTEDCGNRGPSLRTTTASGKLITEWCCRSCTLPPLRYRG 1100

DEN3-H87  1049 DFNYCEGTTVVISENCGTRGPSLRTTTVSGKLIHEWCCRSCTLPPLRYMG 1098
               **   *.****. *.* *********.**. .*******.****. *

DEN4      1100 EDGCWYGMEIRPLSEKEENMVKSQVTAGQGTSETFSMGLLCLTLFVEECL 1149

DEN1-WP   1101 EDGCWYGMEIRPVKEKEENLVKSMVSAGSGEVDSFSLGLLCISIMIEEVM 1150

DEN2-NGC  1101 EDGCWYGMEIRPLKEKEENLVNSLVTAGHGQIDNFSLGVLGMALFLEEML 1150

DEN3-H87  1099 EDGCWYGMEIRPINEKEENMVKSLASAGSGKVDNFTMGVLCLAILFEEVM 1148
               ************.*****.*.** *  .** * .*..*.*  ..  **.

DEN4      1150 RRRVTRKHMILVVVITLCAIILGGLTWMDLLRALIMLGDTMSGRIG-GQI 1198

DEN1-WP   1151 RSRWSRKMLMTGTLAVFLLLTMGQLTWNDLIRLCIMVGANASDKMGMGTT 1200

DEN2-NGC  1151 RTRVGTKHAILLVAVSFVTLITGNMSFRDLGRVMVMVGATMTDDIGMGVT 1200

DEN3-H87  1149 RGKFGKKHMIAGVLFTFVLLLSGQITWRGMAHTLIMIGSNASDRMGMGVT 1198
                  *   *  .              *..       . *.*   . * **

DEN4      1199 HLAIMAVFKMSPGYVLGVFLRKLTSRETALMVIGMAMTTVLSIPHDLMEL 1248

DEN1-WP   1201 YLALMATFRMRPMFAVGLLFRRLTSREVLLLTVGLSLVASVELPNSLEEL 1250

DEN2-NGC  1201 YLALLAAFKVRPTFAAGLLLRKLTSKELMMTTIGIVLLSQSTIPETILEL 1250

DEN3-H87  1199 YLALIATFKIQPFLALGFFLRKLTSRENLLLGVGLAMAATLRLPEDIEQM 1248
                **..*.*.. *   *  *.***.*   .*  .    .*   .  .

DEN4      1249 IDGISLGLILLKIVTQFDNTQVGTLALSLTFIRSTMPLVMAWRTIMAVLF 1298

DEN1-WP   1251 GDGLAMGIMMLKLLTDFQSHQLWATLLSLTFVKTTFSLHYAWKTMAMILS 1300

DEN2-NGC  1251 TDALALGMMVLKMVRKMEKYQLAVTIMAILCVPNAVILQNAWKVSCTILA 1300

DEN3-H87  1249 ANGIALGLMALKLITQFETYQLWTALVSLTCSNTIFTLTVAWRTATLILA 1298
                ...*.. **..     *.   ...      *   **.   .*

DEN4      1299 VVTLIPLCRTSCLQKQSHWVEITALILGAQALPVYLMTLMKGASRRSWPL 1348

DEN1-WP   1301 IVSLFPLCLSTTSQK-TTWLPVLLGSLGCKPLTMFLITENKIWGRKSWPL 1349

DEN2-NGC  1301 VVSVSPLFLTSSQQK-ADWIPLALTIKGLNPTAIFLTTLSRTNKKRSWPL 1349

DEN3-H87  1299 GISLLPVCQSSSMRK-TDWLPMTVAANGVPPLPLFIFSLKDTLKRRSWPL 1347
                ...*.  ... .*  .*. .      *    ...          ..****

DEN4      1349 NEGIMAVGLVSLLGSALLKNDVPLAGPMVAGGLLLAAYVMSGSSADLSLE 1398

DEN1-WP   1350 NEGIMAVGIVSILLSSLLKNDVPLAGPLIAGGMLIACYVISGSSADLSLE 1399

DEN2-NGC  1350 NEAIMAVGMVSILASSLLKNDIPMTGPLVAGGLLTVCYVLTGRSADLELE 1399

DEN3-H87  1348 NEGVMAVGLVSILASSLLRNDVPMAGPLVAGGLLIACYVITGTSADLTVE 1397
               **.****.**.*.*.**.**.**..***.* .**..* ****.*

DEN4      1399 KAANVQWDEMADITGSSPIIEVKQDEDGSFSIRDVEETMMITLLVKLALI 1448

DEN1-WP   1400 KAAEVSWEEEAEHSGASHNILVEVQDDGTMKIKDEERDDTLTILLKATLL 1449

DEN2-NGC  1400 RAADVKWEDQAEISGSSPILSITISEDGSMSIKNEEEEQTLTILIRTGLL 1449

DEN3-H87  1398 KAADVTWEEEAEQTGVSHNLMITVDDDGTMRIKDDETENILTVLLKTALL 1447
                .** *  *.. *.*  .   .    .**. *.  *   .*.*.. *.

DEN4      1449 TVSGLYPLAIPVTMTLWYMWQVKTQRSGALWDVPSPAATKKAALSEGVYR 1498
```

APPENDIX 4-continued

Alignment of dengue virus polyproteins

```
DEN1-WP   1450 AISGVYPMSIPATLFVWYFWQKKKQRSGVLWDTPSPPEVERAVLDDGIYR   1499

DEN2-NGC  1450 VISGLFPVSIPITAAAWYLWEVKKQRAGVLWDVPSPPPVGKAELEDGAYR   1499

DEN3-H87  1448 IVSGIFPYSIPATMLVWHTWQKQTQRSGVLWDVPSPPETQKAELEEGVYR   1497
                .**..*..**.*..*......*....**.*.***.***......*..*.***

DEN4      1499 IMQRGLFGKTQVGVGIHMEGVFHTMWHVTRGSVICHETGRLEPSWADVRN   1548

DEN1-WP   1500 ILQRGLLGRSQVGVGVFQEGVFHTMWHVTRGAVLMYQGKRLEPSWASVKK   1549

DEN2-NGC  1500 IKQKGILGYSQIGAGVYKEGTFHTMWHVTRGAVLMHKGKRIEPSWADVKK   1549

DEN3-H87  1498 IKQQGIFGKTQVGVGVQKEGVFHTMWHVTRGAVLTHNGKRLEPNWASVKK   1547
                *.*.*..*..*.*.*..**.**********.*.......*.**.**.*.

DEN4      1549 DMISYGGGWRLGDKWDKEEDVQVLAIEPGKNPKHVQTKPGLFKTLTGEIG   1598

DEN1-WP   1550 DLISYGGGWRFQGSWNAGEEVQVIAVEPGKNPKNVQTAPGTFKTPEGEVG   1599

DEN2-NGC  1550 DLISYGGGWKLEGEWKEGEEVQVLALEPGKNPRAVQTKPGLFKTNAGTIG   1599

DEN3-H87  1548 DLISYGGGWRLSAQWQKGEEVQVIAVEPGKNPKNFQTMPGIFQTTTGEIG   1597
                *.*******......*...*.***.*.******..**.**.*....*..*

DEN4      1599 AVTLDFKPGTSGSPIINRKGKVIGLYGNGVVTKSGDYVSAITQAERIGEP   1648

DEN1-WP   1600 AIALDFKPGTSGSPIVNREGKIVGLYGNGVVTTSGTYVSAIAQAKASQEG   1649

DEN2-NGC  1600 AVSLDFSPGTSGSPIIDKKGKVVGLYGNGVVTRSGAYVSAIAQTEKSIED   1649

DEN3-H87  1598 AIALDFKPGTSGSPIINREGKVVGLYGNGVVTKNGGYVSGIAQTNAEPDG   1647
                *..***.********...**.**********.*.***.*..

DEN4      1649 -DYEVDEDIFRKKRLTIMDLHPGAGKTKRILPSIVREALKRRLRTLILAP   1697

DEN1-WP   1650 PLPEIEDEVFRKRNLTIMDLHPGSGKTRRYLPAIVREAIRRNVRTLVLAP   1699

DEN2-NGC  1650 -NPEIEDDIFRKRKLTIMDLHPGAGKTKRYLPAIVREAIKRGLRTLILAP   1698

DEN3-H87  1648 PTPELEEEMFKKRNLTIMDLHPGSGKTRKYLPAIVREAIKRRLRTLILAP   1697
                *.....*.*.*.*********.***...**.*****..*..***.***

DEN4      1698 TRVVAAEMEEALRGLPIRYQTPAVKSEHTGREIVDLMCHATFTTRLLSST   1747

DEN1-WP   1700 TRVVASEMAEALKGMPIRYQTTAVKSEHTGKEIVDLMCHATFTMRLLSPV   1749

DEN2-NGC  1699 TRVVAAEMEEALRGLPIRYQTPAIRAEHTGREIVDLMCHATFTMRLLSPV   1748

DEN3-H87  1698 TRVVAAEMEEAMKGLPIRYQTTATKSEHTGREIVDLMCHATFTMRLLSPV   1747
                *****.**.**..*.******.*...****.*************.****

DEN4      1748 RVPNYNLIVMDEAHFTDPSSVAARGYISTRVEMGEAAAIFMTATPPGATD   1797

DEN1-WP   1750 RVPNYNMIIMDEAHFTDPASIAARGYISTRVGMGEAAAIFMTATPPGSVE   1799

DEN2-NGC  1749 RVPNYNLIIMDEAHFTDPASIAARGYISTRVEMGEAAGIFMTATPPGSRD   1798

DEN3-H87  1748 RVPNYNLIIMDEAHFTDPASIAARGYISTRVGMGEAAAIFMTATPPGTAD   1797
                ******.*.*********.*.**********.*****.*********...

DEN4      1798 PFPQSNSPIEDIEREIPERSWNTGFDWITDYQGKTVWFVPSIKAGNDIAN   1847

DEN1-WP   1800 AFPQSNAVIQDEERDIPERSWNSGYDWITDFPGKTVWFVPSIKSGNDIAN   1849

DEN2-NGC  1799 PFPQSNAPIMDEEREIPERSWSSGHEWVTDFKGKTVWFVPSIKAGNDIAA   1848

DEN3-H87  1798 AFPQSNAPIQDEERDIPERSWNSGNEWITDFVGKTVWFVPSIKAGNVIAN   1847
                *****..*..*.**..******..*.*.**.************.**.**

DEN4      1848 CLRKSGKKVIQLSRKTFDTEYPKTKLTDWDFVVTTDISEMGANFRAGRVI   1897

DEN1-WP   1850 CLRKNGKRVVQLSRKTFDTEYQKTKNNDWDYVVTTDISEMGANFRADRVI   1899

DEN2-NGC  1849 CLRKNGKKVIQLSRKTFDSEYVKTRTNDWDFVVTTDISEMGANFKAERVI   1898
```

APPENDIX 4-continued

Alignment of dengue virus polyproteins

```
DEN3-H87 1848 CLRKNGKKVIQLSRKTFDTEYQKTKLNDWDFVVTTDISEMGANFIADRVI 1897
              ****  **.*.********.** **.  ***.************* * ***

DEN4     1898 DPRRCLKPVILPDGPERVILAGPIPVTPASAAQRRGRIGRNPAQEDDQYV 1947

DEN1-WP  1900 DPRRCLKPVILKDGPERVILAGPMPVTVASAAQRRGRIGRNQNKEGDQYI 1949

DEN2-NGC 1899 DPRRCMKPVILTDGEERVILAGPMPVTHSSAAQRRGRIGRNPKNENDQYI 1948

DEN3-H87 1898 DPRRCLKPVILTDGPERVILAGPMPVTVASAAQRRGRVGRNPQKENDQYI 1947
              *****.***** ** *********.***  ********.***   * ***.

DEN4     1948 FSGDPLKNDEDHAHWTEAKMLLDNIYTPEGIIPTLFGPEREKTQAIDGEF 1997

DEN1-WP  1950 YMGQPLNNDEDHAHWTEAKMLLDNINTPEGIIPALFEPEREKSAAIDGEY 1999

DEN2-NGC 1949 YMGEPLENDEDCAHWKEAKMLLDNINTPEGIIPSMFEPEREKVDAIDGEY 1998

DEN3-H87 1948 FMGQPLNKDEDHAHWTEAKMLLDNINTPEGIIPALFEPEREKSAAIDGEY 1997
              . * **  *** *** ********* ******..* *****  *****.

DEN4     1998 RLRGEQRKTFVELMRRGDLPVWLSYKVASAGISYKDREWCFTGERNNQIL 2047

DEN1-WP  2000 RLRGEARKTFVELMRRGDLPVWLSYKVASEGFQYSDRRWCFDGERNNQVL 2049

DEN2-NGC 1999 RLRGEARKTFVDLMRRGDLPVWLAYRVAAEGINYADRRWCFDGIKNNQIL 2048

DEN3-H87 1998 RLKGESRKTFVELMRRGDLPVWLAHKVASEGIKYTDRKWCFDGERNNQIL 2047
              **.** *****.********* .**. *  * ** *** * .***.*

DEN4     2048 EENMEVEIWTREGEKKKLRPRWLDARVYADPMALKDFKEFASGRKSITLD 2097

DEN1-WP  2050 EENMDVEIWTKEGERKKLRPRWLDARTYSDPLALREFKEFAAGRRSVSGD 2099

DEN2-NGC 2049 EENVEVEIWTKEGERKKLKPRWLDARIYSDPLTLKEFKEFAAGRKSLTLN 2098

DEN3-H87 2048 EENMDVEIWTKEGEKKKLRPRWLDARTYSDPLALKEFKDFAAGRKSIALD 2097
              ***..*****.***.*** ******* *.**..*.**.**.**.*...

DEN4     2098 ILTEIASLPTYLSSRAKLALDNIVMLHTTERGGRAYQHALNELPESLETL 2147

DEN1-WP  2100 LILEIGKLPQHLTQRAQNALDNLVMLHNSEQGGKAYRHAMEELPDTIETL 2149

DEN2-NGC 2099 LITEMGRLPTFMTQKARDALDNLAVLHTAEAGGRAYNHALSELPETLETL 2148

DEN3-H87 2098 LVTEIGRVPSHLAHRTRNALDNLVMLHTSEHGGRAYRHAVEELPETMETL 2147
              .. *.  .*  .. ... ****. .**..* **.** **. ***...***

DEN4     2148 MLVALLGAMTAGIFLFFMQGKGIGKLSMGLITIAVASGLLWVAEIQPQWI 2197

DEN1-WP  2150 MLLALIAVLTGGVTLFFLSGRGLGKTSIGLLCVIASSALLWMASVEPHWI 2199

DEN2-NGC 2149 LLLTLLATVTGGIFLFLMSGRGIGKMTLGMCCIITASILLWYAQIQPHWI 2198

DEN3-H87 2148 LLLGLMILLTGGAMLFLISGKGIGKTSIGLICVIASSGMLWMADVPLQWI 2197
              .*. *. .* * ** . *.*.**  ..*.  .. .* .** *   .**

DEN4     2198 AASIILEFFLMVLLIPEPEKQRTPQDNQLIYVILTILTIIGLIAANEMGL 2247

DEN1-WP  2200 AASIILEFFLMVLLIPEPDRQRTPQDNQLAYVVIGLLFMILTAAANEMGL 2249

DEN2-NGC 2199 AASIILEFFLIVLLIPEPEKQRTPQDNQLTYVVIAILTVVAATMANEMGF 2248

DEN3-H87 2198 ASAIVLEFFMMVLLIPEPEKQRTPQDNQLAYVVIGILTLAAIVAANEMGL 2247
              *..*.****.*******..*********  **...* .    *****

DEN4     2248 IEKTKTDFGFY----QVKTETTILDVDLRPASAWTLYAVATTILTPMLRH 2293

DEN1-WP  2250 LETTKKDLGIGHAAAENHHHAAMLDVDLHPASAWTLYAVATTIITPMMRH 2299

DEN2-NGC 2249 LEKTKKDLGLG-SITTQQPESNILDIDLRPASAWTLYAVATTFVTPMLRH 2297

DEN3-H87 2248 LETTKRDLGMS-KEPGVVSPTSYLDVDLHPASAWTLYAVATTVITPMLRH 2296
              .* ** * *           .  **.**.************ .***.**

DEN4     2294 TIENTSANLSLAAIANQAAVLMGLGKGWPLHRMDLGVPLLAMGCYSQVNP 2343
```

APPENDIX 4-continued

Alignment of dengue virus polyproteins

```
DEN1-WP   2300 TIENTTANISLTAIANQAAILMGLDKGWPISKMDIGVPLLALGCYSQVNP 2349

DEN2-NGC  2298 SIENSSVNVSLTAIANQATVLMGLGKGWPLSKMDIGVPLLAIGCYSQVNP 2347

DEN3-H87  2297 TIENSTANVSLAAIANQAVVLMGLDKGWPISKMDLGVPLLALGCYSQVNP 2346
               .***.. *.**.****** .**** ****.. **.****** ********

DEN4      2344 TTLTASLVMLLVHYAIIGPGLQAKATREAQKRTAAGIMKNPTVDGITVID 2393

DEN1-WP   2350 LTLTAAVFMLVAHYAIIGPGLQAKATREAQKRTAAGIMKNPTVDGIVAID 2399

DEN2-NGC  2348 ITLTAALFLLVAHYAIIGPGLQAKATREAQKRAAAGIMKNPTVDGITVID 2397

DEN3-H87  2347 LTLIAAVLLLVTHYAIIGPGLQAKATREAQKRTAAGIMKNPTVDGIMTID 2396
               ** *...*. ********************.************* **

DEN4      2394 LEPISYDPKFEKQLGQVMLLVLCAGQLLLMRTTWAFCEVLTLATGPILTL 2443

DEN1-WP   2400 LDPVVYDAKFEKQLGQIMLLILCTSQILLMRTTWALCESITLATGPLTTL 2449

DEN2-NGC  2398 LDPIPYDPKFEKQLGQVMLLVLCVTQVLMMRTTWALCEALTLATGPISTL 2447

DEN3-H87  2397 LDPVIYDSKFEKQLGQVMLLVLCAVQLLLMRTSWALCEVLTLATGPITTL 2446
               *.*.** ********.***.** *.*.***.** ** .******. **

DEN4      2444 WEGNPGRFWNTTIAVSTANIFRGSYLAGAGLAFSLIKNAQTPRRGTGTTG 2493

DEN1-WP   2450 WEGSPGKFWNTTIAVSMANIFRGSYLAGAGLAFSLMKSLGGGRRGTGAQG 2499

DEN2-NGC  2448 WEGNPGRFWNTTIAVSMANIFRGSYLAGAGLLFSIMKNTTNTRRGTGNIG 2497

DEN3-H87  2447 WEGSPGKFWNTTIAVSMANIFRGSYLAGAGLALSIMKSVGTGKRGTGSQG 2496
               *** **.********* ************* *...*    .**** *

DEN4      2494 ETLGEKWKRQLNSLDRKEFEEYKRSGILEVDRTEAKSALKDGSKIKHAVS 2543

DEN1-WP   2500 ETLGEKWKRQLNQLSKSEFNTYKRSGIIEVDRSEAKEGLKRGEPTKHAVS 2549

DEN2-NGC  2498 ETLGEKWKSRLNALGKSEFQIYKKSGIQEVDRTLAKEGIKRGETDHHAVS 2547

DEN3-H87  2497 ETLGEKWKKKLNQLSRKEFDLYKKSGITEVDRTEAKEGLKRGEITHHAVS 2546
               ********.**.*. ** **.*** ****. **  .* *  .****

DEN4      2544 RGSSKIRWIVERGMVKPKGKVVDLGCGRGGWSYYMATLKNVTEVKGYTKG 2593

DEN1-WP   2550 RGTAKLRWFVERNLVKPEGKVIDLGCGRGGWSYYCAGLKKVTEVKGYTKG 2599

DEN2-NGC  2548 RGSAKLRWFVERNMVTPEGKVVDLGCGRGGWSYYCGGLKNVREVKGLTKG 2597

DEN3-H87  2547 RGSAKLQWFVERNMVIPEGRVIDLGCGRGGWSYYCAGLKKVTEVRGYTKG 2596
               **..*..* ***.* * *.*.************   ** * **.* ***

DEN4      2594 GPGHEEPIPMATYGWNLVKLHSGVDVFYKPTEQVDTLLCDIGESSSNPTI 2643

DEN1-WP   2600 GPGHEEPIPMATYGWNLVKLYSGKDVFFTPPEKCDTLLCDIGESSPNPTI 2649

DEN2-NGC  2598 GPGHEEPIPMSTYGWNLVRLQSGVDVFFTPPEKCDTLLCDIGESSPNPTV 2647

DEN3-H87  2597 GPGHEEPVPMSTYGWNIVKLMSGKDVFYLPPEKCDTLLCDIGESSPSPTV 2646
               *******.**.*****.*.* ** ***. * *.*********** **.

DEN4      2644 EEGRTLRVLKMVEPWLSSKPEFCIKVLNPYMPTVIEELEKLQRKHGGNLV 2693

DEM1-WP   2650 EEGRTLRVLKMVEPWLRGN-QFCIKILNPYMPSVVETLEQMQRKHGGMLV 2698

DEN2-NGC  2648 EAGRTLRVLNLVENWLNNNTQFCIKVLNPYMPSVIEKMEALQRKYGGALV 2697

DEN3-H87  2647 EESRTIRVLKMVEPWLKNN-QFCIKVLNPYMPTVIEHLERLQRKHGGMLV 2695
               *  **.***.**.**    .****.******.*.* .*  .*** ** **

DEN4      2694 RCPLSRNSTHEMYWVSGASGNIVSSVNTTSKMLLNRFTTRHRKPTYEKDV 2743

DEN1-WP   2699 RNPLSRNSTHEMYWVSCGTGNIVSAVNMTSRMLLMRFTMAHRKPTYERDV 2748

DEN2-NGC  2698 RNPLSRNSTHEMYWVSNASGNIVSSVNMISRMLINRFTMRHKKATYEPDV 2747
```

APPENDIX 4-continued

Alignment of dengue virus polyproteins

```
DEN3-H87  2696  RNPLSRNSTHEMYWISNGTGNIVSSVNMVSRLLLNRFTMTHRRPTIEKDV  2745
                *  ************ *   *****.**   *  *.****  *   * **

DEN4      2744  DLGAGTRSVSTETEKPDMTIIGRRLQRLQEEHKETWHYDQENPYRTWAYH  2793

DEN1-WP   2749  DLGAGTRHVAVEPEVANLDIIGQRIENIKNGHKSTWHYDEDNPYKTWAYH  2798

DEN2-NGC  2748  DLGSGTRNIGIESEIPNLDIIGKRIEKIKQEHETSWHYDQDHPYKTWAYH  2797

DEN3-H87  2746  DLGAGTRHVNAEPETPNMDVIGERIKRIKEEHSSTWHYDDENPYKTWAYH  2795
                ***.***  .    * *     .** *. ..  *  .****..**.*****

DEN4      2794  GSYEAPSTGSASSMVNGVVKLLTKPWDVIPMVTQLAMTDTTPFGQQRVFK  2843

DEN1-WP   2799  GSYEVKPSGSASSMVNGVVRLLTKPWDVIPMVTQIAMTDTTPFGQQRVFK  2848

DEN2-NGC  2798  GSYETKQTGSASSMVNGVVRLLTKPWDVVPMVTQMAMTDTTPFGQQRVFK  2847

DEN3-H87  2796  GSYEVKATGSASSMINGVVKLLTKPWDVVPMVTQMANTDTTPFGQQRVFK  2845
                ****  .******.****.******** ***** ****************

DEN4      2844  EKVDTRTPQPKPGTRMVMTTTANWLWALLGKKKNPRLCTREEFISKVRSN  2893

DEN1-WP   2849  EKVDTRTPKAKRGTAQIMEVTARWLWGFLSRNKKPRICTREEFTRKVRSN  2898

DEN2-NGC  2848  EKVDTRTQEPKEGTKKLMKITAEWLWKELGKKKTPRMCTREEFTRKVRSN  2897

DEN3-H87  2846  EKVDTRTPRPMPGTRKVMEITAEWLWRTLGRNKRPRLCTREEFTKKVRTN  2895
                *******         ** .* ** ***  * .* **.****** ***.*

DEN4      2894  AAIGAVFQEEQGWTSASEAVNDSRFWELVDKERALHQEGKCESCVYNMMG  2943

DEN1-WP   2899  AAIGAVFVDENQWNSAKEAVEDERFWDLVHRERELHKQGKCATCVYNMMG  2948

DEN2-NGC  2898  AALGAIFTDENKWKSAREAVEDSRFWELVDKERNLHLEGKCETCVYNMMG  2947

DEN3-H87  2896  AAMGAVFTEENQWDSARAAVEDEEFWKLVDRERELHKLGKCGSCVYNMMG  2945
                **.**.*.*.  *  ** **  ** **.** **  ***  .*******

DEN4      2944  KREKKLGEFGRAKGSRAIWYMWLGARFLEFEALGFLNEDHWFGRENSWSG  2993

DEN1-WP   2949  KREKKLGEFGKAKGSRAIWYMWLGARFLEFEALGFMNEDHWFSRENSLSG  2998

DEN2-NGC  2948  KREKKLGEFGKAKGSRAIWYMWLGARFLEFEALGFLNEDHWFSRENSLSG  2997

DEN3-H87  2946  KREKKLGEFGKAKGSRAIWYMWLGARYLEFEALGFLNEDHWFSRENSYSG  2995
                ********** ****************.*********.******  **

DEN4      2994  VEGEGLHRLGYILEEIDKKDGDLMYADDTAGWDTRITEDDLQNEELITEQ  3043

DEN1-WP   2999  VEGEGLHKLGYILRDISKIPGGNMYADDTAGWDTRITEDDLQNEAKITDI  3048

DEN2-NGC  2998  VEGEGLHKLGYILRDVSKKEGGAMYADDTAGWDTRITLEDLKNEEMVTNH  3047

DEN3-H87  2996  VEGEGLHKLGYILRDISKIPGGAMYADDTAGWDTRITEDDLHNEEKITQQ  3045
                *******.*****  ..  *  * ************* .**.**  .*

DEN4      3044  MAPHHKILAKAIFKLTYQNKVVKVLRPTPRGAVMDIISRKDQRGSGQVGT  3093

DEN1-WP   3049  MEPEHALLATSIFKLTYQNKVVRVQRPAKNGTVMDVISRRDQRGSGQVGT  3098

DEN2-NGC  3048  MEGEHKKLAEAIFKLTYQNKVVRVQRPTPRGTVMDIISRRDQRGSGQVGT  3097

DEN3-H87  3046  MDPEHRQLANAIFKLTYQNKVVKVQRPTPKGTVMDIISRKDQRGSGQVGT  3095
                *   *  **  *********.* **.   *.***.***.**********

DEN4      3094  YGLNTFTNMEVQLIRQMEAEGVITQDDMQNPKGLKERVEKWLKECGVDRL  3143

DEN1-WP   3099  YGLNTFTNMEAQLIRQMESEGIFSPSELETPN-LAERVLDWLKKHGTERL  3147

DEN2-NGC  3098  YGLNTFTNMEAQLIRQMEGEGVFKSIQHLTVT-EEIAVQNWLARVGRERL  3146

DEN3-H87  3096  YGLNTFTNMEAQLIRQMEGEGVLSKADLENPHPLEKKITQWLETKGVERL  3145
                **********.******* **            **       *  .**

DEN4      3144  KRMAISGDDCVVKPLDERFGTSLLFLNDMGKVRKDIPQWEPSKGWKNWQE  3193
```

APPENDIX 4-continued

Alignment of dengue virus polyproteins

```
DEN1-WP   3148 KRMAISGDDCVVKPIDDRFATALTALNDMGKVRKDIPQWEPSKGWNDWQQ  3197

DEN2-NGC  3147 SRMAISGDDCVVKPLDDRFASALTALNDMGKVRKDIQQWEPSRGWNDWTQ  3196

DEN3-H87  3146 KRMAISGDDCVVKPIDDRFANALLALNDMGKVRKDIPQWQPSKGWHDWQQ  3195
               **************.*.**   .*  *********** **.**.**  *  .

DEN4      3194 VPFCSHHFHKIFMKDGRSLVVPCRNQDELIGRARISQGAGWSLRETACLG  3243

DEN1-WP   3198 VPFCSHHFHQLIMKDGREIVVPCRNQDELVGRARVSQGAGWSLRETACLG  3247

DEN2-NGC  3197 VPFCSHHFHELIMKDGRVLVVPCRNQDELIGRARISQGAGWSLRETACLG  3246

DEN3-H87  3196 VPFCSHHFHELIMKDGRKLVVPCRPQDELIGRARISQGAGWSLRETACLG  3245
               *********  . ***** .***** ****.****.**************

DEN4      3244 KAYAQMWSLMYFHRRDLRLASMAICSAVPTEWFPTSRTTWSIHAHHQWMT  3293

DEN1-WP   3248 KSYAQMWQLMYFHRRDLRLAANAICSAVPVDWVPTSRTTWSIHAHHQWMT  3297

DEN2-NGC  3247 KSYAQMWSLMYFHRRDLRLAANAICSAVPSHWVPTSRTTWSIHAKHEWMT  3296

DEN3-H87  3246 KAYAQMWTLMYFHRRDLRLASNAICSAVPVHWVPTSRTTWSIHAHHQWMT  3295
               *.***** ************.  *******   * ************.*.***

DEN4      3294 TEDMLKVWNRVWIEDNPNMTDKTPVHSWEDIPYLGKREDLWCGSLIGLSS  3343

DEN1-WP   3298 TEDMLSVWNRVWIEENPWMEDKTHVSSWEDVPYLGKREDRWCGSLIGLTA  3347

DEN2-NGC  3297 TEDMLTVWNRVWIQENPWMEDKTPVESWEEIPYLGKREDQWCGSLIGLTS  3346

DEN3-N87  3296 TEDMLTVWNRVWIEDNPWMEDKTPVTTWEDVPYLGKREDQWCGSLIGLTS  3345
               ***** *******.** * *** *  .**..******** ********..

DEN4      3344 RATWAKNIHTAITQVRNLIGKEEYVDYMPVMKRYSAPSESEGVL       3387

DEN1-WP   3348 RATWATNIQVAINQVRRLIGNENYLDFMTSMKRFKNESDPEGALW      3392

DEN2-NGC  3347 RATWAKNIQTAINQVRSLIGNEEYTDYMPSMKRFRREEEEAGVLW      3391

DEN3-H87  3346 RATWAQNILTAIQQVRSLIGNEEFLDYMPSMKRFRKEEESEGAIW      3390
               ***** **  ** *** *** *  . *.*  ***.        . * .
```

\* Residue identity
. Residue similarity

While the present invention has been described in some detail for purposes of clarity and understanding, one skilled in the art will appreciate that various changes in form and detail can be made without departing from the true scope of the invention. All figures, tables, and appendices, as well as patents, applications, and publications, referred to above, are hereby incorporated by reference.

SEQUENCE LISTING

<160> NUMBER OF SEQ ID NOS: 70

<210> SEQ ID NO 1
<211> LENGTH: 900
<212> TYPE: PRT
<213> ORGANISM: Dengue 4 virus

<400> SEQUENCE: 1

Gly Thr Gly Thr Thr Gly Glu Thr Leu Gly Glu Lys Trp Lys Arg Gln
 1               5                  10                  15

Leu Asn Ser Leu Asp Arg Lys Glu Phe Glu Glu Tyr Lys Arg Ser Gly
            20                  25                  30

Ile Leu Glu Val Asp Arg Thr Glu Ala Lys Ser Ala Leu Lys Asp Gly
        35                  40                  45

```
Ser Lys Ile Lys His Ala Val Ser Arg Gly Ser Ser Lys Ile Arg Trp
 50                  55                  60

Ile Val Glu Arg Gly Met Val Lys Pro Lys Gly Lys Val Val Asp Leu
 65                  70                  75                  80

Gly Cys Gly Arg Gly Gly Trp Ser Tyr Tyr Met Ala Thr Leu Lys Asn
                 85                  90                  95

Val Thr Glu Val Lys Gly Tyr Thr Lys Gly Pro Gly His Glu Glu
            100                 105                 110

Pro Ile Pro Met Ala Thr Tyr Gly Trp Asn Leu Val Lys Leu His Ser
            115                 120                 125

Gly Val Asp Val Phe Tyr Lys Pro Thr Glu Gln Val Asp Thr Leu Leu
    130                 135                 140

Cys Asp Ile Gly Glu Ser Ser Asn Pro Thr Ile Glu Glu Gly Arg
145                 150                 155                 160

Thr Leu Arg Val Leu Lys Met Val Glu Pro Trp Leu Ser Ser Lys Pro
                165                 170                 175

Glu Phe Cys Ile Lys Val Leu Asn Pro Tyr Met Pro Thr Val Ile Glu
                180                 185                 190

Glu Leu Glu Lys Leu Gln Arg Lys His Gly Gly Asn Leu Val Arg Cys
    195                 200                 205

Pro Leu Ser Arg Asn Ser Thr His Glu Met Tyr Trp Val Ser Gly Ala
    210                 215                 220

Ser Gly Asn Ile Val Ser Ser Val Asn Thr Thr Ser Lys Met Leu Leu
225                 230                 235                 240

Asn Arg Phe Thr Thr Arg His Arg Lys Pro Thr Tyr Glu Lys Asp Val
                245                 250                 255

Asp Leu Gly Ala Gly Thr Arg Ser Val Ser Thr Glu Thr Glu Lys Pro
                260                 265                 270

Asp Met Thr Ile Ile Gly Arg Arg Leu Gln Arg Leu Gln Glu Glu His
                275                 280                 285

Lys Glu Thr Trp His Tyr Asp Gln Glu Asn Pro Tyr Arg Thr Trp Ala
    290                 295                 300

Tyr His Gly Ser Tyr Glu Ala Pro Ser Thr Gly Ser Ala Ser Ser Met
305                 310                 315                 320

Val Asn Gly Val Val Lys Leu Leu Thr Lys Pro Trp Asp Val Ile Pro
                325                 330                 335

Met Val Thr Gln Leu Ala Met Thr Asp Thr Thr Pro Phe Gly Gln Gln
                340                 345                 350

Arg Val Phe Lys Glu Lys Val Asp Thr Arg Thr Pro Gln Pro Lys Pro
                355                 360                 365

Gly Thr Arg Met Val Met Thr Thr Thr Ala Asn Trp Leu Trp Ala Leu
    370                 375                 380

Leu Gly Lys Lys Lys Asn Pro Arg Leu Cys Thr Arg Glu Glu Phe Ile
385                 390                 395                 400

Ser Lys Val Arg Ser Asn Ala Ala Ile Gly Ala Val Phe Gln Glu Glu
                405                 410                 415

Gln Gly Trp Thr Ser Ala Ser Glu Ala Val Asn Asp Ser Arg Phe Trp
                420                 425                 430

Glu Leu Val Asp Lys Glu Arg Ala Leu His Gln Glu Gly Lys Cys Glu
                435                 440                 445

Ser Cys Val Tyr Asn Met Met Gly Lys Arg Glu Lys Lys Leu Gly Glu
    450                 455                 460

Phe Gly Arg Ala Lys Gly Ser Arg Ala Ile Trp Tyr Met Trp Leu Gly
```

-continued

```
            465                 470                 475                 480
Ala Arg Phe Leu Glu Phe Glu Ala Leu Gly Phe Leu Asn Glu Asp His
                    485                 490                 495
Trp Phe Gly Arg Glu Asn Ser Trp Ser Gly Val Glu Gly Gly Leu
                500                 505                 510
His Arg Leu Gly Tyr Ile Leu Glu Glu Ile Asp Lys Lys Asp Gly Asp
            515                 520                 525
Leu Met Tyr Ala Asp Asp Thr Ala Gly Trp Asp Thr Arg Ile Thr Glu
        530                 535                 540
Asp Asp Leu Gln Asn Glu Glu Leu Ile Thr Glu Gln Met Ala Pro His
545                 550                 555                 560
His Lys Ile Leu Ala Lys Ala Ile Phe Lys Leu Thr Tyr Gln Asn Lys
                565                 570                 575
Val Val Lys Val Leu Arg Pro Thr Pro Arg Gly Ala Val Met Asp Ile
                580                 585                 590
Ile Ser Arg Lys Asp Gln Arg Gly Ser Gly Gln Val Gly Thr Tyr Gly
            595                 600                 605
Leu Asn Thr Phe Thr Asn Met Glu Val Gln Leu Ile Arg Gln Met Glu
        610                 615                 620
Ala Glu Gly Val Ile Thr Gln Asp Asp Met Gln Asn Pro Lys Gly Leu
625                 630                 635                 640
Lys Glu Arg Val Glu Lys Trp Leu Lys Glu Cys Gly Val Asp Arg Leu
                645                 650                 655
Lys Arg Met Ala Ile Ser Gly Asp Asp Cys Val Val Lys Pro Leu Asp
                660                 665                 670
Glu Arg Phe Gly Thr Ser Leu Leu Phe Leu Asn Asp Met Gly Lys Val
            675                 680                 685
Arg Lys Asp Ile Pro Gln Trp Glu Pro Ser Lys Gly Trp Lys Asn Trp
        690                 695                 700
Gln Glu Val Pro Phe Cys Ser His His Phe His Lys Ile Phe Met Lys
705                 710                 715                 720
Asp Gly Arg Ser Leu Val Val Pro Cys Arg Asn Gln Asp Glu Leu Ile
                725                 730                 735
Gly Arg Ala Arg Ile Ser Gln Gly Ala Gly Trp Ser Leu Arg Glu Thr
                740                 745                 750
Ala Cys Leu Gly Lys Ala Tyr Ala Gln Met Trp Ser Leu Met Tyr Phe
            755                 760                 765
His Arg Arg Asp Leu Arg Leu Ala Ser Met Ala Ile Cys Ser Ala Val
        770                 775                 780
Pro Thr Glu Trp Phe Pro Thr Ser Arg Thr Thr Trp Ser Ile His Ala
785                 790                 795                 800
His His Gln Trp Met Thr Thr Glu Asp Met Leu Lys Val Trp Asn Arg
                805                 810                 815
Val Trp Ile Glu Asp Asn Pro Asn Met Thr Asp Lys Thr Pro Val His
                820                 825                 830
Ser Trp Glu Asp Ile Pro Tyr Leu Gly Lys Arg Glu Asp Leu Trp Cys
            835                 840                 845
Gly Ser Leu Ile Gly Leu Ser Ser Arg Ala Thr Trp Ala Lys Asn Ile
        850                 855                 860
His Thr Ala Ile Thr Gln Val Arg Asn Leu Ile Gly Lys Glu Glu Tyr
865                 870                 875                 880
Val Asp Tyr Met Pro Val Met Lys Arg Tyr Ser Ala Pro Ser Glu Ser
                885                 890                 895
```

Glu Gly Val Leu
          900

<210> SEQ ID NO 2
<211> LENGTH: 233
<212> TYPE: DNA
<213> ORGANISM: Dengue 4 virus

<400> SEQUENCE: 2
gactagcggt tagaggagac ccctcccatc actgataaaa cgcagcaaaa gggggcccga      60
agccaggagg aagctgtact cctggtggaa ggactagagg ttagaggaga ccccccccaac    120 acaaaaacag catattgacg ctgggaaaga ccagagatcc tgctgtctct gcaacatcaa    180
tccaggcaca gagcgccgca agatggattg gtgttgttga tccaacaggt tct           233

<210> SEQ ID NO 3
<211> LENGTH: 228
<212> TYPE: DNA
<213> ORGANISM: Dengue 1 virus

<400> SEQUENCE: 3
gactagtggt tagaggagac ccctcccaag acacaacgca gcagcggggc ccaacaccag      60
gggaagctgt accctggtgg taaggactag aggttagagg agaccccccg cacaacaaca    120
aacagcatat tgacgctggg agagaccaga gatcctgctg tctctacagc atcattccag    180
gcacagaacg ccaaaaaatg gaatggtgct gttgaatcaa caggttct                  228

<210> SEQ ID NO 4
<211> LENGTH: 230
<212> TYPE: DNA
<213> ORGANISM: Dengue 2 virus

<400> SEQUENCE: 4
gactagcggt tagaggagac ccctccctta caaatcgcag caacaatggg ggcccaaggt      60
gagatgaagc tgtagtctca ctggaaggac tagaggttag aggagacccc cccaaaacaa    120
aaaacagcat attgacgctg ggaaagacca gagatcctgc tgtctcctca gcatcattcc    180
aggcacagaa cgccagaaaa tggaatggtg ctgttgaatc aacaggttct                230

<210> SEQ ID NO 5
<211> LENGTH: 227
<212> TYPE: DNA
<213> ORGANISM: Dengue 3 virus

<400> SEQUENCE: 5
gactagtggt tagaggagac ccctcccatg acacaacgca gcagcggggc ccgagcactg      60
agggaagctg tacctccttg caaaggacta gaggttatag agaccccccg caaacaaaa     120 acagcatatt gacgctggga gagaccagag atcctgctgt ctcctcagca tcattccagg    180
cacagaacgc cagaaaatgg aatggtgctg ttgaatcaac aggttct                   227

<210> SEQ ID NO 6
<211> LENGTH: 227
<212> TYPE: DNA
<213> ORGANISM: West Nile virus

<400> SEQUENCE: 6
gactagaggt tagaggagac cccgcgtaaa aaagtgcacg gcccaacttg gctgaagctg      60
taagccaagg gaaggactag aggttagagg agaccccgtg ccaaaaacac caaaagaaac    120
agcatattga cacctgggat agactagggg atcttctgct ctgcacaacc agccacacgg    180
cacagtgcgc cgacataggt ggctggtggt gctagaacac aggatct                 227

<210> SEQ ID NO 7
<211> LENGTH: 229
<212> TYPE: DNA
<213> ORGANISM: Japanese encephalitis virus

<400> SEQUENCE: 7
gactagaggt tagaggagac cccgtggaaa caacaacatg cggcccaagc cccctcgaag    60
ctgtagagga ggtggaagga ctagaggtta gaggagaccc cgcatttgca tcaaacagca   120
tattgacacc tgggaataga ctgggagatc ttctgctcta tctcaacatc agctactagg   180
cacagagcgc cgaagtatgt acgtggtggt gaggaagaac acaggatct               229

<210> SEQ ID NO 8
<211> LENGTH: 241
<212> TYPE: DNA
<213> ORGANISM: Yellow fever virus

<400> SEQUENCE: 8
aacctggttt ctgggacctc ccaccccaga gtaaaagaa cggagcctcc gctaccaccc     60
tcccacgtgg tggtagaaag acggggtcta gaggttagag gagaccctcc agggaacaaa   120
tagtgggacc atattgacgc cagggaaaga ccggagtggt tctctgcttt tcctccagag   180
gtctgtgagc acagtttgct caagaataag cagacctttg atgacaaac acaaaaccac    240 t                                                                   241

<210> SEQ ID NO 9
<211> LENGTH: 249
<212> TYPE: DNA
<213> ORGANISM: Powassan virus

<400> SEQUENCE: 9
aaacgaactt tgtgagacca aaaggcctcc tggaaggctc accaggagtt aggccgttta    60 ggagccccg agcataactc gggaggaggg aggaagaaaa ttggcaatct tcctcgggat    120
ttttccgcct cctatactaa atttccccca ggaaactggg ggggcggttc ttgttctccc   180
tgagccacca ccatccaggc acagatagcc tgacaaggag atggtgtgtg actcggaaaa   240
acacccgct                                                          249

<210> SEQ ID NO 10
<211> LENGTH: 250
<212> TYPE: DNA
<213> ORGANISM: Louping ill virus

<400> SEQUENCE: 10
tgcaagattt tgcgagaccc cccgccccat gacaaggccg aacatggagc attaaaggga    60
ggcccccgga agcatgcttc cgggaggagg gaagagagaa attggcagct ctcttcaggg   120
tttttcctcc tcctatacca aatttccccc tcgacagagg ggggcggtt cttgttctcc    180 ctgagccacc atcacccaga cacagatagt ctgacaagga ggtgatgtgt gactcggaaa   240
aacacccgct                                                         250

<210> SEQ ID NO 11
<211> LENGTH: 250
<212> TYPE: DNA

<213> ORGANISM: Tick-borne encephalitis virus

<400> SEQUENCE: 11

```
tgaaaaattt tgtgagaccc cctgcatcat gataaggccg aacatggtgc atgaaagggg    60
aggcccccgg aagcacgctt ccgggaggag ggaagagaga aattggcagc tctcttcagg   120
attttttcctc ctcctataca aaattccccc tcggtagagg ggggcggtt cttgttctcc   180
ctgagccacc atcacccaga cacaggtagt ctgacaagga ggtgatgtgt gactcggaaa   240
aacacccgct                                                          250
```

<210> SEQ ID NO 12
<211> LENGTH: 247
<212> TYPE: DNA
<213> ORGANISM: Langat virus

<400> SEQUENCE: 12

```
tgtgaaactt tgtgagaccc cttgcgtcca gagaaggccg aactgggcgt tataaggagg    60
cccccagggg gaaaccccctg ggaggaggga agagagaaat tggcaactct cttcaggata   120
tttcctcctc ctataccaaa ttcccccctcg tcagaggggg ggcggttctt gttctccctg   180
agccaccatc acctagacac agatagtctg aaaaggaggt gatgcgtgtc tcggaaaaac   240
acccgct                                                             247
```

<210> SEQ ID NO 13
<211> LENGTH: 3387
<212> TYPE: PRT
<213> ORGANISM: Dengue 4 virus strain 2A

<400> SEQUENCE: 13

```
Met Asn Gln Arg Lys Lys Val Val Arg Pro Phe Asn Met Leu Lys
  1               5                  10                  15

Arg Glu Arg Asn Arg Val Ser Thr Pro Gln Gly Leu Val Lys Arg Phe
                 20                  25                  30

Ser Thr Gly Leu Phe Ser Gly Lys Gly Pro Leu Arg Met Val Leu Ala
             35                  40                  45

Phe Ile Thr Phe Leu Arg Val Leu Ser Ile Pro Pro Thr Ala Gly Ile
         50                  55                  60

Leu Lys Arg Trp Gly Gln Leu Lys Lys Asn Lys Ala Ile Lys Ile Leu
 65                  70                  75                  80

Ile Gly Phe Arg Lys Glu Ile Gly Arg Met Leu Asn Ile Leu Asn Gly
                 85                  90                  95

Arg Lys Arg Ser Thr Ile Thr Leu Leu Cys Leu Ile Pro Thr Val Met
                100                 105                 110

Ala Phe Ser Leu Ser Thr Arg Asp Gly Glu Pro Leu Met Ile Val Ala
            115                 120                 125

Lys His Glu Arg Gly Arg Pro Leu Leu Phe Lys Thr Thr Glu Gly Ile
        130                 135                 140

Asn Lys Cys Thr Leu Ile Ala Met Asp Leu Gly Glu Met Cys Glu Asp
145                 150                 155                 160

Thr Val Thr Tyr Lys Cys Pro Leu Leu Val Asn Thr Glu Pro Glu Asp
                165                 170                 175

Ile Asp Cys Trp Cys Asn Leu Thr Ser Thr Trp Val Met Tyr Gly Thr
            180                 185                 190

Cys Thr Gln Ser Gly Glu Arg Arg Arg Glu Lys Arg Ser Val Ala Leu
        195                 200                 205
```

```
Thr Pro His Ser Gly Met Gly Leu Glu Thr Arg Ala Glu Thr Trp Met
    210                 215                 220
Ser Ser Glu Gly Ala Trp Lys His Ala Gln Arg Val Glu Ser Trp Ile
225                 230                 235                 240
Leu Arg Asn Pro Gly Phe Ala Leu Leu Ala Gly Phe Met Ala Tyr Met
                245                 250                 255
Ile Gly Gln Thr Gly Ile Gln Arg Thr Val Phe Phe Val Leu Met Met
                260                 265                 270
Leu Val Ala Pro Ser Tyr Gly Met Arg Cys Val Gly Val Gly Asn Arg
            275                 280                 285
Asp Phe Val Glu Gly Val Ser Gly Gly Ala Trp Val Asp Leu Val Leu
    290                 295                 300
Glu His Gly Gly Cys Val Thr Thr Met Ala Gln Gly Lys Pro Thr Leu
305                 310                 315                 320
Asp Phe Glu Leu Thr Lys Thr Thr Ala Lys Glu Val Ala Leu Leu Arg
                325                 330                 335
Thr Tyr Cys Ile Glu Ala Ser Ile Ser Asn Ile Thr Thr Ala Thr Arg
                340                 345                 350
Cys Pro Thr Gln Gly Glu Pro Tyr Leu Lys Glu Glu Gln Asp Gln Gln
            355                 360                 365
Tyr Ile Cys Arg Arg Asp Val Val Asp Arg Gly Trp Gly Asn Gly Cys
    370                 375                 380
Gly Leu Phe Gly Lys Gly Val Val Thr Cys Ala Lys Phe Ser Cys
385                 390                 395                 400
Ser Gly Lys Ile Thr Gly Asn Leu Val Gln Ile Glu Asn Leu Glu Tyr
                405                 410                 415
Thr Val Val Val Thr Val His Asn Gly Asp Thr His Ala Val Gly Asn
            420                 425                 430
Asp Thr Ser Asn His Gly Val Thr Ala Met Ile Thr Pro Arg Ser Pro
    435                 440                 445
Ser Val Glu Val Lys Leu Pro Asp Tyr Gly Glu Leu Thr Leu Asp Cys
450                 455                 460
Glu Pro Arg Ser Gly Ile Asp Phe Asn Glu Met Ile Leu Met Lys Met
465                 470                 475                 480
Lys Lys Lys Thr Trp Leu Val His Lys Gln Trp Phe Leu Asp Leu Pro
                485                 490                 495
Leu Pro Trp Thr Ala Gly Ala Asp Thr Ser Glu Val His Trp Asn Tyr
            500                 505                 510
Lys Glu Arg Met Val Thr Phe Lys Val Pro His Ala Lys Arg Gln Asp
    515                 520                 525
Val Thr Val Leu Gly Ser Gln Glu Gly Ala Met His Ser Ala Leu Ala
    530                 535                 540
Gly Ala Thr Glu Val Asp Ser Gly Asp Gly Asn His Met Phe Ala Gly
545                 550                 555                 560
His Leu Lys Cys Lys Val Arg Met Glu Lys Leu Arg Ile Lys Gly Met
                565                 570                 575
Ser Tyr Thr Met Cys Ser Gly Lys Phe Ser Ile Asp Lys Glu Met Ala
            580                 585                 590
Glu Thr Gln His Gly Thr Thr Val Val Lys Val Lys Tyr Glu Gly Ala
            595                 600                 605
Gly Ala Pro Cys Lys Val Pro Ile Glu Ile Arg Asp Val Asn Lys Glu
    610                 615                 620
Lys Val Val Gly Arg Ile Ile Ser Ser Thr Pro Leu Ala Glu Asn Thr
```

```
                625                 630                 635                 640
Asn Ser Val Thr Asn Ile Glu Leu Glu Pro Pro Phe Gly Asp Ser Tyr
                    645                 650                 655
Ile Val Ile Gly Val Gly Asn Ser Ala Leu Thr Leu His Trp Phe Arg
                    660                 665                 670
Lys Gly Ser Ser Ile Gly Lys Met Phe Glu Ser Thr Tyr Arg Gly Ala
                    675                 680                 685
Lys Arg Met Ala Ile Leu Gly Glu Thr Ala Trp Asp Phe Gly Ser Val
                    690                 695                 700
Gly Gly Leu Phe Thr Ser Leu Gly Lys Ala Val His Gln Val Phe Gly
705                 710                 715                 720
Ser Val Tyr Thr Thr Met Phe Gly Gly Val Ser Trp Met Ile Arg Ile
                    725                 730                 735
Leu Ile Gly Phe Leu Val Leu Trp Ile Gly Thr Asn Ser Arg Asn Thr
                    740                 745                 750
Ser Met Ala Met Thr Cys Ile Ala Val Gly Gly Ile Thr Leu Phe Leu
                    755                 760                 765
Gly Phe Thr Val Gln Ala Asp Met Gly Cys Val Val Ser Trp Ser Gly
                    770                 775                 780
Lys Glu Leu Lys Cys Gly Ser Gly Ile Phe Val Val Asp Asn Val His
785                 790                 795                 800
Thr Trp Thr Glu Gln Tyr Lys Phe Gln Pro Glu Ser Pro Ala Arg Leu
                    805                 810                 815
Ala Ser Ala Ile Leu Asn Ala His Lys Asp Gly Val Cys Gly Ile Arg
                    820                 825                 830
Ser Thr Thr Arg Leu Glu Asn Val Met Trp Lys Gln Ile Thr Asn Glu
                    835                 840                 845
Leu Asn Tyr Val Leu Trp Glu Gly Gly His Asp Leu Thr Val Val Ala
                    850                 855                 860
Gly Asp Val Lys Gly Val Leu Thr Lys Gly Lys Arg Ala Leu Thr Pro
865                 870                 875                 880
Pro Val Ser Asp Leu Lys Tyr Ser Trp Lys Thr Trp Gly Lys Ala Lys
                    885                 890                 895
Ile Phe Thr Pro Glu Ala Arg Asn Ser Thr Phe Leu Ile Asp Gly Pro
                    900                 905                 910
Asp Thr Ser Glu Cys Pro Asn Glu Arg Arg Ala Trp Asn Ser Leu Glu
                    915                 920                 925
Val Glu Asp Tyr Gly Phe Gly Met Phe Thr Thr Asn Ile Trp Met Lys
                    930                 935                 940
Phe Arg Glu Gly Ser Ser Glu Val Cys Asp His Arg Leu Met Ser Ala
945                 950                 955                 960
Ala Ile Lys Asp Gln Lys Ala Val His Ala Asp Met Gly Tyr Trp Ile
                    965                 970                 975
Glu Ser Ser Lys Asn Gln Thr Trp Gln Ile Glu Lys Ala Ser Leu Ile
                    980                 985                 990
Glu Val Lys Thr Cys Leu Trp Pro Lys Thr His Thr Leu Trp Ser Asn
                    995                 1000                1005
Gly Val Leu Glu Ser Gln Met Leu Ile Pro Lys Ser Tyr Ala Gly Pro
      1010                1015                1020
Phe Ser Gln His Asn Tyr Arg Gln Gly Tyr Ala Thr Gln Thr Val Gly
      1025                1030                1035                1040
Pro Trp His Leu Gly Lys Leu Glu Ile Asp Phe Gly Glu Cys Pro Gly
                    1045                1050                1055
```

-continued

```
Thr Thr Val Thr Ile Gln Glu Asp Cys Asp His Arg Gly Pro Ser Leu
        1060                1065                1070

Arg Thr Thr Thr Ala Ser Gly Lys Leu Val Thr Gln Trp Cys Cys Arg
        1075                1080                1085

Ser Cys Thr Met Pro Pro Leu Arg Phe Leu Gly Glu Asp Gly Cys Trp
        1090                1095                1100

Tyr Gly Met Glu Ile Arg Pro Leu Ser Glu Lys Glu Glu Asn Met Val
1105                1110                1115                1120

Lys Ser Gln Val Thr Ala Gly Gln Gly Thr Ser Glu Thr Phe Ser Met
                1125                1130                1135

Gly Leu Leu Cys Leu Thr Leu Phe Val Glu Glu Cys Leu Arg Arg Arg
                1140                1145                1150

Val Thr Arg Lys His Met Ile Leu Val Val Ile Thr Leu Cys Ala
        1155                1160                1165

Ile Ile Leu Gly Gly Leu Thr Trp Met Asp Leu Leu Arg Ala Leu Ile
        1170                1175                1180

Met Leu Gly Asp Thr Met Ser Gly Arg Ile Gly Gly Gln Ile His Leu
1185                1190                1195                1200

Ala Ile Met Ala Val Phe Lys Met Ser Pro Gly Tyr Val Leu Gly Val
                1205                1210                1215

Phe Leu Arg Lys Leu Thr Ser Arg Glu Thr Ala Leu Met Val Ile Gly
        1220                1225                1230

Met Ala Met Thr Thr Val Leu Ser Ile Pro His Asp Leu Met Glu Leu
        1235                1240                1245

Ile Asp Gly Ile Ser Leu Gly Leu Ile Leu Leu Lys Ile Val Thr Gln
        1250                1255                1260

Phe Asp Asn Thr Gln Val Gly Thr Leu Ala Leu Ser Leu Thr Phe Ile
1265                1270                1275                1280

Arg Ser Thr Met Pro Leu Val Met Ala Trp Arg Thr Ile Met Ala Val
                1285                1290                1295

Leu Phe Val Val Thr Leu Ile Pro Leu Cys Arg Thr Ser Cys Leu Gln
                1300                1305                1310

Lys Gln Ser His Trp Val Glu Ile Thr Ala Leu Ile Leu Gly Ala Gln
        1315                1320                1325

Ala Leu Pro Val Tyr Leu Met Thr Leu Met Lys Gly Ala Ser Arg Arg
        1330                1335                1340

Ser Trp Pro Leu Asn Glu Gly Ile Met Ala Val Gly Leu Val Ser Leu
1345                1350                1355                1360

Leu Gly Ser Ala Leu Leu Lys Asn Asp Val Pro Leu Ala Gly Pro Met
                1365                1370                1375

Val Ala Gly Gly Leu Leu Leu Ala Ala Tyr Val Met Ser Gly Ser Ser
                1380                1385                1390

Ala Asp Leu Ser Leu Glu Lys Ala Ala Asn Val Gln Trp Asp Glu Met
        1395                1400                1405

Ala Asp Ile Thr Gly Ser Ser Pro Ile Ile Glu Val Lys Gln Asp Glu
        1410                1415                1420

Asp Gly Ser Phe Ser Ile Arg Asp Val Glu Glu Thr Asn Met Ile Thr
1425                1430                1435                1440

Leu Leu Val Lys Leu Ala Leu Ile Thr Val Ser Gly Leu Tyr Pro Leu
                1445                1450                1455

Ala Ile Pro Val Thr Met Thr Leu Trp Tyr Met Trp Gln Val Lys Thr
        1460                1465                1470
```

-continued

```
Gln Arg Ser Gly Ala Leu Trp Asp Val Pro Ser Pro Ala Ala Thr Lys
        1475                1480                1485

Lys Ala Ala Leu Ser Glu Gly Val Tyr Arg Ile Met Gln Arg Gly Leu
    1490                1495                1500

Phe Gly Lys Thr Gln Val Gly Val Gly Ile His Met Glu Gly Val Phe
1505                1510                1515                1520

His Thr Met Trp His Val Thr Arg Gly Ser Val Ile Cys His Glu Thr
                1525                1530                1535

Gly Arg Leu Glu Pro Ser Trp Ala Asp Val Arg Asn Asp Met Ile Ser
            1540                1545                1550

Tyr Gly Gly Gly Trp Arg Leu Gly Asp Lys Trp Asp Lys Glu Glu Asp
        1555                1560                1565

Val Gln Val Leu Ala Ile Glu Pro Gly Lys Asn Pro Lys His Val Gln
    1570                1575                1580

Thr Lys Pro Gly Leu Phe Lys Thr Leu Thr Gly Glu Ile Gly Ala Val
1585                1590                1595                1600

Thr Leu Asp Phe Lys Pro Gly Thr Ser Gly Ser Pro Ile Ile Asn Arg
                1605                1610                1615

Lys Gly Lys Val Ile Gly Leu Tyr Gly Asn Gly Val Val Thr Lys Ser
            1620                1625                1630

Gly Asp Tyr Val Ser Ala Ile Thr Gln Ala Glu Arg Ile Gly Glu Pro
        1635                1640                1645

Asp Tyr Glu Val Asp Glu Asp Ile Phe Arg Lys Lys Arg Leu Thr Ile
    1650                1655                1660

Met Asp Leu His Pro Gly Ala Gly Lys Thr Lys Arg Ile Leu Pro Ser
1665                1670                1675                1680

Ile Val Arg Glu Ala Leu Lys Arg Arg Leu Arg Thr Leu Ile Leu Ala
                1685                1690                1695

Pro Thr Arg Val Val Ala Ala Glu Met Glu Glu Ala Leu Arg Gly Leu
            1700                1705                1710

Pro Ile Arg Tyr Gln Thr Pro Ala Val Lys Ser Glu His Thr Gly Arg
        1715                1720                1725

Glu Ile Val Asp Leu Met Cys His Ala Thr Phe Thr Thr Arg Leu Leu
    1730                1735                1740

Ser Ser Thr Arg Val Pro Asn Tyr Asn Leu Ile Val Met Asp Glu Ala
1745                1750                1755                1760

His Phe Thr Asp Pro Ser Ser Val Ala Ala Arg Gly Tyr Ile Ser Thr
                1765                1770                1775

Arg Val Glu Met Gly Glu Ala Ala Ile Phe Met Thr Ala Thr Pro
            1780                1785                1790

Pro Gly Ala Thr Asp Pro Phe Pro Gln Ser Asn Ser Pro Ile Glu Asp
        1795                1800                1805

Ile Glu Arg Glu Ile Pro Glu Arg Ser Trp Asn Thr Gly Phe Asp Trp
    1810                1815                1820

Ile Thr Asp Tyr Gln Gly Lys Thr Val Trp Phe Val Pro Ser Ile Lys
1825                1830                1835                1840

Ala Gly Asn Asp Ile Ala Asn Cys Leu Arg Lys Ser Gly Lys Lys Val
                1845                1850                1855

Ile Gln Leu Ser Arg Lys Thr Phe Asp Thr Glu Tyr Pro Lys Thr Lys
            1860                1865                1870

Leu Thr Asp Trp Asp Phe Val Val Thr Thr Asp Ile Ser Glu Met Gly
        1875                1880                1885

Ala Asn Phe Arg Ala Gly Arg Val Ile Asp Pro Arg Arg Cys Leu Lys
```

-continued

```
              1890                1895                1900
Pro Val Ile Leu Pro Asp Gly Pro Glu Arg Val Ile Leu Ala Gly Pro
1905                1910                1915                1920

Ile Pro Val Thr Pro Ala Ser Ala Ala Gln Arg Arg Gly Arg Ile Gly
                    1925                1930                1935

Arg Asn Pro Ala Gln Glu Asp Gln Tyr Val Phe Ser Gly Asp Pro
                1940                1945                1950

Leu Lys Asn Asp Glu Asp His Ala His Trp Thr Glu Ala Lys Met Leu
            1955                1960                1965

Leu Asp Asn Ile Tyr Thr Pro Glu Gly Ile Ile Pro Thr Leu Phe Gly
            1970                1975                1980

Pro Glu Arg Glu Lys Thr Gln Ala Ile Asp Gly Glu Phe Arg Leu Arg
1985                1990                1995                2000

Gly Glu Gln Arg Lys Thr Phe Val Glu Leu Met Arg Arg Gly Asp Leu
                2005                2010                2015

Pro Val Trp Leu Ser Tyr Lys Val Ala Ser Ala Gly Ile Ser Tyr Lys
                2020                2025                2030

Asp Arg Glu Trp Cys Phe Thr Gly Glu Arg Asn Asn Gln Ile Leu Glu
                2035                2040                2045

Glu Asn Met Glu Val Glu Ile Trp Thr Arg Glu Gly Glu Lys Lys Lys
                2050                2055                2060

Leu Arg Pro Arg Trp Leu Asp Ala Arg Val Tyr Ala Asp Pro Met Ala
2065                2070                2075                2080

Leu Lys Asp Phe Lys Glu Phe Ala Ser Gly Arg Lys Ser Ile Thr Leu
                2085                2090                2095

Asp Ile Leu Thr Glu Ile Ala Ser Leu Pro Thr Tyr Leu Ser Ser Arg
                2100                2105                2110

Ala Lys Leu Ala Leu Asp Asn Ile Val Met Leu His Thr Thr Glu Arg
                2115                2120                2125

Gly Gly Arg Ala Tyr Gln His Ala Leu Asn Glu Leu Pro Glu Ser Leu
                2130                2135                2140

Glu Thr Leu Met Leu Val Ala Leu Leu Gly Ala Met Thr Ala Gly Ile
2145                2150                2155                2160

Phe Leu Phe Phe Met Gln Gly Lys Gly Ile Gly Lys Leu Ser Met Gly
                2165                2170                2175

Leu Ile Thr Ile Ala Val Ala Ser Gly Leu Leu Trp Val Ala Glu Ile
                2180                2185                2190

Gln Pro Gln Trp Ile Ala Ala Ser Ile Ile Leu Glu Phe Phe Leu Met
                2195                2200                2205

Val Leu Leu Ile Pro Glu Pro Glu Lys Gln Arg Thr Pro Gln Asp Asn
2210                2215                2220

Gln Leu Ile Tyr Val Ile Leu Thr Ile Leu Thr Ile Ile Gly Leu Ile
                2225                2230                2235                2240

Ala Ala Asn Glu Met Gly Leu Ile Glu Lys Thr Lys Thr Asp Phe Gly
                        2245                2250                2255

Phe Tyr Gln Val Lys Thr Glu Thr Thr Ile Leu Asp Val Asp Leu Arg
                    2260                2265                2270

Pro Ala Ser Ala Trp Thr Leu Tyr Ala Val Ala Thr Thr Ile Leu Thr
                2275                2280                2285

Pro Met Leu Arg His Thr Ile Glu Asn Thr Ser Ala Asn Leu Ser Leu
            2290                2295                2300

Ala Ala Ile Ala Asn Gln Ala Val Leu Met Gly Leu Gly Lys Gly
2305                2310                2315                2320
```

-continued

```
Trp Pro Leu His Arg Met Asp Leu Gly Val Pro Leu Ala Met Gly
            2325                2330                2335

Cys Tyr Ser Gln Val Asn Pro Thr Thr Leu Thr Ala Ser Leu Val Met
            2340                2345                2350

Leu Leu Val His Tyr Ala Ile Ile Gly Pro Gly Leu Gln Ala Lys Ala
            2355                2360                2365

Thr Arg Glu Ala Gln Lys Arg Thr Ala Ala Gly Ile Met Lys Asn Pro
            2370                2375                2380

Thr Val Asp Gly Ile Thr Val Ile Asp Leu Glu Pro Ile Ser Tyr Asp
2385                2390                2395                2400

Pro Lys Phe Glu Lys Gln Leu Gly Gln Val Met Leu Val Leu Cys
            2405                2410                2415

Ala Gly Gln Leu Leu Met Arg Thr Thr Trp Ala Phe Cys Glu Val
            2420                2425                2430

Leu Thr Leu Ala Thr Gly Pro Ile Leu Thr Leu Trp Glu Gly Asn Pro
            2435                2440                2445

Gly Arg Phe Trp Asn Thr Thr Ile Ala Val Ser Thr Ala Asn Ile Phe
            2450                2455                2460

Arg Gly Ser Tyr Leu Ala Gly Ala Gly Leu Ala Phe Ser Leu Ile Lys
2465                2470                2475                2480

Asn Ala Gln Thr Pro Arg Arg Gly Thr Gly Thr Thr Gly Glu Thr Leu
            2485                2490                2495

Gly Glu Lys Trp Lys Arg Gln Leu Asn Ser Leu Asp Arg Lys Glu Phe
            2500                2505                2510

Glu Glu Tyr Lys Arg Ser Gly Ile Leu Glu Val Asp Arg Thr Glu Ala
            2515                2520                2525

Lys Ser Ala Leu Lys Asp Gly Ser Lys Ile Lys His Ala Val Ser Arg
            2530                2535                2540

Gly Ser Ser Lys Ile Arg Trp Ile Val Glu Arg Gly Met Val Lys Pro
2545                2550                2555                2560

Lys Gly Lys Val Val Asp Leu Gly Cys Gly Arg Gly Gly Trp Ser Tyr
            2565                2570                2575

Tyr Met Ala Thr Leu Lys Asn Val Thr Glu Val Lys Gly Tyr Thr Lys
            2580                2585                2590

Gly Gly Pro Gly His Glu Glu Pro Ile Pro Met Ala Thr Tyr Gly Trp
            2595                2600                2605

Asn Leu Val Lys Leu His Ser Gly Val Asp Val Phe Tyr Lys Pro Thr
            2610                2615                2620

Glu Gln Val Asp Thr Leu Leu Cys Asp Ile Gly Glu Ser Ser Ser Asn
2625                2630                2635                2640

Pro Thr Ile Glu Glu Gly Arg Thr Leu Arg Val Leu Lys Met Val Glu
            2645                2650                2655

Pro Trp Leu Ser Ser Lys Pro Glu Phe Cys Ile Lys Val Leu Asn Pro
            2660                2665                2670

Tyr Met Pro Thr Val Ile Glu Glu Leu Glu Lys Leu Gln Arg Lys His
            2675                2680                2685

Gly Gly Asn Leu Val Arg Cys Pro Leu Ser Arg Asn Ser Thr His Glu
            2690                2695                2700

Met Tyr Trp Val Ser Gly Ala Ser Gly Asn Ile Val Ser Ser Val Asn
2705                2710                2715                2720

Thr Thr Ser Lys Met Leu Leu Asn Arg Phe Thr Thr Arg His Arg Lys
            2725                2730                2735
```

-continued

Pro Thr Tyr Glu Lys Asp Val Asp Leu Gly Ala Gly Thr Arg Ser Val
            2740                2745                2750

Ser Thr Glu Thr Glu Lys Pro Asp Met Thr Ile Ile Gly Arg Arg Leu
        2755                2760                2765

Gln Arg Leu Gln Glu Glu His Lys Glu Thr Trp His Tyr Asp Gln Glu
    2770                2775                2780

Asn Pro Tyr Arg Thr Trp Ala Tyr His Gly Ser Tyr Glu Ala Pro Ser
2785                2790                2795                2800

Thr Gly Ser Ala Ser Ser Met Val Asn Gly Val Val Lys Leu Leu Thr
                2805                2810                2815

Lys Pro Trp Asp Val Ile Pro Met Val Thr Gln Leu Ala Met Thr Asp
            2820                2825                2830

Thr Thr Pro Phe Gly Gln Gln Arg Val Phe Lys Glu Lys Val Asp Thr
        2835                2840                2845

Arg Thr Pro Gln Pro Lys Pro Gly Thr Arg Met Val Met Thr Thr Thr
    2850                2855                2860

Ala Asn Trp Leu Trp Ala Leu Leu Gly Lys Lys Lys Asn Pro Arg Leu
2865                2870                2875                2880

Cys Thr Arg Glu Glu Phe Ile Ser Lys Val Arg Ser Asn Ala Ala Ile
                2885                2890                2895

Gly Ala Val Phe Gln Glu Glu Gln Gly Trp Thr Ser Ala Ser Glu Ala
            2900                2905                2910

Val Asn Asp Ser Arg Phe Trp Glu Leu Val Asp Lys Glu Arg Ala Leu
        2915                2920                2925

His Gln Glu Gly Lys Cys Glu Ser Cys Val Tyr Asn Met Met Gly Lys
    2930                2935                2940

Arg Glu Lys Lys Leu Gly Glu Phe Gly Arg Ala Lys Gly Ser Arg Ala
2945                2950                2955                2960

Ile Trp Tyr Met Trp Leu Gly Ala Arg Phe Leu Glu Phe Glu Ala Leu
                2965                2970                2975

Gly Phe Leu Asn Glu Asp His Trp Phe Gly Arg Glu Asn Ser Trp Ser
            2980                2985                2990

Gly Val Glu Gly Glu Gly Leu His Arg Leu Gly Tyr Ile Leu Glu Glu
        2995                3000                3005

Ile Asp Lys Lys Asp Gly Asp Leu Met Tyr Ala Asp Asp Thr Ala Gly
    3010                3015                3020

Trp Asp Thr Arg Ile Thr Glu Asp Asp Leu Gln Asn Glu Glu Leu Ile
3025                3030                3035                3040

Thr Glu Gln Met Ala Pro His His Lys Ile Leu Ala Lys Ala Ile Phe
                3045                3050                3055

Lys Leu Thr Tyr Gln Asn Lys Val Val Lys Val Leu Arg Pro Thr Pro
            3060                3065                3070

Arg Gly Ala Val Met Asp Ile Ile Ser Arg Lys Asp Gln Arg Gly Ser
        3075                3080                3085

Gly Gln Val Gly Thr Tyr Gly Leu Asn Thr Phe Thr Asn Met Glu Val
    3090                3095                3100

Gln Leu Ile Arg Gln Met Glu Ala Glu Gly Val Ile Thr Gln Asp Asp
3105                3110                3115                3120

Met Gln Asn Pro Lys Gly Leu Lys Glu Arg Val Glu Lys Trp Leu Lys
                3125                3130                3135

Glu Cys Gly Val Asp Arg Leu Lys Arg Met Ala Ile Ser Gly Asp Asp
            3140                3145                3150

Cys Val Val Lys Pro Leu Asp Glu Arg Phe Gly Thr Ser Leu Leu Phe

```
                    3155            3160            3165
Leu Asn Asp Met Gly Lys Val Arg Lys Asp Ile Pro Gln Trp Glu Pro
    3170            3175            3180

Ser Lys Gly Trp Lys Asn Trp Gln Glu Val Pro Phe Cys Ser His His
3185            3190            3195            3200

Phe His Lys Ile Phe Met Lys Asp Gly Arg Ser Leu Val Val Pro Cys
            3205            3210            3215

Arg Asn Gln Asp Glu Leu Ile Gly Arg Ala Arg Ile Ser Gln Gly Ala
        3220            3225            3230

Gly Trp Ser Leu Arg Glu Thr Ala Cys Leu Gly Lys Ala Tyr Ala Gln
        3235            3240            3245

Met Trp Ser Leu Met Tyr Phe His Arg Arg Asp Leu Arg Leu Ala Ser
    3250            3255            3260

Met Ala Ile Cys Ser Ala Val Pro Thr Glu Trp Phe Pro Thr Ser Arg
3265            3270            3275            3280

Thr Thr Trp Ser Ile His Ala His His Gln Trp Met Thr Thr Glu Asp
            3285            3290            3295

Met Leu Lys Val Trp Asn Arg Val Trp Ile Glu Asp Asn Pro Asn Met
        3300            3305            3310

Thr Asp Lys Thr Pro Val His Ser Trp Glu Asp Ile Pro Tyr Leu Gly
        3315            3320            3325

Lys Arg Glu Asp Leu Trp Cys Gly Ser Leu Ile Gly Leu Ser Ser Arg
    3330            3335            3340

Ala Thr Trp Ala Lys Asn Ile His Thr Ala Ile Thr Gln Val Arg Asn
3345            3350            3355            3360

Leu Ile Gly Lys Glu Glu Tyr Val Asp Tyr Met Pro Val Met Lys Arg
            3365            3370            3375

Tyr Ser Ala Pro Ser Glu Ser Glu Gly Val Leu
        3380            3385

<210> SEQ ID NO 14
<211> LENGTH: 10649
<212> TYPE: DNA
<213> ORGANISM: Dengue 4 virus strain 2A

<400> SEQUENCE: 14
agttgttagt ctgtgtggac cgacaaggac agttccaaat cggaagcttg cttaacacag     60
ttctaacagt ttgtttgaat agagagcaga tctctggaaa aatgaaccaa cgaaaaaagg    120
tggttagacc acctttcaat atgctgaaac gcgagagaaa ccgcgtatca acccctcaag    180
ggttggtgaa gagattctca accggacttt tttctgggaa aggacccttac ggatggtgc    240 tagcattcat cacgttttg cgagtccttt ccatcccacc aacagcaggg attctgaaga    300 gatgggaca gttgaagaaa aataaggcca tcaagatact gattggattc aggaaggaga    360
taggccgcat gctgaacatc ttgaacggga gaaaaaggtc aacgataaca ttgctgtgct    420
tgattcccac cgtaatggcg ttttccttgt caacaagaga tggcgaaccc ctcatgatag    480
tggcaaaaca tgaaggggg agacctctct tgtttaagac aacagagggg atcaacaaat    540
gcactctcat tgccatggac ttgggtgaaa tgtgtgagga cactgtcacg tataaatgcc    600
ccctactggt caataccgaa cctgaagaca ttgattgctg gtgcaacctc acgtctacct    660
gggtcatgta tggacatgc acccagagcg gagacggag acgagagaag cgctcagtag    720
ctttaacacc acattcagga atgggattgg aaacaagagc tgagcatgg atgtcatcgg    780 aaggggcttg gaagcatgct cagagagtag agagctggat actcagaaac ccaggattcg    840
```

```
cgctcttggc aggatttatg gcttatatga ttgggcaaac aggaatccag cgaactgtct    900
tctttgtcct aatgatgctg gtcgcccat cctacggaat gcgatgcgta ggagtaggaa    960
acagagactt tgtggaagga gtctcaggtg gagcatgggt cgacctggtg ctagaacatg   1020
gaggatgcgt cacaaccatg gcccagggaa accaaccctt ggattttgaa ctgactaaga   1080
caacagccaa ggaagtggct ctgttaagaa cctattgcat tgaagcctca atatcaaaca   1140
taactacggc aacaagatgt ccaacgcaag gagagcctta tctgaaagag gaacaggacc   1200
aacagtacat ttgccggaga gatgtggtag acagagggtg gggcaatggc tgtggcttgt   1260
ttggaaaagg aggagttgtg acatgtgcga agttttcatg ttcggggaag ataacaggca   1320
atttggtcca aattgagaac cttgaataca cagtggttgt aacagtccac aatggagaca   1380
cccatgcagt aggaaatgac acatccaatc atggagttac agccatgata actcccaggt   1440
caccatcggt ggaagtcaaa ttgccggact atggagaact aacactcgat tgtgaaccca   1500
ggtctggaat tgactttaat gagatgattc tgatgaaaat gaaaagaaa acatggctcg   1560
tgcataagca atggttttg gatctgcctc ttccatggac agcaggagca gacacatcag   1620
aggttcactg gaattacaaa gagagaatgg tgacatttaa ggttcctcat gccaagagac   1680
aggatgtgac agtgctggga tctcaggaag gagccatgca ttctgccctc gctggagcca   1740
cagaagtgga ctccggtgat ggaaatcaca tgtttgcagg acatcttaag tgcaaagtcc   1800
gtatggagaa attgagaatc aagggaatgt catacacgat gtgttcagga aagttttcaa   1860
ttgacaaaga gatggcagaa acacagcatg ggacaacagt ggtgaaagtc aagtatgaag   1920
gtgctggagc tccgtgtaaa gtccccatag agataagaga tgtaaacaag gaaaagtgg   1980
ttgggcgtat catctcatcc acccctttgg ctgagaatac caacagtgta accaacatag   2040
aattagaacc cccctttggg gacagctaca tagtgatagg tgttggaaac agcgcattaa   2100
cactccattg gttcaggaaa gggagttcca ttggcaagat gtttgagtcc acatacagag   2160
gtgcaaaacg aatggccatt ctaggtgaaa cagcttggga ttttggttcc gttggtggac   2220
tgttcacatc attgggaaag gctgtgcacc aggttttgg aagtgtgtat acaaccatgt   2280
ttggaggagt ctcatggatg attagaatcc taattgggtt cttagtgttg tggattggca   2340
cgaactcaag gaacacttca atggctatga cgtgcatagc tgttggagga atcactctgt   2400
ttctgggctt cacagttcaa gcagacatgg gttgtgtggt gtcatggagt gggaaagaat   2460
tgaagtgtgg aagcggaatt tttgtggttg acaacgtgca cacttggaca gaacagtaca   2520
aatttcaacc agagtcccca gcgagactag cgtctgcaat attaaatgcc cacaaagatg   2580
gggtctgtgg aattagatca accacgaggc tggaaaatgt catgtggaag caaataacca   2640
acgagctaaa ctatgttctc tgggaaggag acatgacct cactgtagtg gctggggatg   2700
tgaagggggt gttgaccaaa ggcaagagag cactcacacc cccagtgagt gatctgaaat   2760
attcatggaa gacatgggga aaagcaaaaa tcttcacccc agaagcaaga aatagcacat   2820
ttttaataga cggaccagac acctctgaat gccccaatga acgaagagca tggaactctc   2880
ttgaggtgga agactatgga tttggcatgt tcacgaccaa catatggatg aaattccgag   2940
aaggaagttc agaagtgtgt gaccacaggt taatgtcagc tgcaattaaa gatcagaaag   3000
ctgtgcatgc tgacatgggt tattggatag agagctcaaa aaaccagacc tggcagatag   3060
agaaagcatc tcttattgaa gtgaaaacat gtctgtggcc caagacccac acactgtgga   3120
gcaatggagt gctggaaagc cagatgctca ttccaaaatc atatgcgggc ccttttttcac  3180
```

```
agcacaatta ccgccagggc tatgccacgc aaaccgtggg cccatggcac ttaggcaaat    3240
tagagataga cttggagaa tgccccggaa caacagtcac aattcaggag gattgtgacc    3300
atagaggccc atctttgagg accaccactg catctggaaa actagtcacg caatggtgct    3360
gccgctcctg cacgatgcct cccttaaggt tcttgggaga agatgggtgc tggtatggga    3420
tggagattag gcccttgagt gaaaagaag agaacatggt caaatcacag gtgacggccg    3480
gacagggcac atcagaaact ttttctatgg gtctgttgtg cctgaccttg tttgtggaag    3540
aatgcttgag gagaagagtc actaggaaac acatgatatt agttgtggtg atcactcttt    3600
gtgctatcat cctgggaggc ctcacatgga tggacttact acgagccctc atcatgttgg    3660
gggacactat gtctggtaga ataggaggac agatccacct agccatcatg gcagtgttca    3720
agatgtcacc aggatacgtg ctgggtgtgt ttttaaggaa actcacttca agagagacag    3780
cactaatggt aataggaatg gccatgacaa cggtgctttc aattccacat gaccttatgg    3840
aactcattga tggaatatca ctgggactaa ttttgctaaa aatagtaaca cagttttgaca    3900 acacccaagt gggaacctta gctctttcct tgactttcat aagatcaaca atgccattgg    3960
tcatggcttg gaggaccatt atggctgtgt tgtttgtggt cacactcatt cctttgtgca    4020
ggacaagctg tcttcaaaaa cagtctcatt gggtagaaat aacagcactc atcctaggag    4080
cccaagctct gccagtgtac ctaatgactc ttatgaaagg agcctcaaga agatcttggc    4140
ctcttaacga gggcataatg gctgtgggtt tggttagtct cttaggaagc gctcttttaa    4200
agaatgatgt cccttttagct ggcccaatgg tggcaggagg cttacttctg gcggcttacg    4260
tgatgagtgg tagctcagca gatctgtcac tagagaaggc cgccaacgtg cagtgggatg    4320
aaatggcaga cataacaggc tcaagcccaa tcatagaagt gaagcaggat gaagatggct    4380
cttcctccat acgggacgtc gaggaaacca atatgataac ccttttggtg aaactggcac    4440
tgataacagt gtcaggctct tacccctttgg caattccagt cacaatgacc ttatggtaca    4500
tgtggcaagt gaaaacacaa agatcaggag ccctgtggga cgtcccctca cccgctgcca    4560 ctaaaaagc cgcactgtct gaaggagtgt acaggatcat gcaaagaggg ttattcggga    4620
aaactcaggt tggagtaggg atacacatgg aaggtgtatt tcacacaatg tggcatgtaa    4680
caagaggatc agtgatctgc cacgagactg gagattgga gccatcttgg gctgacgtca    4740
ggaatgacat gatatcatac ggtgggggat ggaggcttgg agacaaatgg gacaaagaag    4800
aagacgttca ggtcctcgcc atagaaccag gaaaaaatcc taaacatgtc caaacgaaac    4860
ctggcctttt caagacccta actggagaaa ttggagcagt aacattagat ttcaaacccg    4920
gaacgtctgg ttctcccatc atcaacagga aggaaaagt catcggactc tatgaaatg    4980 gagtagttac caaatcaggt gattacgtca gtgccataac gcaagccgaa agaattggag    5040
agccagatta tgaagtggat gaggacatt ttcgaaagaa aagattaact ataatggact    5100
tacaccccgg agctggaaag acaaaaagaa ttcttccatc aatagtgaga gaagccttaa    5160
aaaggaggct acgaactttg atttagctc ccacgagagt ggtggcggcc gagatggaag    5220
aggccctacg tggactgcca atccgttatc agaccccagc tgtgaaatca gaacacacag    5280
gaagagagat tgtagacctc atgtgtcatg caaccttcac aacaagactt ttgtcatcaa    5340
ccagggttcc aaattacaac cttatagtga tggatgaagc acatttcacc gatcccttcta    5400 gtgtcgcggc tagaggatac atctcgacca gggtggaaat gggagaggca gcagccatct    5460
tcatgaccga aaccccctccc ggagcgcacag atccctttcc ccagagcaac agcccaatag    5520
aagacatcga gagggaaatt ccggaaaggt catggaacac agggttcgac tggataacag    5580
```

```
actaccaagg gaaaactgtg tggtttgttc ccagcataaa agctggaaat gacattgcaa    5640
attgtttgag aaagtcggga agaaagtta  tccagttgag taggaaaacc tttgatacag    5700
agtatccaaa aacgaaactc acggactggg actttgtggt cactacagac atatctgaaa    5760
tgggggccaa ttttagagcc gggagagtga tagaccctag aagatgcctc aagccagtta    5820
tcctaccaga tgggccagag agagtcattt tagcaggtcc tattccagtg actccagcaa    5880
gcgctgctca gagaagaggg cgaataggaa ggaacccagc acaagaagac gaccaatacg    5940 tttctccgg  agacccacta aaaaatgatg aagatcatgc ccactggaca gaagcaaaga    6000
tgctgcttga caatatctac accccagaag ggatcattcc aacattgttt ggtccggaaa    6060
gggaaaaaac ccaagccatt gatggagagt tcgcctcag  aggggaacaa aggaagactt    6120
ttgtggaatt aatgaggaga ggagaccttc cggtgtggct gagctataag gtagcttctg    6180
ctggcatttc ttacaaagat cgggaatggt gcttcacagg ggaaagaaat aaccaaattt    6240
tagaagaaaa catggaggtt gaaatttgga ctagagaggg agaaaagaaa aagctaaggc    6300
caagatggtt agatgcacgt gtatacgctg accccatggc tttgaaggat ttcaaggagt    6360
ttgccagtgg aaggaagagt ataactctcg acatcctaac agagattgcc agtttgccaa    6420
cttacctttc ctctagggcc aagctcgccc ttgataacat agtcatgctc cacacaacag    6480
aaagaggagg gagggcctat caacacgccc tgaacgaact tccggagtca ctggaaacac    6540
tcatgcttgt agctttacta ggtgctatga cagcaggcat cttcctgttt ttcatgcaag    6600
ggaaaggaat agggaaattg tcaatgggtt tgataaccat tgcggtggct agtggcttgc    6660
tctgggtagc agaaattcaa ccccagtgga tagcggcctc aatcatacta gagttttttc    6720
tcatggtact gttgataccg gaaccagaaa aacaaaggac cccacaagac aatcaattga    6780
tctacgtcat attgaccatt ctcaccatca ttggtctaat agcagccaac gagatggggc    6840
tgattgaaaa aacaaaaacg gattttgggt tttaccaggt aaaaacagaa accaccatcc    6900
tcgatgtgga cttgagacca gcttcagcat ggacgctcta tgcagtagcc accacaattc    6960
tgactcccat gctgagacac accatagaaa acacgtcggc caacctatct ctagcagcca    7020
ttgccaacca ggcagccgtc ctaatggggc ttgaaaagg  atggccgctc cacagaatgg    7080
acctcggtgt gccgctgtta gcaatgggat gctattctca agtgaaccca acaaccttga    7140
cagcatcctt agtcatgctt ttagtccatt atgcaataat aggcccagga ttgcaggcaa    7200
aagccacaag agaggcccag aaaaggacag ctgctgggat catgaaaaat cccacagtgg    7260
acgggataac agtaatagat ctagaaccaa tatcctatga cccaaaattt gaaaagcaat    7320
tagggcaggt catgctacta gtcttgtgtg ctggacaact actcttgatg agaacaacat    7380 gggcttctg  tgaagtcttg actttggcca caggaccaat cttgaccttg tgggagggca    7440
acccgggaag gttttggaac acgaccatag ccgtatccac cgccaacatt ttcaggggaa    7500
gttacttggc gggagctgga ctggcttttt cactcataaa gaatgcacaa accctagga    7560 ggggaactgg gaccacagga gagacactgg gagagaagtg gaagagacag ctaaactcat    7620
tagacagaaa agagtttgaa gagtataaaa gaagtggaat actagaagtg gacaggactg    7680
aagccaagtc tgccctgaaa gatgggtcta aaatcaagca tgcagtatct agagggtcca    7740
gtaagatcag atggattgtt gagagaggga tggtaaagcc aaaagggaaa gttgtagatc    7800
ttggctgtgg agaggagga  tggtcttatt acatggcgac actcaagaac gtgactgaag    7860
tgaaagggta tacaaaagga ggtccaggac atgaagaacc gattcccatg gctacttatg    7920
```

```
gttggaattt ggtcaaactc cattcagggg ttgacgtgtt ctacaaaccc acagagcaag    7980
tggacaccct gctctgtgat attggggagt catcttctaa tccaacaata gaggaaggaa    8040
gaacattaag agttttgaag atggtggagc catggctctc ttcaaaacct gaattctgca    8100
tcaaagtcct taacccctac atgccaacag tcatagaaga gctggagaaa ctgcagaaa     8160 aacatggtgg gaaccttgtc agatgcccgc tgtccaggaa ctccacccat gagatgtatt    8220
gggtgtcagg agcgtcggga acattgtga gctctgtgaa cacaacatca aagatgttgt     8280
tgaacaggtt cacaacaagg cataggaaac ccacttatga aaggacgta gatcttgggg     8340 caggaacgag aagtgtctcc actgaaacag aaaaaccaga catgacaatc attgggagaa    8400
ggcttcagcg attgcaagaa gagcacaaag aaacctggca ttatgatcag gaaaacccat    8460
acagaacctg ggcgtatcat ggaagctatg aagctccttc gacaggctct gcatcctcca    8520
tggtgaacgg ggtggtaaaa ctgctaacaa accctggga tgtgattcca atggtgactc     8580
agttagccat gacagataca acccctttg ggcaacaaag agtgttcaaa gagaaggtgg     8640
ataccagaac accacaacca aaacccggta cacgaatggt tatgaccacg acagccaatt    8700
ggctgtgggc cctccttgga aagaagaaaa atcccagact gtgcacaagg gaagagttca    8760
tctcaaaagt tagatcaaac gcagccatag gcgcagtctt tcaggaagaa cagggatgga    8820
catcagccag tgaagctgtg aatgacagcc ggttttggga actggttgac aaagaaaggg    8880
ccctacacca ggaagggaaa tgtgaatcgt gtgtctataa catgatggga aaacgtgaga    8940
aaaagttagg agagtttggc agagccaagg gaagccgagc aatctggtac atgtggctgg    9000
gagcgcggtt tctggaattt gaagccctgg gttttttgaa tgaagatcac tggtttggca    9060
gagaaaattc atggagtgga gtggaagggg aaggtctgca cagattggga tatatcctgg    9120
aggagataga caagaaggat ggagacctaa tgtatgctga tgacacagca ggctgggaca    9180
caagaatcac tgaggatgac cttcaaaatg aggaactgat cacggaacag atggctcccc    9240
accacaagat cctagccaaa gccatttca aactaaccta tcaaaacaaa gtggtgaaag     9300
tcctcagacc cacaccgaga ggagcggtga tggatatcat atccaggaaa gaccaaagag    9360
gtagtggaca agttggaaca tatggtttga acacattcac caacatggaa gttcaactca    9420
tccgccaaat ggaagctgaa ggagtcatca cacaagatga catgcagaac ccaaaagggt    9480
tgaaagaaag agttgagaaa tggctgaaag agtgtggtgt cgacaggtta aagaggatgg    9540
caatcagtgg agacgattgc gtggtgaagc cctagatga gaggtttggc acttccctcc     9600
tcttcttgaa cgacatggga aaggtgagga agacattcc gcagtgggaa ccatctaagg     9660 gatgaaaaa ctggcaagag gttcctttt gctcccacca ctttcacaag atctttatga     9720
aggatggccg ctcactagtt gttccatgta gaaaccagga tgaactgata gggagagcca    9780
gaatctcgca gggagctgga tggagcttaa gagaaacagc ctgcctgggc aaagcttacg    9840
cccagatgtg gtcgcttatg tacttccaca gaagggatct gcgtttagcc tccatggcca    9900
tatgctcagc agttccaacg gaatggtttc caacaagcag aacaacatgg tcaatccacg    9960
ctcatcacca gtggatgacc actgaagata tgctcaaagt gtggaacaga gtgtggtag     10020 aagacaaccc taatatgact gacaagactc cagtccattc gtgggaagat atacttacc    10080 tagggaaag agaggatttg tggtgtggat ccctgattgg actttcttcc agagccacct     10140
gggcgaagaa cattcacacg gccataaccc aggtcaggaa cctgatcgga aaagaggaat    10200
acgtggatta catgccagta atgaaaagat acagtgctcc ttcagagagt gaaggagttc    10260
tgtaattacc aacaacaaac accaaaggct attgaagtca ggccacttgt gccacggttt    10320
```

-continued gagcaaaccg tgctgcctgt agctccgcca ataatgggag gcgtaataat ccccagggag 10380
gccatgcgcc acggaagctg tacgcgtggc atattggact agcggttaga ggagacccct 10440
cccatcactg acaaaacgca gcaaaagggg gcccgaagcc aggaggaagc tgtactcctg 10500
gtggaaggac tagaggttag aggagacccc cccaacacaa aaacagcata ttgacgctgg 10560
gaaagaccag agatcctgct gtctctgcaa catcaatcca ggcacagagc gccgcaagat 10620
ggattggtgt tgttgatcca acaggttct 10649

<210> SEQ ID NO 15
<211> LENGTH: 3387
<212> TYPE: PRT
<213> ORGANISM: Recombinant Dengue 4 virus strain rDEN4

<400> SEQUENCE: 15

Met Asn Gln Arg Lys Lys Val Val Arg Pro Pro Phe Asn Met Leu Lys
1 5 10 15

Arg Glu Arg Asn Arg Val Ser Thr Pro Gln Gly Leu Val Lys Arg Phe
20 25 30

Ser Thr Gly Leu Phe Ser Gly Lys Gly Pro Leu Arg Met Val Leu Ala
35 40 45

Phe Ile Thr Phe Leu Arg Val Leu Ser Ile Pro Pro Thr Ala Gly Ile
50 55 60

Leu Lys Arg Trp Gly Gln Leu Lys Lys Asn Lys Ala Ile Lys Ile Leu
65 70 75 80

Ile Gly Phe Arg Lys Glu Ile Gly Arg Met Leu Asn Ile Leu Asn Gly
85 90 95

Arg Lys Arg Ser Thr Ile Thr Leu Leu Cys Leu Ile Pro Thr Val Met
100 105 110

Ala Phe Ser Leu Ser Thr Arg Asp Gly Glu Pro Leu Met Ile Val Ala
115 120 125

Lys His Glu Arg Gly Arg Pro Leu Leu Phe Lys Thr Thr Glu Gly Ile
130 135 140

Asn Lys Cys Thr Leu Ile Ala Met Asp Leu Gly Glu Met Cys Glu Asp
145 150 155 160

Thr Val Thr Tyr Lys Cys Pro Leu Leu Val Asn Thr Glu Pro Glu Asp
165 170 175

Ile Asp Cys Trp Cys Asn Leu Thr Ser Thr Trp Val Met Tyr Gly Thr
180 185 190

Cys Thr Gln Ser Gly Glu Arg Arg Arg Glu Lys Arg Ser Val Ala Leu
195 200 205

Thr Pro His Ser Gly Met Gly Leu Glu Thr Arg Ala Glu Thr Trp Met
210 215 220

Ser Ser Glu Gly Ala Trp Lys His Ala Gln Arg Val Glu Ser Trp Ile
225 230 235 240

Leu Arg Asn Pro Gly Phe Ala Leu Leu Ala Gly Phe Met Ala Tyr Met
245 250 255

Ile Gly Gln Thr Gly Ile Gln Arg Thr Val Phe Phe Val Leu Met Met
260 265 270

Leu Val Ala Pro Ser Tyr Gly Met Arg Cys Val Gly Val Gly Asn Arg
275 280 285

Asp Phe Val Glu Gly Val Ser Gly Gly Ala Trp Val Asp Leu Val Leu
290 295 300

Glu His Gly Gly Cys Val Thr Thr Met Ala Gln Gly Lys Pro Thr Leu

```
               305                 310                 315                 320
Asp Phe Glu Leu Thr Lys Thr Thr Ala Lys Glu Val Ala Leu Leu Arg
                325                 330                 335
Thr Tyr Cys Ile Glu Ala Ser Ile Ser Asn Ile Thr Thr Ala Thr Arg
                340                 345                 350
Cys Pro Thr Gln Gly Glu Pro Tyr Leu Lys Glu Glu Gln Asp Gln Gln
                355                 360                 365
Tyr Ile Cys Arg Arg Asp Val Val Asp Arg Gly Trp Gly Asn Gly Cys
                370                 375                 380
Gly Leu Phe Gly Lys Gly Val Val Thr Cys Ala Lys Phe Ser Cys
385                 390                 395                 400
Ser Gly Lys Ile Thr Gly Asn Leu Val Gln Ile Glu Asn Leu Glu Tyr
                405                 410                 415
Thr Val Val Val Thr Val His Asn Gly Asp Thr His Ala Val Gly Asn
                420                 425                 430
Asp Thr Ser Asn His Gly Val Thr Ala Met Ile Thr Pro Arg Ser Pro
                435                 440                 445
Ser Val Glu Val Lys Leu Pro Asp Tyr Gly Glu Leu Thr Leu Asp Cys
                450                 455                 460
Glu Pro Arg Ser Gly Ile Asp Phe Asn Glu Met Ile Leu Met Lys Met
465                 470                 475                 480
Lys Lys Lys Thr Trp Leu Val His Lys Gln Trp Phe Leu Asp Leu Pro
                485                 490                 495
Leu Pro Trp Thr Ala Gly Ala Asp Thr Ser Glu Val His Trp Asn Tyr
                500                 505                 510
Lys Glu Arg Met Val Thr Phe Lys Val Pro His Ala Lys Arg Gln Asp
                515                 520                 525
Val Thr Val Leu Gly Ser Gln Glu Gly Ala Met His Ser Ala Leu Ala
                530                 535                 540
Gly Ala Thr Glu Val Asp Ser Gly Asp Gly Asn His Met Phe Ala Gly
545                 550                 555                 560
His Leu Lys Cys Lys Val Arg Met Glu Lys Leu Arg Ile Lys Gly Met
                565                 570                 575
Ser Tyr Thr Met Cys Ser Gly Lys Phe Ser Ile Asp Lys Glu Met Ala
                580                 585                 590
Glu Thr Gln His Gly Thr Thr Val Val Lys Val Lys Tyr Glu Gly Ala
                595                 600                 605
Gly Ala Pro Cys Lys Val Pro Ile Glu Ile Arg Asp Val Asn Lys Glu
                610                 615                 620
Lys Val Val Gly Arg Ile Ile Ser Ser Thr Pro Leu Ala Glu Asn Thr
625                 630                 635                 640
Asn Ser Val Thr Asn Ile Glu Leu Glu Pro Pro Phe Gly Asp Ser Tyr
                645                 650                 655
Ile Val Ile Gly Val Gly Asn Ser Ala Leu Thr Leu His Trp Phe Arg
                660                 665                 670
Lys Gly Ser Ser Ile Gly Lys Met Phe Glu Ser Thr Tyr Arg Gly Ala
                675                 680                 685
Lys Arg Met Ala Ile Leu Gly Glu Thr Ala Trp Asp Phe Gly Ser Val
                690                 695                 700
Gly Gly Leu Phe Thr Ser Leu Gly Lys Ala Val His Gln Val Phe Gly
705                 710                 715                 720
Ser Val Tyr Thr Thr Met Phe Gly Gly Val Ser Trp Met Ile Arg Ile
                725                 730                 735
```

-continued

Leu Ile Gly Phe Leu Val Leu Trp Ile Gly Thr Asn Ser Arg Asn Thr
        740                 745                 750

Ser Met Ala Met Thr Cys Ile Ala Val Gly Gly Ile Thr Leu Phe Leu
        755                 760                 765

Gly Phe Thr Val Gln Ala Asp Met Gly Cys Val Ala Ser Trp Ser Gly
        770                 775                 780

Lys Glu Leu Lys Cys Gly Ser Gly Ile Phe Val Val Asp Asn Val His
785                 790                 795                 800

Thr Trp Thr Glu Gln Tyr Lys Phe Gln Pro Glu Ser Pro Ala Arg Leu
                805                 810                 815

Ala Ser Ala Ile Leu Asn Ala His Lys Asp Gly Val Cys Gly Ile Arg
        820                 825                 830

Ser Thr Thr Arg Leu Glu Asn Val Met Trp Lys Gln Ile Thr Asn Glu
        835                 840                 845

Leu Asn Tyr Val Leu Trp Glu Gly Gly His Asp Leu Thr Val Val Ala
        850                 855                 860

Gly Asp Val Lys Gly Val Leu Thr Lys Gly Lys Arg Ala Leu Thr Pro
865                 870                 875                 880

Pro Val Ser Asp Leu Lys Tyr Ser Trp Lys Thr Trp Gly Lys Ala Lys
                885                 890                 895

Ile Phe Thr Pro Glu Ala Arg Asn Ser Thr Phe Leu Ile Asp Gly Pro
        900                 905                 910

Asp Thr Ser Glu Cys Pro Asn Glu Arg Arg Ala Trp Asn Ser Leu Glu
        915                 920                 925

Val Glu Asp Tyr Gly Phe Gly Met Phe Thr Thr Asn Ile Trp Met Lys
        930                 935                 940

Phe Arg Glu Gly Ser Ser Glu Val Cys Asp His Arg Leu Met Ser Ala
945                 950                 955                 960

Ala Ile Lys Asp Gln Lys Ala Val His Ala Asp Met Gly Tyr Trp Ile
                965                 970                 975

Glu Ser Ser Lys Asn Gln Thr Trp Gln Ile Glu Lys Ala Ser Leu Ile
        980                 985                 990

Glu Val Lys Thr Cys Leu Trp Pro Lys Thr His Thr Leu Trp Ser Asn
        995                 1000                1005

Gly Val Leu Glu Ser Gln Met Leu Ile Pro Lys Ser Tyr Ala Gly Pro
        1010                1015                1020

Phe Ser Gln His Asn Tyr Arg Gln Gly Tyr Ala Thr Gln Thr Val Gly
1025                1030                1035                1040

Pro Trp His Leu Gly Lys Leu Glu Ile Asp Phe Gly Glu Cys Pro Gly
                1045                1050                1055

Thr Thr Val Thr Ile Gln Glu Asp Cys Asp His Arg Gly Pro Ser Leu
        1060                1065                1070

Arg Thr Thr Thr Ala Ser Gly Lys Leu Val Thr Gln Trp Cys Cys Arg
        1075                1080                1085

Ser Cys Thr Met Pro Pro Leu Arg Phe Leu Gly Glu Asp Gly Cys Trp
        1090                1095                1100

Tyr Gly Met Glu Ile Arg Pro Leu Ser Glu Lys Glu Glu Asn Met Val
1105                1110                1115                1120

Lys Ser Gln Val Thr Ala Gly Gln Gly Thr Ser Glu Thr Phe Ser Met
                1125                1130                1135

Gly Leu Leu Cys Leu Thr Leu Phe Val Glu Glu Cys Leu Arg Arg
        1140                1145                1150

-continued

```
Val Thr Arg Lys His Met Ile Leu Val Val Ile Thr Leu Cys Ala
        1155                1160                1165
Ile Ile Leu Gly Gly Leu Thr Trp Met Asp Leu Leu Arg Ala Leu Ile
        1170                1175                1180
Met Leu Gly Asp Thr Met Ser Gly Arg Ile Gly Gly Gln Ile His Leu
1185                1190                1195                1200
Ala Ile Met Ala Val Phe Lys Met Ser Pro Gly Tyr Val Leu Gly Val
            1205                1210                1215
Phe Leu Arg Lys Leu Thr Ser Arg Glu Thr Ala Leu Met Val Ile Gly
            1220                1225                1230
Met Ala Met Thr Thr Val Leu Ser Ile Pro His Asp Leu Met Glu Leu
            1235                1240                1245
Ile Asp Gly Ile Ser Leu Gly Leu Ile Leu Lys Ile Val Thr Gln
            1250                1255                1260
Phe Asp Asn Thr Gln Val Gly Thr Leu Ala Leu Ser Leu Thr Phe Ile
1265                1270                1275                1280
Arg Ser Thr Met Pro Leu Val Met Ala Trp Arg Thr Ile Met Ala Val
            1285                1290                1295
Leu Phe Val Val Thr Leu Ile Pro Leu Cys Arg Thr Ser Cys Leu Gln
            1300                1305                1310
Lys Gln Ser His Trp Val Glu Ile Thr Ala Leu Ile Leu Gly Ala Gln
            1315                1320                1325
Ala Leu Pro Val Tyr Leu Met Thr Leu Met Lys Gly Ala Ser Arg Arg
            1330                1335                1340
Ser Trp Pro Leu Asn Glu Gly Ile Met Ala Val Gly Leu Val Ser Leu
1345                1350                1355                1360
Leu Gly Ser Ala Leu Leu Lys Asn Asp Val Pro Leu Ala Gly Pro Met
            1365                1370                1375
Val Ala Gly Gly Leu Leu Leu Ala Ala Tyr Val Met Ser Gly Ser Ser
            1380                1385                1390
Ala Asp Leu Ser Leu Glu Lys Ala Ala Asn Val Gln Trp Asp Glu Met
            1395                1400                1405
Ala Asp Ile Thr Gly Ser Ser Pro Ile Val Glu Val Lys Gln Asp Glu
        1410                1415                1420
Asp Gly Ser Phe Ser Ile Arg Asp Val Glu Glu Thr Asn Met Ile Thr
1425                1430                1435                1440
Leu Leu Val Lys Leu Ala Leu Ile Thr Val Ser Gly Leu Tyr Pro Leu
            1445                1450                1455
Ala Ile Pro Val Thr Met Thr Leu Trp Tyr Met Trp Gln Val Lys Thr
            1460                1465                1470
Gln Arg Ser Gly Ala Leu Trp Asp Val Pro Ser Pro Ala Ala Thr Lys
            1475                1480                1485
Lys Ala Ala Leu Ser Glu Gly Val Tyr Arg Ile Met Gln Arg Gly Leu
            1490                1495                1500
Phe Gly Lys Thr Gln Val Gly Val Gly Ile His Met Glu Gly Val Phe
1505                1510                1515                1520
His Thr Met Trp His Val Thr Arg Gly Ser Val Ile Cys His Glu Thr
            1525                1530                1535
Gly Arg Leu Glu Pro Ser Trp Ala Asp Val Arg Asn Asp Met Ile Ser
            1540                1545                1550
Tyr Gly Gly Gly Trp Arg Leu Gly Asp Lys Trp Asp Lys Glu Glu Asp
            1555                1560                1565
Val Gln Val Leu Ala Ile Glu Pro Gly Lys Asn Pro Lys His Val Gln
```

-continued

```
                1570            1575            1580
Thr Lys Pro Gly Leu Phe Lys Thr Leu Thr Gly Glu Ile Gly Ala Val
1585            1590            1595            1600

Thr Leu Asp Phe Lys Pro Gly Thr Ser Gly Ser Pro Ile Ile Asn Arg
                1605            1610            1615

Lys Gly Lys Val Ile Gly Leu Tyr Gly Asn Gly Val Val Thr Lys Ser
                1620            1625            1630

Gly Asp Tyr Val Ser Ala Ile Thr Gln Ala Glu Arg Ile Gly Glu Pro
                1635            1640            1645

Asp Tyr Glu Val Asp Asp Ile Phe Arg Lys Lys Arg Leu Thr Ile
1650            1655            1660

Met Asp Leu His Pro Gly Ala Gly Lys Thr Lys Arg Ile Leu Pro Ser
1665            1670            1675            1680

Ile Val Arg Glu Ala Leu Lys Arg Arg Leu Arg Thr Leu Ile Leu Ala
                1685            1690            1695

Pro Thr Arg Val Val Ala Ala Glu Met Glu Glu Ala Leu Arg Gly Leu
                1700            1705            1710

Pro Ile Arg Tyr Gln Thr Pro Ala Val Lys Ser Glu His Thr Gly Arg
                1715            1720            1725

Glu Ile Val Asp Leu Met Cys His Ala Thr Phe Thr Thr Arg Leu Leu
                1730            1735            1740

Ser Ser Thr Arg Val Pro Asn Tyr Asn Leu Ile Val Met Asp Glu Ala
1745            1750            1755            1760

His Phe Thr Asp Pro Ser Ser Val Ala Ala Arg Gly Tyr Ile Ser Thr
                1765            1770            1775

Arg Val Glu Met Gly Glu Ala Ala Ile Phe Met Thr Ala Thr Pro
                1780            1785            1790

Pro Gly Ala Thr Asp Pro Phe Pro Gln Ser Asn Ser Pro Ile Glu Asp
                1795            1800            1805

Ile Glu Arg Glu Ile Pro Glu Arg Ser Trp Asn Thr Gly Phe Asp Trp
                1810            1815            1820

Ile Thr Asp Tyr Gln Gly Lys Thr Val Trp Phe Val Pro Ser Ile Lys
1825            1830            1835            1840

Ala Gly Asn Asp Ile Ala Asn Cys Leu Arg Lys Ser Gly Lys Lys Val
                1845            1850            1855

Ile Gln Leu Ser Arg Lys Thr Phe Asp Thr Glu Tyr Pro Lys Thr Lys
                1860            1865            1870

Leu Thr Asp Trp Asp Phe Val Val Thr Thr Asp Ile Ser Glu Met Gly
                1875            1880            1885

Ala Asn Phe Arg Ala Gly Arg Val Ile Asp Pro Arg Arg Cys Leu Lys
                1890            1895            1900

Pro Val Ile Leu Pro Asp Gly Pro Glu Arg Val Ile Leu Ala Gly Pro
1905            1910            1915            1920

Ile Pro Val Thr Pro Ala Ser Ala Ala Gln Arg Arg Gly Arg Ile Gly
                1925            1930            1935

Arg Asn Pro Ala Gln Glu Asp Asp Gln Tyr Val Phe Ser Gly Asp Pro
                1940            1945            1950

Leu Lys Asn Asp Glu Asp His Ala His Trp Thr Glu Ala Lys Met Leu
                1955            1960            1965

Leu Asp Asn Ile Tyr Thr Pro Glu Gly Ile Ile Pro Thr Leu Phe Gly
                1970            1975            1980

Pro Glu Arg Glu Lys Thr Gln Ala Ile Asp Gly Glu Phe Arg Leu Arg
1985            1990            1995            2000
```

-continued

Gly Glu Gln Arg Lys Thr Phe Val Glu Leu Met Arg Arg Gly Asp Leu
                2005                2010                2015
Pro Val Trp Leu Ser Tyr Lys Val Ala Ser Ala Gly Ile Ser Tyr Glu
                2020                2025                2030
Asp Arg Glu Trp Cys Phe Thr Gly Glu Arg Asn Asn Gln Ile Leu Glu
                2035                2040            2045
Glu Asn Met Glu Val Glu Ile Trp Thr Arg Gly Glu Lys Lys Lys
            2050                2055                2060
Leu Arg Pro Arg Trp Leu Asp Ala Arg Val Tyr Ala Asp Pro Met Ala
2065                2070                2075                2080
Leu Lys Asp Phe Lys Glu Phe Ala Ser Gly Arg Lys Ser Ile Thr Leu
                2085                2090                2095
Asp Ile Leu Thr Glu Ile Ala Ser Leu Pro Thr Tyr Leu Ser Ser Arg
                2100                2105                2110
Ala Lys Leu Ala Leu Asp Asn Ile Val Met Leu His Thr Thr Glu Arg
                2115                2120                2125
Gly Gly Arg Ala Tyr Gln His Ala Leu Asn Glu Leu Pro Glu Ser Leu
                2130                2135            2140
Glu Thr Leu Met Leu Val Ala Leu Leu Gly Ala Met Thr Ala Gly Ile
2145                2150                2155                2160
Phe Leu Phe Phe Met Gln Gly Lys Gly Ile Gly Lys Leu Ser Met Gly
                2165                2170                2175
Leu Ile Thr Ile Ala Val Ala Ser Gly Leu Leu Trp Val Ala Glu Ile
                2180                2185                2190
Gln Pro Gln Trp Ile Ala Ala Ser Ile Ile Leu Glu Phe Phe Leu Met
                2195                2200                2205
Val Leu Leu Ile Pro Glu Pro Glu Lys Gln Arg Thr Pro Gln Asp Asn
                2210                2215                2220
Gln Leu Ile Tyr Val Ile Leu Thr Ile Leu Thr Ile Ile Gly Leu Ile
2225                2230                2235                2240
Ala Ala Asn Glu Met Gly Leu Ile Glu Lys Thr Lys Thr Asp Phe Gly
                2245                2250                2255
Phe Tyr Gln Val Lys Thr Glu Thr Thr Ile Leu Asp Val Asp Leu Arg
                2260                2265                2270
Pro Ala Ser Ala Trp Thr Leu Tyr Ala Val Ala Thr Thr Ile Leu Thr
                2275                2280                2285
Pro Met Leu Arg His Thr Ile Glu Asn Thr Ser Ala Asn Leu Ser Leu
                2290                2295                2300
Ala Ala Ile Ala Asn Gln Ala Ala Val Leu Met Gly Leu Gly Lys Gly
2305                2310                2315                2320
Trp Pro Leu His Arg Met Asp Leu Gly Val Pro Leu Leu Ala Met Gly
                2325                2330                2335
Cys Tyr Ser Gln Val Asn Pro Thr Thr Leu Thr Ala Ser Leu Val Met
                2340                2345                2350
Leu Leu Val His Tyr Ala Ile Ile Gly Pro Gly Leu Gln Ala Lys Ala
                2355                2360                2365
Thr Arg Glu Ala Gln Lys Arg Thr Ala Ala Gly Ile Met Lys Asn Pro
                2370                2375                2380
Thr Val Asp Gly Ile Thr Val Ile Asp Leu Glu Pro Ile Ser Tyr Asp
2385                2390                2395                2400
Pro Lys Phe Glu Lys Gln Leu Gly Gln Val Met Leu Leu Val Leu Cys
                2405                2410                2415

-continued

```
Ala Gly Gln Leu Leu Met Arg Thr Thr Trp Ala Phe Cys Glu Val
            2420                2425                2430

Leu Thr Leu Ala Thr Gly Pro Ile Leu Thr Leu Trp Glu Gly Asn Pro
        2435                2440                2445

Gly Arg Phe Trp Asn Thr Thr Ile Ala Val Ser Thr Ala Asn Ile Phe
    2450                2455                2460

Arg Gly Ser Tyr Leu Ala Gly Ala Gly Leu Ala Phe Ser Leu Ile Lys
2465                2470                2475                2480

Asn Ala Gln Thr Pro Arg Arg Gly Thr Gly Thr Thr Gly Glu Thr Leu
            2485                2490                2495

Gly Glu Lys Trp Lys Arg Gln Leu Asn Ser Leu Asp Arg Lys Glu Phe
            2500                2505                2510

Glu Glu Tyr Lys Arg Ser Gly Ile Leu Glu Val Asp Arg Thr Glu Ala
            2515                2520                2525

Lys Ser Ala Leu Lys Asp Gly Ser Lys Ile Lys His Ala Val Ser Arg
            2530                2535                2540

Gly Ser Ser Lys Ile Arg Trp Ile Val Glu Arg Gly Met Val Lys Pro
2545                2550                2555                2560

Lys Gly Lys Val Val Asp Leu Gly Cys Gly Arg Gly Gly Trp Ser Tyr
            2565                2570                2575

Tyr Met Ala Thr Leu Lys Asn Val Thr Glu Val Lys Gly Tyr Thr Lys
            2580                2585                2590

Gly Gly Pro Gly His Glu Glu Pro Ile Pro Met Ala Thr Tyr Gly Trp
            2595                2600                2605

Asn Leu Val Lys Leu His Ser Gly Val Asp Val Phe Tyr Lys Pro Thr
        2610                2615                2620

Glu Gln Val Asp Thr Leu Leu Cys Asp Ile Gly Glu Ser Ser Ser Asn
2625                2630                2635                2640

Pro Thr Ile Glu Glu Gly Arg Thr Leu Arg Val Leu Lys Met Val Glu
            2645                2650                2655

Pro Trp Leu Ser Ser Lys Pro Glu Phe Cys Ile Lys Val Leu Asn Pro
            2660                2665                2670

Tyr Met Pro Thr Val Ile Glu Glu Leu Glu Lys Leu Gln Arg Lys His
            2675                2680                2685

Gly Gly Asn Leu Val Arg Cys Pro Leu Ser Arg Asn Ser Thr His Glu
            2690                2695                2700

Met Tyr Trp Val Ser Gly Ala Ser Gly Asn Ile Val Ser Ser Val Asn
2705                2710                2715                2720

Thr Thr Ser Lys Met Leu Leu Asn Arg Phe Thr Thr Arg His Arg Lys
            2725                2730                2735

Pro Thr Tyr Glu Lys Asp Val Asp Leu Gly Ala Gly Thr Arg Ser Val
            2740                2745                2750

Ser Thr Glu Thr Glu Lys Pro Asp Met Thr Ile Ile Gly Arg Arg Leu
            2755                2760                2765

Gln Arg Leu Gln Glu Glu His Lys Glu Thr Trp His Tyr Asp Gln Glu
            2770                2775                2780

Asn Pro Tyr Arg Thr Trp Ala Tyr His Gly Ser Tyr Glu Ala Pro Ser
2785                2790                2795                2800

Thr Gly Ser Ala Ser Ser Met Val Asn Gly Val Val Lys Leu Leu Thr
            2805                2810                2815

Lys Pro Trp Asp Val Ile Pro Met Val Thr Gln Leu Ala Met Thr Asp
            2820                2825                2830

Thr Thr Pro Phe Gly Gln Gln Arg Val Phe Lys Glu Lys Val Asp Thr
```

-continued

```
               2835                2840                2845
Arg Thr Pro Gln Pro Lys Pro Gly Thr Arg Met Val Met Thr Thr Thr
           2850                2855                2860
Ala Asn Trp Leu Trp Ala Leu Leu Gly Lys Lys Lys Asn Pro Arg Leu
2865                2870                2875                2880
Cys Thr Arg Glu Glu Phe Ile Ser Lys Val Arg Ser Asn Ala Ala Ile
               2885                2890                2895
Gly Ala Val Phe Gln Glu Gln Gly Trp Thr Ser Ala Ser Glu Ala
           2900                2905                2910
Val Asn Asp Ser Arg Phe Trp Glu Leu Val Asp Lys Glu Arg Ala Leu
           2915                2920                2925
His Gln Glu Gly Lys Cys Glu Ser Cys Val Tyr Asn Met Met Gly Lys
           2930                2935                2940
Arg Glu Lys Lys Leu Gly Glu Phe Gly Arg Ala Lys Gly Ser Arg Ala
2945                2950                2955                2960
Ile Trp Tyr Met Trp Leu Gly Ala Arg Phe Leu Glu Phe Glu Ala Leu
               2965                2970                2975
Gly Phe Leu Asn Glu Asp His Trp Phe Gly Arg Glu Asn Ser Trp Ser
           2980                2985                2990
Gly Val Glu Gly Glu Gly Leu His Arg Leu Gly Tyr Ile Leu Glu Glu
           2995                3000                3005
Ile Asp Lys Lys Asp Gly Asp Leu Met Tyr Ala Asp Thr Ala Gly
           3010                3015                3020
Trp Asp Thr Arg Ile Thr Glu Asp Asp Leu Gln Asn Glu Glu Leu Ile
3025                3030                3035                3040
Thr Glu Gln Met Ala Pro His His Lys Ile Leu Ala Lys Ala Ile Phe
               3045                3050                3055
Lys Leu Thr Tyr Gln Asn Lys Val Val Lys Val Leu Arg Pro Thr Pro
           3060                3065                3070
Arg Gly Ala Val Met Asp Ile Ser Arg Lys Asp Gln Arg Gly Ser
           3075                3080                3085
Gly Gln Val Gly Thr Tyr Gly Leu Asn Thr Phe Thr Asn Met Glu Val
           3090                3095                3100
Gln Leu Ile Arg Gln Met Glu Ala Glu Gly Val Ile Thr Gln Asp Asp
3105                3110                3115                3120
Met Gln Asn Pro Lys Gly Leu Lys Glu Arg Val Glu Lys Trp Leu Lys
               3125                3130                3135
Glu Cys Gly Val Asp Arg Leu Lys Arg Met Ala Ile Ser Gly Asp Asp
           3140                3145                3150
Cys Val Val Lys Pro Leu Asp Glu Arg Phe Gly Thr Ser Leu Leu Phe
           3155                3160                3165
Leu Asn Asp Met Gly Lys Val Arg Lys Asp Ile Pro Gln Trp Glu Pro
           3170                3175                3180
Ser Lys Gly Trp Lys Asn Trp Gln Glu Val Pro Phe Cys Ser His His
3185                3190                3195                3200
Phe His Lys Ile Phe Met Lys Asp Gly Arg Ser Leu Val Val Pro Cys
               3205                3210                3215
Arg Asn Gln Asp Glu Leu Ile Gly Arg Ala Arg Ile Ser Gln Gly Ala
           3220                3225                3230
Gly Trp Ser Leu Arg Glu Thr Ala Cys Leu Gly Lys Ala Tyr Ala Gln
           3235                3240                3245
Met Trp Ser Leu Met Tyr Phe His Arg Arg Asp Leu Arg Leu Ala Ser
           3250                3255                3260
```

-continued

```
Met Ala Ile Cys Ser Ala Val Pro Thr Glu Trp Phe Pro Thr Ser Arg
3265                3270                3275                3280

Thr Thr Trp Ser Ile His Ala His His Gln Trp Met Thr Thr Glu Asp
            3285                3290                3295

Met Leu Lys Val Trp Asn Arg Val Trp Ile Glu Asp Asn Pro Asn Met
        3300                3305                3310

Thr Asp Lys Thr Pro Val His Ser Trp Glu Asp Ile Pro Tyr Leu Gly
    3315                3320                3325

Lys Arg Glu Asp Leu Trp Cys Gly Ser Leu Ile Gly Leu Ser Ser Arg
3330                3335                3340

Ala Thr Trp Ala Lys Asn Ile His Thr Ala Ile Thr Gln Val Arg Asn
3345                3350                3355                3360

Leu Ile Gly Lys Glu Glu Tyr Val Asp Tyr Met Pro Val Met Lys Arg
            3365                3370                3375

Tyr Ser Ala Pro Ser Glu Ser Glu Gly Val Leu
            3380                3385
```

<210> SEQ ID NO 16
<211> LENGTH: 10649
<212> TYPE: DNA
<213> ORGANISM: Recombinant Dengue 4 virus strain rDEN4

<400> SEQUENCE: 16

| | | | |
|---|---|---|---|
| agttgttagt ctgtgtggac cgacaaggac agttccaaat cggaagcttg cttaacacag | 60 |
| ttctaacagt ttgtttgaat agagagcaga tctctgaaa atgaaccaa cgaaaaagg | 120 |
| tggttagacc acctttcaat atgctgaaac gcgagagaaa ccgcgtatca accctcaag | 180 |
| ggttggtgaa gagattctca accggacttt tttctgggaa aggaccctta cggatggtgc | 240 |
| tagcattcat cacgtttttg cgagtccttt ccatcccacc aacagcaggg attctgaaga | 300 |
| gatggggaca gttgaagaaa ataaggcca tcaagatact gattggattc aggaaggaga | 360 |
| taggccgcat gctgaacatc ttgaacggga gaaaaggtc aacgataaca ttgctgtgct | 420 |
| tgattcccac cgtaatggcg ttttccctca gcacaagaga tggcgaaccc ctcatgatag | 480 |
| tggcaaaaca tgaagggggg agacctctct tgtttaagac aacagagggg atcaacaaat | 540 |
| gcactctcat tgccatggac ttgggtgaaa tgtgtgagga cactgtcacg tataaatgcc | 600 |
| ccctactggt caataccgaa cctgaagaca ttgattgctg gtgcaacctc acgtctacct | 660 |
| gggtcatgta tgggacatgc acccagagcg agaacggag cgagagaag cgctcagtag | 720 |
| ctttaacacc acattcagga atgggattgg aaacaagagc tgagacatgg atgtcatcgg | 780 |
| aagggcttg gaagcatgct cagagagtag agagctggat actcagaaac ccaggattcg | 840 |
| cgctcttggc aggatttatg cttatatga ttgggcaaac aggaatccag cgaactgtct | 900 |
| tctttgtcct aatgatgctg gtcgccccat cctacgaat gcgatgcgta ggagtaggaa | 960 |
| acagagactt tgtggaagga gtctcaggtg gagcatgggt cgacctggtg ctagaacatg | 1020 |
| gaggatgcgt cacaaccatg gcccagggaa aaccaacctt ggattttgaa ctgactaaga | 1080 |
| caacagccaa ggaagtggct ctgttaagaa cctattgcat tgaagcctca atatcaaaca | 1140 |
| taactacggc aacaagatgt ccaacgcaag gagagcctta tctgaaagag aacaggacc | 1200 |
| aacagtacat ttgccggaga gatgtggtag acagagggtg gggcaatggc tgtggcttgt | 1260 |
| ttggaaaagg aggagttgtg acatgtgcga gttttcatg ttcggggaag ataacaggca | 1320 |
| atttggtcca aattgagaac cttgaataca cagtggttgt aacagtccac aatggagaca | 1380 |

```
cccatgcagt aggaaatgac acatccaatc atggagttac agccatgata actcccaggt   1440
caccatcggt ggaagtcaaa ttgccggact atggagaact aacactcgat tgtgaaccca   1500
ggtctggaat tgactttaat gagatgattc tgatgaaaat gaaaagaaa acatggctcg    1560 tgcataagca atggtttttg gatctgcctc ttccatggac agcaggagca gacacatcag   1620
aggttcactg gaattacaaa gagagaatgg tgacatttaa ggttcctcat gccaagagac   1680
aggatgtgac agtgctggga tctcaggaag gagccatgca ttctgccctc gctggagcca   1740
cagaagtgga ctccggtgat ggaaatcaca tgtttgcagg acatcttaag tgcaaagtcc   1800
gtatggagaa attgagaatc aagggaatgt catacacgat gtgttcagga agttttcaa    1860 ttgacaaaga gatggcagaa acacagcatg gacaacagt ggtgaaagtc aagtatgaag    1920
gtgctggagc tccgtgtaaa gtccccatag agataagaga tgtaaacaag gaaaagtgg    1980 ttgggcgtat catctcatcc accccttTgg ctgagaatac caacagtgta accaacatag   2040
aattagaacc cccctttggg gacagctaca tagtgatagg tgttggaaac agcgcattaa    2100
cactccattg gttcaggaaa gggagttcca ttggcaagat gtttgagtcc acatacagag   2160
gtgcaaaacg aatggccatt ctaggtgaaa cagcttggga ttttggttcc gttggtggac   2220
tgttcacatc attgggaaag gctgtgcacc aggttttgg aagtgtgtat acaaccatgt    2280
ttggaggagt ctcatggatg attagaatcc taattgggtt cttagtgttg tggattggca   2340
cgaactcgag gaacacttca atggctatga cgtgcatagc tgttggagga atcactctgt   2400
ttctgggctt cacagttcaa gcagacatgg gttgtgtggc gtcatggagt gggaaagaat   2460
tgaagtgtgg aagcggaatt tttgtggttg acaacgtgca cacttggaca gaacagtaca   2520
aatttcaacc agagtcccca gcgagactag cgtctgcaat attaaatgcc cacaaagatg   2580
gggtctgtgg aattagatca accacgaggc tggaaaatgt catgtggaag caaataacca   2640
acgagctaaa ctatgttctc tgggaaggag gacatgacct cactgtagtg ctggggatg    2700 tgaagggggt gttgaccaaa ggcaagagag cactcacacc cccagtgagt gatctgaaat   2760
attcatggaa gacatgggga aaagcaaaaa tcttcacccc agaagcaaga aatagcacat   2820
ttttaataga cggaccagac acctctgaat gccccaatga cgaagagca tggaactctc     2880 ttgaggtgga agactatgga tttgcatgt tcacgaccaa catatggatg aaattccgag    2940
aaggaagttc agaagtgtgt gaccacaggt taatgtcagc tgcaattaaa gatcagaaag   3000
ctgtgcatgc tgacatgggt tattggatag agagctcaaa aaaccagacc tggcagatag   3060
agaaagcatc tcttattgaa gtgaaaacat gtctgtggcc caagacccac acactgtgga   3120 gcaatgagt gctggaaagc cagatgctca ttccaaaatc atatgcgggc cttttttcac    3180
agcacaatta ccgccagggc tatgccacgc aaaccgtggg cccatggcac ttaggcaaat   3240
tagagataga cttttggaga atgccccgaa caacagtcac aattcaggag gattgtgacc   3300
atagaggccc atctttgagg accaccactg catctgaaa actagtcacg caatggtgct    3360
gccgctcctg cacgatgcct cccttaaggt tcttgggaga agatgggtgc tggtatggga   3420
tggagattag gcccttgagt gaaaagaag agaaacatggt caaatcacag gtgacggccg    3480
gacagggcac atcagaaact ttttctatgg gtctgttgtg cctgaccttg tttgtggaag    3540
aatgcttgag gagaagagtc actaggaaac acatgatatt agttgtggtg atcactcttt    3600
gtgctatcat cctgggaggc ctcacatgga tggacttact acgagccctc atcatgttgg    3660
gggacactat gtctggtaga ataggaggac agatccacct agccatcatg gcagtgttca   3720
agatgtcacc aggatacgtg ctgggtgtgt ttttaaggaa actcacttca agagagacag   3780
```

```
cactaatggt aataggaatg gccatgacaa cggtgctttc aattccacat gaccttatgg    3840
aactcattga tggaatatca ctgggactaa ttttgctaaa aatagtaaca cagtttgaca    3900
acacccaagt gggaacctta gctctttcct tgactttcat aagatcaaca atgccattgg    3960
tcatggcttg gaggaccatt atggctgtgt tgtttgtggt cacactcatt cctttgtgca    4020
ggacaagctg tcttcaaaaa cagtctcatt gggtagaaat aacagcactc atcctaggag    4080
cccaagctct gccagtgtac ctaatgactc ttatgaaagg agcctcaaga agatcttggc    4140
ctcttaacga gggcataatg gctgtgggtt tggttagtct cttaggaagc gctcttttaa    4200
agaatgatgt cccctttagct ggcccaatgg tggcaggagg cttacttctg gcggcttacg    4260
tgatgagtgg tagctcagca gatctgtcac tagagaaggc cgccaacgtg cagtgggatg    4320
aaatggcaga cataacaggc tcaagcccaa tcgtagaagt gaagcaggat gaagatggct    4380 cttttctccat acgggacgtc gaggaaacca atatgataac ccttttggtg aaactggcac    4440
tgataacagt gtcaggtctc taccccttgg caattccagt cacaatgacc ttatggtaca    4500
tgtggcaagt gaaaacacaa agatcaggag ccctgtggga cgtcccctca cccgctgcca    4560
ctaaaaaagc cgcactgtct gaaggagtgt acaggatcat gcaaagaggg ttattcggga    4620
aaactcaggt tggagtaggg atacacatgg aaggtgtatt tcacacaatg tggcatgtaa    4680
caagaggatc agtgatctgc cacgagactg ggagattgga gccatcttgg gctgacgtca    4740
ggaatgacat gatatcatac ggtgggggat ggaggcttgg agacaaatgg gacaaagaag    4800
aagacgttca ggtcctcgcc atagaaccag gaaaaaatcc taaacatgtc caaacgaaac    4860
ctggcctttt caagacccta actggagaaa ttggagcagt aacattagat ttcaaacccg    4920
gaacgtctgg ttctcccatc atcaacagga aggaaaagt catcggactc tatggaaatg    4980
gagtagttac caaatcaggt gattacgtca gtgccataac gcaagccgaa agaattggag    5040
agccagatta tgaagtggat gaggacattt ttcgaaagaa aagattaact ataatggact    5100
tacaccccgg agctggaaag acaaaaagaa ttcttccatc aatagtgaga gaagccttaa    5160
aaaggaggct acgaactttg atttagctc ccacgagagt ggtggcggcc gagatggaag    5220
aggccctacg tggactgcca atccgttatc agaccccagc tgtgaaatca gaacacacag    5280
gaagagagat tgtagacctc atgtgtcatg caaccttcac aacaagactt ttgtcatcaa    5340
ccagggttcc aaattacaac cttatagtga tggatgaagc acatttcacc gatccttcta    5400
gtgtcgcggc tagaggatac atctcgacca gggtggaaat gggagaggca gcagccatct    5460
tcatgaccgc aaccccctccc ggagcgacag atccctttcc ccagagcaac agcccaatag    5520
aagacatcga gagggaaatt ccggaaaggt catggaacac agggttcgac tggataacag    5580
actaccaagg gaaaactgtg tggtttgttc ccagcataaa agctggaaat gacattgcaa    5640
attgtttgag aaagtcggga aagaaagtta tccagttgag taggaaaaccc tttgatacag    5700 agtatccaaa aacgaaactc acggactggg actttgtggt cactacagac atatctgaaa    5760
tgggggccaa ttttagagcc gggagagtga tagaccctag aagatgcctc aagccagtta    5820
tcctaccaga tgggccagag agagtcattt tagcaggtcc tattccagtg actccagcaa    5880
gcgctgctca gagaagaggg cgaataggaa ggaaccagc acaagaagac gaccaatacg    5940
ttttctccgg agacccacta aaaaatgatg aagatcatgc ccactggaca gaagcaaaga    6000
tgctgcttga caatatctac acccccagaag ggatcattcc aacattgttt ggtccggaaa    6060
gggaaaaaac ccaagccatt gatggagagt ttcgcctcag aggggaacaa aggaagactt    6120
```

```
ttgtggaatt aatgaggaga ggagaccttc cggtgtggct gagctataag gtagcttctg    6180
ctggcatttc ttacgaagat cgggaatggt gcttcacagg ggaaagaaat aaccaaattt    6240
tagaagaaaa catggaggtt gaaatttgga ctagagaggg agaaaagaaa aagctaaggc    6300
caagatggtt agatgcacgt gtatacgctg accccatggc tttgaaggat ttcaaggagt    6360
ttgccagtgg aaggaagagt ataactctcg acatcctaac agagattgcc agtttgccaa    6420
cttacctttc ctctagggcc aagctcgccc ttgataacat agtcatgctc cacacaacag    6480
aaagaggagg gagggcctat caacacgccc tgaacgaact tccggagtca ctggaaacac    6540
tcatgcttgt agctttacta ggtgctatga cagcaggcat cttcctgttt ttcatgcaag    6600
ggaaaggaat agggaaattg tcaatgggtt tgataaccat tgcggtggct agtggcttgc    6660
tctgggtagc agaaattcaa ccccagtgga tagcggcctc aatcatacta gagttttttc    6720
tcatggtact gttgataccg gaaccagaaa acaaaggac cccacaagac aatcaattga    6780
tctacgtcat attgaccatt ctcaccatca ttggtctaat agcagccaac agatggggc    6840 tgattgaaaa aacaaaaacg gattttgggt tttaccaggt aaaaacagaa accaccatcc    6900
tcgatgtgga cttgagacca gcttcagcat ggacgctcta tgcagtagcc accacaattc    6960
tgactcccat gctgagacac accatagaaa acacgtcggc caacctatct ctagcagcca    7020
ttgccaacca gcagccgtc ctaatggggc ttggaaaagg atggccgctc cacagaatgg    7080
acctcggtgt gccgctgtta gcaatgggat gctattctca agtgaaccca acaaccttga    7140
cagcatcctt agtcatgctt ttagtccatt atgcaataat aggcccagga ttgcaggcaa    7200
aagccacaag agaggcccag aaaaggacag ctgctgggat catgaaaaat cccacagtgg    7260
acgggataac agtaatagat ctagaaccaa tatcctatga cccaaaattt gaaaagcaat    7320
tagggcaggt catgctacta gtcttgtgtg ctggacaact actcttgatg agaacaacat    7380 gggcttctg tgaagtcttg acttggcca caggaccaat cttgaccttg tgggagggca    7440
acccgggaag gttttggaac acgaccatag ccgtatccac cgccaacatt tcagggaa    7500 gttacttggc gggagctgga ctggcttttt cactcataaa gaatgcacaa accctagga    7560 ggggaactgg gaccacagga gagacactgg gagagaagtg gagagacag ctaaactcat    7620 tagacagaaa agagtttgaa gagtataaaa gaagtggaat actagaagtg gacaggactg    7680
aagccaagtc tgccctgaaa gatgggtcta aaatcaagca tgcagtatca agagggtcca    7740
gtaagatcag atggattgtt gagagaggga tggtaaagcc aaaagggaaa gttgtagatc    7800
ttggctgtgg gagaggagga tggtcttatt acatggcgac actcaagaac gtgactgaag    7860
tgaaagggta cacaaaagga ggtccaggac atgaagaacc gattcccatg gctacttatg    7920
gttggaattt ggtcaaactc cattcagggg ttgacgtgtt ctacaaaccc acagagcaag    7980
tggacaccct gctctgtgat attggggagt catcttctaa tccaacaata gaggaaggaa    8040
gaacattaag agttttgaag atggtggagc catggctctc ttcaaaacct gaattctgca    8100
tcaaagtcct taaccctac atgccaacag tcatagaaga gctggagaaa ctgcagagaa    8160
aacatggtgg gaaccttgtc agatgccgc tgtccaggaa ctccacccat gagatgtatt    8220
gggtgtcagg agcgtcggga aacattgtga gctctgtgaa cacaacatca agatgttgt    8280 tgaacaggtt cacaacaagg cataggaaac ccacttatga aaggacgta gatcttgggg    8340 caggaacgag aagtgtctcc actgaaacag aaaaaccaga catgacaatc attgggagaa    8400
ggcttcagcg attgcaagaa gagcacaaag aaacctggca ttatgatcag gaaaacccat    8460
acagaacctg ggcgtatcat ggaagctatg aagctccttc gacaggctct gcatcctcca    8520
```

```
tggtgaacgg ggtggtaaaa ctgctaacaa accctgggc tgtgattcca atggtgactc    8580
agttagccat gacagataca accccttttg gcaacaaag agtgttcaaa gagaaggtgg    8640
ataccagaac accacaacca aaacccggta cacgaatggt tatgaccacg acagccaatt    8700
ggctgtgggc cctccttgga aagaagaaaa atcccagact gtgcacaagg aagagttca    8760
tctcaaaagt tagatcaaac gcagccatag gcgcagtctt tcaggaagaa cagggatgga    8820
catcagccag tgaagctgtg aatgacagcc ggttttggga actggttgac aaagaaaggg    8880
ccctacacca ggaagggaaa tgtgaatcgt gtgtctataa catgatggga aaacgtgaga    8940
aaaagttagg agagtttggc agagccaagg gaagccgagc aatctggtac atgtggctgg    9000
gagcgcggtt tctggaattt gaagccctgg gtttttgaa tgaagatcac tggtttggca    9060
gagaaaattc atggagtgga gtggaagggg aaggtctgca cagattggga tatatcctgg    9120
aggagataga caagaaggat ggagacctaa tgtatgctga tgacacagca ggctgggaca    9180
caagaatcac tgaggatgac cttcaaaatg aggaactgat cacggaacag atggctcccc    9240
accacaagat cctagccaaa gccattttca aactaaccta tcaaaacaaa gtggtgaaag    9300
tcctcagacc cacaccgcgg ggagcggtga tggatatcat atccaggaaa gaccaaagag    9360
gtagtggaca agttggaaca tatggtttga acacattcac caacatggaa gttcaactca    9420
tccgccaaat ggaagctgaa ggagtcatca cacaagatga catgcagaac ccaaaagggt    9480
tgaaagaaag agttgagaaa tggctgaaag gtgtggtgt cgacaggtta agaggatgg    9540
caatcagtgg agacgattgc gtggtgaagc ccctagatga gaggtttgc acttccctcc    9600
tcttcttgaa cgacatggga aaggtgagga agacattcc gcagtgggaa ccatctaagg    9660
gatgaaaaaa ctggcaagag gttccttttt gctcccacca ctttcacaag atctttatga    9720
aggatggccg ctcactagtt gttccatgta gaaaccagga tgaactgata gggagagca    9780
gaatctcgca gggagctgga tggagcttaa gagaaacagc ctgcctgggc aaagcttacg    9840
cccagatgtg gtcgcttatg tacttccaca aagggatct gcgtttagcc tccatggcca    9900
tatgctcagc agttccaacg gaatggtttc caacaagcag aacaacatgg tcaatccacg    9960
ctcatcacca gtggatgacc actgaagata tgctcaaagt gtggaacaga gtgtggatag   10020
aagcaaccc taatatgact gacaagactc cagtccattc gtgggaagat ataccttacc   10080
tagggaaaag agaggatttg tggtgtggat ccctgattgg actttcttcc agagccacct   10140
gggcgaagaa cattcatacg gccataaccc aggtcaggaa cctgatcgga aaagaggaat   10200
acgtggatta catgccagta atgaaaagat acagtgctcc ttcagagagt gaaggagttc   10260
tgtaattacc aacaacaaac accaaggct attgaagtca ggccacttgt gccacggttt   10320
gagcaaaccg tgctgcctgt agctccgcca ataatgggag gcgtaataat ccccagggag   10380
gccatgcgcc acgaagctg tacgcgtggc atattggact agcggttaga ggagacccct   10440
cccatcactg ataaaacgca gcaaaggggg cccgaagcc aggaggaagc tgtactcctg   10500
gtggaaggac tagaggttag aggagacccc cccaacacaa aaacagcata ttgacgctgg   10560
gaaagaccag agatcctgct gtctctgcaa catcaatcca ggcacagagc gccgcaagat   10620
ggattggtgt tgttgatcca acaggttct                                   10649
```

<210> SEQ ID NO 17
<211> LENGTH: 3388
<212> TYPE: PRT
<213> ORGANISM: Recombinant Dengue rDEN2/4d30

```
<400> SEQUENCE: 17

Met Asn Asn Gln Arg Lys Lys Ala Arg Asn Thr Pro Phe Asn Met Leu
 1               5                  10                  15

Lys Arg Glu Arg Asn Arg Val Ser Thr Val Gln Gln Leu Thr Lys Arg
            20                  25                  30

Phe Ser Leu Gly Met Leu Gln Gly Arg Gly Pro Leu Lys Leu Phe Met
        35                  40                  45

Ala Leu Val Ala Phe Leu Arg Phe Leu Thr Ile Pro Pro Thr Ala Gly
    50                  55                  60

Ile Leu Lys Arg Trp Gly Thr Ile Lys Ser Lys Ala Ile Asn Val
65                  70                  75                  80

Leu Arg Gly Phe Arg Lys Glu Ile Gly Arg Met Leu Asn Ile Leu Asn
                85                  90                  95

Arg Arg Arg Arg Thr Ala Gly Met Ile Ile Met Leu Ile Pro Thr Val
            100                 105                 110

Met Ala Phe His Leu Thr Thr Arg Asn Gly Glu Pro His Met Ile Val
        115                 120                 125

Ser Arg Gln Glu Lys Gly Lys Ser Leu Leu Phe Lys Thr Glu Asp Gly
    130                 135                 140

Val Asn Met Cys Thr Leu Met Ala Met Asp Leu Gly Glu Leu Cys Glu
145                 150                 155                 160

Asp Thr Ile Thr Tyr Lys Cys Pro Leu Leu Arg Gln Asn Glu Pro Glu
                165                 170                 175

Asp Ile Asp Cys Trp Cys Asn Ser Thr Ser Thr Trp Val Thr Tyr Gly
            180                 185                 190

Thr Cys Thr Thr Thr Gly Glu His Arg Arg Glu Lys Arg Ser Val Ala
        195                 200                 205

Leu Val Pro His Val Gly Met Gly Leu Glu Thr Arg Thr Glu Thr Trp
    210                 215                 220

Met Ser Ser Glu Gly Ala Trp Lys His Ala Gln Arg Ile Glu Thr Trp
225                 230                 235                 240

Ile Leu Arg His Pro Gly Phe Thr Ile Met Ala Ala Ile Leu Ala Tyr
                245                 250                 255

Thr Ile Gly Thr Thr His Phe Gln Arg Ala Leu Ile Phe Ile Leu Leu
            260                 265                 270

Thr Ala Val Ala Pro Ser Met Thr Met Arg Cys Ile Gly Ile Ser Asn
        275                 280                 285

Arg Asp Phe Val Glu Gly Val Ser Gly Gly Ser Trp Val Asp Ile Val
    290                 295                 300

Leu Glu His Gly Ser Cys Val Thr Thr Met Ala Lys Asn Lys Pro Thr
305                 310                 315                 320

Leu Asp Phe Glu Leu Ile Lys Thr Glu Ala Lys Gln Pro Ala Thr Leu
                325                 330                 335

Arg Lys Tyr Cys Ile Glu Ala Lys Leu Thr Asn Thr Thr Thr Glu Ser
            340                 345                 350

Arg Cys Pro Thr Gln Gly Glu Pro Ser Leu Asn Glu Glu Gln Asp Lys
        355                 360                 365

Arg Phe Val Cys Lys His Ser Met Val Asp Arg Gly Trp Gly Asn Gly
    370                 375                 380

Cys Gly Leu Phe Gly Lys Gly Gly Ile Val Thr Cys Ala Met Phe Thr
385                 390                 395                 400

Cys Lys Lys Asn Met Glu Gly Lys Val Val Gln Pro Glu Asn Leu Glu
                405                 410                 415
```

```
Tyr Thr Ile Val Ile Thr Pro His Ser Gly Glu Glu His Ala Val Gly
            420                 425                 430

Asn Asp Thr Gly Lys His Gly Lys Glu Ile Lys Ile Thr Pro Gln Ser
        435                 440                 445

Ser Ile Thr Glu Ala Glu Leu Thr Gly Tyr Gly Thr Val Thr Met Glu
    450                 455                 460

Cys Ser Pro Arg Thr Gly Leu Asp Phe Asn Glu Met Val Leu Leu Gln
465                 470                 475                 480

Met Glu Asn Lys Ala Trp Leu Val His Arg Gln Trp Phe Leu Asp Leu
                485                 490                 495

Pro Leu Pro Trp Leu Pro Gly Ala Asp Thr Gln Gly Ser Asn Trp Ile
            500                 505                 510

Gln Lys Glu Thr Leu Val Thr Phe Lys Asn Pro His Ala Lys Lys Gln
        515                 520                 525

Asp Val Val Leu Gly Ser Gln Glu Gly Ala Met His Thr Ala Leu
    530                 535                 540

Thr Gly Ala Thr Glu Ile Gln Met Ser Ser Gly Asn Leu Leu Phe Thr
545                 550                 555                 560

Gly His Leu Lys Cys Arg Leu Arg Met Asp Lys Leu Gln Leu Lys Gly
                565                 570                 575

Met Ser Tyr Ser Met Cys Thr Gly Lys Phe Lys Val Val Lys Glu Ile
            580                 585                 590

Ala Glu Thr Gln His Gly Thr Ile Val Ile Arg Val Gln Tyr Glu Gly
        595                 600                 605

Asp Gly Ser Pro Cys Lys Ile Pro Phe Glu Ile Met Asp Leu Glu Lys
    610                 615                 620

Arg His Val Leu Gly Arg Leu Ile Thr Val Asn Pro Ile Val Thr Glu
625                 630                 635                 640

Lys Asp Ser Pro Val Asn Ile Glu Ala Glu Pro Pro Phe Gly Asp Ser
                645                 650                 655

Tyr Ile Ile Ile Gly Val Glu Pro Gly Gln Leu Lys Leu Asn Trp Phe
            660                 665                 670

Lys Lys Gly Ser Ser Ile Gly Gln Met Phe Glu Thr Thr Met Arg Gly
        675                 680                 685

Ala Lys Arg Met Ala Ile Leu Gly Asp Thr Ala Trp Asp Phe Gly Ser
    690                 695                 700

Leu Gly Gly Val Phe Thr Ser Ile Gly Lys Ala Leu His Gln Val Phe
705                 710                 715                 720

Gly Ala Ile Tyr Gly Ala Ala Phe Ser Gly Val Ser Trp Thr Met Lys
                725                 730                 735

Ile Leu Ile Gly Val Ile Ile Thr Trp Ile Gly Met Asn Ser Arg Asn
            740                 745                 750

Thr Ser Met Ala Met Thr Cys Ile Ala Val Gly Ile Thr Leu Phe
        755                 760                 765

Leu Gly Phe Thr Val Gln Ala Asp Met Gly Cys Val Ala Ser Trp Ser
770                 775                 780

Gly Lys Glu Leu Lys Cys Gly Ser Gly Ile Phe Val Val Asp Asn Val
785                 790                 795                 800

His Thr Trp Thr Glu Gln Tyr Lys Phe Gln Pro Glu Ser Pro Ala Arg
                805                 810                 815

Leu Ala Ser Ala Ile Leu Asn Ala His Lys Asp Gly Val Cys Gly Ile
            820                 825                 830
```

-continued

Arg Ser Thr Thr Arg Leu Glu Asn Val Met Trp Lys Gln Ile Thr Asn
    835                 840                 845

Glu Leu Asn Tyr Val Leu Trp Glu Gly Gly His Asp Leu Thr Val Val
    850                 855                 860

Ala Gly Asp Val Lys Gly Val Leu Thr Lys Gly Lys Arg Ala Leu Thr
865                 870                 875                 880

Pro Pro Val Ser Asp Leu Lys Tyr Ser Trp Lys Thr Trp Gly Lys Ala
            885                 890                 895

Lys Ile Phe Thr Pro Glu Ala Arg Asn Ser Thr Phe Leu Ile Asp Gly
                900                 905                 910

Pro Asp Thr Ser Glu Cys Pro Asn Glu Arg Arg Ala Trp Asn Ser Leu
            915                 920                 925

Glu Val Glu Asp Tyr Gly Phe Gly Met Phe Thr Thr Asn Ile Trp Met
    930                 935                 940

Lys Phe Arg Glu Gly Ser Ser Glu Val Cys Asp His Arg Leu Met Ser
945                 950                 955                 960

Ala Ala Ile Lys Asp Gln Lys Ala Val His Ala Asp Met Gly Tyr Trp
                965                 970                 975

Ile Glu Ser Ser Lys Asn Gln Thr Trp Gln Ile Glu Lys Ala Ser Leu
            980                 985                 990

Ile Glu Val Lys Thr Cys Leu Trp Pro Lys Thr His Thr Leu Trp Ser
            995                 1000                1005

Asn Gly Val Leu Glu Ser Gln Met Leu Ile Pro Lys Ser Tyr Ala Gly
    1010                1015                1020

Pro Phe Ser Gln His Asn Tyr Arg Gln Gly Tyr Ala Thr Gln Thr Val
1025                1030                1035                1040

Gly Pro Trp His Leu Gly Lys Leu Glu Ile Asp Phe Gly Glu Cys Pro
            1045                1050                1055

Gly Thr Thr Val Thr Ile Gln Glu Asp Cys Asp His Arg Gly Pro Ser
            1060                1065                1070

Leu Arg Thr Thr Thr Ala Ser Gly Lys Leu Val Thr Gln Trp Cys Cys
    1075                1080                1085

Arg Ser Cys Thr Met Pro Pro Leu Arg Phe Leu Gly Glu Asp Gly Cys
    1090                1095                1100

Trp Tyr Gly Met Glu Ile Arg Pro Leu Ser Glu Lys Glu Glu Asn Met
1105                1110                1115                1120

Val Lys Ser Gln Val Thr Ala Gly Gln Gly Thr Ser Glu Thr Phe Ser
            1125                1130                1135

Met Gly Leu Leu Cys Leu Thr Leu Phe Val Glu Glu Cys Leu Arg Arg
                1140                1145                1150

Arg Val Thr Arg Lys His Met Ile Leu Val Val Val Ile Thr Leu Cys
            1155                1160                1165

Ala Ile Ile Leu Gly Gly Leu Thr Trp Met Asp Leu Leu Arg Ala Leu
    1170                1175                1180

Ile Met Leu Gly Asp Thr Met Ser Gly Arg Ile Gly Gly Gln Ile His
1185                1190                1195                1200

Leu Ala Ile Met Ala Val Phe Lys Met Ser Pro Gly Tyr Val Leu Gly
                1205                1210                1215

Val Phe Leu Arg Lys Leu Thr Ser Arg Glu Thr Ala Leu Met Val Ile
            1220                1225                1230

Gly Met Ala Met Thr Thr Val Leu Ser Ile Pro His Asp Leu Met Glu
    1235                1240                1245

Leu Ile Asp Gly Ile Ser Leu Gly Leu Ile Leu Leu Lys Ile Val Thr

-continued

```
            1250                1255                1260
Gln Phe Asp Asn Thr Gln Val Gly Thr Leu Ala Leu Ser Leu Thr Phe
1265                1270                1275                1280

Ile Arg Ser Thr Met Pro Leu Val Met Ala Trp Arg Thr Ile Met Ala
                1285                1290                1295

Val Leu Phe Val Val Thr Leu Ile Pro Leu Cys Arg Thr Ser Cys Leu
            1300                1305                1310

Gln Lys Gln Ser His Trp Val Glu Ile Thr Ala Leu Ile Leu Gly Ala
                1315                1320                1325

Gln Ala Leu Pro Val Tyr Leu Met Thr Leu Met Lys Gly Ala Ser Arg
            1330                1335                1340

Arg Ser Trp Pro Leu Asn Glu Gly Ile Met Ala Val Gly Leu Val Ser
1345                1350                1355                1360

Leu Leu Gly Ser Ala Leu Leu Lys Asn Asp Val Pro Leu Ala Gly Pro
                1365                1370                1375

Met Val Ala Gly Gly Leu Leu Leu Ala Ala Tyr Val Met Ser Gly Ser
            1380                1385                1390

Ser Ala Asp Leu Ser Leu Glu Lys Ala Ala Asn Val Gln Trp Asp Glu
            1395                1400                1405

Met Ala Asp Ile Thr Gly Ser Ser Pro Ile Val Glu Val Lys Gln Asp
1410                1415                1420

Glu Asp Gly Ser Phe Ser Ile Arg Asp Val Glu Glu Thr Asn Met Ile
1425                1430                1435                1440

Thr Leu Leu Val Lys Leu Ala Leu Ile Thr Val Ser Gly Leu Tyr Pro
                1445                1450                1455

Leu Ala Ile Pro Val Thr Met Thr Leu Trp Tyr Met Trp Gln Val Lys
                1460                1465                1470

Thr Gln Arg Ser Gly Ala Leu Trp Asp Val Pro Ser Pro Ala Ala Thr
            1475                1480                1485

Lys Lys Ala Ala Leu Ser Glu Gly Val Tyr Arg Ile Met Gln Arg Gly
            1490                1495                1500

Leu Phe Gly Lys Thr Gln Val Gly Val Gly Ile His Met Glu Gly Val
1505                1510                1515                1520

Phe His Thr Met Trp His Val Thr Arg Gly Ser Val Ile Cys His Glu
                1525                1530                1535

Thr Gly Arg Leu Glu Pro Ser Trp Ala Asp Val Arg Asn Asp Met Ile
                1540                1545                1550

Ser Tyr Gly Gly Gly Trp Arg Leu Gly Asp Lys Trp Asp Lys Glu Glu
            1555                1560                1565

Asp Val Gln Val Leu Ala Ile Glu Pro Gly Lys Asn Pro Lys His Val
            1570                1575                1580

Gln Thr Lys Pro Gly Leu Phe Lys Thr Leu Thr Gly Glu Ile Gly Ala
1585                1590                1595                1600

Val Thr Leu Asp Phe Lys Pro Gly Thr Ser Gly Ser Pro Ile Ile Asn
                1605                1610                1615

Arg Lys Gly Lys Val Ile Gly Leu Tyr Gly Asn Gly Val Val Thr Lys
                1620                1625                1630

Ser Gly Asp Tyr Val Ser Ala Ile Thr Gln Ala Glu Arg Ile Gly Glu
            1635                1640                1645

Pro Asp Tyr Glu Val Asp Glu Asp Ile Phe Arg Lys Arg Leu Thr
            1650                1655                1660

Ile Met Asp Leu His Pro Gly Ala Gly Lys Thr Lys Arg Ile Leu Pro
1665                1670                1675                1680
```

```
Ser Ile Val Arg Glu Ala Leu Lys Arg Arg Leu Arg Thr Leu Ile Leu
            1685                1690                1695

Ala Pro Thr Arg Val Ala Ala Glu Met Glu Glu Ala Leu Arg Gly
            1700                1705                1710

Leu Pro Ile Arg Tyr Gln Thr Pro Ala Val Lys Ser Glu His Thr Gly
            1715                1720                1725

Arg Glu Ile Val Asp Leu Met Cys His Ala Thr Phe Thr Thr Arg Leu
            1730                1735                1740

Leu Ser Ser Thr Arg Val Pro Asn Tyr Asn Leu Ile Val Met Asp Glu
1745                1750                1755                1760

Ala His Phe Thr Asp Pro Ser Ser Val Ala Ala Arg Gly Tyr Ile Ser
            1765                1770                1775

Thr Arg Val Glu Met Gly Glu Ala Ala Ile Phe Met Thr Ala Thr
            1780                1785                1790

Pro Pro Gly Ala Thr Asp Pro Phe Pro Gln Ser Asn Ser Pro Ile Glu
            1795                1800                1805

Asp Ile Glu Arg Glu Ile Pro Glu Arg Ser Trp Asn Thr Gly Phe Asp
            1810                1815                1820

Trp Ile Thr Asp Tyr Gln Gly Lys Thr Val Trp Phe Val Pro Ser Ile
1825                1830                1835                1840

Lys Ala Gly Asn Asp Ile Ala Asn Cys Leu Arg Lys Ser Gly Lys Lys
            1845                1850                1855

Val Ile Gln Leu Ser Arg Lys Thr Phe Asp Thr Glu Tyr Pro Lys Thr
            1860                1865                1870

Lys Leu Thr Asp Trp Asp Phe Val Val Thr Thr Asp Ile Ser Glu Met
            1875                1880                1885

Gly Ala Asn Phe Arg Ala Gly Arg Val Ile Asp Pro Arg Arg Cys Leu
            1890                1895                1900

Lys Pro Val Ile Leu Pro Asp Gly Pro Glu Arg Val Ile Leu Ala Gly
1905                1910                1915                1920

Pro Ile Pro Val Thr Pro Ala Ser Ala Ala Gln Arg Arg Gly Arg Ile
            1925                1930                1935

Gly Arg Asn Pro Ala Gln Glu Asp Asp Gln Tyr Val Phe Ser Gly Asp
            1940                1945                1950

Pro Leu Lys Asn Asp Glu Asp His Ala His Trp Thr Glu Ala Lys Met
            1955                1960                1965

Leu Leu Asp Asn Ile Tyr Thr Pro Glu Gly Ile Ile Pro Thr Leu Phe
            1970                1975                1980

Gly Pro Glu Arg Glu Lys Thr Gln Ala Ile Asp Gly Glu Phe Arg Leu
1985                1990                1995                2000

Arg Gly Glu Gln Arg Lys Thr Phe Val Glu Leu Met Arg Arg Gly Asp
            2005                2010                2015

Leu Pro Val Trp Leu Ser Tyr Lys Val Ala Ser Ala Gly Ile Ser Tyr
            2020                2025                2030

Glu Asp Arg Glu Trp Cys Phe Thr Gly Glu Arg Asn Asn Gln Ile Leu
            2035                2040                2045

Glu Glu Asn Met Glu Val Glu Ile Trp Thr Arg Glu Gly Glu Lys Lys
            2050                2055                2060

Lys Leu Arg Pro Arg Trp Leu Asp Ala Arg Val Tyr Ala Asp Pro Met
2065                2070                2075                2080

Ala Leu Lys Asp Phe Lys Glu Phe Ala Ser Gly Arg Lys Ser Ile Thr
            2085                2090                2095
```

```
Leu Asp Ile Leu Thr Glu Ile Ala Ser Leu Pro Thr Tyr Leu Ser Ser
        2100                2105                2110

Arg Ala Lys Leu Ala Leu Asp Asn Ile Val Met Leu His Thr Thr Glu
        2115                2120                2125

Arg Gly Gly Arg Ala Tyr Gln His Ala Leu Asn Glu Leu Pro Glu Ser
        2130                2135                2140

Leu Glu Thr Leu Met Leu Val Ala Leu Leu Gly Ala Met Thr Ala Gly
2145                2150                2155                2160

Ile Phe Leu Phe Phe Met Gln Gly Lys Gly Ile Gly Lys Leu Ser Met
            2165                2170                2175

Gly Leu Ile Thr Ile Ala Val Ala Ser Gly Leu Leu Trp Val Ala Glu
        2180                2185                2190

Ile Gln Pro Gln Trp Ile Ala Ala Ser Ile Ile Leu Glu Phe Phe Leu
        2195                2200                2205

Met Val Leu Leu Ile Pro Glu Pro Glu Lys Gln Arg Thr Pro Gln Asp
        2210                2215                2220

Asn Gln Leu Ile Tyr Val Ile Leu Thr Ile Leu Thr Ile Ile Gly Leu
2225                2230                2235                2240

Ile Ala Ala Asn Glu Met Gly Leu Ile Glu Lys Thr Lys Thr Asp Phe
            2245                2250                2255

Gly Phe Tyr Gln Val Lys Thr Glu Thr Thr Ile Leu Asp Val Asp Leu
        2260                2265                2270

Arg Pro Ala Ser Ala Trp Thr Leu Tyr Ala Val Ala Thr Thr Ile Leu
        2275                2280                2285

Thr Pro Met Leu Arg His Thr Ile Glu Asn Thr Ser Ala Asn Leu Ser
        2290                2295                2300

Leu Ala Ala Ile Ala Asn Gln Ala Ala Val Leu Met Gly Leu Gly Lys
2305                2310                2315                2320

Gly Trp Pro Leu His Arg Met Asp Leu Gly Val Pro Leu Leu Ala Met
            2325                2330                2335

Gly Cys Tyr Ser Gln Val Asn Pro Thr Thr Leu Thr Ala Ser Leu Val
            2340                2345                2350

Met Leu Leu Val His Tyr Ala Ile Ile Gly Pro Gly Leu Gln Ala Lys
            2355                2360                2365

Ala Thr Arg Glu Ala Gln Lys Arg Thr Ala Ala Gly Ile Met Lys Asn
        2370                2375                2380

Pro Thr Val Asp Gly Ile Thr Val Ile Asp Leu Glu Pro Ile Ser Tyr
2385                2390                2395                2400

Asp Pro Lys Phe Glu Lys Gln Leu Gly Gln Val Met Leu Leu Val Leu
            2405                2410                2415

Cys Ala Gly Gln Leu Leu Leu Met Arg Thr Thr Trp Ala Phe Cys Glu
            2420                2425                2430

Val Leu Thr Leu Ala Thr Gly Pro Ile Leu Thr Leu Trp Glu Gly Asn
            2435                2440                2445

Pro Gly Arg Phe Trp Asn Thr Thr Ile Ala Val Ser Thr Ala Asn Ile
        2450                2455                2460

Phe Arg Gly Ser Tyr Leu Ala Gly Ala Gly Leu Ala Phe Ser Leu Ile
2465                2470                2475                2480

Lys Asn Ala Gln Thr Pro Arg Arg Gly Thr Gly Thr Gly Glu Thr
            2485                2490                2495

Leu Gly Glu Lys Trp Lys Arg Gln Leu Asn Ser Leu Asp Arg Lys Glu
        2500                2505                2510

Phe Glu Glu Tyr Lys Arg Ser Gly Ile Leu Glu Val Asp Arg Thr Glu
```

-continued

```
            2515                2520                2525
Ala Lys Ser Ala Leu Lys Asp Gly Ser Lys Ile Lys His Ala Val Ser
        2530                2535                2540
Arg Gly Ser Ser Lys Ile Arg Trp Ile Val Glu Arg Gly Met Val Lys
2545                2550                2555                2560
Pro Lys Gly Lys Val Val Asp Leu Gly Cys Gly Arg Gly Gly Trp Ser
            2565                2570                2575
Tyr Tyr Met Ala Thr Leu Lys Asn Val Thr Glu Val Lys Gly Tyr Thr
        2580                2585                2590
Lys Gly Gly Pro Gly His Glu Glu Pro Ile Pro Met Ala Thr Tyr Gly
        2595                2600                2605
Trp Asn Leu Val Lys Leu His Ser Gly Val Asp Val Phe Tyr Lys Pro
        2610                2615                2620
Thr Glu Gln Val Asp Thr Leu Leu Cys Asp Ile Gly Glu Ser Ser Ser
2625                2630                2635                2640
Asn Pro Thr Ile Glu Glu Gly Arg Thr Leu Arg Val Leu Lys Met Val
            2645                2650                2655
Glu Pro Trp Leu Ser Ser Lys Pro Glu Phe Cys Ile Lys Val Leu Asn
            2660                2665                2670
Pro Tyr Met Pro Thr Val Ile Glu Glu Leu Glu Lys Leu Gln Arg Lys
        2675                2680                2685
His Gly Gly Asn Leu Val Arg Cys Pro Leu Ser Arg Asn Ser Thr His
        2690                2695                2700
Glu Met Tyr Trp Val Ser Gly Ala Ser Gly Asn Ile Val Ser Ser Val
2705                2710                2715                2720
Asn Thr Thr Ser Lys Met Leu Leu Asn Arg Phe Thr Thr Arg His Arg
            2725                2730                2735
Lys Pro Thr Tyr Glu Lys Asp Val Asp Leu Gly Ala Gly Thr Arg Ser
            2740                2745                2750
Val Ser Thr Glu Thr Glu Lys Pro Asp Met Thr Ile Ile Gly Arg Arg
        2755                2760                2765
Leu Gln Arg Leu Gln Glu Glu His Lys Glu Thr Trp His Tyr Asp Gln
        2770                2775                2780
Glu Asn Pro Tyr Arg Thr Trp Ala Tyr His Gly Ser Tyr Glu Ala Pro
2785                2790                2795                2800
Ser Thr Gly Ser Ala Ser Ser Met Val Asn Gly Val Val Lys Leu Leu
            2805                2810                2815
Thr Lys Pro Trp Asp Val Ile Pro Met Val Thr Gln Leu Ala Met Thr
            2820                2825                2830
Asp Thr Thr Pro Phe Gly Gln Gln Arg Val Phe Lys Glu Lys Val Asp
        2835                2840                2845
Thr Arg Thr Pro Gln Pro Lys Pro Gly Thr Arg Met Val Met Thr Thr
        2850                2855                2860
Thr Ala Asn Trp Leu Trp Ala Leu Leu Gly Lys Lys Lys Asn Pro Arg
2865                2870                2875                2880
Leu Cys Thr Arg Glu Glu Phe Ile Ser Lys Val Arg Ser Asn Ala Ala
            2885                2890                2895
Ile Gly Ala Val Phe Gln Glu Glu Gln Gly Trp Thr Ser Ala Ser Glu
            2900                2905                2910
Ala Val Asn Asp Ser Arg Phe Trp Glu Leu Val Asp Lys Glu Arg Ala
        2915                2920                2925
Leu His Gln Glu Gly Lys Cys Glu Ser Cys Val Tyr Asn Met Met Gly
        2930                2935                2940
```

```
Lys Arg Glu Lys Lys Leu Gly Glu Phe Gly Arg Ala Lys Gly Ser Arg
2945                2950                2955                2960

Ala Ile Trp Tyr Met Trp Leu Gly Ala Arg Phe Leu Glu Phe Glu Ala
                2965                2970                2975

Leu Gly Phe Leu Asn Glu Asp His Trp Phe Gly Arg Glu Asn Ser Trp
            2980                2985                2990

Ser Gly Val Glu Gly Gly Leu His Arg Leu Gly Tyr Ile Leu Glu
        2995                3000                3005

Glu Ile Asp Lys Lys Asp Gly Asp Leu Met Tyr Ala Asp Asp Thr Ala
    3010                3015                3020

Gly Trp Asp Thr Arg Ile Thr Glu Asp Leu Gln Asn Glu Glu Leu
3025                3030                3035                3040

Ile Thr Glu Gln Met Ala Pro His His Lys Ile Leu Ala Lys Ala Ile
                3045                3050                3055

Phe Lys Leu Thr Tyr Gln Asn Lys Val Val Lys Val Leu Arg Pro Thr
            3060                3065                3070

Pro Arg Gly Ala Val Met Asp Ile Ile Ser Arg Lys Asp Gln Arg Gly
        3075                3080                3085

Ser Gly Gln Val Gly Thr Tyr Gly Leu Asn Thr Phe Thr Asn Met Glu
    3090                3095                3100

Val Gln Leu Ile Arg Gln Met Glu Ala Glu Gly Val Ile Thr Gln Asp
3105                3110                3115                3120

Asp Met Gln Asn Pro Lys Gly Leu Lys Glu Arg Val Glu Lys Trp Leu
                3125                3130                3135

Lys Glu Cys Gly Val Asp Arg Leu Lys Arg Met Ala Ile Ser Gly Asp
            3140                3145                3150

Asp Cys Val Val Lys Pro Leu Asp Glu Arg Phe Gly Thr Ser Leu Leu
        3155                3160                3165

Phe Leu Asn Asp Met Gly Lys Val Arg Lys Asp Ile Pro Gln Trp Glu
    3170                3175                3180

Pro Ser Lys Gly Trp Lys Asn Trp Gln Glu Val Pro Phe Cys Ser His
3185                3190                3195                3200

His Phe His Lys Ile Phe Met Lys Asp Gly Arg Ser Leu Val Val Pro
                3205                3210                3215

Cys Arg Asn Gln Asp Glu Leu Ile Gly Arg Ala Arg Ile Ser Gln Gly
            3220                3225                3230

Ala Gly Trp Ser Leu Arg Glu Thr Ala Cys Leu Gly Lys Ala Tyr Ala
        3235                3240                3245

Gln Met Trp Ser Leu Met Tyr Phe His Arg Arg Asp Leu Arg Leu Ala
    3250                3255                3260

Ser Met Ala Ile Cys Ser Ala Val Pro Thr Glu Trp Phe Pro Thr Ser
3265                3270                3275                3280

Arg Thr Thr Trp Ser Ile His Ala His His Gln Trp Met Thr Thr Glu
                3285                3290                3295

Asp Met Leu Lys Val Trp Asn Arg Val Trp Ile Glu Asp Asn Pro Asn
            3300                3305                3310

Met Thr Asp Lys Thr Pro Val His Ser Trp Glu Asp Ile Pro Tyr Leu
        3315                3320                3325

Gly Lys Arg Glu Asp Leu Trp Cys Gly Ser Leu Ile Gly Leu Ser Ser
    3330                3335                3340

Arg Ala Thr Trp Ala Lys Asn Ile His Thr Ala Ile Thr Gln Val Arg
3345                3350                3355                3360
```

Asn Leu Ile Gly Lys Glu Glu Tyr Val Asp Tyr Met Pro Val Met Lys
              3365                3370                3375

Arg Tyr Ser Ala Pro Ser Glu Ser Glu Gly Val Leu
              3380                3385

<210> SEQ ID NO 18
<211> LENGTH: 10616
<212> TYPE: DNA
<213> ORGANISM: Recombinant dengue virus rDEN2/4d30

<400> SEQUENCE: 18

| | | | | |
|---|---|---|---|---|
| agttgttagt | ctgtgtggac | cgacaaggac | agttccaaat | cggaagcttg | cttaacacag | 60 |
| ttctaacagt | ttgtttgaat | agagagcaga | tctctgatga | ataaccaacg | aaaaaaggcg | 120 |
| agaaatacgc | ctttcaatat | gctgaaacgc | gagagaaacc | gcgtgtcgac | tgtacaacag | 180 |
| ctgacaaaga | gattctcact | tggaatgctg | cagggacgag | gaccattaaa | actgttcatg | 240 |
| gccctggtgg | cgttccttcg | tttcctaaca | atcccaccaa | cagcagggat | actgaagaga | 300 |
| tggggaacaa | ttaaaaaatc | aaaagccatt | aatgttttga | gagggttcag | gaaagagatt | 360 |
| ggaaggatgc | tgaacatctt | gaacaggaga | cgcagaactg | caggcatgat | cattatgctg | 420 |
| attccaacag | tgatggcgtt | ccatttaacc | acacgtaacg | gagaaccaca | catgatcgtc | 480 |
| agtagacaag | agaaagggaa | agtcttctg | tttaaaacag | aggatggtgt | gaacatgtgt | 540 |
| accctcatgg | ccatggacct | tggtgaattg | tgtgaagata | caatcacgta | caagtgtcct | 600 |
| cttctcaggc | agaatgaacc | agaagacata | gattgttggt | gcaactctac | gtccacatgg | 660 |
| gtaacttatg | ggacgtgtac | caccacagga | gaacacagaa | gagaaaaaag | atcagtggca | 720 |
| ctcgttccac | atgtgggaat | gggactggag | acacgaactg | aaacatggat | gtcatcagaa | 780 |
| ggggcctgga | acatgcccca | gagaattgaa | acttggatct | tgagacatcc | aggctttacc | 840 |
| ataatggcag | caatcctggc | atacaccata | ggaacgacac | atttccaaag | agccctgatt | 900 |
| ttcatcttac | tgacagctgt | cgctccttca | atgacaatgc | gttgcatagg | aatatcaaat | 960 |
| agagactttg | tagaaggggt | ttcaggagga | agctgggttg | acatagtctt | agaacatgga | 1020 |
| agctgtgtga | cgacgatggc | aaaaaacaaa | ccaacattgg | attttgaact | gataaaaaca | 1080 |
| gaagccaaac | aacctgccac | tctaaggaag | tactgtatag | aggcaaagct | gaccaacaca | 1140 |
| acaacagaat | ctcgctgccc | aacacaagga | gaacctagcc | taaatgaaga | gcaggacaaa | 1200 |
| aggttcgtct | gcaaacactc | catggtggac | agaggatggg | gaaatggatg | tggattattt | 1260 |
| ggaaaaggag | gcattgtgac | ctgtgctatg | ttcacatgca | aaaagaacat | ggaaggaaaa | 1320 |
| gtcgtgcaac | cagaaaactt | ggaatacacc | attgtgataa | caccctcactc | agggggaagag | 1380 |
| catgcagtcg | gaaatgacac | aggaaaacat | ggcaaggaaa | tcaaaataac | accacagagt | 1440 |
| tccatcacag | aagcagagtt | gacaggctat | ggcactgtca | cgatggagtg | ctctccgaga | 1500 |
| acgggcctcg | acttcaatga | gatggtgttg | ctgcaaatgg | aaaataaagc | ttggctggtg | 1560 |
| cacaggcaat | ggttcctaga | cctgccgttg | ccatggctgc | ccggagcgga | cacacaagga | 1620 |
| tcaaattgga | tacagaaaga | gacattggtc | actttcaaaa | atccccatgc | gaagaaacag | 1680 |
| gatgttgttg | ttttgggatc | ccaagaaggg | gccatgcaca | cagcactcac | aggggccaca | 1740 |
| gaaatccaga | tgtcatcagg | aaacttactg | ttcacaggac | atctcaagtg | caggctgagg | 1800 |
| atggacaaac | tacagctcaa | aggaatgtca | tactctatgt | gcacaggaaa | gtttaaagtt | 1860 |
| gtgaaggaaa | tagcagaaac | acaacatgga | acaatagtta | tcagagtaca | atatgaaggg | 1920 |
| gacggttctc | catgtaagat | ccccttttga | gataatggatt | tggaaaaaag | acatgttta | 1980 |

```
ggtcgcctga ttacagtcaa cccaatcgta acagaaaaag atagcccagt caacatagaa    2040
gcagaacctc cattcggaga cagctacatc atcataggag tagagccggg acaattgaag    2100
ctcaactggt ttaagaaagg aagttctatc ggccaaatgt ttgagacaac aatgagggga    2160
gcgaagagaa tggccatttt aggtgacaca gcttgggatt ttggatccct gggaggagtg    2220
tttacatcta taggaaaggc tctccaccaa gttttcggag caatctatgg ggctgccttc    2280
agtggggtct catggactat gaaaatcctc ataggagtca ttatcacatg gataggaatg    2340
aactcgagga acacttcaat ggctatgacg tgcatagctg ttggaggaat cactctgttt    2400
ctgggcttca cagttcaagc agacatgggt tgtgtggcgt catggagtgg gaaagaattg    2460
aagtgtggaa gcggaatttt tgtggttgac aacgtgcaca cttggacaga acagtacaaa    2520
tttcaaccag agtccccagc gagactagcg tctgcaatat aaatgccca caaagatggg    2580 gtctgtggaa ttagatcaac cacgaggctg gaaaatgtca tgtggaagca ataaccaac    2640 gagctaaaact atgttctctg ggaaggagga catgacctca ctgtagtggc tggggatgtg    2700
aagggggtgt tgaccaaagg caagagagca ctcacacccc cagtgagtga tctgaaatat    2760
tcatggaaga catggggaaa agcaaaaatc ttcaccccag aagcaagaaa tagcacattt    2820
ttaatagacg gaccagacac ctctgaatgc cccaatgaac gaagagcatg gaactctctt    2880
gaggtggaag actatggatt tggcatgttc acgaccaaca tatggatgaa attccgagaa    2940
ggaagttcag aagtgtgtga ccacaggtta atgtcagctg caattaaaga tcagaaagct    3000
gtgcatgctg acatgggtta ttggatagag agctcaaaaa accagaccctg gcagatagag    3060 aaagcatctc ttattgaagt gaaaacatgt ctgtggccca gacccacac actgtggagc    3120 aatgagtgc tggaaagcca gatgctcatt ccaaaatcat atgcgggccc tttttcacag    3180
cacaattacc gccagggcta tgccacgcaa accgtgggcc catggcactt aggcaaatta    3240
gagatagact ttgagaatg ccccggaaca acagtcacaa ttcaggagga ttgtgaccat    3300
agaggcccat ctttgaggac caccactgca tctggaaaac tagtcacgca atggtgctgc    3360
cgctcctgca cgatgcctcc cttaaggttc ttggagaag atgggtgctg gtatgggatg    3420
gagattaggc ccttgagtga aaaagaagag aacatggtca aatcacaggt gacggccgga    3480
cagggcacat cagaaacttt ttctatgggt ctgttgtgcc tgaccttgtt tgtggaagaa    3540
tgcttgagga gaagagtcac taggaaacac atgatattag ttgtggtgat cactctttgt    3600
gctatcatcc tgggaggcct cacatggatg gacttactac gagccctcat catgttgggg    3660
gacactatgt ctggtagaat aggaggacag atccacctag ccatcatggc agtgttcaag    3720
atgtcaccag gatacgtgct gggtgtgttt ttaaggaaac tcacttcaag agagacagca    3780
ctaatggtaa taggaatggc catgacaacg gtgctttcaa ttccacatga ccttatggaa    3840
ctcattgatg gaatatcact gggactaatt ttgctaaaaa tagtaacaca gtttgacaac    3900
acccaagtgg gaaccttagc tctttccttg actttcataa gatcaacaat gccattggtc    3960
atggcttgga ggaccattat ggctgtgttg tttgtggtca cactcattcc tttgtgcagg    4020
acaagctgtc ttcaaaaaca gtctcattgg gtagaaataa cagcactcat cctaggagcc    4080
caagctctgc cagtgtacct aatgactctt atgaaggagg cctcaagaag atcttggcct    4140
cttaacgagg gcataatggc tgtgggtttg gttagtctct taggaagcgc tctttttaaag    4200 aatgatgtcc cttagctgg cccaatggtg gcaggaggct tacttctggc ggcttacgtg    4260
atgagtggta gctcagcaga tctgtcacta gagaaggccg ccaacgtgca gtgggatgaa    4320
```

```
atggcagaca taacaggctc aagcccaatc atagaagtga agcaggatga agatggctct    4380
ttctccatac gggacgtcga ggaaaccaat atgataaccc ttttggtgaa actggcactg    4440
ataacagtgt caggtctcta ccccttggca attccagtca caatgacctt atggtacatg    4500
tggcaagtga aaacacaaag atcaggagcc ctgtgggacg tcccctcacc cgctgccact    4560
aaaaaagccg cactgtctga aggagtgtac aggatcatgc aaagagggtt attcgggaaa    4620
actcaggttg gagtagggat acacatggaa ggtgtatttc acacaatgtg gcatgtaaca    4680
agaggatcag tgatctgcca cgagactggg agattggagc catcttgggc tgacgtcagg    4740
aatgacatga tatcatacgg tggggggatgg aggcttggag acaaatggga caaagaagaa    4800
gacgttcagg tcctcgccat agaaccagga aaaaatccta acatgtcca acgaaaacct    4860 ggcctttca agaccctaac tggagaaatt ggagcagtaa cattagattt caaacccgga    4920
acgtctggtt ctcccatcat caacaggaaa ggaaaagtca tcggactcta tggaaatgga    4980
gtagttacca aatcaggtga ttacgtcagt gccataacgc aagccgaaag aattggagag    5040
ccagattatg aagtggatga ggacattttt cgaagaaaa gattaactat aatggactta    5100 cacccccggag ctggaaagac aaaaagaatt cttccatcaa tagtgagaga agccttaaaa    5160
aggaggctac gaactttgat tttagctccc acgagagtgg tggcggccga gatggaagag    5220
gccctacgtg gactgccaat ccgttatcag accccagctg tgaaatcaga acacacagga    5280
agagagattg tagacctcat gtgtcatgca accttcacaa caagacttt gtcatcaacc    5340 agggttccaa attacaacct tatagtgatg atgaagcac atttcaccga tcctctagt    5400 gtcgcggcta gaggatacat ctcgaccagg gtggaaatgg gagaggcagc agccatcttc    5460
atgaccgcaa cccctcccgg agcgacagat ccctttcccc agagcaacag cccaatagaa    5520
gacatcgaga gggaaattcc ggaaaggtca tggaacacag ggttcgactg gataacagac    5580
taccaaggga aaactgtgtg gtttgttccc agcataaaag ctggaaatga cattgcaaat    5640
tgtttgagaa agtcgggaaa gaaagttatc cagttgagta ggaaaacctt tgatacagag    5700
tatccaaaaa cgaaactcac ggactgggac tttgtggtca ctacagacat atctgaaatg    5760
ggggccaatt ttagagccgg agagtgata cccctagaa gatgcctcaa gccagttatc    5820 ctaccgatg ggccagagag agtcattta gcaggtccta ttccagtgac tccagcaagc    5880
gctgctcaga aagagggcg aataggaagg aacccagcac aagaagacga ccaatacgtt    5940
ttctccggag acccactaaa aaatgatgaa gatcatgccc actggacaga agcaaagatg    6000
ctgcttgaca atatctacac cccagaaggg atcattccaa cattgtttgg tccggaaagg    6060 gaaaaaccc aagccattga tggagagttt cgcctcagag gggacaaag gaagactttt    6120 gtggaattaa tgaggagagg agaccttccg gtgtggctga ctataaggt agcttctgct    6180 ggcatttctt acaagatcg ggaatggtgc ttcacagggg aaagaaataa ccaaattta    6240 gaagaaaaca tggaggttga aatttggact agagaggag aaaagaaaaa gctaaggcca    6300
agatggttag atgcacgtgt atacgctgac cccatggctt tgaaggattt caaggagttt    6360
gccagtggaa ggaagagtat aactctcgac atcctaacag agattgccag tttgccaact    6420 taccttcct ctagggccaa gctcgcccct gataacatag tcatgctcca cacaacagaa    6480
agaggaggga gggcctatca acacgccctg aacgaacttc cggagtcact ggaaacactc    6540
atgcttgtag cttactaggt gctatgaca gcaggcatct tcctgttttt catgcaaggg    6600
aaaggaatag ggaaattgtc aatgggtttg ataaccattg cggtggctag tggcttgctc    6660
tgggtagcag aaattcaacc ccagtggata gcggcctcaa tcatactaga gttttttctc    6720
```

```
atggtactgt tgataccgga accagaaaaa caaaggaccc cacaagacaa tcaattgatc    6780
tacgtcatat tgaccattct caccatcatt ggtctaatag cagccaacga gatgggctg    6840 attgaaaaaa caaaaacgga ttttgggttt taccaggtaa aaacagaaac caccatcctc    6900
gatgtggact tgagaccagc ttcagcatgg acgctctatg cagtagccac cacaattctg    6960
actcccatgc tgagacacac catagaaaac acgtcggcca acctatctct agcagccatt    7020
gccaaccagg cagccgtcct aatggggctt ggaaaaggat ggccgctcca cagaatggac    7080
ctcggtgtgc cgctgttagc aatgggatgc tattctcaag tgaacccaac aaccttgaca    7140
gcatccttag tcatgctttt agtccattat gcaataatag gcccaggatt gcaggcaaaa    7200
gccacaagag aggcccagaa aaggacagct gctgggatca tgaaaaatcc cacagtggac    7260
gggataacag taatagatct agaaccaata tcctatgacc aaaatttga aaagcaatta    7320 gggcaggtca tgctactagt cttgtgtgct ggacaactac tcttgatgag aacaacatgg    7380
gctttctgtg aagtcttgac tttggccaca ggaccaatct tgaccttgtg ggagggcaac    7440 ccggaaggt tttggaacac gaccatagcc gtatccaccg ccaacatttt caggggaagt    7500
tacttggcgg gagctggact ggcttttttca ctcataaaga atgcacaaac ccctaggagg    7560
ggaactggga ccacaggaga gacactggga gagaagtgga gagacagct aaactcatta    7620 gacagaaaag agtttgaaga gtataaaaga agtggaatac tagaagtgga caggactgaa    7680
gccaagtctg ccctgaaaga tgggtctaaa atcaagcatg cagtatcaag agggtccagt    7740
aagatcagat ggattgttga gagagggatg gtaaagccaa aagggaaagt tgtagatctt    7800
ggctgtggga gaggaggatg gtcttattac atggcgacac tcaagaacgt gactgaagtg    7860
aaagggtata caaaaggag tccaggacat gaagaaccga ttcccatggc tacttatggt    7920
tggaatttgg tcaaactcca ttcagggggtt gacgtgttct acaaacccac agagcaagtg    7980 gacacectgc tctgtgatat tggggagtca tcttctaatc caacaatagca ggaaggaaga    8040 acattaagag tttttgaagat ggtggagcca tggctctctt caaaacctga attctgcatc    8100
aaagtcctta ccccctacat gccaacagtc atagaagagc tggagaaact gcagagaaaa    8160
catggtggga accttgtcag atgccegctg tccaggaact ccaccecatga atgttattgg    8220 gtgtcaggag cgtcgggaaa cattgtgagc tctgtgaaca acatcaaa gatgttgttg    8280 aacaggttca caacaaggca taggaaaccc acttatgaga aggacgtaga tcttgggca    8340 ggaacgagaa gtgtctccac tgaaacgaaa aaaccagaca tgacaatcat gggagaagg    8400 cttcagcgat tgcaagaaga gcacaaagaa acctggcatt atgatcagga aacccatac    8460 agaacctggg cgtatcatgg aagctatgaa gctccttcga caggctctgc atcctccatg    8520
gtgaacgggg tggtaaaact gctaacaaaa ccctgggatg tgattccaat ggtgactcag    8580
ttagccatga cagatacaac cccttttggg caacaaagag tgttcaaaga aaggtggat    8640 accagaacac cacaaccaaa acccggtaca cgaatggtta tgaccacgac agccaattgg    8700
ctgtgggccc tccttggaaa gaagaaaaat cccagactgt gcacaagga agagttcatc    8760 tcaaaagtta gatcaaacgc agccataggc gcagtctttc aggaagaaca gggatggaca    8820
tcagccagtg aagctgtgaa tgacagccgg ttttgggaac tggttgacaa agaagggcc    8880 ctacaccagg aagggaaatg tgaatcgtgt gtctataaca tgatgggaaa acgtgagaaa    8940
aagttaggag agtttggcag agccaaggga agccgagcaa tctggtacat gtggctggga    9000
gcgcggtttc tggaatttga agccctgggt ttttgaatg aagatcactg gtttggcaga    9060
```

-continued

```
gaaaattcat ggagtggagt ggaaggggaa ggtctgcaca gattgggata tatcctggag      9120
gagatagaca agaaggatgg agacctaatg tatgctgatg acacagcagg ctgggacaca      9180
agaatcactg aggatgacct tcaaaatgag gaactgatca cggaacagat ggctccccac      9240
cacaagatcc tagccaaagc cattttcaaa ctaacctatc aaaacaaagt ggtgaaagtc      9300
ctcagaccca caccgcgggg agcggtgatg gatatcatat ccaggaaaga ccaaagaggt      9360
agtggacaag ttggaacata tggtttgaac acattcacca catggaagt tcaactcatc       9420 cgccaaatgg aagctgaagg agtcatcaca caagatgaca tgcagaaccc aaaagggttg      9480
aaagaaagag ttgagaaatg gctgaaagag tgtggtgtcg acaggttaaa gaggatggca      9540
atcagtggag acgattgcgt ggtgaagccc ctagatgaga ggtttggcac ttccctcctc      9600
ttcttgaacg acatgggaaa ggtgaggaaa gacattccgc agtgggaacc atctaaggga      9660
tggaaaaact ggcaagaggt tcctttttgc tcccaccact ttcacaagat ctttatgaag      9720
gatggccgct cactagttgt tccatgtaga aaccaggatg aactgatagg agagccaga       9780 atctcgcagg gagctggatg gagcttaaga gaaacagcct gcctgggcaa agcttacgcc      9840
cagatgtggt cgcttatgta cttccacaga agggatctgc gtttagcctc catggccata      9900
tgctcagcag ttccaacgga atggtttcca acaagcagaa caacatggtc aatccacgct      9960
catcaccagt ggatgaccac tgaagatatg ctcaaagtgt ggaacagagt gtggataaga     10020 gacaaccta atatgactga caagactcca gtccattcgt gggaagatat accttaccta     10080
gggaaaagag aggatttgtg tgtgtggatcc ctgattggac tttcttccag agccacctgg    10140
gcgaagaaca ttcacacggc cataacccag gtcaggaacc tgatcggaaa agaggaatac     10200
gtggattaca tgccagtaat gaaaagatac agtgctcctt cagagagtga aggagttctg     10260
taattaccaa caacaaacac caaaggctat tgaagtcagg ccacttgtgc cacggtttga     10320
gcaaaccgtg ctgcctgtag ctccgccaat aatgggaggc gtaataatcc ccagggaggc     10380
catgcgccac ggaagctgta cgcgtggcat attggactag cggttagagg agaccctcc      10440 catcactgac aaaacgcagc aaaaggggc ccaagactag aggttagagg agaccccccc      10500
aacacaaaaa cagcatattg acgctgggaa agaccagaga tcctgctgtc tctgcaacat     10560
caatccaggc acagagcgcc gcaagatgga ttggtgttgt tgatccaaca ggttct         10616
```

<210> SEQ ID NO 19
<211> LENGTH: 3387
<212> TYPE: PRT
<213> ORGANISM: Dengue 4 virus

<400> SEQUENCE: 19

```
Met Asn Gln Arg Lys Lys Val Val Arg Pro Phe Asn Met Leu Lys
  1               5                  10                  15

Arg Glu Arg Asn Arg Val Ser Thr Pro Gln Gly Leu Val Lys Arg Phe
                 20                  25                  30

Ser Thr Gly Leu Phe Ser Gly Lys Gly Pro Leu Arg Met Val Leu Ala
             35                  40                  45

Phe Ile Thr Phe Leu Arg Val Leu Ser Ile Pro Thr Ala Gly Ile
         50                  55                  60

Leu Lys Arg Trp Gly Gln Leu Lys Lys Asn Lys Ala Ile Lys Ile Leu
 65                  70                  75                  80

Ile Gly Phe Arg Lys Glu Ile Gly Arg Met Leu Asn Ile Leu Asn Gly
                 85                  90                  95

Arg Lys Arg Ser Thr Ile Thr Leu Leu Cys Leu Ile Pro Thr Val Met
```

-continued

```
                100                 105                 110
Ala Phe Ser Leu Ser Thr Arg Asp Gly Glu Pro Leu Met Ile Val Ala
                115                 120                 125

Lys His Glu Arg Gly Arg Pro Leu Leu Phe Lys Thr Thr Glu Gly Ile
            130                 135                 140

Asn Lys Cys Thr Leu Ile Ala Met Asp Leu Gly Glu Met Cys Glu Asp
145                 150                 155                 160

Thr Val Thr Tyr Lys Cys Pro Leu Leu Val Asn Thr Glu Pro Glu Asp
                165                 170                 175

Ile Asp Cys Trp Cys Asn Leu Thr Ser Thr Trp Val Met Tyr Gly Thr
            180                 185                 190

Cys Thr Gln Ser Gly Glu Arg Arg Glu Lys Arg Ser Val Ala Leu
                195                 200                 205

Thr Pro His Ser Gly Met Gly Leu Glu Thr Arg Ala Glu Thr Trp Met
        210                 215                 220

Ser Ser Glu Gly Ala Trp Lys His Ala Gln Arg Val Glu Ser Trp Ile
225                 230                 235                 240

Leu Arg Asn Pro Gly Phe Ala Leu Leu Ala Gly Phe Met Ala Tyr Met
                245                 250                 255

Ile Gly Gln Thr Gly Ile Gln Arg Thr Val Phe Phe Val Leu Met Met
            260                 265                 270

Leu Val Ala Pro Ser Tyr Gly Met Arg Cys Val Gly Val Gly Asn Arg
        275                 280                 285

Asp Phe Val Glu Gly Val Ser Gly Gly Ala Trp Val Asp Leu Val Leu
        290                 295                 300

Glu His Gly Gly Cys Val Thr Thr Met Ala Gln Gly Lys Pro Thr Leu
305                 310                 315                 320

Asp Phe Glu Leu Thr Lys Thr Thr Ala Lys Glu Val Ala Leu Leu Arg
                325                 330                 335

Thr Tyr Cys Ile Glu Ala Ser Ile Ser Asn Ile Thr Thr Ala Thr Arg
            340                 345                 350

Cys Pro Thr Gln Gly Glu Pro Tyr Leu Lys Glu Glu Gln Asp Gln Gln
        355                 360                 365

Tyr Ile Cys Arg Arg Asp Val Val Asp Arg Gly Trp Gly Asn Gly Cys
    370                 375                 380

Gly Leu Phe Gly Lys Gly Gly Val Val Thr Cys Ala Lys Phe Ser Cys
385                 390                 395                 400

Ser Gly Lys Ile Thr Gly Asn Leu Val Gln Ile Glu Asn Leu Glu Tyr
                405                 410                 415

Thr Val Val Val Thr Val His Asn Gly Asp Thr His Ala Val Gly Asn
            420                 425                 430

Asp Thr Ser Asn His Gly Val Thr Ala Met Ile Thr Pro Arg Ser Pro
        435                 440                 445

Ser Val Glu Val Lys Leu Pro Asp Tyr Gly Glu Leu Thr Leu Asp Cys
        450                 455                 460

Glu Pro Arg Ser Gly Ile Asp Phe Asn Glu Met Ile Leu Met Lys Met
465                 470                 475                 480

Lys Lys Lys Thr Trp Leu Val His Lys Gln Trp Phe Leu Asp Leu Pro
                485                 490                 495

Leu Pro Trp Thr Ala Gly Ala Asp Thr Ser Glu Val His Trp Asn Tyr
            500                 505                 510

Lys Glu Arg Met Val Thr Phe Lys Val Pro His Ala Lys Arg Gln Asp
        515                 520                 525
```

-continued

```
Val Thr Val Leu Gly Ser Gln Glu Gly Ala Met His Ser Ala Leu Ala
    530                 535                 540
Gly Ala Thr Glu Val Asp Ser Gly Asp Gly Asn His Met Phe Ala Gly
545                 550                 555                 560
His Leu Lys Cys Lys Val Arg Met Glu Lys Leu Arg Ile Lys Gly Met
                565                 570                 575
Ser Tyr Thr Met Cys Ser Gly Lys Phe Ser Ile Asp Lys Glu Met Ala
            580                 585                 590
Glu Thr Gln His Gly Thr Thr Val Val Lys Val Lys Tyr Glu Gly Ala
        595                 600                 605
Gly Ala Pro Cys Lys Val Pro Ile Glu Ile Arg Asp Val Asn Lys Glu
610                 615                 620
Lys Val Val Gly Arg Ile Ile Ser Ser Thr Pro Leu Ala Glu Asn Thr
625                 630                 635                 640
Asn Ser Val Thr Asn Ile Glu Leu Glu Pro Pro Phe Gly Asp Ser Tyr
                645                 650                 655
Ile Val Ile Gly Val Gly Asn Ser Ala Leu Thr Leu His Trp Phe Arg
            660                 665                 670
Lys Gly Ser Ser Ile Gly Lys Met Phe Glu Ser Thr Tyr Arg Gly Ala
        675                 680                 685
Lys Arg Met Ala Ile Leu Gly Glu Thr Ala Trp Asp Phe Gly Ser Val
690                 695                 700
Gly Gly Leu Phe Thr Ser Leu Gly Lys Ala Val His Gln Val Phe Gly
705                 710                 715                 720
Ser Val Tyr Thr Thr Met Phe Gly Gly Val Ser Trp Met Ile Arg Ile
                725                 730                 735
Leu Ile Gly Phe Leu Val Leu Trp Ile Gly Thr Asn Ser Arg Asn Thr
            740                 745                 750
Ser Met Ala Met Thr Cys Ile Ala Val Gly Gly Ile Thr Leu Phe Leu
        755                 760                 765
Gly Phe Thr Val Gln Ala Asp Met Gly Cys Val Ala Ser Trp Ser Gly
770                 775                 780
Lys Glu Leu Lys Cys Gly Ser Gly Ile Phe Val Val Asp Asn Val His
785                 790                 795                 800
Thr Trp Thr Glu Gln Tyr Lys Phe Gln Pro Glu Ser Pro Ala Arg Leu
                805                 810                 815
Ala Ser Ala Ile Leu Asn Ala His Lys Asp Gly Val Cys Gly Ile Arg
            820                 825                 830
Ser Thr Thr Arg Leu Glu Asn Val Met Trp Lys Gln Ile Thr Asn Glu
        835                 840                 845
Leu Asn Tyr Val Leu Trp Glu Gly His Asp Leu Thr Val Val Ala
850                 855                 860
Gly Asp Val Lys Gly Val Leu Thr Lys Gly Lys Arg Ala Leu Thr Pro
865                 870                 875                 880
Pro Val Ser Asp Leu Lys Tyr Ser Trp Lys Thr Trp Gly Lys Ala Lys
                885                 890                 895
Ile Phe Thr Pro Glu Ala Arg Asn Ser Thr Phe Leu Ile Asp Gly Pro
            900                 905                 910
Asp Thr Ser Glu Cys Pro Asn Glu Arg Arg Ala Trp Asn Ser Leu Glu
        915                 920                 925
Val Glu Asp Tyr Gly Phe Gly Met Phe Thr Thr Asn Ile Trp Met Lys
930                 935                 940
```

-continued

```
Phe Arg Glu Gly Ser Ser Val Cys Asp His Arg Leu Met Ser Ala
945                 950                 955                 960

Ala Ile Lys Asp Gln Lys Ala Val His Ala Asp Met Gly Tyr Trp Ile
            965                 970                 975

Glu Ser Ser Lys Asn Gln Thr Trp Gln Ile Glu Lys Ala Ser Leu Ile
        980                 985                 990

Glu Val Lys Thr Cys Leu Trp Pro Lys Thr His Thr Leu Trp Ser Asn
    995                 1000                1005

Gly Val Leu Glu Ser Gln Met Leu Ile Pro Lys Ser Tyr Ala Gly Pro
1010                1015                1020

Phe Ser Gln His Asn Tyr Arg Gln Gly Tyr Ala Thr Gln Thr Val Gly
1025                1030                1035                1040

Pro Trp His Leu Gly Lys Leu Glu Ile Asp Phe Gly Glu Cys Pro Gly
                1045                1050                1055

Thr Thr Val Thr Ile Gln Glu Asp Cys Asp His Arg Gly Pro Ser Leu
                1060                1065                1070

Arg Thr Thr Thr Ala Ser Gly Lys Leu Val Thr Gln Trp Cys Cys Arg
            1075                1080                1085

Ser Cys Thr Met Pro Pro Leu Arg Phe Leu Gly Glu Asp Gly Cys Trp
1090                1095                1100

Tyr Gly Met Glu Ile Arg Pro Leu Ser Glu Lys Glu Glu Asn Met Val
1105                1110                1115                1120

Lys Ser Gln Val Thr Ala Gly Gln Gly Thr Ser Glu Thr Phe Ser Met
                1125                1130                1135

Gly Leu Leu Cys Leu Thr Leu Phe Val Glu Glu Cys Leu Arg Arg Arg
            1140                1145                1150

Val Thr Arg Lys His Met Ile Leu Val Val Ile Thr Leu Cys Ala
        1155                1160                1165

Ile Ile Leu Gly Gly Leu Thr Trp Met Asp Leu Leu Arg Ala Leu Ile
1170                1175                1180

Met Leu Gly Asp Thr Met Ser Gly Arg Ile Gly Gly Gln Ile His Leu
1185                1190                1195                1200

Ala Ile Met Ala Val Phe Lys Met Ser Pro Gly Tyr Val Leu Gly Val
                1205                1210                1215

Phe Leu Arg Lys Leu Thr Ser Arg Glu Thr Ala Leu Met Val Ile Gly
            1220                1225                1230

Met Ala Met Thr Thr Val Leu Ser Ile Pro His Asp Leu Met Glu Leu
        1235                1240                1245

Ile Asp Gly Ile Ser Leu Gly Leu Ile Leu Leu Lys Ile Val Thr Gln
1250                1255                1260

Phe Asp Asn Thr Gln Val Gly Leu Ala Leu Ser Leu Thr Phe Ile
1265                1270                1275                1280

Arg Ser Thr Met Pro Leu Val Met Ala Trp Arg Thr Ile Met Ala Val
                1285                1290                1295

Leu Phe Val Val Thr Leu Ile Pro Leu Cys Arg Thr Ser Cys Leu Gln
            1300                1305                1310

Lys Gln Ser His Trp Val Glu Ile Thr Ala Leu Ile Leu Gly Ala Gln
        1315                1320                1325

Ala Leu Pro Val Tyr Leu Met Thr Leu Met Lys Gly Ala Ser Arg Arg
    1330                1335                1340

Ser Trp Pro Leu Asn Glu Gly Ile Met Ala Val Gly Leu Val Ser Leu
1345                1350                1355                1360

Leu Gly Ser Ala Leu Leu Lys Asn Asp Val Pro Leu Ala Gly Pro Met
```

-continued

```
                1365                1370                1375
Val Ala Gly Gly Leu Leu Ala Ala Tyr Val Met Ser Gly Ser Ser
            1380                1385                1390
Ala Asp Leu Ser Leu Glu Lys Ala Ala Asn Val Gln Trp Asp Glu Met
            1395                1400                1405
Ala Asp Ile Thr Gly Ser Ser Pro Ile Ile Glu Val Lys Gln Asp Glu
            1410                1415                1420
Asp Gly Ser Phe Ser Ile Arg Asp Val Glu Glu Thr Asn Met Ile Thr
1425                1430                1435                1440
Leu Leu Val Lys Leu Ala Leu Ile Thr Val Ser Gly Leu Tyr Pro Leu
                1445                1450                1455
Ala Ile Pro Val Thr Met Thr Leu Trp Tyr Met Trp Gln Val Lys Thr
                1460                1465                1470
Gln Arg Ser Gly Ala Leu Trp Asp Val Pro Ser Pro Ala Ala Thr Lys
                1475                1480                1485
Lys Ala Ala Leu Ser Glu Gly Val Tyr Arg Ile Met Gln Arg Gly Leu
            1490                1495                1500
Phe Gly Lys Thr Gln Val Gly Val Gly Ile His Met Glu Gly Val Phe
1505                1510                1515                1520
His Thr Met Trp His Val Thr Arg Gly Ser Val Ile Cys His Glu Thr
                1525                1530                1535
Gly Arg Leu Glu Pro Ser Trp Ala Asp Val Arg Asn Asp Met Ile Ser
                1540                1545                1550
Tyr Gly Gly Gly Trp Arg Leu Gly Asp Lys Trp Asp Lys Glu Glu Asp
                1555                1560                1565
Val Gln Val Leu Ala Ile Glu Pro Gly Lys Asn Pro Lys His Val Gln
            1570                1575                1580
Thr Lys Pro Gly Leu Phe Lys Thr Leu Thr Gly Glu Ile Gly Ala Val
1585                1590                1595                1600
Thr Leu Asp Phe Lys Pro Gly Thr Ser Gly Ser Pro Ile Ile Asn Arg
                1605                1610                1615
Lys Gly Lys Val Ile Gly Leu Tyr Gly Asn Gly Val Val Thr Lys Ser
                1620                1625                1630
Gly Asp Tyr Val Ser Ala Ile Thr Gln Ala Glu Arg Ile Gly Glu Pro
                1635                1640                1645
Asp Tyr Glu Val Asp Glu Asp Ile Phe Arg Lys Lys Arg Leu Thr Ile
                1650                1655                1660
Met Asp Leu His Pro Gly Ala Gly Lys Thr Lys Arg Ile Leu Pro Ser
1665                1670                1675                1680
Ile Val Arg Glu Ala Leu Lys Arg Arg Leu Arg Thr Leu Ile Leu Ala
                1685                1690                1695
Pro Thr Arg Val Val Ala Ala Glu Met Glu Glu Ala Leu Arg Gly Leu
            1700                1705                1710
Pro Ile Arg Tyr Gln Thr Pro Ala Val Lys Ser Glu His Thr Gly Arg
            1715                1720                1725
Glu Ile Val Asp Leu Met Cys His Ala Thr Phe Thr Thr Arg Leu Leu
            1730                1735                1740
Ser Ser Thr Arg Val Pro Asn Tyr Asn Leu Ile Val Met Asp Glu Ala
1745                1750                1755                1760
His Phe Thr Asp Pro Ser Ser Val Ala Ala Arg Gly Tyr Ile Ser Thr
                1765                1770                1775
Arg Val Glu Met Gly Glu Ala Ala Ile Phe Met Thr Ala Thr Pro
                1780                1785                1790
```

```
Pro Gly Ala Thr Asp Pro Phe Pro Gln Ser Asn Ser Pro Ile Glu Asp
        1795                1800                1805

Ile Glu Arg Glu Ile Pro Glu Arg Ser Trp Asn Thr Gly Phe Asp Trp
        1810                1815                1820

Ile Thr Asp Tyr Gln Gly Lys Thr Val Trp Phe Val Pro Ser Ile Lys
1825                1830                1835                1840

Ala Gly Asn Asp Ile Ala Asn Cys Leu Arg Lys Ser Gly Lys Lys Val
        1845                1850                1855

Ile Gln Leu Ser Arg Lys Thr Phe Asp Thr Glu Tyr Pro Lys Thr Lys
        1860                1865                1870

Leu Thr Asp Trp Asp Phe Val Val Thr Thr Asp Ile Ser Glu Met Gly
        1875                1880                1885

Ala Asn Phe Arg Ala Gly Arg Val Ile Asp Pro Arg Arg Cys Leu Lys
        1890                1895                1900

Pro Val Ile Leu Pro Asp Gly Pro Glu Arg Val Ile Leu Ala Gly Pro
1905                1910                1915                1920

Ile Pro Val Thr Pro Ala Ser Ala Ala Gln Arg Arg Gly Arg Ile Gly
        1925                1930                1935

Arg Asn Pro Ala Gln Glu Asp Asp Gln Tyr Val Phe Ser Gly Asp Pro
        1940                1945                1950

Leu Lys Asn Asp Glu Asp His Ala His Trp Thr Glu Ala Lys Met Leu
        1955                1960                1965

Leu Asp Asn Ile Tyr Thr Pro Glu Gly Ile Ile Pro Thr Leu Phe Gly
        1970                1975                1980

Pro Glu Arg Glu Lys Thr Gln Ala Ile Asp Gly Glu Phe Arg Leu Arg
1985                1990                1995                2000

Gly Glu Gln Arg Lys Thr Phe Val Glu Leu Met Arg Arg Gly Asp Leu
        2005                2010                2015

Pro Val Trp Leu Ser Tyr Lys Val Ala Ser Ala Gly Ile Ser Tyr Lys
        2020                2025                2030

Asp Arg Glu Trp Cys Phe Thr Gly Glu Arg Asn Asn Gln Ile Leu Glu
        2035                2040                2045

Glu Asn Met Glu Val Glu Ile Trp Thr Arg Glu Gly Glu Lys Lys Lys
        2050                2055                2060

Leu Arg Pro Arg Trp Leu Asp Ala Arg Val Tyr Ala Asp Pro Met Ala
2065                2070                2075                2080

Leu Lys Asp Phe Lys Glu Phe Ala Ser Gly Arg Lys Ser Ile Thr Leu
        2085                2090                2095

Asp Ile Leu Thr Glu Ile Ala Ser Leu Pro Thr Tyr Leu Ser Ser Arg
        2100                2105                2110

Ala Lys Leu Ala Leu Asp Asn Ile Val Met Leu His Thr Thr Glu Arg
        2115                2120                2125

Gly Gly Arg Ala Tyr Gln His Ala Leu Asn Glu Leu Pro Glu Ser Leu
        2130                2135                2140

Glu Thr Leu Met Leu Val Ala Leu Leu Gly Ala Met Thr Ala Gly Ile
2145                2150                2155                2160

Phe Leu Phe Phe Met Gln Gly Lys Gly Ile Gly Lys Leu Ser Met Gly
        2165                2170                2175

Leu Ile Thr Ile Ala Val Ala Ser Gly Leu Leu Trp Val Ala Glu Ile
        2180                2185                2190

Gln Pro Gln Trp Ile Ala Ala Ser Ile Ile Leu Glu Phe Phe Leu Met
        2195                2200                2205
```

-continued

```
Val Leu Leu Ile Pro Glu Pro Glu Lys Gln Arg Thr Pro Gln Asp Asn
2210                2215                2220

Gln Leu Ile Tyr Val Ile Leu Thr Ile Leu Thr Ile Ile Gly Leu Ile
2225                2230                2235                2240

Ala Ala Asn Glu Met Gly Leu Ile Glu Lys Thr Lys Thr Asp Phe Gly
                2245                2250                2255

Phe Tyr Gln Val Lys Thr Glu Thr Thr Ile Leu Asp Val Asp Leu Arg
                2260                2265                2270

Pro Ala Ser Ala Trp Thr Leu Tyr Ala Val Ala Thr Thr Ile Leu Thr
            2275                2280                2285

Pro Met Leu Arg His Thr Ile Glu Asn Thr Ser Ala Asn Leu Ser Leu
            2290                2295                2300

Ala Ala Ile Ala Asn Gln Ala Ala Val Leu Met Gly Leu Gly Lys Gly
2305                2310                2315                2320

Trp Pro Leu His Arg Met Asp Leu Gly Val Pro Leu Leu Ala Met Gly
                2325                2330                2335

Cys Tyr Ser Gln Val Asn Pro Thr Thr Leu Thr Ala Ser Leu Val Met
                2340                2345                2350

Leu Leu Val His Tyr Ala Ile Ile Gly Pro Gly Leu Gln Ala Lys Ala
            2355                2360                2365

Thr Arg Glu Ala Gln Lys Arg Thr Ala Ala Gly Ile Met Lys Asn Pro
    2370                2375                2380

Thr Val Asp Gly Ile Thr Val Ile Asp Leu Glu Pro Ile Ser Tyr Asp
2385                2390                2395                2400

Pro Lys Phe Glu Lys Gln Leu Gly Gln Val Met Leu Leu Val Leu Cys
                2405                2410                2415

Ala Gly Gln Leu Leu Leu Met Arg Thr Thr Trp Ala Phe Cys Glu Val
            2420                2425                2430

Leu Thr Leu Ala Thr Gly Pro Ile Leu Thr Leu Trp Glu Gly Asn Pro
            2435                2440                2445

Gly Arg Phe Trp Asn Thr Thr Ile Ala Val Ser Thr Ala Asn Ile Phe
    2450                2455                2460

Arg Gly Ser Tyr Leu Ala Gly Ala Gly Leu Ala Phe Ser Leu Ile Lys
2465                2470                2475                2480

Asn Ala Gln Thr Pro Arg Arg Gly Thr Gly Thr Thr Gly Glu Thr Leu
                2485                2490                2495

Gly Glu Lys Trp Lys Arg Gln Leu Asn Ser Leu Asp Arg Lys Glu Phe
                2500                2505                2510

Glu Glu Tyr Lys Arg Ser Gly Ile Leu Glu Val Asp Arg Thr Glu Ala
            2515                2520                2525

Lys Ser Ala Leu Lys Asp Gly Ser Lys Ile Lys His Ala Val Ser Arg
            2530                2535                2540

Gly Ser Ser Lys Ile Arg Trp Ile Val Glu Arg Gly Met Val Lys Pro
2545                2550                2555                2560

Lys Gly Lys Val Val Asp Leu Gly Cys Gly Arg Gly Gly Trp Ser Tyr
                2565                2570                2575

Tyr Met Ala Thr Leu Lys Asn Val Thr Glu Val Lys Gly Tyr Thr Lys
            2580                2585                2590

Gly Gly Pro Gly His Glu Glu Pro Ile Pro Met Ala Thr Tyr Gly Trp
            2595                2600                2605

Asn Leu Val Lys Leu His Ser Gly Val Asp Val Phe Tyr Lys Pro Thr
    2610                2615                2620

Glu Gln Val Asp Thr Leu Leu Cys Asp Ile Gly Glu Ser Ser Ser Asn
```

-continued

```
            2625                2630                2635                2640
Pro Thr Ile Glu Glu Gly Arg Thr Leu Arg Val Leu Lys Met Val Glu
                2645                2650                2655
Pro Trp Leu Ser Ser Lys Pro Glu Phe Cys Ile Lys Val Leu Asn Pro
                2660                2665                2670
Tyr Met Pro Thr Val Ile Glu Glu Leu Glu Lys Leu Gln Arg Lys His
                2675                2680                2685
Gly Gly Asn Leu Val Arg Cys Pro Leu Ser Arg Asn Ser Thr His Glu
                2690                2695                2700
Met Tyr Trp Val Ser Gly Ala Ser Gly Asn Ile Val Ser Ser Val Asn
2705                2710                2715                2720
Thr Thr Ser Lys Met Leu Leu Asn Arg Phe Thr Thr Arg His Arg Lys
                2725                2730                2735
Pro Thr Tyr Glu Lys Asp Val Asp Leu Gly Ala Gly Thr Arg Ser Val
                2740                2745                2750
Ser Thr Glu Thr Glu Lys Pro Asp Met Thr Ile Ile Gly Arg Arg Leu
                2755                2760                2765
Gln Arg Leu Gln Glu Glu His Lys Glu Thr Trp His Tyr Asp Gln Glu
                2770                2775                2780
Asn Pro Tyr Arg Thr Trp Ala Tyr His Gly Ser Tyr Glu Ala Pro Ser
2785                2790                2795                2800
Thr Gly Ser Ala Ser Ser Met Val Asn Gly Val Val Lys Leu Leu Thr
                2805                2810                2815
Lys Pro Trp Asp Val Ile Pro Met Val Thr Gln Leu Ala Met Thr Asp
                2820                2825                2830
Thr Thr Pro Phe Gly Gln Gln Arg Val Phe Lys Glu Lys Val Asp Thr
                2835                2840                2845
Arg Thr Pro Gln Pro Lys Pro Gly Thr Arg Met Val Met Thr Thr Thr
                2850                2855                2860
Ala Asn Trp Leu Trp Ala Leu Leu Gly Lys Lys Lys Asn Pro Arg Leu
2865                2870                2875                2880
Cys Thr Arg Glu Glu Phe Ile Ser Lys Val Arg Ser Asn Ala Ala Ile
                2885                2890                2895
Gly Ala Val Phe Gln Glu Glu Gln Gly Trp Thr Ser Ala Ser Glu Ala
                2900                2905                2910
Val Asn Asp Ser Arg Phe Trp Glu Leu Val Asp Lys Glu Arg Ala Leu
                2915                2920                2925
His Gln Glu Gly Lys Cys Glu Ser Cys Val Tyr Asn Met Met Gly Lys
                2930                2935                2940
Arg Glu Lys Lys Leu Gly Glu Phe Gly Arg Ala Lys Gly Ser Arg Ala
2945                2950                2955                2960
Ile Trp Tyr Met Trp Leu Gly Ala Arg Phe Leu Glu Phe Glu Ala Leu
                2965                2970                2975
Gly Phe Leu Asn Glu Asp His Trp Phe Gly Arg Glu Asn Ser Trp Ser
                2980                2985                2990
Gly Val Glu Gly Glu Gly Leu His Arg Leu Gly Tyr Ile Leu Glu Glu
                2995                3000                3005
Ile Asp Lys Lys Asp Gly Asp Leu Met Tyr Ala Asp Asp Thr Ala Gly
                3010                3015                3020
Trp Asp Thr Arg Ile Thr Glu Asp Asp Leu Gln Asn Glu Glu Leu Ile
3025                3030                3035                3040
Thr Glu Gln Met Ala Pro His His Lys Ile Leu Ala Lys Ala Ile Phe
                3045                3050                3055
```

```
Lys Leu Thr Tyr Gln Asn Lys Val Val Lys Val Leu Arg Pro Thr Pro
            3060                3065                3070

Arg Gly Ala Val Met Asp Ile Ile Ser Arg Lys Asp Gln Arg Gly Ser
        3075                3080                3085

Gly Gln Val Gly Thr Tyr Gly Leu Asn Thr Phe Thr Asn Met Glu Val
    3090                3095                3100

Gln Leu Ile Arg Gln Met Glu Ala Glu Gly Val Ile Thr Gln Asp Asp
3105                3110                3115                3120

Met Gln Asn Pro Lys Gly Leu Lys Glu Arg Val Glu Lys Trp Leu Lys
                3125                3130                3135

Glu Cys Gly Val Asp Arg Leu Lys Arg Met Ala Ile Ser Gly Asp Asp
            3140                3145                3150

Cys Val Val Lys Pro Leu Asp Glu Arg Phe Gly Thr Ser Leu Leu Phe
        3155                3160                3165

Leu Asn Asp Met Gly Lys Val Arg Lys Asp Ile Pro Gln Trp Glu Pro
    3170                3175                3180

Ser Lys Gly Trp Lys Asn Trp Gln Glu Val Pro Phe Cys Ser His His
3185                3190                3195                3200

Phe His Lys Ile Phe Met Lys Asp Gly Arg Ser Leu Val Val Pro Cys
                3205                3210                3215

Arg Asn Gln Asp Glu Leu Ile Gly Arg Ala Arg Ile Ser Gln Gly Ala
            3220                3225                3230

Gly Trp Ser Leu Arg Glu Thr Ala Cys Leu Gly Lys Ala Tyr Ala Gln
        3235                3240                3245

Met Trp Ser Leu Met Tyr Phe His Arg Arg Asp Leu Arg Leu Ala Ser
    3250                3255                3260

Met Ala Ile Cys Ser Ala Val Pro Thr Glu Trp Phe Pro Thr Ser Arg
3265                3270                3275                3280

Thr Thr Trp Ser Ile His Ala His His Gln Trp Met Thr Thr Glu Asp
                3285                3290                3295

Met Leu Lys Val Trp Asn Arg Val Trp Ile Glu Asp Asn Pro Asn Met
            3300                3305                3310

Thr Asp Lys Thr Pro Val His Ser Trp Glu Asp Ile Pro Tyr Leu Gly
        3315                3320                3325

Lys Arg Glu Asp Leu Trp Cys Gly Ser Leu Ile Gly Leu Ser Ser Arg
    3330                3335                3340

Ala Thr Trp Ala Lys Asn Ile His Thr Ala Ile Thr Gln Val Arg Asn
3345                3350                3355                3360

Leu Ile Gly Lys Glu Glu Tyr Val Asp Tyr Met Pro Val Met Lys Arg
                3365                3370                3375

Tyr Ser Ala Pro Ser Glu Ser Glu Gly Val Leu
            3380                3385

<210> SEQ ID NO 20
<211> LENGTH: 3392
<212> TYPE: PRT
<213> ORGANISM: Dengue 1 virus strain WP

<400> SEQUENCE: 20

Met Asn Asn Gln Arg Lys Lys Thr Gly Arg Pro Ser Phe Asn Met Leu
 1               5                  10                  15

Lys Arg Ala Arg Asn Arg Val Ser Thr Val Ser Gln Leu Ala Lys Arg
            20                  25                  30

Phe Ser Lys Gly Leu Leu Ser Gly Gln Gly Pro Met Lys Leu Val Met
```

```
                 35                  40                  45
Ala Phe Ile Ala Phe Leu Arg Phe Leu Ala Ile Pro Pro Thr Ala Gly
 50                  55                  60

Ile Leu Ala Arg Trp Gly Ser Phe Lys Lys Asn Gly Ala Ile Lys Val
 65                  70                  75                  80

Leu Arg Gly Phe Lys Lys Glu Ile Ser Asn Met Leu Asn Ile Met Asn
                 85                  90                  95

Arg Arg Lys Arg Ser Val Thr Met Leu Leu Met Leu Leu Pro Thr Ala
                100                 105                 110

Leu Ala Phe His Leu Thr Thr Arg Gly Gly Glu Pro His Met Ile Val
                115                 120                 125

Ser Lys Gln Glu Arg Gly Lys Ser Leu Leu Phe Lys Thr Ser Ala Gly
    130                 135                 140

Val Asn Met Cys Thr Leu Ile Ala Met Asp Leu Gly Glu Leu Cys Glu
145                 150                 155                 160

Asp Thr Met Thr Tyr Lys Cys Pro Arg Ile Thr Glu Thr Glu Pro Asp
                165                 170                 175

Asp Val Asp Cys Trp Cys Asn Ala Thr Glu Thr Trp Val Thr Tyr Gly
                180                 185                 190

Thr Cys Ser Gln Thr Gly Glu His Arg Arg Asp Lys Arg Ser Val Ala
                195                 200                 205

Leu Ala Pro His Val Gly Leu Gly Leu Glu Thr Arg Thr Glu Thr Trp
    210                 215                 220

Met Ser Ser Glu Gly Ala Trp Lys Gln Ile Gln Lys Val Glu Thr Trp
225                 230                 235                 240

Ala Leu Arg His Pro Gly Phe Thr Val Ile Ala Leu Phe Leu Ala His
                245                 250                 255

Ala Ile Gly Thr Ser Ile Thr Gln Lys Gly Ile Ile Phe Ile Leu Leu
                260                 265                 270

Met Leu Val Thr Pro Ser Met Ala Met Arg Cys Val Gly Ile Gly Asn
                275                 280                 285

Arg Asp Phe Val Glu Gly Leu Ser Gly Ala Thr Trp Val Asp Val Val
    290                 295                 300

Leu Glu His Gly Ser Cys Val Thr Thr Met Ala Lys Asp Lys Pro Thr
305                 310                 315                 320

Leu Asp Ile Glu Leu Leu Lys Thr Glu Val Thr Asn Pro Ala Val Leu
                325                 330                 335

Arg Lys Leu Cys Ile Glu Ala Lys Ile Ser Asn Thr Thr Thr Asp Ser
                340                 345                 350

Arg Cys Pro Thr Gln Gly Glu Ala Thr Leu Val Glu Glu Gln Asp Thr
                355                 360                 365

Asn Phe Val Cys Arg Arg Thr Phe Val Asp Arg Gly Trp Gly Asn Gly
    370                 375                 380

Cys Gly Leu Phe Gly Lys Gly Ser Leu Ile Thr Cys Ala Lys Phe Lys
385                 390                 395                 400

Cys Val Thr Lys Leu Glu Gly Lys Ile Val Gln Tyr Glu Asn Leu Lys
                405                 410                 415

Tyr Ser Val Ile Val Thr Val His Thr Gly Asp Gln His Gln Val Gly
                420                 425                 430

Asn Glu Thr Thr Glu His Gly Thr Thr Ala Thr Ile Thr Pro Gln Ala
    435                 440                 445

Pro Thr Ser Glu Ile Gln Leu Thr Asp Tyr Gly Ala Leu Thr Leu Asp
    450                 455                 460
```

-continued

```
Cys Ser Pro Arg Thr Gly Leu Asp Phe Asn Glu Met Val Leu Leu Thr
465                 470                 475                 480

Met Glu Lys Lys Ser Trp Leu Val His Lys Gln Trp Phe Leu Asp Leu
                485                 490                 495

Pro Leu Pro Trp Thr Ser Gly Ala Ser Thr Ser Gln Glu Thr Trp Asn
                500                 505                 510

Arg Gln Asp Leu Leu Val Thr Phe Lys Thr Ala His Ala Lys Lys Gln
                515                 520                 525

Glu Val Val Leu Gly Ser Gln Glu Gly Ala Met His Thr Ala Leu
                530                 535                 540

Thr Gly Ala Thr Glu Ile Gln Thr Ser Gly Thr Thr Ile Phe Ala
545                 550                 555                 560

Gly His Leu Lys Cys Arg Leu Lys Met Asp Lys Leu Thr Leu Lys Gly
                565                 570                 575

Met Ser Tyr Val Met Cys Thr Gly Ser Phe Lys Leu Glu Lys Glu Val
                580                 585                 590

Ala Glu Thr Gln His Gly Thr Val Leu Val Gln Val Lys Tyr Glu Gly
                595                 600                 605

Thr Asp Ala Pro Cys Lys Ile Pro Phe Ser Ser Gln Asp Glu Lys Gly
                610                 615                 620

Val Thr Gln Asn Gly Arg Leu Ile Thr Ala Asn Pro Ile Val Thr Asp
625                 630                 635                 640

Lys Glu Lys Pro Val Asn Ile Glu Ala Glu Pro Pro Phe Gly Glu Ser
                645                 650                 655

Tyr Ile Val Val Gly Ala Gly Glu Lys Ala Leu Lys Leu Ser Trp Phe
                660                 665                 670

Lys Lys Gly Ser Ser Ile Gly Lys Met Phe Glu Ala Thr Ala Arg Gly
                675                 680                 685

Ala Arg Arg Met Ala Ile Leu Gly Asp Thr Ala Trp Asp Phe Gly Ser
                690                 695                 700

Ile Gly Gly Val Phe Thr Ser Val Gly Lys Leu Ile His Gln Ile Phe
705                 710                 715                 720

Gly Thr Ala Tyr Gly Val Leu Phe Ser Gly Val Ser Trp Thr Met Lys
                725                 730                 735

Ile Gly Ile Gly Ile Leu Leu Thr Trp Leu Gly Leu Asn Ser Arg Ser
                740                 745                 750

Thr Ser Leu Ser Met Thr Cys Ile Ala Val Gly Met Val Thr Leu Tyr
                755                 760                 765

Leu Gly Val Met Val Gln Ala Asp Ser Gly Cys Val Ile Asn Trp Lys
                770                 775                 780

Gly Arg Glu Leu Lys Cys Gly Ser Gly Ile Phe Val Thr Asn Glu Val
785                 790                 795                 800

His Thr Trp Thr Glu Gln Tyr Lys Phe Gln Ala Asp Ser Pro Lys Arg
                805                 810                 815

Leu Ser Ala Ala Ile Gly Lys Ala Trp Glu Glu Gly Val Cys Gly Ile
                820                 825                 830

Arg Ser Ala Thr Arg Leu Glu Asn Ile Met Trp Lys Gln Ile Ser Asn
                835                 840                 845

Glu Leu Asn His Ile Leu Leu Glu Asn Asp Met Lys Phe Thr Val Val
                850                 855                 860

Val Gly Asp Val Ser Gly Ile Leu Ala Gln Gly Lys Lys Met Ile Arg
865                 870                 875                 880
```

-continued

```
Pro Gln Pro Met Glu His Lys Tyr Ser Trp Lys Ser Trp Gly Lys Ala
                885                 890                 895
Lys Ile Ile Gly Ala Asp Val Gln Asn Thr Thr Phe Ile Ile Asp Gly
            900                 905                 910
Pro Asn Thr Pro Glu Cys Pro Asp Asn Gln Arg Ala Trp Asn Ile Trp
        915                 920                 925
Glu Val Glu Asp Tyr Gly Phe Gly Ile Phe Thr Thr Asn Ile Trp Leu
    930                 935                 940
Lys Leu Arg Asp Ser Tyr Thr Gln Val Cys Asp His Arg Leu Met Ser
945                 950                 955                 960
Ala Ala Ile Lys Asp Ser Lys Ala Val His Ala Asp Met Gly Tyr Trp
                965                 970                 975
Ile Glu Ser Glu Lys Asn Glu Thr Trp Lys Leu Ala Arg Ala Ser Phe
            980                 985                 990
Ile Glu Val Lys Thr Cys Ile Trp Pro Lys Ser His Thr Leu Trp Ser
        995                 1000                1005
Asn Gly Val Leu Glu Ser Glu Met Ile Ile Pro Lys Ile Tyr Gly Gly
    1010                1015                1020
Pro Ile Ser Gln His Asn Tyr Arg Pro Gly Tyr Phe Thr Gln Thr Ala
1025                1030                1035                1040
Gly Pro Trp His Leu Gly Lys Leu Glu Leu Asp Phe Asp Leu Cys Glu
                1045                1050                1055
Gly Thr Thr Val Val Asp Glu His Cys Gly Asn Arg Gly Pro Ser
            1060                1065                1070
Leu Arg Thr Thr Thr Val Thr Gly Lys Thr Ile His Glu Trp Cys Cys
        1075                1080                1085
Arg Ser Cys Thr Leu Pro Pro Leu Arg Phe Lys Gly Glu Asp Gly Cys
    1090                1095                1100
Trp Tyr Gly Met Glu Ile Arg Pro Val Lys Glu Lys Glu Glu Asn Leu
1105                1110                1115                1120
Val Lys Ser Met Val Ser Ala Gly Ser Gly Glu Val Asp Ser Phe Ser
                1125                1130                1135
Leu Gly Leu Leu Cys Ile Ser Ile Met Ile Glu Glu Val Met Arg Ser
            1140                1145                1150
Arg Trp Ser Arg Lys Met Leu Met Thr Gly Thr Leu Ala Val Phe Leu
        1155                1160                1165
Leu Leu Thr Met Gly Gln Leu Thr Trp Asn Asp Leu Ile Arg Leu Cys
    1170                1175                1180
Ile Met Val Gly Ala Asn Ala Ser Asp Lys Met Gly Met Gly Thr Thr
1185                1190                1195                1200
Tyr Leu Ala Leu Met Ala Thr Phe Arg Met Arg Pro Met Phe Ala Val
                1205                1210                1215
Gly Leu Leu Phe Arg Arg Leu Thr Ser Arg Glu Val Leu Leu Leu Thr
            1220                1225                1230
Val Gly Leu Ser Leu Val Ala Ser Val Glu Leu Pro Asn Ser Leu Glu
        1235                1240                1245
Glu Leu Gly Asp Gly Leu Ala Met Gly Ile Met Met Leu Lys Leu Leu
    1250                1255                1260
Thr Asp Phe Gln Ser His Gln Leu Trp Ala Thr Leu Leu Ser Leu Thr
1265                1270                1275                1280
Phe Val Lys Thr Thr Phe Ser Leu His Tyr Ala Trp Lys Thr Met Ala
                1285                1290                1295
Met Ile Leu Ser Ile Val Ser Leu Phe Pro Leu Cys Leu Ser Thr Thr
```

```
                1300                1305                1310
Ser Gln Lys Thr Thr Trp Leu Pro Val Leu Leu Gly Ser Leu Gly Cys
        1315                1320                1325

Lys Pro Leu Thr Met Phe Leu Ile Thr Glu Asn Lys Ile Trp Gly Arg
        1330                1335            1340

Lys Ser Trp Pro Leu Asn Glu Gly Ile Met Ala Val Gly Ile Val Ser
1345                1350                1355                1360

Ile Leu Leu Ser Ser Leu Leu Lys Asn Asp Val Pro Leu Ala Gly Pro
                1365                1370                1375

Leu Ile Ala Gly Gly Met Leu Ile Ala Cys Tyr Val Ile Ser Gly Ser
            1380                1385                1390

Ser Ala Asp Leu Ser Leu Glu Lys Ala Ala Glu Val Ser Trp Glu Glu
        1395                1400                1405

Glu Ala Glu His Ser Gly Ala Ser His Asn Ile Leu Glu Val Gln
    1410                1415                1420

Asp Asp Gly Thr Met Lys Ile Lys Asp Glu Arg Asp Asp Thr Leu
1425                1430                1435                1440

Thr Ile Leu Leu Lys Ala Thr Leu Leu Ala Ile Ser Gly Val Tyr Pro
                1445                1450                1455

Met Ser Ile Pro Ala Thr Leu Phe Val Trp Tyr Phe Trp Gln Lys Lys
            1460                1465                1470

Lys Gln Arg Ser Gly Val Leu Trp Asp Thr Pro Ser Pro Pro Glu Val
        1475                1480                1485

Glu Arg Ala Val Leu Asp Asp Gly Ile Tyr Arg Ile Leu Gln Arg Gly
        1490                1495                1500

Leu Leu Gly Arg Ser Gln Val Gly Val Gly Val Phe Gln Glu Gly Val
1505                1510                1515                1520

Phe His Thr Met Trp His Val Thr Arg Gly Ala Val Leu Met Tyr Gln
                1525                1530                1535

Gly Lys Arg Leu Glu Pro Ser Trp Ala Ser Val Lys Lys Asp Leu Ile
            1540                1545                1550

Ser Tyr Gly Gly Gly Trp Arg Phe Gln Gly Ser Trp Asn Ala Gly Glu
        1555                1560                1565

Glu Val Gln Val Ile Ala Val Glu Pro Gly Lys Asn Pro Lys Asn Val
    1570                1575                1580

Gln Thr Ala Pro Gly Thr Phe Lys Thr Pro Glu Gly Glu Val Gly Ala
1585                1590                1595                1600

Ile Ala Leu Asp Phe Lys Pro Gly Thr Ser Gly Ser Pro Ile Val Asn
                1605                1610                1615

Arg Glu Gly Lys Ile Val Gly Leu Tyr Gly Asn Gly Val Val Thr Thr
            1620                1625                1630

Ser Gly Thr Tyr Val Ser Ala Ile Ala Gln Ala Lys Ala Ser Gln Glu
        1635                1640                1645

Gly Pro Leu Pro Glu Ile Glu Asp Glu Val Phe Arg Lys Arg Asn Leu
    1650                1655                1660

Thr Ile Met Asp Leu His Pro Gly Ser Gly Lys Thr Arg Arg Tyr Leu
1665                1670                1675                1680

Pro Ala Ile Val Arg Glu Ala Ile Arg Arg Asn Val Arg Thr Leu Val
                1685                1690                1695

Leu Ala Pro Thr Arg Val Val Ala Ser Glu Met Ala Glu Ala Leu Lys
            1700                1705                1710

Gly Met Pro Ile Arg Tyr Gln Thr Thr Ala Val Lys Ser Glu His Thr
        1715                1720                1725
```

```
Gly Lys Glu Ile Val Asp Leu Met Cys His Ala Thr Phe Thr Met Arg
    1730                1735                1740

Leu Leu Ser Pro Val Arg Val Pro Asn Tyr Asn Met Ile Ile Met Asp
1745                1750                1755                1760

Glu Ala His Phe Thr Asp Pro Ala Ser Ile Ala Ala Arg Gly Tyr Ile
                1765                1770                1775

Ser Thr Arg Val Gly Met Gly Glu Ala Ala Ile Phe Met Thr Ala
            1780                1785                1790

Thr Pro Pro Gly Ser Val Glu Ala Phe Pro Gln Ser Asn Ala Val Ile
            1795                1800                1805

Gln Asp Glu Glu Arg Asp Ile Pro Glu Arg Ser Trp Asn Ser Gly Tyr
            1810                1815                1820

Asp Trp Ile Thr Asp Phe Pro Gly Lys Thr Val Trp Phe Val Pro Ser
1825                1830                1835                1840

Ile Lys Ser Gly Asn Asp Ile Ala Asn Cys Leu Arg Lys Asn Gly Lys
                1845                1850                1855

Arg Val Val Gln Leu Ser Arg Lys Thr Phe Asp Thr Glu Tyr Gln Lys
            1860                1865                1870

Thr Lys Asn Asn Asp Trp Asp Tyr Val Val Thr Thr Asp Ile Ser Glu
            1875                1880                1885

Met Gly Ala Asn Phe Arg Ala Asp Arg Val Ile Asp Pro Arg Arg Cys
    1890                1895                1900

Leu Lys Pro Val Ile Leu Lys Asp Gly Pro Glu Arg Val Ile Leu Ala
1905                1910                1915                1920

Gly Pro Met Pro Val Thr Val Ala Ser Ala Ala Gln Arg Arg Gly Arg
            1925                1930                1935

Ile Gly Arg Asn Gln Asn Lys Glu Gly Asp Gln Tyr Ile Tyr Met Gly
            1940                1945                1950

Gln Pro Leu Asn Asn Asp Glu Asp His Ala His Trp Thr Glu Ala Lys
            1955                1960                1965

Met Leu Leu Asp Asn Ile Asn Thr Pro Glu Gly Ile Ile Pro Ala Leu
    1970                1975                1980

Phe Glu Pro Glu Arg Glu Lys Ser Ala Ala Ile Asp Gly Glu Tyr Arg
1985                1990                1995                2000

Leu Arg Gly Glu Ala Arg Lys Thr Phe Val Glu Leu Met Arg Arg Gly
                2005                2010                2015

Asp Leu Pro Val Trp Leu Ser Tyr Lys Val Ala Ser Glu Gly Phe Gln
            2020                2025                2030

Tyr Ser Asp Arg Arg Trp Cys Phe Asp Gly Glu Arg Asn Asn Gln Val
            2035                2040                2045

Leu Glu Glu Asn Met Asp Val Glu Ile Trp Thr Lys Glu Gly Glu Arg
    2050                2055                2060

Lys Lys Leu Arg Pro Arg Trp Leu Asp Ala Arg Thr Tyr Ser Asp Pro
2065                2070                2075                2080

Leu Ala Leu Arg Glu Phe Lys Glu Phe Ala Ala Gly Arg Arg Ser Val
                2085                2090                2095

Ser Gly Asp Leu Ile Leu Glu Ile Gly Lys Leu Pro Gln His Leu Thr
            2100                2105                2110

Gln Arg Ala Gln Asn Ala Leu Asp Asn Leu Val Met Leu His Asn Ser
            2115                2120                2125

Glu Gln Gly Gly Lys Ala Tyr Arg His Ala Met Glu Glu Leu Pro Asp
    2130                2135                2140
```

-continued

```
Thr Ile Glu Thr Leu Met Leu Ala Leu Ile Ala Val Leu Thr Gly
2145                2150                2155                2160

Gly Val Thr Leu Phe Phe Leu Ser Gly Arg Gly Leu Gly Lys Thr Ser
            2165                2170                2175

Ile Gly Leu Leu Cys Val Ile Ala Ser Ser Ala Leu Leu Trp Met Ala
        2180                2185                2190

Ser Val Glu Pro His Trp Ile Ala Ala Ser Ile Ile Leu Glu Phe Phe
        2195                2200                2205

Leu Met Val Leu Leu Ile Pro Glu Pro Asp Arg Gln Arg Thr Pro Gln
    2210                2215                2220

Asp Asn Gln Leu Ala Tyr Val Val Ile Gly Leu Leu Phe Met Ile Leu
2225                2230                2235                2240

Thr Ala Ala Ala Asn Glu Met Gly Leu Leu Glu Thr Thr Lys Lys Asp
                2245                2250                2255

Leu Gly Ile Gly His Ala Ala Ala Glu Asn His His His Ala Ala Met
                2260                2265                2270

Leu Asp Val Asp Leu His Pro Ala Ser Ala Trp Thr Leu Tyr Ala Val
            2275                2280                2285

Ala Thr Thr Ile Ile Thr Pro Met Met Arg His Thr Ile Glu Asn Thr
    2290                2295                2300

Thr Ala Asn Ile Ser Leu Thr Ala Ile Ala Asn Gln Ala Ala Ile Leu
2305                2310                2315                2320

Met Gly Leu Asp Lys Gly Trp Pro Ile Ser Lys Met Asp Ile Gly Val
            2325                2330                2335

Pro Leu Leu Ala Leu Gly Cys Tyr Ser Gln Val Asn Pro Leu Thr Leu
        2340                2345                2350

Thr Ala Ala Val Phe Met Leu Val Ala His Tyr Ala Ile Ile Gly Pro
        2355                2360                2365

Gly Leu Gln Ala Lys Ala Thr Arg Glu Ala Gln Lys Arg Thr Ala Ala
    2370                2375                2380

Gly Ile Met Lys Asn Pro Thr Val Asp Gly Ile Val Ala Ile Asp Leu
2385                2390                2395                2400

Asp Pro Val Val Tyr Asp Ala Lys Phe Glu Lys Gln Leu Gly Gln Ile
                2405                2410                2415

Met Leu Leu Ile Leu Cys Thr Ser Gln Ile Leu Leu Met Arg Thr Thr
            2420                2425                2430

Trp Ala Leu Cys Glu Ser Ile Thr Leu Ala Thr Gly Pro Leu Thr Thr
            2435                2440                2445

Leu Trp Glu Gly Ser Pro Gly Lys Phe Trp Asn Thr Thr Ile Ala Val
    2450                2455                2460

Ser Met Ala Asn Ile Phe Arg Gly Ser Tyr Leu Ala Gly Ala Gly Leu
2465                2470                2475                2480

Ala Phe Ser Leu Met Lys Ser Leu Gly Gly Gly Arg Arg Gly Thr Gly
            2485                2490                2495

Ala Gln Gly Glu Thr Leu Gly Glu Lys Trp Lys Arg Gln Leu Asn Gln
        2500                2505                2510

Leu Ser Lys Ser Glu Phe Asn Thr Tyr Lys Arg Ser Gly Ile Ile Glu
        2515                2520                2525

Val Asp Arg Ser Glu Ala Lys Glu Gly Leu Lys Arg Gly Glu Pro Thr
    2530                2535                2540

Lys His Ala Val Ser Arg Gly Thr Ala Lys Leu Arg Trp Phe Val Glu
2545                2550                2555                2560

Arg Asn Leu Val Lys Pro Glu Gly Lys Val Ile Asp Leu Gly Cys Gly
```

-continued

```
            2565                2570                2575
Arg Gly Gly Trp Ser Tyr Tyr Cys Ala Gly Leu Lys Lys Val Thr Glu
            2580                2585                2590

Val Lys Gly Tyr Thr Lys Gly Gly Pro Gly His Glu Glu Pro Ile Pro
            2595                2600                2605

Met Ala Thr Tyr Gly Trp Asn Leu Val Lys Leu Tyr Ser Gly Lys Asp
            2610                2615                2620

Val Phe Phe Thr Pro Pro Glu Lys Cys Asp Thr Leu Leu Cys Asp Ile
2625                2630                2635                2640

Gly Glu Ser Ser Pro Asn Pro Thr Ile Glu Glu Gly Arg Thr Leu Arg
            2645                2650                2655

Val Leu Lys Met Val Glu Pro Trp Leu Arg Gly Asn Gln Phe Cys Ile
            2660                2665                2670

Lys Ile Leu Asn Pro Tyr Met Pro Ser Val Val Glu Thr Leu Glu Gln
            2675                2680                2685

Met Gln Arg Lys His Gly Gly Met Leu Val Arg Asn Pro Leu Ser Arg
            2690                2695                2700

Asn Ser Thr His Glu Met Tyr Trp Val Ser Cys Gly Thr Gly Asn Ile
2705                2710                2715                2720

Val Ser Ala Val Asn Met Thr Ser Arg Met Leu Leu Asn Arg Phe Thr
            2725                2730                2735

Met Ala His Arg Lys Pro Thr Tyr Glu Arg Asp Val Asp Leu Gly Ala
            2740                2745                2750

Gly Thr Arg His Val Ala Val Glu Pro Glu Val Ala Asn Leu Asp Ile
            2755                2760                2765

Ile Gly Gln Arg Ile Glu Asn Ile Lys Asn Gly His Lys Ser Thr Trp
            2770                2775                2780

His Tyr Asp Glu Asp Asn Pro Tyr Lys Thr Trp Ala Tyr His Gly Ser
2785                2790                2795                2800

Tyr Glu Val Lys Pro Ser Gly Ser Ala Ser Ser Met Val Asn Gly Val
            2805                2810                2815

Val Arg Leu Leu Thr Lys Pro Trp Asp Val Ile Pro Met Val Thr Gln
            2820                2825                2830

Ile Ala Met Thr Asp Thr Thr Pro Phe Gly Gln Gln Arg Val Phe Lys
            2835                2840                2845

Glu Lys Val Asp Thr Arg Thr Pro Lys Ala Lys Arg Gly Thr Ala Gln
            2850                2855                2860

Ile Met Glu Val Thr Ala Arg Trp Leu Trp Gly Phe Leu Ser Arg Asn
2865                2870                2875                2880

Lys Lys Pro Arg Ile Cys Thr Arg Glu Glu Phe Thr Arg Lys Val Arg
            2885                2890                2895

Ser Asn Ala Ala Ile Gly Ala Val Phe Val Asp Glu Asn Gln Trp Asn
            2900                2905                2910

Ser Ala Lys Glu Ala Val Glu Asp Glu Arg Phe Trp Asp Leu Val His
            2915                2920                2925

Arg Glu Arg Glu Leu His Lys Gln Gly Lys Cys Ala Thr Cys Val Tyr
            2930                2935                2940

Asn Met Met Gly Lys Arg Glu Lys Lys Leu Gly Glu Phe Gly Lys Ala
2945                2950                2955                2960

Lys Gly Ser Arg Ala Ile Trp Tyr Met Trp Leu Gly Ala Arg Phe Leu
            2965                2970                2975

Glu Phe Glu Ala Leu Gly Phe Met Asn Glu Asp His Trp Phe Ser Arg
            2980                2985                2990
```

-continued

```
Glu Asn Ser Leu Ser Gly Val Glu Gly Glu Gly Leu His Lys Leu Gly
            2995                3000                3005
Tyr Ile Leu Arg Asp Ile Ser Lys Ile Pro Gly Gly Asn Met Tyr Ala
        3010                3015                3020
Asp Asp Thr Ala Gly Trp Asp Thr Arg Ile Thr Glu Asp Asp Leu Gln
3025                3030                3035                3040
Asn Glu Ala Lys Ile Thr Asp Ile Met Glu Pro Glu His Ala Leu Leu
            3045                3050                3055
Ala Thr Ser Ile Phe Lys Leu Thr Tyr Gln Asn Lys Val Val Arg Val
            3060                3065                3070
Gln Arg Pro Ala Lys Asn Gly Thr Val Met Asp Val Ile Ser Arg Arg
            3075                3080                3085
Asp Gln Arg Gly Ser Gly Gln Val Gly Thr Tyr Gly Leu Asn Thr Phe
            3090                3095                3100
Thr Asn Met Glu Ala Gln Leu Ile Arg Gln Met Glu Ser Gly Ile
3105                3110                3115                3120
Phe Ser Pro Ser Glu Leu Glu Thr Pro Asn Leu Ala Glu Arg Val Leu
            3125                3130                3135
Asp Trp Leu Lys Lys His Gly Thr Glu Arg Leu Lys Arg Met Ala Ile
            3140                3145                3150
Ser Gly Asp Asp Cys Val Val Lys Pro Ile Asp Asp Arg Phe Ala Thr
            3155                3160                3165
Ala Leu Thr Ala Leu Asn Asp Met Gly Lys Val Arg Lys Asp Ile Pro
            3170                3175                3180
Gln Trp Glu Pro Ser Lys Gly Trp Asn Asp Trp Gln Gln Val Pro Phe
3185                3190                3195                3200
Cys Ser His His Phe His Gln Leu Ile Met Lys Asp Gly Arg Glu Ile
            3205                3210                3215
Val Val Pro Cys Arg Asn Gln Asp Glu Leu Val Gly Arg Ala Arg Val
            3220                3225                3230
Ser Gln Gly Ala Gly Trp Ser Leu Arg Glu Thr Ala Cys Leu Gly Lys
            3235                3240                3245
Ser Tyr Ala Gln Met Trp Gln Leu Met Tyr Phe His Arg Arg Asp Leu
            3250                3255                3260
Arg Leu Ala Ala Asn Ala Ile Cys Ser Ala Val Pro Val Asp Trp Val
3265                3270                3275                3280
Pro Thr Ser Arg Thr Thr Trp Ser Ile His Ala His His Gln Trp Met
            3285                3290                3295
Thr Thr Glu Asp Met Leu Ser Val Trp Asn Arg Val Trp Ile Glu Glu
            3300                3305                3310
Asn Pro Trp Met Glu Asp Lys Thr His Val Ser Ser Trp Glu Asp Val
            3315                3320                3325
Pro Tyr Leu Gly Lys Arg Glu Asp Arg Trp Cys Gly Ser Leu Ile Gly
            3330                3335                3340
Leu Thr Ala Arg Ala Thr Trp Ala Thr Asn Ile Gln Val Ala Ile Asn
3345                3350                3355                3360
Gln Val Arg Arg Leu Ile Gly Asn Glu Asn Tyr Leu Asp Phe Met Thr
            3365                3370                3375
Ser Met Lys Arg Phe Lys Asn Glu Ser Asp Pro Glu Gly Ala Leu Trp
            3380                3385                3390
```

<210> SEQ ID NO 21
<211> LENGTH: 3391

<212> TYPE: PRT
<213> ORGANISM: Dengue 2 virus strain NGC

<400> SEQUENCE: 21

```
Met Asn Asn Gln Arg Lys Lys Ala Arg Asn Thr Pro Phe Asn Met Leu
 1               5                  10                  15

Lys Arg Glu Arg Asn Arg Val Ser Thr Val Gln Gln Leu Thr Lys Arg
            20                  25                  30

Phe Ser Leu Gly Met Leu Gln Gly Arg Gly Pro Leu Lys Leu Phe Met
        35                  40                  45

Ala Leu Val Ala Phe Leu Arg Phe Leu Thr Ile Pro Pro Thr Ala Gly
    50                  55                  60

Ile Leu Lys Arg Trp Gly Thr Ile Lys Ser Lys Ala Ile Asn Val
65                  70                  75                  80

Leu Arg Gly Phe Arg Lys Glu Ile Gly Arg Met Leu Asn Ile Leu Asn
                85                  90                  95

Arg Arg Arg Arg Thr Ala Gly Met Ile Ile Met Leu Ile Pro Thr Val
            100                 105                 110

Met Ala Phe His Leu Thr Thr Arg Asn Gly Glu Pro His Met Ile Val
        115                 120                 125

Ser Arg Gln Glu Lys Gly Lys Ser Leu Leu Phe Lys Thr Glu Asp Gly
    130                 135                 140

Val Asn Met Cys Thr Leu Met Ala Met Asp Leu Gly Glu Leu Cys Glu
145                 150                 155                 160

Asp Thr Ile Thr Tyr Lys Cys Pro Phe Leu Arg Gln Asn Glu Pro Glu
                165                 170                 175

Asp Ile Asp Cys Trp Cys Asn Ser Thr Ser Thr Trp Val Thr Tyr Gly
            180                 185                 190

Thr Cys Thr Thr Thr Gly Glu His Arg Arg Glu Lys Arg Ser Val Ala
        195                 200                 205

Leu Val Pro His Val Gly Met Gly Leu Glu Thr Arg Thr Glu Thr Trp
    210                 215                 220

Met Ser Ser Glu Gly Ala Trp Lys His Ala Gln Arg Ile Glu Thr Trp
225                 230                 235                 240

Ile Leu Arg His Pro Gly Phe Thr Ile Met Ala Ala Ile Leu Ala Tyr
                245                 250                 255

Thr Ile Gly Thr Thr His Phe Gln Arg Ala Leu Ile Phe Ile Leu Leu
            260                 265                 270

Thr Ala Val Ala Pro Ser Met Thr Met Arg Cys Ile Gly Ile Ser Asn
        275                 280                 285

Arg Asp Phe Val Glu Gly Val Ser Gly Gly Ser Trp Val Asp Ile Val
    290                 295                 300

Leu Glu His Gly Ser Cys Val Thr Thr Met Ala Lys Asn Lys Pro Thr
305                 310                 315                 320

Leu Asp Phe Glu Leu Ile Lys Thr Glu Ala Lys Gln Pro Ala Thr Leu
                325                 330                 335

Arg Lys Tyr Cys Ile Glu Ala Lys Leu Thr Asn Thr Thr Thr Asp Ser
            340                 345                 350

Arg Cys Pro Thr Gln Gly Glu Pro Ser Leu Asn Glu Glu Gln Asp Lys
        355                 360                 365

Arg Phe Val Cys Lys His Ser Met Val Asp Arg Gly Trp Gly Asn Gly
    370                 375                 380

Cys Gly Leu Phe Gly Lys Gly Gly Ile Val Thr Cys Ala Met Phe Thr
385                 390                 395                 400
```

```
Cys Lys Lys Asn Met Lys Gly Lys Val Val Gln Pro Glu Asn Leu Glu
            405                 410                 415

Tyr Thr Ile Val Ile Thr Pro His Ser Gly Glu Glu His Ala Val Gly
            420                 425                 430

Asn Asp Thr Gly Lys His Gly Lys Glu Ile Lys Ile Thr Pro Gln Ser
            435                 440                 445

Ser Ile Thr Glu Ala Glu Leu Thr Gly Tyr Gly Thr Val Thr Met Glu
    450                 455                 460

Cys Ser Pro Arg Thr Gly Leu Asp Phe Asn Glu Met Val Leu Leu Gln
465                 470                 475                 480

Met Glu Asn Lys Ala Trp Leu Val His Arg Gln Trp Phe Leu Asp Leu
            485                 490                 495

Pro Leu Pro Trp Leu Pro Gly Ala Asp Thr Gln Gly Ser Asn Trp Ile
            500                 505                 510

Gln Lys Glu Thr Leu Val Thr Phe Lys Asn Pro His Ala Lys Lys Gln
            515                 520                 525

Asp Val Val Leu Gly Ser Gln Glu Gly Ala Met His Thr Ala Leu
            530                 535                 540

Thr Gly Ala Thr Glu Ile Gln Met Ser Ser Gly Asn Leu Leu Phe Thr
545                 550                 555                 560

Gly His Leu Lys Cys Arg Leu Arg Met Asp Lys Leu Gln Leu Lys Gly
            565                 570                 575

Met Ser Tyr Ser Met Cys Thr Gly Lys Phe Lys Val Val Lys Glu Ile
            580                 585                 590

Ala Glu Thr Gln His Gly Thr Ile Val Ile Arg Val Gln Tyr Glu Gly
            595                 600                 605

Asp Gly Ser Pro Cys Lys Ile Pro Phe Glu Ile Met Asp Leu Glu Lys
            610                 615                 620

Arg His Val Leu Gly Arg Leu Ile Thr Val Asn Pro Ile Val Thr Glu
625                 630                 635                 640

Lys Asp Ser Pro Val Asn Ile Glu Ala Glu Pro Pro Phe Gly Asp Ser
            645                 650                 655

Tyr Ile Ile Ile Gly Val Glu Pro Gly Gln Leu Lys Leu Asn Trp Phe
            660                 665                 670

Lys Lys Gly Ser Ser Ile Gly Gln Met Ile Glu Thr Thr Met Arg Gly
            675                 680                 685

Ala Lys Arg Met Ala Ile Leu Gly Asp Thr Ala Trp Asp Phe Gly Ser
            690                 695                 700

Leu Gly Gly Val Phe Thr Ser Ile Gly Lys Ala Leu His Gln Val Phe
705                 710                 715                 720

Gly Ala Ile Tyr Gly Ala Ala Phe Ser Gly Val Ser Trp Thr Met Lys
            725                 730                 735

Ile Leu Ile Gly Val Ile Ile Thr Trp Ile Gly Met Asn Ser Arg Ser
            740                 745                 750

Thr Ser Leu Ser Val Ser Leu Val Leu Val Gly Val Val Thr Leu Tyr
            755                 760                 765

Leu Gly Val Met Val Gln Ala Asp Ser Gly Cys Val Val Ser Trp Lys
            770                 775                 780

Asn Lys Glu Leu Lys Cys Gly Ser Gly Ile Phe Ile Thr Asp Asn Val
785                 790                 795                 800

His Thr Trp Thr Glu Gln Tyr Lys Phe Gln Pro Glu Ser Pro Ser Lys
            805                 810                 815
```

-continued

```
Leu Ala Ser Ala Ile Gln Lys Ala His Glu Glu Gly Ile Cys Gly Ile
            820                 825                 830
Arg Ser Val Thr Arg Leu Glu Asn Leu Met Trp Lys Gln Ile Thr Pro
        835                 840                 845
Glu Leu Asn His Ile Leu Ser Glu Asn Glu Val Lys Leu Thr Ile Met
    850                 855                 860
Thr Gly Asp Ile Lys Gly Ile Met Gln Ala Gly Lys Arg Ser Leu Gln
865                 870                 875                 880
Pro Gln Pro Thr Glu Leu Lys Tyr Ser Trp Lys Thr Trp Gly Lys Ala
                885                 890                 895
Lys Met Leu Ser Thr Glu Ser His Asn Gln Thr Phe Leu Ile Asp Gly
            900                 905                 910
Pro Glu Thr Ala Glu Cys Pro Asn Thr Asn Arg Ala Trp Asn Ser Leu
        915                 920                 925
Glu Val Glu Asp Tyr Gly Phe Gly Val Phe Thr Thr Asn Ile Trp Leu
    930                 935                 940
Lys Leu Arg Glu Lys Gln Asp Val Phe Cys Asp Ser Lys Leu Met Ser
945                 950                 955                 960
Ala Ala Ile Lys Asp Asn Arg Ala Val His Ala Asp Met Gly Tyr Trp
                965                 970                 975
Ile Glu Ser Ala Leu Asn Asp Thr Trp Lys Ile Glu Lys Ala Ser Phe
            980                 985                 990
Ile Glu Val Lys Ser Cys His Trp Pro Lys Ser His Thr Leu Trp Ser
        995                 1000                1005
Asn Gly Val Leu Glu Ser Glu Met Ile Ile Pro Lys Asn Phe Ala Gly
    1010                1015                1020
Pro Val Ser Gln His Asn Tyr Arg Pro Gly Tyr His Thr Gln Thr Ala
1025                1030                1035                1040
Gly Pro Trp His Leu Gly Lys Leu Glu Met Asp Phe Asp Phe Cys Glu
                1045                1050                1055
Gly Thr Thr Val Val Val Thr Glu Asp Cys Gly Asn Arg Gly Pro Ser
            1060                1065                1070
Leu Arg Thr Thr Thr Ala Ser Gly Lys Leu Ile Thr Glu Trp Cys Cys
        1075                1080                1085
Arg Ser Cys Thr Leu Pro Pro Leu Arg Tyr Arg Gly Glu Asp Gly Cys
    1090                1095                1100
Trp Tyr Gly Met Glu Ile Arg Pro Leu Lys Glu Lys Glu Glu Asn Leu
1105                1110                1115                1120
Val Asn Ser Leu Val Thr Ala Gly His Gly Gln Ile Asp Asn Phe Ser
                1125                1130                1135
Leu Gly Val Leu Gly Met Ala Leu Phe Leu Glu Glu Met Leu Arg Thr
            1140                1145                1150
Arg Val Gly Thr Lys His Ala Ile Leu Leu Val Ala Val Ser Phe Val
        1155                1160                1165
Thr Leu Ile Thr Gly Asn Met Ser Phe Arg Asp Leu Gly Arg Val Met
    1170                1175                1180
Val Met Val Gly Ala Thr Met Thr Asp Asp Ile Gly Met Gly Val Thr
1185                1190                1195                1200
Tyr Leu Ala Leu Leu Ala Ala Phe Lys Val Arg Pro Thr Phe Ala Ala
                1205                1210                1215
Gly Leu Leu Leu Arg Lys Leu Thr Ser Lys Glu Leu Met Met Thr Thr
            1220                1225                1230
Ile Gly Ile Val Leu Leu Ser Gln Ser Thr Ile Pro Glu Thr Ile Leu
```

-continued

```
            1235                1240                1245
Glu Leu Thr Asp Ala Leu Ala Leu Gly Met Met Val Leu Lys Met Val
    1250                1255                1260
Arg Lys Met Glu Lys Tyr Gln Leu Ala Val Thr Ile Met Ala Ile Leu
1265                1270                1275                1280
Cys Val Pro Asn Ala Val Ile Leu Gln Asn Ala Trp Lys Val Ser Cys
            1285                1290                1295
Thr Ile Leu Ala Val Val Ser Val Ser Pro Leu Phe Leu Thr Ser Ser
                1300                1305                1310
Gln Gln Lys Ala Asp Trp Ile Pro Leu Ala Leu Thr Ile Lys Gly Leu
        1315                1320                1325
Asn Pro Thr Ala Ile Phe Leu Thr Thr Leu Ser Arg Thr Asn Lys Lys
    1330                1335                1340
Arg Ser Trp Pro Leu Asn Glu Ala Ile Met Ala Val Gly Met Val Ser
1345                1350                1355                1360
Ile Leu Ala Ser Ser Leu Leu Lys Asn Asp Ile Pro Met Thr Gly Pro
            1365                1370                1375
Leu Val Ala Gly Gly Leu Leu Thr Val Cys Tyr Val Leu Thr Gly Arg
            1380                1385                1390
Ser Ala Asp Leu Glu Leu Glu Arg Ala Ala Asp Val Lys Trp Glu Asp
            1395                1400                1405
Gln Ala Glu Ile Ser Gly Ser Ser Pro Ile Leu Ser Ile Thr Ile Ser
    1410                1415                1420
Glu Asp Gly Ser Met Ser Ile Lys Asn Glu Glu Glu Gln Thr Leu
1425                1430                1435                1440
Thr Ile Leu Ile Arg Thr Gly Leu Leu Val Ile Ser Gly Leu Phe Pro
                1445                1450                1455
Val Ser Ile Pro Ile Thr Ala Ala Ala Trp Tyr Leu Trp Glu Val Lys
            1460                1465                1470
Lys Gln Arg Ala Gly Val Leu Trp Asp Val Pro Ser Pro Pro Pro Val
        1475                1480                1485
Gly Lys Ala Glu Leu Glu Asp Gly Ala Tyr Arg Ile Lys Gln Lys Gly
    1490                1495                1500
Ile Leu Gly Tyr Ser Gln Ile Gly Ala Gly Val Tyr Lys Glu Gly Thr
1505                1510                1515                1520
Phe His Thr Met Trp His Val Thr Arg Gly Ala Val Leu Met His Lys
            1525                1530                1535
Gly Lys Arg Ile Glu Pro Ser Trp Ala Asp Val Lys Lys Asp Leu Ile
        1540                1545                1550
Ser Tyr Gly Gly Gly Trp Lys Leu Glu Gly Glu Trp Lys Glu Gly Glu
        1555                1560                1565
Glu Val Gln Val Leu Ala Leu Glu Pro Gly Lys Asn Pro Arg Ala Val
    1570                1575                1580
Gln Thr Lys Pro Gly Leu Phe Lys Thr Asn Ala Gly Thr Ile Gly Ala
1585                1590                1595                1600
Val Ser Leu Asp Phe Ser Pro Gly Thr Ser Gly Ser Pro Ile Ile Asp
            1605                1610                1615
Lys Lys Gly Lys Val Val Gly Leu Tyr Gly Asn Gly Val Val Thr Arg
            1620                1625                1630
Ser Gly Ala Tyr Val Ser Ala Ile Ala Gln Thr Glu Lys Ser Ile Glu
        1635                1640                1645
Asp Asn Pro Glu Ile Glu Asp Asp Ile Phe Arg Lys Arg Lys Leu Thr
    1650                1655                1660
```

```
Ile Met Asp Leu His Pro Gly Ala Gly Lys Thr Lys Arg Tyr Leu Pro
1665                1670                1675                1680

Ala Ile Val Arg Glu Ala Ile Lys Arg Gly Leu Arg Thr Leu Ile Leu
                1685                1690                1695

Ala Pro Thr Arg Val Val Ala Ala Glu Met Glu Ala Leu Arg Gly
            1700                1705                1710

Leu Pro Ile Arg Tyr Gln Thr Pro Ala Ile Arg Ala Glu His Thr Gly
            1715                1720                1725

Arg Glu Ile Val Asp Leu Met Cys His Ala Thr Phe Thr Met Arg Leu
1730                1735                1740

Leu Ser Pro Val Arg Val Pro Asn Tyr Asn Leu Ile Ile Met Asp Glu
1745                1750                1755                1760

Ala His Phe Thr Asp Pro Ala Ser Ile Ala Ala Arg Gly Tyr Ile Ser
                1765                1770                1775

Thr Arg Val Glu Met Gly Glu Ala Ala Gly Ile Phe Met Thr Ala Thr
            1780                1785                1790

Pro Pro Gly Ser Arg Asp Pro Phe Pro Gln Ser Asn Ala Pro Ile Met
            1795                1800                1805

Asp Glu Glu Arg Glu Ile Pro Glu Arg Ser Trp Ser Ser Gly His Glu
1810                1815                1820

Trp Val Thr Asp Phe Lys Gly Lys Thr Val Trp Phe Val Pro Ser Ile
1825                1830                1835                1840

Lys Ala Gly Asn Asp Ile Ala Ala Cys Leu Arg Lys Asn Gly Lys Lys
                1845                1850                1855

Val Ile Gln Leu Ser Arg Lys Thr Phe Asp Ser Glu Tyr Val Lys Thr
            1860                1865                1870

Arg Thr Asn Asp Trp Asp Phe Val Val Thr Thr Asp Ile Ser Glu Met
            1875                1880                1885

Gly Ala Asn Phe Lys Ala Glu Arg Val Ile Asp Pro Arg Arg Cys Met
1890                1895                1900

Lys Pro Val Ile Leu Thr Asp Gly Glu Glu Arg Val Ile Leu Ala Gly
1905                1910                1915                1920

Pro Met Pro Val Thr His Ser Ser Ala Ala Gln Arg Arg Gly Arg Ile
            1925                1930                1935

Gly Arg Asn Pro Lys Asn Glu Asn Asp Gln Tyr Ile Tyr Met Gly Glu
            1940                1945                1950

Pro Leu Glu Asn Asp Glu Asp Cys Ala His Trp Lys Glu Ala Lys Met
            1955                1960                1965

Leu Leu Asp Asn Ile Asn Thr Pro Glu Gly Ile Ile Pro Ser Met Phe
1970                1975                1980

Glu Pro Glu Arg Glu Lys Val Asp Ala Ile Asp Gly Glu Tyr Arg Leu
1985                1990                1995                2000

Arg Gly Glu Ala Arg Lys Thr Phe Val Asp Leu Met Arg Arg Gly Asp
                2005                2010                2015

Leu Pro Val Trp Leu Ala Tyr Arg Val Ala Ala Glu Gly Ile Asn Tyr
            2020                2025                2030

Ala Asp Arg Arg Trp Cys Phe Asp Gly Ile Lys Asn Asn Gln Ile Leu
            2035                2040                2045

Glu Glu Asn Val Glu Val Glu Ile Trp Thr Lys Glu Gly Glu Arg Lys
            2050                2055                2060

Lys Leu Lys Pro Arg Trp Leu Asp Ala Arg Ile Tyr Ser Asp Pro Leu
2065                2070                2075                2080
```

```
Thr Leu Lys Glu Phe Lys Glu Phe Ala Ala Gly Arg Lys Ser Leu Thr
            2085                2090                2095

Leu Asn Leu Ile Thr Glu Met Gly Arg Leu Pro Thr Phe Met Thr Gln
            2100                2105                2110

Lys Ala Arg Asp Ala Leu Asp Asn Leu Ala Val Leu His Thr Ala Glu
            2115                2120                2125

Ala Gly Gly Arg Ala Tyr Asn His Ala Leu Ser Glu Leu Pro Glu Thr
            2130                2135                2140

Leu Glu Thr Leu Leu Leu Leu Thr Leu Leu Ala Thr Val Thr Gly Gly
2145                2150                2155                2160

Ile Phe Leu Phe Leu Met Ser Gly Arg Gly Ile Gly Lys Met Thr Leu
            2165                2170                2175

Gly Met Cys Cys Ile Ile Thr Ala Ser Ile Leu Leu Trp Tyr Ala Gln
            2180                2185                2190

Ile Gln Pro His Trp Ile Ala Ala Ser Ile Ile Leu Glu Phe Phe Leu
            2195                2200                2205

Ile Val Leu Leu Ile Pro Glu Pro Glu Lys Gln Arg Thr Pro Gln Asp
            2210                2215                2220

Asn Gln Leu Thr Tyr Val Val Ile Ala Ile Leu Thr Val Val Ala Ala
2225                2230                2235                2240

Thr Met Ala Asn Glu Met Gly Phe Leu Glu Lys Thr Lys Lys Asp Leu
            2245                2250                2255

Gly Leu Gly Ser Ile Thr Thr Gln Gln Pro Glu Ser Asn Ile Leu Asp
            2260                2265                2270

Ile Asp Leu Arg Pro Ala Ser Ala Trp Thr Leu Tyr Ala Val Ala Thr
            2275                2280                2285

Thr Phe Val Thr Pro Met Leu Arg His Ser Ile Glu Asn Ser Ser Val
            2290                2295                2300

Asn Val Ser Leu Thr Ala Ile Ala Asn Gln Ala Thr Val Leu Met Gly
2305                2310                2315                2320

Leu Gly Lys Gly Trp Pro Leu Ser Lys Met Asp Ile Gly Val Pro Leu
            2325                2330                2335

Leu Ala Ile Gly Cys Tyr Ser Gln Val Asn Pro Ile Thr Leu Thr Ala
            2340                2345                2350

Ala Leu Phe Leu Leu Val Ala His Tyr Ala Ile Ile Gly Pro Gly Leu
            2355                2360                2365

Gln Ala Lys Ala Thr Arg Glu Ala Gln Lys Arg Ala Ala Ala Gly Ile
            2370                2375                2380

Met Lys Asn Pro Thr Val Asp Gly Ile Thr Val Ile Asp Leu Asp Pro
2385                2390                2395                2400

Ile Pro Tyr Asp Pro Lys Phe Glu Lys Gln Leu Gly Gln Val Met Leu
            2405                2410                2415

Leu Val Leu Cys Val Thr Gln Val Leu Met Met Arg Thr Thr Trp Ala
            2420                2425                2430

Leu Cys Glu Ala Leu Thr Leu Ala Thr Gly Pro Ile Ser Thr Leu Trp
            2435                2440                2445

Glu Gly Asn Pro Gly Arg Phe Trp Asn Thr Thr Ile Ala Val Ser Met
            2450                2455                2460

Ala Asn Ile Phe Arg Gly Ser Tyr Leu Ala Gly Ala Gly Leu Leu Phe
2465                2470                2475                2480

Ser Ile Met Lys Asn Thr Thr Asn Thr Arg Arg Gly Thr Gly Asn Ile
            2485                2490                2495

Gly Glu Thr Leu Gly Glu Lys Trp Lys Ser Arg Leu Asn Ala Leu Gly
```

-continued

```
                2500                2505                2510
Lys Ser Glu Phe Gln Ile Tyr Lys Lys Ser Gly Ile Gln Glu Val Asp
            2515                2520                2525

Arg Thr Leu Ala Lys Glu Gly Ile Lys Arg Gly Glu Thr Asp His His
        2530                2535                2540

Ala Val Ser Arg Gly Ser Ala Lys Leu Arg Trp Phe Val Glu Arg Asn
2545                2550                2555                2560

Met Val Thr Pro Glu Gly Lys Val Val Asp Leu Gly Cys Gly Arg Gly
                2565                2570                2575

Gly Trp Ser Tyr Tyr Cys Gly Gly Leu Lys Asn Val Arg Glu Val Lys
            2580                2585                2590

Gly Leu Thr Lys Gly Gly Pro Gly His Glu Glu Pro Ile Pro Met Ser
        2595                2600                2605

Thr Tyr Gly Trp Asn Leu Val Arg Leu Gln Ser Gly Val Asp Val Phe
    2610                2615                2620

Phe Thr Pro Pro Glu Lys Cys Asp Thr Leu Leu Cys Asp Ile Gly Glu
2625                2630                2635                2640

Ser Ser Pro Asn Pro Thr Val Glu Ala Gly Arg Thr Leu Arg Val Leu
                2645                2650                2655

Asn Leu Val Glu Asn Trp Leu Asn Asn Asn Thr Gln Phe Cys Ile Lys
            2660                2665                2670

Val Leu Asn Pro Tyr Met Pro Ser Val Ile Glu Lys Met Glu Ala Leu
        2675                2680                2685

Gln Arg Lys Tyr Gly Gly Ala Leu Val Arg Asn Pro Leu Ser Arg Asn
    2690                2695                2700

Ser Thr His Glu Met Tyr Trp Val Ser Asn Ala Ser Gly Asn Ile Val
2705                2710                2715                2720

Ser Ser Val Asn Met Ile Ser Arg Met Leu Ile Asn Arg Phe Thr Met
                2725                2730                2735

Arg His Lys Lys Ala Thr Tyr Glu Pro Asp Val Asp Leu Gly Ser Gly
            2740                2745                2750

Thr Arg Asn Ile Gly Ile Glu Ser Glu Ile Pro Asn Leu Asp Ile Ile
        2755                2760                2765

Gly Lys Arg Ile Glu Lys Ile Lys Gln Glu His Glu Thr Ser Trp His
    2770                2775                2780

Tyr Asp Gln Asp His Pro Tyr Lys Thr Trp Ala Tyr His Gly Ser Tyr
2785                2790                2795                2800

Glu Thr Lys Gln Thr Gly Ser Ala Ser Ser Met Val Asn Gly Val Val
                2805                2810                2815

Arg Leu Leu Thr Lys Pro Trp Asp Val Val Pro Met Val Thr Gln Met
            2820                2825                2830

Ala Met Thr Asp Thr Thr Pro Phe Gly Gln Gln Arg Val Phe Lys Glu
        2835                2840                2845

Lys Val Asp Thr Arg Thr Gln Glu Pro Lys Glu Gly Thr Lys Lys Leu
    2850                2855                2860

Met Lys Ile Thr Ala Glu Trp Leu Trp Lys Glu Leu Gly Lys Lys Lys
2865                2870                2875                2880

Thr Pro Arg Met Cys Thr Arg Glu Glu Phe Thr Arg Lys Val Arg Ser
                2885                2890                2895

Asn Ala Ala Leu Gly Ala Ile Phe Thr Asp Glu Asn Lys Trp Lys Ser
            2900                2905                2910

Ala Arg Glu Ala Val Glu Asp Ser Arg Phe Trp Glu Leu Val Asp Lys
        2915                2920                2925
```

```
Glu Arg Asn Leu His Leu Glu Gly Lys Cys Glu Thr Cys Val Tyr Asn
    2930                2935                2940
Met Met Gly Lys Arg Glu Lys Lys Leu Gly Phe Gly Lys Ala Lys
2945                2950                2955                2960
Gly Ser Arg Ala Ile Trp Tyr Met Trp Leu Gly Ala Arg Phe Leu Glu
                2965                2970                2975
Phe Glu Ala Leu Gly Phe Leu Asn Glu Asp His Trp Phe Ser Arg Glu
            2980                2985                2990
Asn Ser Leu Ser Gly Val Glu Gly Gly Leu His Lys Leu Gly Tyr
        2995                3000                3005
Ile Leu Arg Asp Val Ser Lys Lys Glu Gly Gly Ala Met Tyr Ala Asp
    3010                3015                3020
Asp Thr Ala Gly Trp Asp Thr Arg Ile Thr Leu Glu Asp Leu Lys Asn
3025                3030                3035                3040
Glu Glu Met Val Thr Asn His Met Glu Gly Glu His Lys Lys Leu Ala
                3045                3050                3055
Glu Ala Ile Phe Lys Leu Thr Tyr Gln Asn Lys Val Val Arg Val Gln
            3060                3065                3070
Arg Pro Thr Pro Arg Gly Thr Val Met Asp Ile Ile Ser Arg Arg Asp
        3075                3080                3085
Gln Arg Gly Ser Gly Gln Val Gly Thr Tyr Gly Leu Asn Thr Phe Thr
    3090                3095                3100
Asn Met Glu Ala Gln Leu Ile Arg Gln Met Glu Gly Glu Gly Val Phe
3105                3110                3115                3120
Lys Ser Ile Gln His Leu Thr Val Thr Glu Glu Ile Ala Val Gln Asn
                3125                3130                3135
Trp Leu Ala Arg Val Gly Arg Glu Arg Leu Ser Arg Met Ala Ile Ser
            3140                3145                3150
Gly Asp Asp Cys Val Val Lys Pro Leu Asp Asp Arg Phe Ala Ser Ala
        3155                3160                3165
Leu Thr Ala Leu Asn Asp Met Gly Lys Val Arg Lys Asp Ile Gln Gln
    3170                3175                3180
Trp Glu Pro Ser Arg Gly Trp Asn Asp Trp Thr Gln Val Pro Phe Cys
3185                3190                3195                3200
Ser His His Phe His Glu Leu Ile Met Lys Asp Gly Arg Val Leu Val
                3205                3210                3215
Val Pro Cys Arg Asn Gln Asp Glu Leu Ile Gly Arg Ala Arg Ile Ser
            3220                3225                3230
Gln Gly Ala Gly Trp Ser Leu Arg Glu Thr Ala Cys Leu Gly Lys Ser
        3235                3240                3245
Tyr Ala Gln Met Trp Ser Leu Met Tyr Phe His Arg Arg Asp Leu Arg
    3250                3255                3260
Leu Ala Ala Asn Ala Ile Cys Ser Ala Val Pro Ser His Trp Val Pro
3265                3270                3275                3280
Thr Ser Arg Thr Thr Trp Ser Ile His Ala Lys His Glu Trp Met Thr
                3285                3290                3295
Thr Glu Asp Met Leu Thr Val Trp Asn Arg Val Trp Ile Gln Glu Asn
            3300                3305                3310
Pro Trp Met Glu Asp Lys Thr Pro Val Glu Ser Trp Glu Glu Ile Pro
        3315                3320                3325
Tyr Leu Gly Lys Arg Glu Asp Gln Trp Cys Gly Ser Leu Ile Gly Leu
    3330                3335                3340
```

Thr Ser Arg Ala Thr Trp Ala Lys Asn Ile Gln Thr Ala Ile Asn Gln
3345                3350                3355                3360

Val Arg Ser Leu Ile Gly Asn Glu Glu Tyr Thr Asp Tyr Met Pro Ser
            3365                3370                3375

Met Lys Arg Phe Arg Arg Glu Glu Glu Ala Gly Val Leu Trp
        3380                3385                3390

<210> SEQ ID NO 22
<211> LENGTH: 3390
<212> TYPE: PRT
<213> ORGANISM: Dengue 3 virus strain H87

<400> SEQUENCE: 22

Met Asn Asn Gln Arg Lys Lys Thr Gly Lys Pro Ser Ile Asn Met Leu
1               5                   10                  15

Lys Arg Val Arg Asn Arg Val Ser Thr Gly Ser Gln Leu Ala Lys Arg
            20                  25                  30

Phe Ser Arg Gly Leu Leu Asn Gly Gln Gly Pro Met Lys Leu Val Met
        35                  40                  45

Ala Phe Ile Ala Phe Leu Arg Phe Leu Ala Ile Pro Pro Thr Ala Gly
50                  55                  60

Val Leu Ala Arg Trp Gly Thr Phe Lys Lys Ser Gly Ala Ile Lys Val
65                  70                  75                  80

Leu Lys Gly Phe Lys Lys Glu Ile Ser Asn Met Leu Ser Ile Ile Asn
            85                  90                  95

Lys Arg Lys Lys Thr Ser Leu Cys Leu Met Met Met Leu Pro Ala Thr
        100                 105                 110

Leu Ala Phe His Leu Thr Ser Arg Asp Gly Glu Pro Arg Met Ile Val
    115                 120                 125

Gly Lys Asn Glu Arg Gly Lys Ser Leu Leu Phe Lys Thr Ala Ser Gly
130                 135                 140

Ile Asn Met Cys Thr Leu Ile Ala Met Asp Leu Gly Glu Met Cys Asp
145                 150                 155                 160

Asp Thr Val Thr Tyr Lys Cys Pro His Ile Thr Glu Val Glu Pro Glu
            165                 170                 175

Asp Ile Asp Cys Trp Cys Asn Leu Thr Ser Thr Trp Val Thr Tyr Gly
        180                 185                 190

Thr Cys Asn Gln Ala Gly Glu His Arg Arg Asp Lys Arg Ser Val Ala
    195                 200                 205

Leu Ala Pro His Val Gly Met Gly Leu Asp Thr Arg Thr Gln Thr Trp
210                 215                 220

Met Ser Ala Glu Gly Ala Trp Arg Gln Val Glu Lys Val Glu Thr Trp
225                 230                 235                 240

Ala Leu Arg His Pro Gly Phe Thr Ile Leu Ala Leu Phe Leu Ala His
            245                 250                 255

Tyr Ile Gly Thr Ser Leu Thr Gln Lys Val Val Ile Phe Ile Leu Leu
        260                 265                 270

Met Leu Val Thr Pro Ser Met Thr Met Arg Cys Val Gly Val Gly Asn
    275                 280                 285

Arg Asp Phe Val Glu Gly Leu Ser Gly Ala Thr Trp Val Asp Val Val
290                 295                 300

Leu Glu His Gly Gly Cys Val Thr Thr Met Ala Lys Asn Lys Pro Thr
305                 310                 315                 320

Leu Asp Ile Glu Leu Gln Lys Thr Glu Ala Thr Gln Leu Ala Thr Leu
            325                 330                 335

-continued

Arg Lys Leu Cys Ile Glu Gly Lys Ile Thr Asn Ile Thr Thr Asp Ser
            340                 345                 350

Arg Cys Pro Thr Gln Gly Glu Ala Ile Leu Pro Glu Glu Gln Asp Gln
            355                 360                 365

Asn Tyr Val Cys Lys His Thr Tyr Val Asp Arg Gly Trp Gly Asn Gly
            370                 375                 380

Cys Gly Leu Phe Gly Lys Gly Ser Leu Val Thr Cys Ala Lys Phe Gln
385                 390                 395                 400

Cys Leu Glu Ser Ile Glu Gly Lys Val Val Gln His Glu Asn Leu Lys
                405                 410                 415

Tyr Thr Val Ile Ile Thr Val His Thr Gly Asp Gln His Gln Val Gly
            420                 425                 430

Asn Glu Thr Gln Gly Val Thr Ala Glu Ile Thr Ser Gln Ala Ser Thr
            435                 440                 445

Ala Glu Ala Ile Leu Pro Glu Tyr Gly Thr Leu Gly Leu Glu Cys Ser
450                 455                 460

Pro Arg Thr Gly Leu Asp Phe Asn Glu Met Ile Leu Leu Thr Met Lys
465                 470                 475                 480

Asn Lys Ala Trp Met Val His Arg Gln Trp Phe Asp Leu Pro Leu
                485                 490                 495

Pro Trp Thr Ser Gly Ala Thr Thr Lys Thr Pro Thr Trp Asn Arg Lys
            500                 505                 510

Glu Leu Leu Val Thr Phe Lys Asn Ala His Ala Lys Lys Gln Glu Val
            515                 520                 525

Val Val Leu Gly Ser Gln Glu Gly Ala Met His Thr Ala Leu Thr Gly
            530                 535                 540

Ala Thr Glu Ile Gln Thr Ser Gly Gly Thr Ser Ile Phe Ala Gly His
545                 550                 555                 560

Leu Lys Cys Arg Leu Lys Met Asp Lys Leu Lys Leu Lys Gly Met Ser
                565                 570                 575

Tyr Ala Met Cys Leu Asn Thr Phe Val Leu Lys Lys Glu Val Ser Glu
            580                 585                 590

Thr Gln His Gly Thr Ile Leu Ile Lys Val Glu Tyr Lys Gly Glu Asp
            595                 600                 605

Ala Pro Cys Lys Ile Pro Phe Ser Thr Glu Asp Gly Gln Gly Lys Ala
            610                 615                 620

His Asn Gly Arg Leu Ile Thr Ala Asn Pro Val Val Thr Lys Lys Glu
625                 630                 635                 640

Glu Pro Val Asn Ile Glu Ala Glu Pro Pro Phe Gly Glu Ser Asn Ile
                645                 650                 655

Val Ile Gly Ile Gly Asp Lys Ala Leu Lys Ile Asn Trp Tyr Arg Lys
            660                 665                 670

Gly Ser Ser Ile Gly Lys Met Phe Glu Ala Thr Ala Arg Gly Ala Arg
            675                 680                 685

Arg Met Ala Ile Leu Gly Asp Thr Ala Trp Asp Phe Gly Ser Val Gly
690                 695                 700

Gly Val Leu Asn Ser Leu Gly Lys Met Val His Gln Ile Phe Gly Ser
705                 710                 715                 720

Ala Tyr Thr Ala Leu Phe Ser Gly Val Ser Trp Ile Met Lys Ile Gly
                725                 730                 735

Ile Gly Val Leu Leu Thr Trp Ile Gly Leu Asn Ser Lys Asn Thr Ser
            740                 745                 750

-continued

```
Met Ser Phe Ser Cys Ile Ala Ile Gly Ile Ile Thr Leu Tyr Leu Gly
        755                 760                 765

Val Val Val Gln Ala Asp Met Gly Cys Val Ile Asn Trp Lys Gly Lys
        770                 775                 780

Glu Leu Lys Cys Gly Ser Gly Ile Phe Val Thr Asn Glu Val His Thr
785                 790                 795                 800

Trp Thr Glu Gln Tyr Lys Phe Gln Ala Asp Ser Pro Lys Arg Val Ala
                805                 810                 815

Thr Ala Ile Ala Gly Ala Trp Glu Asn Gly Val Cys Gly Ile Arg Ser
            820                 825                 830

Thr Thr Arg Met Glu Asn Leu Leu Trp Lys Gln Ile Ala Asn Glu Leu
            835                 840                 845

Asn Tyr Ile Leu Trp Glu Asn Asp Ile Lys Leu Thr Val Val Val Gly
        850                 855                 860

Asp Ile Thr Gly Val Leu Glu Gln Gly Lys Arg Thr Leu Thr Pro Gln
865                 870                 875                 880

Pro Met Glu Leu Lys Tyr Ser Trp Lys Thr Trp Gly Leu Ala Lys Ile
                885                 890                 895

Val Thr Ala Glu Thr Gln Asn Ser Ser Phe Ile Ile Asp Gly Pro Ser
            900                 905                 910

Thr Pro Glu Cys Pro Ser Ala Ser Arg Ala Trp Asn Val Trp Glu Val
        915                 920                 925

Glu Asp Tyr Gly Phe Gly Val Phe Thr Thr Asn Ile Trp Leu Lys Leu
        930                 935                 940

Arg Glu Val Tyr Thr Gln Leu Cys Asp His Arg Leu Met Ser Ala Ala
945                 950                 955                 960

Val Lys Asp Glu Arg Ala Val His Ala Asp Met Gly Tyr Trp Ile Glu
                965                 970                 975

Ser Gln Lys Asn Gly Ser Trp Lys Leu Glu Lys Ala Ser Leu Ile Glu
            980                 985                 990

Val Lys Thr Cys Thr Trp Pro Lys Ser His Thr Leu Trp Ser Asn Gly
        995                 1000                1005

Val Leu Glu Ser Asp Met Ile Ile Pro Lys Ser Leu Ala Gly Pro Ile
        1010                1015                1020

Ser Gln His Asn His Arg Pro Gly Tyr His Thr Gln Thr Ala Gly Pro
1025                1030                1035                1040

Trp His Leu Gly Lys Leu Glu Leu Asp Phe Asn Tyr Cys Glu Gly Thr
                1045                1050                1055

Thr Val Val Ile Ser Glu Asn Cys Gly Thr Arg Gly Pro Ser Leu Arg
            1060                1065                1070

Thr Thr Thr Val Ser Gly Lys Leu Ile His Glu Trp Cys Cys Arg Ser
            1075                1080                1085

Cys Thr Leu Pro Pro Leu Arg Tyr Met Gly Glu Asp Gly Cys Trp Tyr
        1090                1095                1100

Gly Met Glu Ile Arg Pro Ile Asn Glu Lys Glu Glu Asn Met Val Lys
1105                1110                1115                1120

Ser Leu Ala Ser Ala Gly Ser Gly Lys Val Asp Asn Phe Thr Met Gly
                1125                1130                1135

Val Leu Cys Leu Ala Ile Leu Phe Glu Glu Val Met Arg Gly Lys Phe
            1140                1145                1150

Gly Lys Lys His Met Ile Ala Gly Val Leu Phe Thr Phe Val Leu Leu
            1155                1160                1165

Leu Ser Gly Gln Ile Thr Trp Arg Gly Met Ala His Thr Leu Ile Met
```

```
          1170           1175           1180
Ile Gly Ser Asn Ala Ser Asp Arg Met Gly Met Gly Val Thr Tyr Leu
1185               1190               1195               1200

Ala Leu Ile Ala Thr Phe Lys Ile Gln Pro Phe Leu Ala Leu Gly Phe
               1205               1210               1215

Phe Leu Arg Lys Leu Thr Ser Arg Glu Asn Leu Leu Gly Val Gly
           1220               1225               1230

Leu Ala Met Ala Ala Thr Leu Arg Leu Pro Glu Asp Ile Glu Gln Met
               1235               1240               1245

Ala Asn Gly Ile Ala Leu Gly Leu Met Ala Leu Lys Leu Ile Thr Gln
       1250               1255               1260

Phe Glu Thr Tyr Gln Leu Trp Thr Ala Leu Val Ser Leu Thr Cys Ser
1265               1270               1275               1280

Asn Thr Ile Phe Thr Leu Thr Val Ala Trp Arg Thr Ala Thr Leu Ile
               1285               1290               1295

Leu Ala Gly Ile Ser Leu Leu Pro Val Cys Gln Ser Ser Ser Met Arg
               1300               1305               1310

Lys Thr Asp Trp Leu Pro Met Thr Val Ala Ala Met Gly Val Pro Pro
           1315               1320               1325

Leu Pro Leu Phe Ile Phe Ser Leu Lys Asp Thr Leu Lys Arg Arg Ser
           1330               1335               1340

Trp Pro Leu Asn Glu Gly Val Met Ala Val Gly Leu Val Ser Ile Leu
1345               1350               1355               1360

Ala Ser Ser Leu Leu Arg Asn Asp Val Pro Met Ala Gly Pro Leu Val
               1365               1370               1375

Ala Gly Gly Leu Leu Ile Ala Cys Tyr Val Ile Thr Gly Thr Ser Ala
               1380               1385               1390

Asp Leu Thr Val Glu Lys Ala Ala Asp Val Thr Trp Glu Glu Glu Ala
               1395               1400               1405

Glu Gln Thr Gly Val Ser His Asn Leu Met Ile Thr Val Asp Asp Asp
           1410               1415               1420

Gly Thr Met Arg Ile Lys Asp Asp Glu Thr Glu Asn Ile Leu Thr Val
1425               1430               1435               1440

Leu Leu Lys Thr Ala Leu Leu Ile Val Ser Gly Ile Phe Pro Tyr Ser
               1445               1450               1455

Ile Pro Ala Thr Met Leu Val Trp His Thr Trp Gln Lys Gln Thr Gln
               1460               1465               1470

Arg Ser Gly Val Leu Trp Asp Val Pro Ser Pro Pro Glu Thr Gln Lys
           1475               1480               1485

Ala Glu Leu Glu Glu Gly Val Tyr Arg Ile Lys Gln Gln Gly Ile Phe
           1490               1495               1500

Gly Lys Thr Gln Val Gly Val Gly Val Gln Lys Glu Gly Val Phe His
1505               1510               1515               1520

Thr Met Trp His Val Thr Arg Gly Ala Val Leu Thr His Asn Gly Lys
                   1525               1530               1535

Arg Leu Glu Pro Asn Trp Ala Ser Val Lys Lys Asp Leu Ile Ser Tyr
               1540               1545               1550

Gly Gly Gly Trp Arg Leu Ser Ala Gln Trp Gln Lys Gly Glu Glu Val
           1555               1560               1565

Gln Val Ile Ala Val Glu Pro Gly Lys Asn Pro Lys Asn Phe Gln Thr
           1570               1575               1580

Met Pro Gly Ile Phe Gln Thr Thr Thr Gly Glu Ile Gly Ala Ile Ala
1585               1590               1595               1600
```

```
Leu Asp Phe Lys Pro Gly Thr Ser Gly Ser Pro Ile Ile Asn Arg Glu
            1605                1610                1615

Gly Lys Val Val Gly Leu Tyr Gly Asn Gly Val Val Thr Lys Asn Gly
        1620                1625                1630

Gly Tyr Val Ser Gly Ile Ala Gln Thr Asn Ala Glu Pro Asp Gly Pro
        1635                1640                1645

Thr Pro Glu Leu Glu Glu Met Phe Lys Arg Asn Leu Thr Ile
    1650                1655                1660

Met Asp Leu His Pro Gly Ser Gly Lys Thr Arg Lys Tyr Leu Pro Ala
1665                1670                1675                1680

Ile Val Arg Glu Ala Ile Lys Arg Arg Leu Arg Thr Leu Ile Leu Ala
            1685                1690                1695

Pro Thr Arg Val Val Ala Ala Glu Met Glu Glu Ala Met Lys Gly Leu
        1700                1705                1710

Pro Ile Arg Tyr Gln Thr Thr Ala Thr Lys Ser Glu His Thr Gly Arg
        1715                1720                1725

Glu Ile Val Asp Leu Met Cys His Ala Thr Phe Thr Met Arg Leu Leu
    1730                1735                1740

Ser Pro Val Arg Val Pro Asn Tyr Asn Leu Ile Ile Met Asp Glu Ala
1745                1750                1755                1760

His Phe Thr Asp Pro Ala Ser Ile Ala Ala Arg Gly Tyr Ile Ser Thr
            1765                1770                1775

Arg Val Gly Met Gly Glu Ala Ala Ile Phe Met Thr Ala Thr Pro
        1780                1785                1790

Pro Gly Thr Ala Asp Ala Phe Pro Gln Ser Asn Ala Pro Ile Gln Asp
        1795                1800                1805

Glu Glu Arg Asp Ile Pro Glu Arg Ser Trp Asn Ser Gly Asn Glu Trp
    1810                1815                1820

Ile Thr Asp Phe Val Gly Lys Thr Val Trp Phe Val Pro Ser Ile Lys
1825                1830                1835                1840

Ala Gly Asn Val Ile Ala Asn Cys Leu Arg Lys Asn Gly Lys Lys Val
            1845                1850                1855

Ile Gln Leu Ser Arg Lys Thr Phe Asp Thr Glu Tyr Gln Lys Thr Lys
        1860                1865                1870

Leu Asn Asp Trp Asp Phe Val Val Thr Thr Asp Ile Ser Glu Met Gly
        1875                1880                1885

Ala Asn Phe Ile Ala Asp Arg Val Ile Asp Pro Arg Arg Cys Leu Lys
    1890                1895                1900

Pro Val Ile Leu Thr Asp Gly Pro Glu Arg Val Ile Leu Ala Gly Pro
1905                1910                1915                1920

Met Pro Val Thr Val Ala Ser Ala Ala Gln Arg Arg Gly Arg Val Gly
            1925                1930                1935

Arg Asn Pro Gln Lys Glu Asn Asp Gln Tyr Ile Phe Met Gly Gln Pro
        1940                1945                1950

Leu Asn Lys Asp Glu Asp His Ala His Trp Thr Glu Ala Lys Met Leu
        1955                1960                1965

Leu Asp Asn Ile Asn Thr Pro Glu Gly Ile Ile Pro Ala Leu Phe Glu
    1970                1975                1980

Pro Glu Arg Glu Lys Ser Ala Ala Ile Asp Gly Glu Tyr Arg Leu Lys
1985                1990                1995                2000

Gly Glu Ser Arg Lys Thr Phe Val Glu Leu Met Arg Arg Gly Asp Leu
            2005                2010                2015
```

```
Pro Val Trp Leu Ala His Lys Val Ala Ser Glu Gly Ile Lys Tyr Thr
            2020                2025                2030

Asp Arg Lys Trp Cys Phe Asp Gly Glu Arg Asn Asn Gln Ile Leu Glu
            2035                2040            2045

Glu Asn Met Asp Val Glu Ile Trp Thr Lys Gly Glu Lys Lys Lys
            2050                2055            2060

Leu Arg Pro Arg Trp Leu Asp Ala Arg Thr Tyr Ser Asp Pro Leu Ala
2065            2070                2075                2080

Leu Lys Glu Phe Lys Asp Phe Ala Ala Gly Arg Lys Ser Ile Ala Leu
            2085                2090                2095

Asp Leu Val Thr Glu Ile Gly Arg Val Pro Ser His Leu Ala His Arg
            2100                2105                2110

Thr Arg Asn Ala Leu Asp Asn Leu Val Met Leu His Thr Ser Glu His
            2115                2120            2125

Gly Gly Arg Ala Tyr Arg His Ala Val Glu Glu Leu Pro Glu Thr Met
            2130                2135            2140

Glu Thr Leu Leu Leu Leu Gly Leu Met Ile Leu Leu Thr Gly Gly Ala
2145            2150                2155                2160

Met Leu Phe Leu Ile Ser Gly Lys Gly Ile Gly Lys Thr Ser Ile Gly
            2165                2170                2175

Leu Ile Cys Val Ile Ala Ser Ser Gly Met Leu Trp Met Ala Asp Val
            2180                2185                2190

Pro Leu Gln Trp Ile Ala Ser Ala Ile Val Leu Glu Phe Phe Met Met
            2195                2200            2205

Val Leu Leu Ile Pro Glu Pro Glu Lys Gln Arg Thr Pro Gln Asp Asn
            2210                2215            2220

Gln Leu Ala Tyr Val Val Ile Gly Ile Leu Thr Leu Ala Ala Ile Val
2225            2230                2235                2240

Ala Ala Asn Glu Met Gly Leu Leu Glu Thr Thr Lys Arg Asp Leu Gly
            2245                2250                2255

Met Ser Lys Glu Pro Gly Val Val Ser Pro Thr Ser Tyr Leu Asp Val
            2260                2265            2270

Asp Leu His Pro Ala Ser Ala Trp Thr Leu Tyr Ala Val Ala Thr Thr
            2275                2280                2285

Val Ile Thr Pro Met Leu Arg His Thr Ile Glu Asn Ser Thr Ala Asn
            2290                2295            2300

Val Ser Leu Ala Ala Ile Ala Asn Gln Ala Val Val Leu Met Gly Leu
2305            2310                2315                2320

Asp Lys Gly Trp Pro Ile Ser Lys Met Asp Leu Gly Val Pro Leu Leu
            2325                2330            2335

Ala Leu Gly Cys Tyr Ser Gln Val Asn Pro Leu Thr Leu Ile Ala Ala
            2340                2345            2350

Val Leu Leu Leu Val Thr His Tyr Ala Ile Ile Gly Pro Gly Leu Gln
            2355                2360            2365

Ala Lys Ala Thr Arg Glu Ala Gln Lys Arg Thr Ala Ala Gly Ile Met
            2370                2375            2380

Lys Asn Pro Thr Val Asp Gly Ile Met Thr Ile Asp Leu Asp Pro Val
2385            2390                2395                2400

Ile Tyr Asp Ser Lys Phe Glu Lys Gln Leu Gly Gln Val Met Leu Leu
            2405                2410                2415

Val Leu Cys Ala Val Gln Leu Leu Leu Met Arg Thr Ser Trp Ala Leu
            2420                2425                2430

Cys Glu Val Leu Thr Leu Ala Thr Gly Pro Ile Thr Thr Leu Trp Glu
```

```
                  2435                2440                2445
Gly Ser Pro Gly Lys Phe Trp Asn Thr Thr Ile Ala Val Ser Met Ala
    2450                2455                2460

Asn Ile Phe Arg Gly Ser Tyr Leu Ala Gly Ala Gly Leu Ala Leu Ser
2465                2470                2475                2480

Ile Met Lys Ser Val Gly Thr Gly Lys Arg Gly Thr Gly Ser Gln Gly
                2485                2490                2495

Glu Thr Leu Gly Glu Lys Trp Lys Lys Leu Asn Gln Leu Ser Arg
    2500                2505                2510

Lys Glu Phe Asp Leu Tyr Lys Lys Ser Gly Ile Thr Glu Val Asp Arg
    2515                2520                2525

Thr Glu Ala Lys Glu Gly Leu Lys Arg Gly Glu Ile Thr His His Ala
    2530                2535                2540

Val Ser Arg Gly Ser Ala Lys Leu Gln Trp Phe Val Glu Arg Asn Met
2545                2550                2555                2560

Val Ile Pro Glu Gly Arg Val Ile Asp Leu Gly Cys Gly Arg Gly Gly
                2565                2570                2575

Trp Ser Tyr Tyr Cys Ala Gly Leu Lys Lys Val Thr Glu Val Arg Gly
                2580                2585                2590

Tyr Thr Lys Gly Gly Pro Gly His Glu Glu Pro Val Pro Met Ser Thr
                2595                2600                2605

Tyr Gly Trp Asn Ile Val Lys Leu Met Ser Gly Lys Asp Val Phe Tyr
    2610                2615                2620

Leu Pro Pro Glu Lys Cys Asp Thr Leu Leu Cys Asp Ile Gly Glu Ser
2625                2630                2635                2640

Ser Pro Ser Pro Thr Val Glu Glu Ser Arg Thr Ile Arg Val Leu Lys
                2645                2650                2655

Met Val Glu Pro Trp Leu Lys Asn Asn Gln Phe Cys Ile Lys Val Leu
                2660                2665                2670

Asn Pro Tyr Met Pro Thr Val Ile Glu His Leu Glu Arg Leu Gln Arg
                2675                2680                2685

Lys His Gly Gly Met Leu Val Arg Asn Pro Leu Ser Arg Asn Ser Thr
    2690                2695                2700

His Glu Met Tyr Trp Ile Ser Asn Gly Thr Gly Asn Ile Val Ser Ser
2705                2710                2715                2720

Val Asn Met Val Ser Arg Leu Leu Leu Asn Arg Phe Thr Met Thr His
                2725                2730                2735

Arg Arg Pro Thr Ile Glu Lys Asp Val Asp Leu Gly Ala Gly Thr Arg
                2740                2745                2750

His Val Asn Ala Glu Pro Glu Thr Pro Asn Met Asp Val Ile Gly Glu
    2755                2760                2765

Arg Ile Lys Arg Ile Lys Glu Glu His Ser Ser Thr Trp His Tyr Asp
    2770                2775                2780

Asp Glu Asn Pro Tyr Lys Thr Trp Ala Tyr His Gly Ser Tyr Glu Val
2785                2790                2795                2800

Lys Ala Thr Gly Ser Ala Ser Ser Met Ile Asn Gly Val Val Lys Leu
                2805                2810                2815

Leu Thr Lys Pro Trp Asp Val Val Pro Met Val Thr Gln Met Ala Met
                2820                2825                2830

Thr Asp Thr Thr Pro Phe Gly Gln Gln Arg Val Phe Lys Glu Lys Val
    2835                2840                2845

Asp Thr Arg Thr Pro Arg Pro Met Pro Gly Thr Arg Lys Val Met Glu
    2850                2855                2860
```

```
Ile Thr Ala Glu Trp Leu Trp Arg Thr Leu Gly Arg Asn Lys Arg Pro
2865                2870                2875                2880

Arg Leu Cys Thr Arg Glu Glu Phe Thr Lys Lys Val Arg Thr Asn Ala
            2885                2890                2895

Ala Met Gly Ala Val Phe Thr Glu Glu Asn Gln Trp Asp Ser Ala Arg
        2900                2905                2910

Ala Ala Val Glu Asp Glu Glu Phe Trp Lys Leu Val Asp Arg Glu Arg
    2915                2920                2925

Glu Leu His Lys Leu Gly Lys Cys Gly Ser Cys Val Tyr Asn Met Met
2930                2935                2940

Gly Lys Arg Glu Lys Lys Leu Gly Glu Phe Gly Lys Ala Lys Gly Ser
2945                2950                2955                2960

Arg Ala Ile Trp Tyr Met Trp Leu Gly Ala Arg Tyr Leu Glu Phe Glu
                2965                2970                2975

Ala Leu Gly Phe Leu Asn Glu Asp His Trp Phe Ser Arg Glu Asn Ser
            2980                2985                2990

Tyr Ser Gly Val Glu Gly Glu Gly Leu His Lys Leu Gly Tyr Ile Leu
        2995                3000                3005

Arg Asp Ile Ser Lys Ile Pro Gly Gly Ala Met Tyr Ala Asp Asp Thr
    3010                3015                3020

Ala Gly Trp Asp Thr Arg Ile Thr Glu Asp Asp Leu His Asn Glu Glu
3025                3030                3035                3040

Lys Ile Thr Gln Gln Met Asp Pro Glu His Arg Gln Leu Ala Asn Ala
                3045                3050                3055

Ile Phe Lys Leu Thr Tyr Gln Asn Lys Val Val Lys Val Gln Arg Pro
            3060                3065                3070

Thr Pro Lys Gly Thr Val Met Asp Ile Ile Ser Arg Lys Asp Gln Arg
        3075                3080                3085

Gly Ser Gly Gln Val Gly Thr Tyr Gly Leu Asn Thr Phe Thr Asn Met
    3090                3095                3100

Glu Ala Gln Leu Ile Arg Gln Met Glu Gly Glu Gly Val Leu Ser Lys
3105                3110                3115                3120

Ala Asp Leu Glu Asn Pro His Pro Leu Glu Lys Lys Ile Thr Gln Trp
                3125                3130                3135

Leu Glu Thr Lys Gly Val Glu Arg Leu Lys Arg Met Ala Ile Ser Gly
            3140                3145                3150

Asp Asp Cys Val Val Lys Pro Ile Asp Asp Arg Phe Ala Asn Ala Leu
        3155                3160                3165

Leu Ala Leu Asn Asp Met Gly Lys Val Arg Lys Asp Ile Pro Gln Trp
    3170                3175                3180

Gln Pro Ser Lys Gly Trp His Asp Trp Gln Gln Val Pro Phe Cys Ser
3185                3190                3195                3200

His His Phe His Glu Leu Ile Met Lys Asp Gly Arg Lys Leu Val Val
                3205                3210                3215

Pro Cys Arg Pro Gln Asp Glu Leu Ile Gly Arg Ala Arg Ile Ser Gln
            3220                3225                3230

Gly Ala Gly Trp Ser Leu Arg Glu Thr Ala Cys Leu Gly Lys Ala Tyr
        3235                3240                3245

Ala Gln Met Trp Thr Leu Met Tyr Phe His Arg Arg Asp Leu Arg Leu
    3250                3255                3260

Ala Ser Asn Ala Ile Cys Ser Ala Val Pro Val His Trp Val Pro Thr
3265                3270                3275                3280
```

```
Ser Arg Thr Thr Trp Ser Ile His Ala His His Gln Trp Met Thr Thr
            3285                3290                3295

Glu Asp Met Leu Thr Val Trp Asn Arg Val Trp Ile Glu Asp Asn Pro
        3300                3305                3310

Trp Met Glu Asp Lys Thr Pro Val Thr Thr Trp Glu Asp Val Pro Tyr
    3315                3320                3325

Leu Gly Lys Arg Glu Asp Gln Trp Cys Gly Ser Leu Ile Gly Leu Thr
            3330                3335                3340

Ser Arg Ala Thr Trp Ala Gln Asn Ile Leu Thr Ala Ile Gln Gln Val
3345                3350                3355                3360

Arg Ser Leu Ile Gly Asn Glu Glu Phe Leu Asp Tyr Met Pro Ser Met
            3365                3370                3375

Lys Arg Phe Arg Lys Glu Glu Glu Ser Glu Gly Ala Ile Trp
            3380                3385                3390

<210> SEQ ID NO 23
<211> LENGTH: 21
<212> TYPE: DNA
<213> ORGANISM: Artificial Sequence
<220> FEATURE:
<223> OTHER INFORMATION: Oligonucleotide

<400> SEQUENCE: 23
cagttccaaa ccggaagctt g                                          21

<210> SEQ ID NO 24
<211> LENGTH: 27
<212> TYPE: DNA
<213> ORGANISM: Artificial Sequence
<220> FEATURE:
<223> OTHER INFORMATION: Oligonucleotide

<400> SEQUENCE: 24
ccaacgagct atcgtacgtt ctctggg                                    27

<210> SEQ ID NO 25
<211> LENGTH: 27
<212> TYPE: DNA
<213> ORGANISM: Artificial Sequence
<220> FEATURE:
<223> OTHER INFORMATION: Oligonucleotide

<400> SEQUENCE: 25
gattgtgacc atggcggccc atctttg                                    27

<210> SEQ ID NO 26
<211> LENGTH: 31
<212> TYPE: DNA
<213> ORGANISM: Artificial Sequence
<220> FEATURE:
<223> OTHER INFORMATION: Oligonucleotide

<400> SEQUENCE: 26
ggagattagg ccgctgagcg gtaaagaaga g                               31

<210> SEQ ID NO 27
<211> LENGTH: 26
<212> TYPE: DNA
<213> ORGANISM: Artificial Sequence
<220> FEATURE:
<223> OTHER INFORMATION: Oligonucleotide

<400> SEQUENCE: 27
```

| | |
|---|---|
| gtttgtggaa aaatgtctga ggagaa | 26 |

<210> SEQ ID NO 28
<211> LENGTH: 27
<212> TYPE: DNA
<213> ORGANISM: Artificial Sequence
<220> FEATURE:
<223> OTHER INFORMATION: Oligonucleotide

<400> SEQUENCE: 28

| | |
|---|---|
| ctaggaaaca cataatatta gttgtgg | 27 |

<210> SEQ ID NO 29
<211> LENGTH: 27
<212> TYPE: DNA
<213> ORGANISM: Artificial Sequence
<220> FEATURE:
<223> OTHER INFORMATION: Oligonucleotide

<400> SEQUENCE: 29

| | |
|---|---|
| cagatccacc taaccataat ggcagtg | 27 |

<210> SEQ ID NO 30
<211> LENGTH: 25
<212> TYPE: DNA
<213> ORGANISM: Artificial Sequence
<220> FEATURE:
<223> OTHER INFORMATION: Oligonucleotide

<400> SEQUENCE: 30

| | |
|---|---|
| ggaaactcac ctcgggagag acagc | 25 |

<210> SEQ ID NO 31
<211> LENGTH: 26
<212> TYPE: DNA
<213> ORGANISM: Artificial Sequence
<220> FEATURE:
<223> OTHER INFORMATION: Oligonucleotide

<400> SEQUENCE: 31

| | |
|---|---|
| ttgggtagag gtcaccgcac tcatcc | 26 |

<210> SEQ ID NO 32
<211> LENGTH: 25
<212> TYPE: DNA
<213> ORGANISM: Artificial Sequence
<220> FEATURE:
<223> OTHER INFORMATION: Oligonucleotide

<400> SEQUENCE: 32

| | |
|---|---|
| gtagaaatag ccgctctcat cctag | 25 |

<210> SEQ ID NO 33
<211> LENGTH: 30
<212> TYPE: DNA
<213> ORGANISM: Artificial Sequence
<220> FEATURE:
<223> OTHER INFORMATION: Oligonucleotide

<400> SEQUENCE: 33

| | |
|---|---|
| ggcggcttac gtaatgggag gtagctcagc | 30 |

<210> SEQ ID NO 34
<211> LENGTH: 27
<212> TYPE: DNA
<213> ORGANISM: Artificial Sequence

```
<220> FEATURE:
<223> OTHER INFORMATION: Oligonucleotide

<400> SEQUENCE: 34
ctagagaagg cagcttctgt gcagtgg                                          27

<210> SEQ ID NO 35
<211> LENGTH: 25
<212> TYPE: DNA
<213> ORGANISM: Artificial Sequence
<220> FEATURE:
<223> OTHER INFORMATION: Oligonucleotide

<400> SEQUENCE: 35
ccttggccat tccagcaaca atgac                                            25

<210> SEQ ID NO 36
<211> LENGTH: 26
<212> TYPE: DNA
<213> ORGANISM: Artificial Sequence
<220> FEATURE:
<223> OTHER INFORMATION: Oligonucleotide

<400> SEQUENCE: 36
gacgttcaaa ttttagccat agaacc                                           26

<210> SEQ ID NO 37
<211> LENGTH: 27
<212> TYPE: DNA
<213> ORGANISM: Artificial Sequence
<220> FEATURE:
<223> OTHER INFORMATION: Oligonucleotide

<400> SEQUENCE: 37
ctggagaaac gggcgccgta acattag                                          27

<210> SEQ ID NO 38
<211> LENGTH: 27
<212> TYPE: DNA
<213> ORGANISM: Artificial Sequence
<220> FEATURE:
<223> OTHER INFORMATION: Oligonucleotide

<400> SEQUENCE: 38
gaaattggat cggtaacctt agatttc                                          27

<210> SEQ ID NO 39
<211> LENGTH: 27
<212> TYPE: DNA
<213> ORGANISM: Artificial Sequence
<220> FEATURE:
<223> OTHER INFORMATION: Oligonucleotide

<400> SEQUENCE: 39
ggagcagtaa cgtttgattt caaaccc                                          27

<210> SEQ ID NO 40
<211> LENGTH: 24
<212> TYPE: DNA
<213> ORGANISM: Artificial Sequence
<220> FEATURE:
<223> OTHER INFORMATION: Oligonucleotide

<400> SEQUENCE: 40
gttaccaaac ctggggatta cgtc                                             24
```

```
<210> SEQ ID NO 41
<211> LENGTH: 25
<212> TYPE: DNA
<213> ORGANISM: Artificial Sequence
<220> FEATURE:
<223> OTHER INFORMATION: Oligonucleotide

<400> SEQUENCE: 41
gattaactat catgaactta caccc                                          25

<210> SEQ ID NO 42
<211> LENGTH: 25
<212> TYPE: DNA
<213> ORGANISM: Artificial Sequence
<220> FEATURE:
<223> OTHER INFORMATION: Oligonucleotide

<400> SEQUENCE: 42
ggaaaacctt tggcaccgag tatcc                                          25

<210> SEQ ID NO 43
<211> LENGTH: 26
<212> TYPE: DNA
<213> ORGANISM: Artificial Sequence
<220> FEATURE:
<223> OTHER INFORMATION: Oligonucleotide

<400> SEQUENCE: 43
tccagtgata ccggctagcg ctgctc                                         26

<210> SEQ ID NO 44
<211> LENGTH: 23
<212> TYPE: DNA
<213> ORGANISM: Artificial Sequence
<220> FEATURE:
<223> OTHER INFORMATION: Oligonucleotide

<400> SEQUENCE: 44
gcctcagagg tggccaaagg aag                                            23

<210> SEQ ID NO 45
<211> LENGTH: 26
<212> TYPE: DNA
<213> ORGANISM: Artificial Sequence
<220> FEATURE:
<223> OTHER INFORMATION: Oligonucleotide

<400> SEQUENCE: 45
acatggaggc agagatctgg actaga                                         26

<210> SEQ ID NO 46
<211> LENGTH: 23
<212> TYPE: DNA
<213> ORGANISM: Artificial Sequence
<220> FEATURE:
<223> OTHER INFORMATION: Oligonucleotide

<400> SEQUENCE: 46
aaagcatggc caaggatgct gtc                                            23

<210> SEQ ID NO 47
<211> LENGTH: 28
<212> TYPE: DNA
<213> ORGANISM: Artificial Sequence
<220> FEATURE:
<223> OTHER INFORMATION: Oligonucleotide
```

-continued

```
<400> SEQUENCE: 47
gcataatgga cgctaagcat gactaagg                                              28

<210> SEQ ID NO 48
<211> LENGTH: 26
<212> TYPE: DNA
<213> ORGANISM: Artificial Sequence
<220> FEATURE:
<223> OTHER INFORMATION: Oligonucleotide

<400> SEQUENCE: 48
ttattgcata gtgcacgaaa agcatg                                                26

<210> SEQ ID NO 49
<211> LENGTH: 23
<212> TYPE: DNA
<213> ORGANISM: Artificial Sequence
<220> FEATURE:
<223> OTHER INFORMATION: Oligonucleotide

<400> SEQUENCE: 49
gggcctatta ttacgtaatg gac                                                   23

<210> SEQ ID NO 50
<211> LENGTH: 24
<212> TYPE: DNA
<213> ORGANISM: Artificial Sequence
<220> FEATURE:
<223> OTHER INFORMATION: Oligonucleotide

<400> SEQUENCE: 50
ctgcaatcct ggtgatatta ttgc                                                  24

<210> SEQ ID NO 51
<211> LENGTH: 23
<212> TYPE: DNA
<213> ORGANISM: Artificial Sequence
<220> FEATURE:
<223> OTHER INFORMATION: Oligonucleotide

<400> SEQUENCE: 51
ctcataaaga acgttcaaac cct                                                   23

<210> SEQ ID NO 52
<211> LENGTH: 24
<212> TYPE: DNA
<213> ORGANISM: Artificial Sequence
<220> FEATURE:
<223> OTHER INFORMATION: Oligonucleotide

<400> SEQUENCE: 52
cattagacag acgcgagttt gaag                                                  24

<210> SEQ ID NO 53
<211> LENGTH: 27
<212> TYPE: DNA
<213> ORGANISM: Artificial Sequence
<220> FEATURE:
<223> OTHER INFORMATION: Oligonucleotide

<400> SEQUENCE: 53
tggcgacgct caagatagtg actgaag                                               27

<210> SEQ ID NO 54
```

<210> SEQ ID NO 54
<211> LENGTH: 25
<212> TYPE: DNA
<213> ORGANISM: Artificial Sequence
<220> FEATURE:
<223> OTHER INFORMATION: Oligonucleotide

<400> SEQUENCE: 54
gagtcatcat cgataccaac aatag                                    25

<210> SEQ ID NO 55
<211> LENGTH: 27
<212> TYPE: DNA
<213> ORGANISM: Artificial Sequence
<220> FEATURE:
<223> OTHER INFORMATION: Oligonucleotide

<400> SEQUENCE: 55
cttcaaaacc tggcttctgc atcaaag                                  27

<210> SEQ ID NO 56
<211> LENGTH: 28
<212> TYPE: DNA
<213> ORGANISM: Artificial Sequence
<220> FEATURE:
<223> OTHER INFORMATION: Oligonucleotide

<400> SEQUENCE: 56
caaagatgtt gagcaacagg ttcacaac                                 28

<210> SEQ ID NO 57
<211> LENGTH: 27
<212> TYPE: DNA
<213> ORGANISM: Artificial Sequence
<220> FEATURE:
<223> OTHER INFORMATION: Oligonucleotide

<400> SEQUENCE: 57
ggaaagaaga aacacccgag actgtgc                                  27

<210> SEQ ID NO 58
<211> LENGTH: 25
<212> TYPE: DNA
<213> ORGANISM: Artificial Sequence
<220> FEATURE:
<223> OTHER INFORMATION: Oligonucleotide

<400> SEQUENCE: 58
gggaactggt cgatcgagaa agggc                                    25

<210> SEQ ID NO 59
<211> LENGTH: 28
<212> TYPE: DNA
<213> ORGANISM: Artificial Sequence
<220> FEATURE:
<223> OTHER INFORMATION: Oligonucleotide

<400> SEQUENCE: 59
ccagtggatt actacagaag atatgctc                                 28

<210> SEQ ID NO 60
<211> LENGTH: 29
<212> TYPE: DNA
<213> ORGANISM: Artificial Sequence
<220> FEATURE:
<223> OTHER INFORMATION: Oligonucleotide

<400> SEQUENCE: 60
caggaacctg accggtaaag aggaatacg                                    29

<210> SEQ ID NO 61
<211> LENGTH: 28
<212> TYPE: DNA
<213> ORGANISM: Artificial Sequence
<220> FEATURE:
<223> OTHER INFORMATION: Oligonucleotide

<400> SEQUENCE: 61
ctgtaattac caacatcaaa caccaaag                                     28

<210> SEQ ID NO 62
<211> LENGTH: 26
<212> TYPE: DNA
<213> ORGANISM: Artificial Sequence
<220> FEATURE:
<223> OTHER INFORMATION: Oligonucleotide

<400> SEQUENCE: 62
ccaacaacaa ccaccaaagg ctattg                                       26

<210> SEQ ID NO 63
<211> LENGTH: 25
<212> TYPE: DNA
<213> ORGANISM: Artificial Sequence
<220> FEATURE:
<223> OTHER INFORMATION: Oligonucleotide

<400> SEQUENCE: 63
ggattggtgt tgtcgatcca acagg                                        25

<210> SEQ ID NO 64
<211> LENGTH: 24
<212> TYPE: DNA
<213> ORGANISM: Artificial Sequence
<220> FEATURE:
<223> OTHER INFORMATION: Primer

<400> SEQUENCE: 64
ctggtggaag cccaacacaa aaac                                         24

<210> SEQ ID NO 65
<211> LENGTH: 45
<212> TYPE: DNA
<213> ORGANISM: Artificial Sequence
<220> FEATURE:
<223> OTHER INFORMATION: Primer

<400> SEQUENCE: 65
ctggtggaag gaagagagaa attggcaact ccccaacaca aaaac                  45

<210> SEQ ID NO 66
<211> LENGTH: 22
<212> TYPE: DNA
<213> ORGANISM: Artificial Sequence
<220> FEATURE:
<223> OTHER INFORMATION: Primer

<400> SEQUENCE: 66
agaccccccc aagcatattg ac                                           22

<210> SEQ ID NO 67
<211> LENGTH: 39
<212> TYPE: DNA

```
<213> ORGANISM: Artificial Sequence
<220> FEATURE:
<223> OTHER INFORMATION: Primer

<400> SEQUENCE: 67
agaccccccc aatatttcct cctcctatag catattgac                    39

<210> SEQ ID NO 68
<211> LENGTH: 21
<212> TYPE: DNA
<213> ORGANISM: Artificial Sequence
<220> FEATURE:
<223> OTHER INFORMATION: Primer

<400> SEQUENCE: 68
cccaacacaa agcatattga c                                       21

<210> SEQ ID NO 69
<211> LENGTH: 6
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (1)...(6)
<223> OTHER INFORMATION: n = A,T,C or G

<400> SEQUENCE: 69 gcagcn                                                         6

<210> SEQ ID NO 70
<211> LENGTH: 5
<212> TYPE: DNA
<213> ORGANISM: Artificial Sequence
<220> FEATURE:
<223> OTHER INFORMATION: Oligonucleotide

<400> SEQUENCE: 70 gcagc                                                          5
```

What is claimed is:

1. An attenuated dengue virus comprising
a mutation at nucleotide position 4995 of the NS3 gene;
wherein said numbering is based upon a prototypical DEN4 isolate strain 814669 (Dominica 1981);
wherein said mutation results in a nucleotide substitution from T to C; and
wherein said attenuated dengue virus is attenuated as compared to a wildtype dengue virus.

2. The attenuated dengue virus of claim 1, further comprising a Δ30 mutation.

3. The attenuated dengue virus of claim 1, wherein the attenuated dengue virus is a dengue virus type 1.

4. The attenuated dengue virus of claim 1, wherein the attenuated dengue virus is a dengue virus type 2.

5. The attenuated dengue virus of claim 1, wherein the attenuated dengue virus is a dengue virus type 3.

6. The attenuated dengue virus of claim 1, wherein the attenuated dengue virus is a dengue virus type 4.

7. The attenuated dengue virus of claim 1, wherein the attenuated dengue virus is a chimeric virus.

8. The chimeric virus of claim 7 having a dengue 1 backbone.

9. The chimeric virus of claim 7 having a dengue 2 backbone.

10. The chimeric virus of claim 7 having a dengue 3 backbone.

11. The chimeric virus of claim 7 having a dengue 4 backbone.

12. The attenuated dengue virus of claim 1, wherein the mutation at nucleotide position 4995 results in a viral polypeptide having a substitution of a proline for a serine at position 1632 of the polypeptide.

13. The attenuated dengue virus of claim 1, wherein the mutation at nucleotide position 4995 results in a viral polypeptide having a substitution of a proline for an asparagine at position 1632 of the polypeptide.

14. An attenuated dengue virus comprising
- a mutation wherein the mutation results in the expression of an NS3 protein having an amino acid substitution from serine or asparagine to proline at amino acid position 1632;
- wherein said numbering is based upon a viral polypeptide encoded by a prototypical DEN4 isolate strain 814669 (Dominica 1981);
- wherein said attenuated dengue virus is attenuated as compared to a wildtype dengue virus.

15. The attenuated dengue virus of claim 14, wherein said attenuated dengue virus is temperature sensitive.

16. The attenuated dengue virus of claim 12, wherein said attenuated dengue virus comprises a deletion of nucleotides 10,478-10,507 in the 3' untranslated region.

* * * * *